United States Patent
Serra Comas et al.

(10) Patent No.: US 7,423,172 B2
(45) Date of Patent: Sep. 9, 2008

(54) TYROSINE DERIVATIVES AS PPAR-γ-MODULATORS

(75) Inventors: Carmen Serra Comas, L'Hospitalet De Llobregat (ES); Anna Fernández Serrat, Cagnes sur Mer (FR); Dolors Balsa López, Badalona (ES); Isabel Masip Masip, Barcelona (ES); Juan Lorenzo Catena Ruiz, L'Hospitalet De Llobregat (ES); José Hidalgo Rodriguez, Sant Fost De Campsentelles (ES); Carmen Lagunas Arnal, Barcelona (ES); Carolina Salcedo Roca, Corbera (ES); Andrés Fernández García, Barcelona (ES)

(73) Assignee: Laboratorios Salvat, S.A., Barcelona (ES)

( * ) Notice: Subject to any disclaimer, the term of this patent is extended or adjusted under 35 U.S.C. 154(b) by 0 days.

(21) Appl. No.: 11/658,856

(22) PCT Filed: Jul. 29, 2005

(86) PCT No.: PCT/EP2005/053728

§ 371 (c)(1),
(2), (4) Date: Mar. 22, 2007

(87) PCT Pub. No.: WO2006/010775

PCT Pub. Date: Feb. 2, 2006

(65) Prior Publication Data

US 2007/0276043 A1 Nov. 29, 2007

(30) Foreign Application Priority Data

Jul. 30, 2004 (ES) ................................ 200401966

(51) Int. Cl.
C07C 233/88 (2006.01)
C07C 229/36 (2006.01)
C07C 233/20 (2006.01)
C07C 233/69 (2006.01)

(52) U.S. Cl. ...................... 562/445; 562/433; 562/443; 562/444

(58) Field of Classification Search ........................ None
See application file for complete search history.

(56) References Cited

U.S. PATENT DOCUMENTS 6,274,608 B1 8/2001 Sauerberg et al.

FOREIGN PATENT DOCUMENTS

| EP | 0 875 510 A1 | 11/1998 |
| WO | WO 94/29285 A1 | 12/1994 |
| WO | WO 9429285 A1 | 12/1994 |
| WO | WO 97/31907 A1 | 9/1997 |
| WO | WO 9731907 A1 | 9/1997 |
| WO | WO 01/30343 A1 | 5/2001 |
| WO | WO 02/08188 A1 | 1/2002 |
| WO | WO 03/011814 A1 | 2/2003 |
| WO | WO 03/011834 A1 | 2/2003 |
| WO | WO 03011814 A1 | 2/2003 |
| WO | WO 03011834 A1 | 2/2003 |
| WO | WO 03/053966 A3 | 7/2003 |
| WO | WO 2004/020408 A1 | 3/2004 |

OTHER PUBLICATIONS

Cobb et al, "N-(2-Benzoylphenyl)-L-Tyrosine PPARγ Agonists," J. Med. Chem., vol. 41, No. 25, 1998, pp. 5055-5069, XP002355939.
Li, Y. et al, "T0903131 (T131): A Selective Modulator of PPAR?", 2004, Abstract No. 659-P, San Francisco, CA.
Reifel-Miller, A. et al, "LY519818: A Novel Non-TZD, PPAR[gamma]-Dominant Agonist with Improved Insulin Sensitization and Unique Co-Factor Recruitment and Response Element Activation Profiles," 2003, Abstract No. 614-P, Indianapolis, IN; San Diego, CA.
Wright, H. et al, "A Synthetic Antagonist for the Peroxisome Proliferator-activated Receptor γ Inhibits Adipocyte Differentiation," *The Journal of Biological Chemistry*, vol. 275, No. 3, Issue of Jan. 21, pp. 1873-1877, 2000, USA; 2000 by The American Society for Biochemistry and Molecular Biology, Inc.
Lehmann, J. et al, "An Antidiabetic Thiazolidinedione Is a High Affinity Ligand for Peroxisome Proliferator-activated Receptor γ (PPARγ)," *The Journal of Biological Chemistry*, vol. 270, No. 22, Issue of Jun. 2, pp. 12953-12956, 1995; 1995 by The American Society of Biochemistry and Molecular Biologi, Inc., USA.
Harland, P. et al, "Synthesis of Primary Amines via Alkylation of the Sodium Salt of Trifluoroacetamide: An Alternative to the Gabriel Synthesis," *Communications*, Nov. 1984, pp. 941-943; Department of Chemistry, University of Lancaster, Great Britain; Lancaster Synthesis, Ltd., Great Britain.
Lin, X. et al, "Utilization of Fukuyama's sulfonamide protecting group for the synthesis of N-substituted α-amino acids and derivatives," *Tetrahedron Letters 41* (2000), pp. 3309-3313, Abstract; 2000 Elsevier Science Ltd.; Chiron Corporation, CA, USA.

(Continued)

*Primary Examiner*—Yvonne Eyler
*Assistant Examiner*—Yevegeny Valenrod
(74) *Attorney, Agent, or Firm*—Rothwell, Figg, Ernst & Manbeck, p.c.

(57) ABSTRACT

Compounds of general formula I, and the salts and solvates thereof, wherein R1 represents the radical 2-benzoylphenylamino; R2 represents —$(CH_2)_s$—$N(COR_3)$-A-J-T or —$(CH_2)_s$—$N(R_4)$—B-J-T; and s. R3, R4, A, B, J and T have the meanings disclosed in the description. These compounds are PPARγ modulators and, therefore, are useful for the treatment or prevention of a condition or a disease mediated by these receptors.

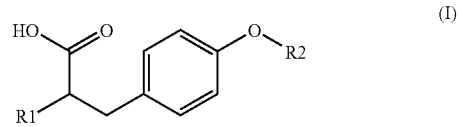

(I)

10 Claims, No Drawings

OTHER PUBLICATIONS

Fajas, L. et al, "The Organization, Promoter Analysis, and Expression of the Human PPARγ Gene," *The Journal of Biological Chemistry*, vol. 272, No. 30, Issue of Jul. 25, pp. 18779-18789, 1997, USA; 1997 by The American Society for Biochemistry and Molecular Biology, Inc.

Fajas, L. et al, "PPARγ3 mRNA: a distinct PPARγ mRNA subtype transcribed from an independent promoter," *FEBS Letters 438* (1998), pp. 55-60, FEBS 21031; 1998 Federation of European Biochemical Societies; Département d' Athérosclérose, France.

Vamecq, J. et al, "Medical significance of peroxisome proliferator-activated receptors," *The Lancet*, vol. 354, Jul. 10, 1999, pp. 141-148; Neuropaediatrics Department of Professor Jean-Pierre Nuyts, France; Laboratory of Molecular and Cell Biology, University of Burgundy, Dijon.

Grimaldi, P., "The roles of PPARs in adipocyte differentiation," *Progress in Lipid Research 40* (2001), pp. 269-281; 2001 Elsevier Science Ltd.; Centre de Biochimie, University of Nice-Sophia Antipolis, France.

Schiller, P. et al, "Inhibition of Gap-Junctional Communication Induces the Trans-differentiation of Osteoblasts to an Adipocytic Phenotype in Vitro," *The Journal of Biological Chemistry*, vol. 276, No. 17, Issue of Apr. 27, pp. 14133-14138, 2001, USA; Published, JBC Papers in Press, Jan. 25, 2001.

Berger, J. et al, "PPARs: therapeutic targets for metabolic disease," *Trends in Pharmacological Sciences*, vol. 26, No. 5, May 2005; 2005 Merck Research Laboratories—Published by Elsevier Ltd.

Minoura, H. et al, "Pharmacological characteristrics of a novel nonthiazolidinedione insulin sensitizer, FK614," *European Journal of Pharmacology 494* (2004), pp. 273-281; Abstract; 2004 Elsevier B.V.; Research Division, Fujisawa Pharmaceutical Co., Ltd., Japan; Tsukuba Research Center, Daicel Chemical Industries, Ltd., Japan.

Kurtz, T.W., "Treating the metabolic syndrome: telmisartan as a peroxisome proliferator-activated receptor-gamma activator," *Acta Diabetol*, 2005, vol. 42, pp. S9-S16; supplied by the British Library—"The world's knowledge; Laboratory of Medicine, San Francisco, CA; supplied by The British Library—The world's knowledge".

Henke, B. et al, "N-(2-Benzoylphenyl)-L-tyrosine PPARγ Agonists. 1. Discovery of a Novel Series of Potent Antihyperglycemic and Antihyperlipidemic Agents," *Journal of Medicinal Chemistry*, 1998, vol. 41, No. 25, pp. 5020-5036; 1998 American Chemical Society; published on Web Nov. 11, 1998.

Collins, J. et al, "N-(2-Benzoylphenyl)-L-tyrosine PPARγ Agonists. 2. Structure-Activity Relationship and Optimization of the Phenyl Alkyl Ether Moiety," *Journal of Medicinal Chemistry*, 1998, vol. 41, No. 25, pp. 5037-5054; 1998 American Chemical Society; published on Web Nov. 6, 1998; Published on Web Nov. 6, 1998.

Cobb, J. et al, "N-(2-Benzoylphenyl)-L-tyrosine PPARγ Agonists. 3. Structure-Activitiy Relationship and Optimization of the N-Aryl Substituent," *Journal of Medicinal Chemistry*, 1998, vol. 41, No. 25, pp. 5055-5069; 1998 American Chemical Society; published on Web Nov. 7, 1998.

Bal-Tembe, S., et al, "HL 752: A Potent and Long-Acting Antispasmodic Agent," *Bioorganic & Medicinal Chemistry*, vol. 5, No. 7, pp. 1381-1387, 1997; 1997 Elsevier Science Ltd., Great Britain.

Cantello, B. et al, "[[ω-(Heterocyclylamino)alkoxy]benzyl]-2,4-thiazolidinediones as Potent Antihyperglycemic Agents," *Journal of Medicinal Chemistry*, 1994, vol. 37, No. 23, pp. 3977-3985; 1994 American Chemical Society.

Mitsunobu, Oyo, "The Use of Diethyl Azodicarboxylate and Triphenylphosphine in Synthesis and Transformation of Natural Products," *Synthesis*, Jan. 1981, pp. 1-28; 1981 Georg Thieme Verlag, Stuttgart, New York.

Daoud, K.M. et al, "Synthesis of Biologically Active Compounds of Amino Ester Hydrochlorides derived from Substituted-cinchophen," *Journal of the Indian Chemical Society*, vol. 66, May 1989, pp. 316-318; supplied by The British Library—"The world's knowledge".

Hirschmann, R. et al, "De Novo Design and Synthesis of Somatostatin Non-Peptide Peptidomimetics Utilizing β-D-Glucose as a Novel Scaffolding," *Journal of the American Chemical Society*, 1993, vol. 115, No. 26, pp. 12550-12568; 1993 American Chemical Society.

Elbrecht, A. et al, "L-764406 Is a Partial Agonist of Human Peroxisome Proliferator-activated Receptor γ," *The Journal of Biological Chemistry*, vol. 274, No. 12, Issue of Mar. 19, pp. 7913-7922, 1999, USA; 1999 by The American Society for Biochemistry and Molecular Biology, Inc.

TYROSINE DERIVATIVES AS PPAR-γ-MODULATORS

CROSS-REFERENCE TO RELATED APPLICATION

The present application is a national stage filing under 35 U.S.C. §371 of PCT/EP2005/053728, filed on 29 Jul. 2005. The present application also claims priority under 35 U.S.C. §119 to Spain patent application Serial No. 200401966 filed on 30 Jul. 2004.

The present invention relates to new tyrosine derivatives acting as PPARγ modulators, as well as to processes and intermediates useful for their preparation, to pharmaceutical compositions containing them and their application in medicine.

BACKGROUND ART

Peroxisome proliferator activated receptors (PPARs) belong to the superfamily of transcription factors known as nuclear receptors. This family includes steroid, retinoid and thyroid hormone receptors. Three sub-types of PPARs have been identified in humans, rodents and *Xenopus laevis*. They are PPARα, PPARβ/δ and PPARγ, each encoded by a different gene and showing different tissue distribution.

The gene encoding for PPARγ is transcribed in humans in three different mRNA isoforms (PPARγ1, PPARγ2 and PPARγ3) through different splicing and promoter usage (Fajas et al., *J. Biol. Chem.* 1997, vol. 272, p. 18779-18789). The PPARγ1 isoform shows a wide tissular distribution, while PPARγ2 and PPARγ3 are confined to certain tissues: PPARγ2 is expressed only in adipose tissue and PPARγ3 in adipose tissue as well as in macrophages (Fajas et al., *FEBS Lett.* 1998, vol. 438, p. 55-60).

Differences detected in tissue distribution as well as in the activation profile of the PPARγ isoforms suggest they are involved in a variety of physiological functions playing a central role in glucose homeostasis and lipid metabolism (Vamecq et al., *Lancet* 1999, vol. 354, p, 141-148). These functions include, for example, lipidic transport in plasma and catabolism of fatty acids, regulation of insulin sensitivity and blood glucose levels, differentiation of macrophages that form atherosclerotic plaques, inflammatory response, carcinogenesis, hyperplasia, and adipocyte differentiation, the latter being the most verified function of the PPARγ (Grimaldi, *Prog. Lipid Res.* 2001, vol. 40, p. 269-281; Schiller et al., *J. Biol. Chem.* 2001, vol. 276, p. 14133-14137). Thus, the discovery of these transcription factors has provided new pharmacological targets for the development of useful therapeutic agents for the prevention and treatment of metabolic diseases such as diabetes, obesity and dyslipidaemia.

Non-insulin dependent diabetes mellitus (NIDDM) or type 2 diabetes is characterized by an insulin resistance in peripheral tissues, including muscle, liver, and adipose tissue. Glitazones, selective PPARγ agonist compounds, are drugs that reduce insulin resistance and lower blood glucose levels. Currently two products belonging to this family, rosiglitazone and pioglitazone, have been approved for the treatment of type 2 diabetes in humans.

A great effort has been made in recent years to design new drugs that improve the side effect profile of the first glitazones, show a greater affinity as a PPARγ ligands, and increase their potency in type 2 diabetes. This rational design has yielded structurally diverse compounds that show great potency and selectivity (e.g. farglitazar).

PPARγ agonists have had shortcomings which have so far detracted from their attractiveness, such as liver toxicity (especially troglitazone), weigh gain, edema, heart weight gain (in rodents) and adiposity, as well as modest efficacy in monotherapy for type 2 diabetes. These facts have provided an incentive to develop improved insulin sensitizers.

Compounds totally or partially blocking PPARγ activity have demonstrated to inhibit adipocyte differentiation. Thus, full antagonists constitute an effective treatment for obesity. Moreover, compounds that are partial agonists in addition of being antagonists may be particularly desirable because they are effective in treating not only obesity but also in controlling hyperglycemia. The PPARγ antagonists/partial agonists are therefore effective in treating obesity and other symptoms that generally occur in non-insulin dependent diabetes, such as elevated plasma levels of glucose, tryglicerides, and insulin.

Recently, there have been reports of compounds that are PPARγ antagonists or partial agonists (WO01/30343, WO02/08188, WO2004/020408), which are useful for the treatment of obesity and type 2 diabetes, with reduced side effects (Berger et al., *Trends Pharmacol. Sci.* 2005, vol. 26, p. 244-51).

Examples of partial agonists in clinical development for diabetes are (−)-halofenate (metaglidasen), FK 614 (Minoura et al., *Eur. J. Pharmacol.* 2004, vol. 494, p. 273-8), T131 (Li et al., 64th *Annu. Meet Sci. Sess. Am. Diabetes Assoc.* (June 4-June 8, Orlando) 2004, Abst 659-P), LY818 (Reifel-Miller et al., *Diabetes* 2003, 52 (Suppl. 1): Abst 614-P) and telmisartan, an angiotensin II blocker approved for the treatment of hypertension, with PPAR partial agonistic activity at concentrations achievable at plasmatic levels during treatment (Kurtz et al., *Acta Diabetol.* 2005; vol. 42 Suppl 1: S 9-16) which are currently in phase II of clinical development.

In Henkel et al., *J. Med. Chem.* 1998, vol. 41, p. 5020-5036; Collins et al., *J. Med. Chem.* 1998, vol. 41, p. 5037-5054; Cobb et al., *J. Med. Chem.* 1998, vol. 41, p. 5055-5069, WO 94/29285 and in WO 97/31907 de N-(2-benzoylphenyl)-L-tyrosine derivatives are described as being potent and selective PPARγ agonists. Documents WO 03/011814 and WO 03/011834 disclose N-(2-benzoylphenyl)-L-tyrosine derivatives as partial PPARγ agonists. Document U.S. Pat. No. 6,274,608 describes N-(2-benzoylphenyl)-L-tyrosine derivatives as being useful in the treatment and/or prevention of conditions mediated by Retinoid X Receptor (RXR) and the PPAR families.

Obviously, it is of great interest to provide new therapeutic agents that modulate PPARγ.

SUMMARY OF THE INVENTION

One aspect of the present invention relates to the provision of new compounds of general formula I,

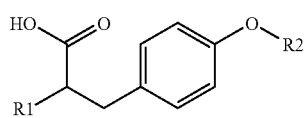

their stereoisomers and mixtures thereof, their polymorphs and mixtures thereof, and the pharmaceutically acceptable solvates and addition salts of all of them, wherein R1 represents the radical 2-benzoylphenylamino;

R2 represents $-(CH_2)_s-N(COR3)-A-J-T$ or $-(CH_2)_s-N(R4)-B-J-T$;

R3 represents $-(C_1-C_{10})$alkyl optionally substituted by one or more substituents selected from $-F$, $-Cl$, $-Br$ and $-O(C_1-C_4)$alkyl; $-(C_2-C_6)$alkenyl; $-(C_2-C_6)$alkynyl; $-(C_1-C_3)$alkylene-Y; $-(C_2-C_3)$alkenylene-Y; $-(C_2-C_3)$alkynylene-Y or $-Y$;

R4 represents —(C$_4$-C$_{10}$)alkyl optionally substituted by one or more substituents selected from —F, —Cl, —Br and —O(C$_1$-C$_4$)alkyl; —(C$_2$-C$_6$)alkenyl; —(C$_2$-C$_6$)alkynyl; —(C$_1$-C$_4$)alkylene-Y; —(C$_2$-C$_4$)alkenylene-Y; —(C$_2$-C$_4$)alkynylene-Y or —Y;

s represents 2 or 3;

A represents —(C$_1$-C$_4$)alkylene-; —(C$_2$-C$_4$)alkenylene-; —(C$_2$-C$_4$)alkynylene-; —(C$_1$-C$_4$)alkylene-Z-, wherein the alkylene part is attached to the N atom and Z is attached to J; or -Z-;

B represents —(C$_4$)alkylene-; —(C$_2$-C$_4$)alkenylene-; —(C$_2$-C$_4$)alkynylene-; —(C$_1$-C$_4$)alkylene-Z-, wherein the alkylene part is attached to the N atom and Z is attached to J; or -Z-;

J represents a single bond or a biradical selected from the following groups:
  a) —(CH$_2$)$_{1-4}$—, —O—, —S—, —SO—, —SO$_2$—, —CO—, —OCO—, —COO—, —OCONR5-, —NR5COO—, —CONR5-, —NR5CO—, —NR5-, —NR5SO$_2$—, —SO$_2$NR5-; and
  b) —O(C$_1$-C$_4$)alkyl-, —(C$_1$-C$_4$)alkyl-O—, —S(C$_1$-C$_4$)alkyl-, —(C$_1$-C$_4$)alkyl-S—, —SO(C$_1$-C$_4$)alkyl-, —(C$_1$-C$_4$)alkyl-SO—, —SO$_2$(C$_1$-C$_4$)alkyl-, —(C$_1$-C$_4$)alkyl-SO$_2$—, —OCO—C$_1$-C$_4$)alkyl-, —COO—(C$_1$-C$_4$)alkyl-, —(C$_1$-C$_4$)alkyl-OCO—, —(C$_1$-C$_4$)alkyl-COO—, —OCONR5-(C$_1$-C$_4$)alkyl-, —NR5COO—(C$_1$-C$_4$)alkyl-, —(C$_1$-C$_4$)alkyl-OCONR5-, —(C$_1$-C$_4$)alkyl-NR5COO—, —CONR5-(C$_1$-C$_4$)alkyl-, —NR5CO—(C$_1$-C$_4$)alkyl-, —(C$_1$-C$_4$)alkyl-CONR5-, —(C$_1$-C$_4$)alkyl-NR5CO—, —NR5-(C$_1$-C$_4$)alkyl-, —(C$_1$-C$_4$)alkyl-NR5-, —SO$_2$NR5-(C$_1$-C$_4$)alkyl-, —NR5SO$_2$—(C$_1$-C$_4$)alkyl-, —(C$_1$-C$_4$)alkyl-SO$_2$NR5-, —(C$_1$-C$_4$)alkyl-NR5SO$_2$—;

T represents —H, —C$_1$-C$_4$)alkyl, —(C$_2$-C$_4$)alkenyl, —(C$_2$-C$_4$)alkynyl or —Y;

Y represents a monoradical coming from a cycle selected from a (C$_3$-C$_6$)cycloalkane, cyclohexene, a heterocycle, benzene and a bicycle, wherein all these cycles can be optionally substituted with one or more substituents selected from the group —OH, —CHO, —SH, —NO$_2$, —CN, —F, —Cl, —Br, —CO(C$_1$-C$_4$)alkyl, —COO(C$_1$-C$_4$)alkyl, —OCO(C$_1$-C$_4$)alkyl, —S(C$_1$-C$_4$)alkyl, —SO(C$_1$-C$_4$)alkyl, —SO$_2$(C$_1$-C$_4$)alkyl, —SO$_2$—O(C$_1$-C$_4$)alkyl, —O—SO$_2$(C$_1$-C$_4$)alkyl, —NR5R6, —CONR5R6, —(C$_1$-C$_4$)alkyl optionally substituted by one or more —OH or —F and —O(C$_1$-C$_4$)alkyl optionally substituted by one or more —OH or —F, and wherein the cycles (C$_3$-C$_6$)cycloalkane, cyclohexene and bicycle can also be optionally substituted with one or more substituents oxo (=O);

Z represents a biradical coming from a cycle selected from a (C$_3$-C$_6$)cycloalkane, cyclohexene, a heterocycle, benzene and a bicycle, wherein all these cycles can be optionally substituted with one or more substituents selected from the group —OH, —CHO, —SH, —NO$_2$, —CN, —F, —Cl, —Br, —CO(C$_1$-C$_4$)alkyl, —COO(C$_1$-C$_4$)alkyl, —OCO(C$_1$-C$_4$)alkyl, —S(C$_1$-C$_4$)alkyl, —SO(C$_1$-C$_4$)alkyl, —SO$_2$(C$_1$-C$_4$)alkyl, —SO$_2$—O(C$_1$-C$_4$)alkyl, —O—SO$_2$(C$_1$-C$_4$)alkyl, —NR5R6, —CONR5R6, —(C$_1$-C$_4$)alkyl optionally substituted by one or more —OH or —F and —O(C$_1$-C$_4$)alkyl optionally substituted by one or more —OH or —F, and wherein the cycles (C$_3$-C$_6$)cycloalkane, cyclohexene and bicycle can also be optionally substituted with one or more substituents oxo (=O);

R5 and R6 independently represent —H or —(C$_1$-C$_4$)alkyl;

a heterocycle in the above definitions represents a five- or six-membered aromatic ring containing from one to three heteroatoms independently selected from O, S and N, wherein said ring can be attached to the rest of the molecule through a carbon or a nitrogen atom; and a bicycle in the above definitions represents a partially unsaturated, saturated or aromatic seven- to ten-membered ring optionally containing from one to three heteroatoms independently selected from O, S and N, wherein said ring or rings can be attached to the rest of the molecule through a carbon or a nitrogen atom.

The compounds of formula I are PPARγ modulators and, therefore, useful as active pharmaceutical substances.

Thus, another aspect of this invention relates to the pharmaceutical compositions which comprise an effective amount of a compound of formula I or a pharmaceutically acceptable salt or solvate thereof and one or more pharmaceutical acceptable excipients.

Another aspect of the present invention relates to the use of a compound of formula I for the manufacture of a medicament for the treatment or prevention of diseases mediated by PPARγ. Another aspect of the present invention relates to the use of a compound of formula I for the manufacture of a medicament for the treatment or prevention of metabolic diseases in a subject in need thereof, including a human. Another aspect of the present invention relates to the use of a compound of formula I or a pharmaceutically acceptable salt or solvate thereof for the manufacture of a medicament for the treatment or prevention of metabolic diseases selected from non-insulin-dependent diabetes mellitus and obesity in a subject in need thereof, including a human. Another aspect of the present invention relates to the use of a compound of formula I or a pharmaceutically acceptable salt or solvate thereof for the manufacture of a medicament for the treatment or prevention of cardiovascular diseases associated with metabolic syndrome, inflammatory diseases, cancer, bone diseases, skin wound healing, cutaneous disorders associated with an anomalous differentiation of epidermic cells, and other disorders where insulin resistance is a component in a subject in need thereof, including a human.

Another aspect of the present invention relates to the method for the treatment or prevention of diseases mediated by PPARγ comprising the administration to a mammal, including a human, an effective amount of a compound of formula I or a pharmaceutically acceptable salt or solvate thereof. Another aspect of the present invention relates to the method for the treatment or prevention of metabolic diseases comprising the administration to a mammal, including a human, an effective amount of a compound of formula I or a pharmaceutically acceptable salt or solvate thereof. Another aspect of the present invention relates to the method for the treatment or prevention of metabolic diseases selected from non-insulin-dependent diabetes mellitus and obesity comprising the administration to a mammal, including a human, an effective amount of a compound of formula I or a pharmaceutically acceptable salt or solvate thereof. Another aspect of the present invention relates to the method for the treatment or prevention of cardiovascular diseases associated with metabolic syndrome, inflammatory diseases, cancer, bone diseases, skin wound healing, cutaneous disorders associated with an anomalous differentiation of epidermic cells and other disorders where insulin resistance is a component, comprising the administration to a mammal, including a human, an effective amount of a compound of formula I or a pharmaceutically acceptable salt or solvate thereof.

In the previous definitions, the terms "alkyl" and "alkylene" mean respectively a monoradical or biradical straight or branched saturated hydrocarbon chain having the indicated number of carbon atoms. Examples of alkyl include, but are not limited to, methyl, ethyl, propyl, isopropyl, butyl, isobutyl, sec-butyl, tert-butyl, pentyl, isopentyl, neopentyl, hexyl, heptyl, octyl, nonyl, decyl and the like.

The terms "alkenyl" and "alkenylene", as used herein, mean respectively a monoradical or biradical straight or branched unsaturated hydrocarbon chain, having the indicated number of carbon atoms and also containing one or more double bonds. Examples of alkenyl include, but are not limited to, ethenyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl and the like.

The terms "alkynyl" and "alkynylene", as used herein, mean respectively a monoradical or biradical straight or branched unsaturated hydrocarbon chain, having the indicated number of carbon atoms and also containing one or more triple bonds. Examples of alkynyl include, but are not limited to, ethynyl, 1-propynyl, 2-propynyl, 1-butynyl, 2-butynyl, 3-butynyl, 1,3-butadiynyl, 1-pentynyl, 2-pentynyl, 3-pentynyl, 4-pentynyl, 1-hexynyl, 2-hexynyl, 3-hexynyl, 4-hexynyl, 5-hexynyl and the like.

The term heterocycle as used herein refers to a five- or six-membered monocyclic aromatic ring containing from one to three heteroatoms independently selected from O, S and N. As mentioned previously, these heterocycles can be optionally substituted with one or more substituents, which can be placed on any available position of the cycle, and can be attached to the rest of the molecule via any available carbon or nitrogen atoms. Examples include, but are not limited to, 1, 2, 4-oxadiazole, 1, 2, 4-thiadiazole, 1,3,4-oxadiazole, 1,3,4-thiadiazole, furan, imidazole, isoxazole, isothiazole, oxazole, pyrazol, pyrrole, thiazole, thiophene, 1,2,3-triazole, 1,2,4-triazole, pyrazine, pyridazine, pyridine, pyrimidine and the like.

The term $(C_3-C_6)$cycloalkane as used herein refers to saturated monocyclic carbocyclic ring having the indicated number of carbon atoms. As mentioned previously, it can be optionally substituted with one or more substituents, which can be placed on any available position of the cycle. Examples of $(C_3-C_6)$cycloalkanes include, but are not limited to, cyclopropane, cyclobutane, cyclopentane and cyclohexane.

The term bicycle, as used herein refers to a partially unsaturated, saturated or aromatic seven- to ten-membered ring optionally containing from one to three heteroatoms independently selected from O, S and N, wherein said ring or rings can be attached to the rest of the molecule through a carbon or a nitrogen atom. As mentioned previously, it can be optionally substituted with one or more substituents, which can be placed on any available position of the cycle. Examples of bicyclic groups include, among others, naphthalene, 1,2,3,4-tetrahydronaphthalene, quinoline, 1,2,3,4-tetrahydroquinoline, isoquinoline, benzofuran, 2,3-dihydrobenzofuran, benzothiophene, indole, benzimidazole, benzotriazol, bicyclo[2.2.1]heptane, bicyclo[3.2.1]octane and bicyclo[3.2.2]nonane.

The expression "optionally substituted with one or more" means that a group can be unsubstituted or substituted with one or more, preferably with 1, 2, 3 or 4 substituents, provided that this group has 1, 2, 3 or 4 positions susceptible of being substituted.

Throughout the description and claims the word "comprise" and variations of the word, such as "comprising", are not intended to exclude other additives, components, elements or steps. The disclosures in the abstract accompanying this application and in the application from which priority is claimed, are incorporated herein as reference.

As used therein the term "treatment" includes treatment, prevention and management of such condition. The term "pharmaceutically acceptable" as used herein refers to those compounds, compositions, and/or dosage forms which are, within the scope of medical judgement, suitable for use in contact with the tissues of humans and animals without excessive toxicity, irritation, allergic response, or other problem or complication, commensurate with a reasonable benefit/risk ratio.

Compounds of formula I of the present invention comprise at least one chiral center. The present invention includes both the racemic compounds and the enantiomeric compounds, i.e. compounds of formula Ia (wherein the configuration of the chiral carbon attached to R1 is (S)) and compounds of formula Ib (wherein the configuration of the chiral carbon attached to R1 is (R)) as shown below.

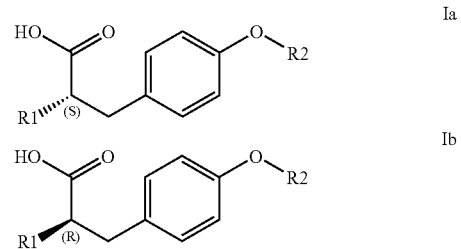

In a particular embodiment of the invention the configuration of the chiral carbon attached to R1 is (S).

In another embodiment in a compound of formula I or Ia, R2 represents —$(CH_2)_s$—N(COR3)-A-J-T. In another embodiment in a compound of formula I or Ia, R2 represents —$(CH_2)_s$—N(R4)-B-J-T. In another embodiment in a compound of formula I or Ia, J represents a single bond and T represents —H. In another embodiment in a compound of formula I or Ia, J represents —$(CH_2)_{1-4}$—, —O—, —S—, —SO—, —$SO_2$—, —O($C_1$-$C_4$)alkyl- or —S($C_1$-$C_4$)alkyl-. In another embodiment in a compound of formula I or Ia, T represents —H or —($C_1$-$C_4$)alkyl.

In another embodiment in a compound of formula I or Ia, R2 represents —$(CH_2)_s$—N(COR3)-A-J-T; R3 represents —($C_1$-$C_{10}$)alkyl optionally substituted by one or more substituents selected from —F, —Cl, —Br and —O($C_1$-$C_4$)alkyl; —($C_2$-$C_6$)alkenyl; —($C_1$-$C_3$)alkylene-Y; —($C_2$-$C_3$)alkenylene-Y; —($C_2$-$C_3$)alkynylene-Y or —Y; and Y in R3 represents a monoradical coming from a cycle selected from a ($C_3$-$C_6$)cycloalkane, a heterocycle, benzene and a bicycle, wherein all these cycles can be optionally substituted as defined above.

In another embodiment in a compound of formula I or Ia, R2 represents —$(CH_2)_s$—N(COR3)-A-J-T; A represents —($C_1$-$C_4$)alkylene-; —($C_1$-$C_4$)alkylene-Z- or -Z-; Z in A represents a biradical coming from a cycle selected from a ($C_3$-$C_6$)cycloalkane, a heterocycle, benzene and a bicycle, wherein all these cycles can be optionally substituted with one or more substituents selected from the group —F, —Cl, —Br, —S($C_1$-$C_4$)alkyl, —($C_1$-$C_4$)alkyl optionally substituted by one or more —OH or —F and —O($C_1$-$C_4$)alkyl optionally substituted by one or more —OH or —F; J represents a single bond; and T represents —H.

In another embodiment in a compound of formula I or Ia, R2 represents —$(CH_2)_s$—N(COR3)-A-J-T; A represents —($C_1$-$C_4$)alkylene-; —($C_1$-$C_4$)alkylene-Z- or -Z-; Z in A represents an unsubstituted biradical coming from a cycle selected from a ($C_3$-$C_6$)cycloalkane and benzene; J represents a single bond; and T represents —H.

In another embodiment in a compound of formula I or Ia, R2 represents —($CH_2$)$_s$—N(R4)-B-J-T; R4 represents —($C_4$-$C_{10}$)alkyl optionally substituted by one or more substituents selected from —F, —Cl, —Br and —O($C_1$-$C_4$)alkyl; —($C_1$-$C_4$)alkylene-Y; or —Y; and Y in R4 represents a monoradical coming from a cycle selected from a ($C_3$-$C_6$)cycloalkane, a heterocycle, benzene and a bicycle, wherein all these cycles can be optionally substituted as defined above.

In another embodiment in a compound of formula I or Ia, R2 represents —($CH_2$)$_s$—N(R4)-B-J-T, B represents —($C_1$-$C_4$)alkylene-Z- or -Z-; Z in B represents a biradical coming from a cycle selected from a ($C_3$-$C_6$)cycloalkane, a heterocycle, benzene and a bicycle, wherein all these cycles can be optionally substituted as defined above; J represents a single bond; and T represents —H.

Furthermore, all possible combinations of the above-mentioned embodiments form also part of this invention.

The compounds of the present invention may contain one or more basic nitrogen atoms and, therefore, they may form salts with acids, that also form part of this invention. Examples of pharmaceutically acceptable salts include, among others, addition salts with inorganic acids such as hydrochloric, hydrobromic, hydroiodic, nitric, perchloric, sulphuric and phosphoric acid, as well as addition salts of organic acids such as acetic, methanesulfonic, trifluoromethanesulfonic, ethanesulfonic, benzenesulfonic, p-toluenesulfonic, benzoic, camphorsulfonic, mandelic, oxalic, succinic, fumaric, tartaric, and maleic acid. Likewise, compounds of the present invention may contain one or more acid protons and, therefore, they may form salts with bases, that also form part of this invention. Examples of these salts include salts with metal cations, such as for example an alkaline metal ion, an alkaline-earth metal ion or an aluminium ion; or it may be coordinated with an organic with an organic or inorganic base. An acceptable organic base includes among others diethylamine and triethylamine. An acceptable inorganic base includes aluminium hydroxide, calcium hydroxide, potassium hydroxide, sodium carbonate, and sodium hydroxide. There may be more than one cation or anion depending on the number of functions with charge and on the valency of cations and anions.

Salts derived from pharmaceutically acceptable organic nontoxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

There is no limitation on the type of salt that can be used provided that these are pharmaceutically acceptable when they are used for therapeutic purposes. Salts can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, such as ether, ethyl acetate, ethanol, isopropanol, or acetonitrile or in a mixture of the two. The compounds of formula I and their salts differ in some physical properties but they are equivalent for the purposes of the present invention.

Some of the compounds of formula I of the present invention may exist in unsolvated as well as solvated forms such as, for example, hydrates. The present invention encompasses all such above-mentioned forms which are pharmaceutically active.

Some of the compounds of general formula I may exhibit polymorphism, encompassing the present invention all the possible polymorphic forms, and mixtures thereof. Various polymorphs may be prepared by crystallization under different conditions or by heating or melting the compound followed by gradual or fast cooling. The presence of polymorphs may be determined by solid NMR spectroscopy, IR spectroscopy, differential scanning calorimetry, powder X-ray diffraction or such other techniques.

Compounds of formula I of the present invention comprise at least one chiral center. Additionally, compounds of formula I of the present invention may have further chiral centres. The present invention includes each one of the possible stereoisomers and mixtures thereof, particularly racemic mixtures thereof. A single enantiomer may be prepared by any of the commonly used processes, for example, by chromatographic separation of the racemic mixture on a stationary chiral phase, by resolution of the racemic mixture by fractional crystallisation techniques of the diastereomeric salts thereof, by chiral synthesis, by enzymatic resolution or by biotransformation. This resolution can be carried out on any chiral synthetic intermediate or on products of general Formula I. Alternatively, any enantiomer of a compound of the general Formula I may be obtained by enantiospecific synthesis using optically pure starting materials or reagents of known configuration.

Some of the compounds of the present invention may exist as several diastereoisomers, which may be separated by conventional techniques such as chromatography or fractional crystallization. Some compounds of the present invention may exhibit cis/trans isomers. The present invention includes each of the geometric isomers and its mixtures. The present invention covers all isomers and mixtures thereof (for example racemic mixtures) whether obtained by synthesis and also by physically mixing them.

The present invention relates to a process for the preparation of the above said novel compounds, their derivatives, their analogues, their tautomeric forms, their stereoisomers, their polymorphs or their pharmaceutical acceptable salts and solvates.

The compounds of the present invention may be synthesized using the methods described below, as well as other processes known in the field of organic synthesis. Preferred methods include, but are not limited to, the general processes shown in the attached schemes. Unless otherwise stated the groups R1, R2, R3, R4, R5, R6, s, A, B, J, and T have the meaning described in general formula I.

A compound of formula I may be obtained in general by hydrolysis of a compound of formula II, wherein R7 represents ($C_1$-$C_4$)alkyl. This reaction can be carried out in the presence of a base such as an alkaline hydroxide in a solvent such as tetrahydrofuran, aqueous methanol or a mixture thereof, at a temperature comprised between room temperature and the temperature of the boiling point of the solvent, preferably at room temperature.

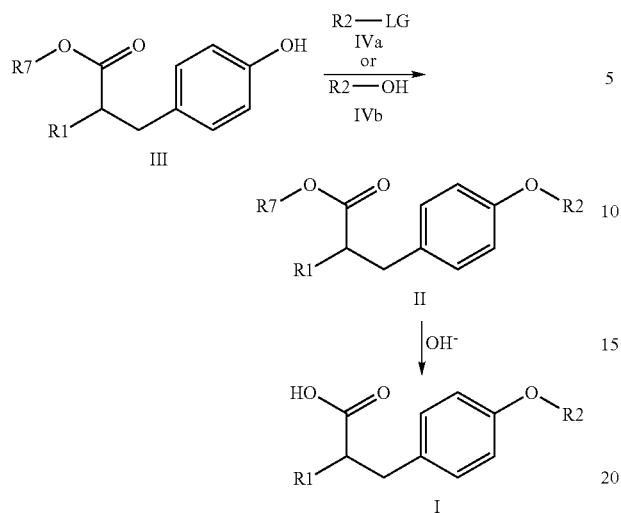

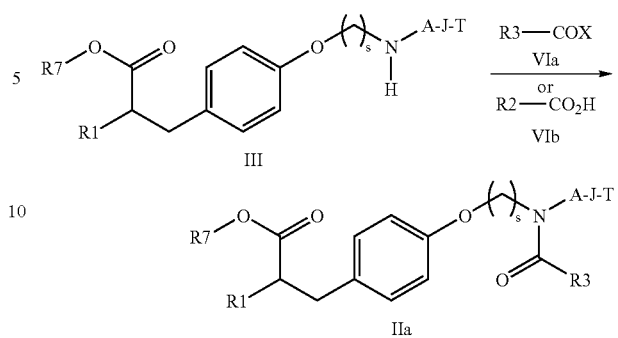

A compound of formula II may be obtained as shown in the above scheme by Williamson ether synthesis (see for instance Bal-Tembe et al., *Bioorg. Med. Chem.* 1997, 5, 1381-1388; Cantello et al., *J. Med. Chem.* 1994, vol. 37, p. 3977-3985 or EP 875510) or by Mitsunobu conditions (Mitsunobu, *Synthesis* 1981, 1; Hughes, *Org. React.* 1992, 42, 335).

In the first case, phenol ester III may be reacted with R2-LG (IVa), wherein LG represents a leaving group, such as for instance a halogen including —Cl, —Br, —I or an alkylsulfonate or arylsulfonate, including mesylate, tosylate or nosylate. This reaction is carried out in the presence of a base, such as NaH, $K_2CO_3$ or $Cs_2CO_3$, in a solvent such as N,N-dimethylformamide, acetone or ethyl acetate, at a temperature comprised between room temperature and the temperature of the boiling point of the solvent, preferably heating.

In the second case, a compound of formula III may be reacted with an alcohol of formula R2-OH (IVb) using for example, diethyl azodicarboxylate (DEAD) and triphenylphosphine in tetrahydrofuran as a solvent, at a temperature comprised between room temperature and the temperature of the boiling point of the solvent, preferably at room temperature.

Isolated enantiomeric forms of formula Ia and Ib can be obtained either by chiral resolution of a compound of formula I or starting from the corresponding chiral compounds IIIa and IIIb respectively.

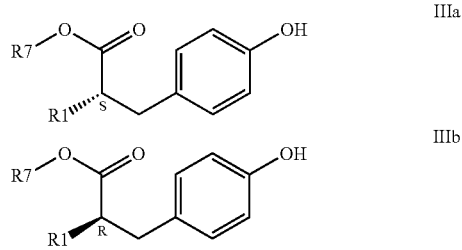

A compound of formula II wherein R2 represents —(CH$_2$)$_s$—N(COR3)-A-J-T (i.e. compound of formula IIa) may also be obtained by acylation of a compound of formula Va with a compound of formula R3-COX (VIa), wherein X represents halogen, preferably Cl.

This reaction is carried out in the presence of a base such as triethylamine, in a solvent such as dichloromethane or ethyl acetate, at a temperature comprised between room temperature and the temperature of the boiling point of the solvent.

Some compounds of formula IIa can also be obtained by reacting a compound Va with the corresponding acid of formula VIb (see for instance Elmore, *Amino Acids Pep. Proteins* 2001, 32, 107-162). This reaction is carried out in the presence of a coupling agent, such as the combination of 1-(3-dimethylaminopropyl)-3-ethylcarbodiimide (EDC) and 1-hydroxybenzotriazol (HOBT) in the presence of a base such as triethylamine, in a solvent such as ethyl acetate or tetrahydrofuran, at a temperature comprised between room temperature and the temperature of the boiling point of the solvent.

Some compounds of formula II wherein R2 represents —(CH$_2$)$_s$—N(R4)-B-J-T (i.e. compounds of formula IIb) may also be obtained by reacting a compound of formula Vb with an alkylating agent of formula R4-LG (VII), wherein LG has the meaning previously described.

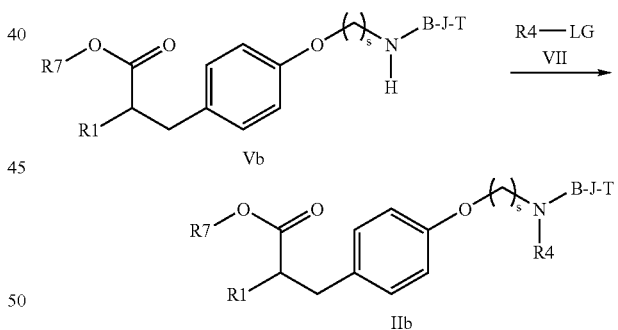

This reaction is carried out in the presence of a base, such as $K_2CO_3$, in a suitable solvent, such as N,N-dimethylformamide or acetonitrile, at a temperature and the temperature of the boiling point of the solvent, preferably room temperature.

Alternatively compounds of formula II can be obtained by solid synthesis using different types of polimeric solid resins, such as Wang or 2-chlorotrityl resins (Collins et al. *J. Med. Chem.* 1998, 41, 5037-5054). Compounds of formula III can be prepared following similar procedures to those described in Cobb et al., *J. Med. Chem.* 1998, 41, 5055-69.

Compounds IVa and IVb wherein R2 represents —(CH$_2$)$_s$—N(R4)-B-J-T (i.e. compounds of formula IVaa and IVba respectively) may be obtained as shown in the following scheme:

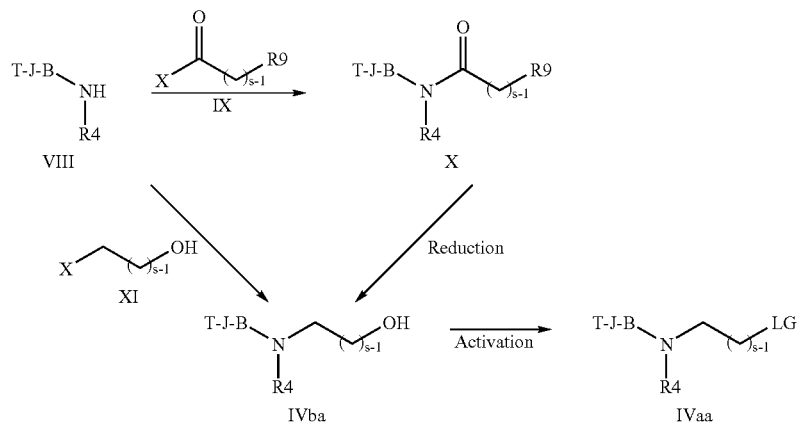

Compound VIII is acylated with a compound of formula IX to yield a compound of formula X, wherein R9 represents —CO$_2$(C$_1$-C$_4$)alkyl or —OCO(C$_1$-C$_4$)alkyl, under the same conditions as the reaction of compound Va with VIa to give compound. IIa. Reduction of compound X with a reducing agent such as lithium aluminium hydride in diethyl ether affords compound IVba.

Alternatively, compound VIII can be reacted with an alkylating agent of formula XI to afford compound IVba (Daoud et al., *J. Indian Chem. Soc.* 1989, 66, 316-318). Compound of formula IVaa is obtained by converting the hydroxyl group of compound IVba into a leaving group. This reaction may be carried out using a sulfonyl halide such as methanesulfonyl chloride in the presence of a base, such as pyridine or triethylamine in a solvent such as dichloromethane or chloroform. Alternatively, compound IVba can be reacted with a halogenating agent such as SOCl$_2$ in a a solvent such as tetrahydrofuran.

Compound VIII can be also converted directly into a compound of formula IVaa by reaction with a compound of formula XII, wherein each LG independently represents a leaving group as defined above, in the same conditions as described for the conversion of VIII into IVba.

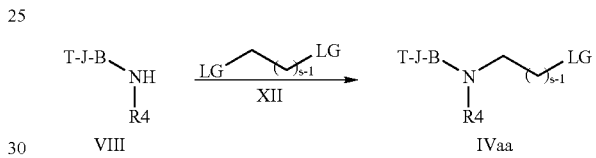

A compound of formula V (including compounds of formula Va and Vb) may be obtained using two different synthetic sequences as shown in the following scheme:

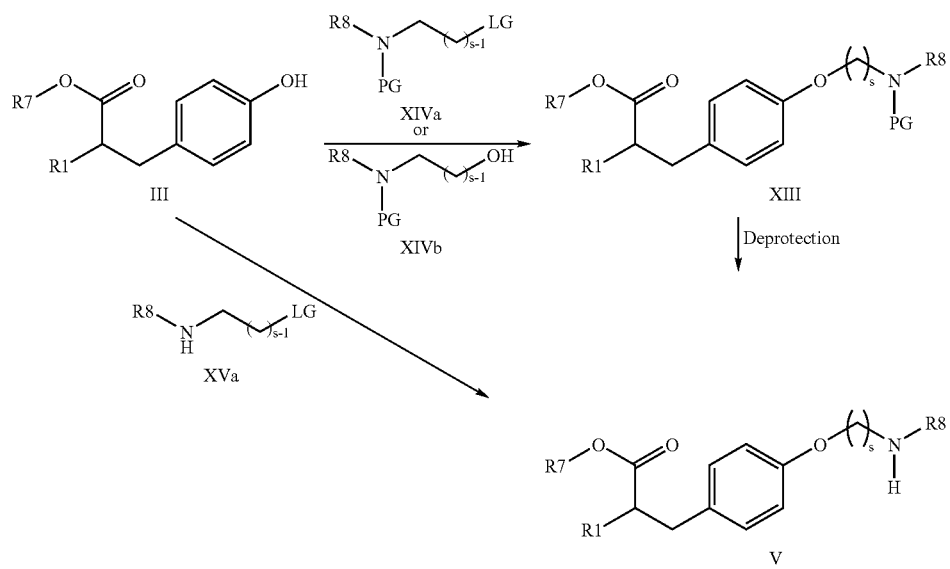

Phenol III can be reacted with a protected amine of formula XIVa or XIVb, to yield a compound of formula XIII, wherein R8 represents -A-J-T or —B-J-T, LG represents a leaving group as previously described and PG represents a protecting group, such as for example, trifluoroacetyl or 2-nitrobenzenesulfonyl. The reaction is carried out under the same conditions described for the conversion of a compound of formula III into a compound of formula II. Compound V is subsequently obtained by deprotection of compound XIII. This reaction is carried out under different conditions depending upon the nature of the protecting group (see for instance Harland et al. *Synthesis* 1984, 941-43, Hirschmann et al. *J. Amer. Chem. Soc.* 1993, 12550-12568 for the group trifluoroacetamide and Lin et al. *Tetrahedron Letters* 2000, 3309-3313 for the 2-nitrobenzenesulfonylamide group).

Alternatively a compound of formula V can be obtained by reacting phenol III with a secondary amine of formula XVa by Williamson ether synthesis. Compounds of formula VIII are commercially available or can be prepared by methods similar to those described for instance in WO 03/53966 or EP 875510. Compounds XIVa and XIVb can be obtained by reaction of the corresponding unprotected amine of formula XV and a protecting group (see Protective Groups in Organic Synthesis, John Wiley & Sons, 3rd Edition, 1999).

A compound of formula XV can be obtained using the following synthetic scheme:

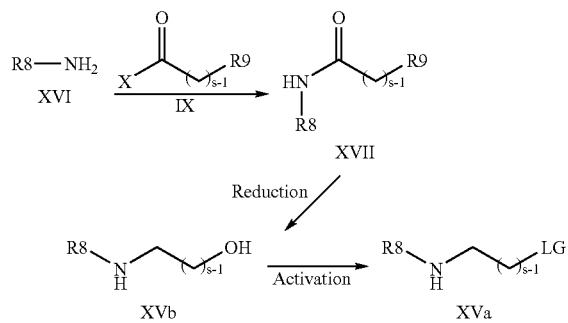

Compound XVI is acylated to afford compound XVII under the same conditions for the reaction of compound Va and VIa to give compound IIa. Reduction of compound XVII gives compound XVb under the conditions described for the reduction of compound X. Compounds XVb wherein the amino group is less reactive than the hydroxyl group can be converted into compounds XVa under the conditions described for the conversion of IVba into IVaa.

Moreover, a compound of formula XVc can be obtained starting from a compound of formula XVIII.

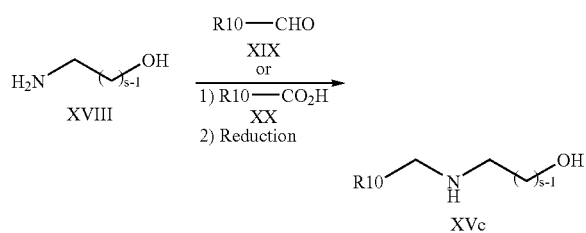

This conversion can be carried out by reaction with an aldehyde of formula R10-CHO (XIX), wherein R10 represents R8 wherein the group attached to the N is —CH$_2$, in the presence of a reducing agent, such as triacetoxyborohydride or cyanoborohydride in a solvent such as 1,2-dichloroethane. Alternatively, compound XVIII can be reacted with compound XX or a derivative thereof to afford the corresponding amide as previously described. The reduction of the resulting product gives rise a compound of formula XVc. Compounds VIa, VIb, VII, IX, XI, XII, XVI, XVIII, XIX and XX are commercially available or can be easily obtained by conventional methods.

As it will be obvious to a person skilled in the art some of the reactions described above can also be carried out on compounds of formula I.

The compounds of the present invention are ligands of the PPARγ receptor. Therefore, they are expectedly useful for the treatment or prevention of a condition mediated by PPARγ in a subject in need thereof, including a human.

Thus, the present invention relates to the use of these compounds for the preparation of a medicament for the treatment or prevention of metabolic diseases, cardiovascular diseases associated with metabolic syndrome (including vascular restenosis), inflammatory diseases, cancer, bone diseases (particularly osteoporosis), skin wound healing, cutaneous disorders associated with an anomalous differentiation of epidermic cells, particularly the formation of keloids, and other disorders where insulin resistance is a component, including Syndrome X.

As an example, metabolic diseases that can be treated or prevented include non-insulin-dependent diabetes mellitus, obesity, hypercholesterolaemia (including raising HDL levels), dyslipidemia (including hyperlipidemia and hypertrigyceridemia), and other lipid-mediated pathologies.

As an example, inflammatory diseases that can be treated or prevented include rheumatoid arthritis, atherosclerosis, psoriasis, inflammatory bowel disease and pancreatitis.

The compounds described herein may be used to treat these diseases or conditions separately, or may be used to treat them concurrently with the treatment of obesity.

The present invention further provides for pharmaceutical compositions comprising a compound of formula I or a pharmaceutical salt or solvate thereof together with one or more pharmaceutically acceptable excipients, in either single or multiple doses. The examples of the excipients mentioned below are given by way of illustration only and are not to be construed as limiting the scope of the invention.

The compounds of the present invention can be administered in the form of any pharmaceutical formulation. The pharmaceutical formulation will depend upon the nature of the active compound and its route of administration. Any route of administration may be used, for example such as oral, buccal, pulmonary, topical, parenteral (including subcutaneous, intramuscular, and intravenous), transdermal, ocular (ophthalmic), inhalation, intranasal, otic, transmucosal, implant or rectal administration. However oral, topical or parenteral administration are preferred.

Solid compositions for oral administration include among others tablets, granulates and hard gelatin capsules, formulated both as immediate release or modified release formulations.

The manufacturing method may be based on a simple mixture, dry granulation, wet granulation or lyophilization of the active compound with excipients. These excipients may be binding agents, such as syrup, acacia, gelatin, sorbitol, gum tragacanth, corn starch or polyvinylpyrrolidone; fillers such as lactose, sugar, microcrystalline cellulose, maize-starch, calcium phosphate or sorbitol; lubricants such as magnesium stearate, stearic acid, talc, polyethylene glycol or silica; disintegrants such as potato starch, alginic acid or sodium starch glycollate; wetting agents, such as sodium lauryl sulfate, sweetening agents such as sucrose, lactose, dextrose, mannitol, sorbitol or saccharin; bioadhesive agents such as hydroxypropyl cellulose, poly(vinyl alcohol), poly (isobutylene), sodium carboxymethyl cellulose; glidants such as magnesium trisilicate, powdered cellulose, starch, talc or tribasic calcium phosphate; flow enhancers such as colloidal silicon dioxide; release modifiers such as xanthan gum, ethylcellulose, carbomer, hydroxypropyl methyl cellulose or wax or osmotic agents such as potassium bicarbonate or sodium chloride.

The tablets may be coated according to methods well-known in the art such as aqueous dispersion coating, solvent-based coating or drying coating. The active compound can also be incorporated by coating onto inert pellets using film-coating agents, by extrusion and spheronization process, by hot melting pelletization or it can be in the form of a troche or lozenge. When a dosage unit form is a capsule, it may contain, in addition to materials of the above type, a liquid carrier such as a fatty oil or wax.

Powders and granulates for the preparation of oral suspensions by the addition of water can be obtained by mixing the active compound with dispersing or wetting agents; suspending agents, anticaking agents, buffering agents and preservatives. Other excipients may also be added, for example sweetening, flavouring and colouring agents.

Alternatively, the compounds of the present invention may be incorporated into oral liquid preparations such as emulsions, solutions, dispersions, suspensions, syrups, elixirs or in the form of soft gelatin capsules. They may contain commonly-used inert diluents, such as purified water, ethanol, sorbitol, glycerol, polyethylene glycols (macrogols) and propylene glycol. Aid compositions can also contain coadjuvants such as wetting, suspending, sweetening, flavouring agents, preservatives, buffers, chelating agents and antioxidants.

Solutions or suspensions may be prepared in water suitably mixed with a surfactant such as sodium lauryl sulfate. Dispersions may also be prepared in glycerol, liquid polyethylene glycols and mixtures thereof in oils. Under ordinary conditions of storage and use, these preparations contain a preservative to prevent the growth of microorganisms. Moreover, formulations containing these compounds may be presented as a dry product constitution with water or other suitable vehicle before use.

Injectable preparations for parenteral administration comprise sterile solutions, suspensions or emulsions in oily or aqueous vehicles, and may contain coadjuvants, such as suspending, stabilizing, tonicity agents or dispersing agents.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

The compound can also be formulated for its topical application. Formulations include creams, lotions, gels, powders, solutions, shampoo preparations, oral paste, mouth wash preparations and patches wherein the compound is dispersed or dissolved in suitable excipients. These excipients may be antimicrobial preservatives such as imidurea, propylparaben, propylene glycol or methylparaben; emulsifying agents such as cetyl alcohol, methylcellulose, poloxamer or medium-chain triglycerids; emulsion stabilizers such as glyceril monostearate, magnesium aluminium silicate, cyclodextrins or wax; humectants such as triacetin, glycerin, propylene glycol or sorbitol; penetrants enhancing agents such as isopropyl miristate; buffering agents such as malic acid, potassium citrate or sodium phosphate dibasic; surfactants such as docusate sodium, sodium lauryl sulfate, polysorbates or sorbitan esters; thickening agents such as hydroxyethyl cellulose, hydroxypropyl cellulose or polyethylene oxide.

The effective dosage of active ingredient may vary depending on the particular compound administered, the route of administration, the nature and severity of the disease to be treated, as well as the age, the general condition and body weight of the patient, among other factors. A representative example of a suitable dosage range is from about 0.001 to about 100 mg/Kg body weight per day, which can be administered as a single or divided doses. However, the dosage administered will be generally left to the discretion of the physician.

PPARγ2 Binding Assay

The cDNA encoding for the open reading frame of the hPPARγ2 was amplified by PCR (polymerase chain reaction) and inserted in the plasmid pGEX-4T-2. This construction (pGEX-hPPARγ) was introduced into $E.$ $coli$ where it was overexpressed and semipurified as a fusion protein with glutathione S-transferase (GST) (Elbrecht et al., $J.$ $Biol.$ $Chem.$ 1999, 274, 7913-7922). The binding of the compounds to the GST-hPPARγ2 s was determined by modifications in the method described by Lehmann et al. ($J.$ $Biol.$ $Chem.$ 1995, 270, 12953-12957). The receptors (2.5 μg) were incubated in 96-well plates in the presence or in the absence of the products with [$^3$H]BRL-49853 (100 nM) for 3 h at 4° C., in a final volume of 200 μL of buffer Tris-HCl 10 mM pH:8.0, containing KCl 50 mM and DTT 10 mM. Non-specific binding was determined in the presence of BRL49853 100 μM. The reaction mixture was transferred to a Multiscreen Durapore (Millipore) microplate containing glutathione-Sepharose 4B in every well. The reaction mixture was left to incubate with the resin during 10 min, and then centrifuged at 735 g during 2 min. To dissociate the receptor bound to the resin, reduced glutathione 10 mM is added and incubated during 10 min. The receptor was eluted by centrifugation. Then, scintillation liquid was added to the elution and the contained radioactivity was quantified by liquid scintillation spectroscopy (Microbeta Wallac, Perkin Elmer).

LBD-hPPARs Transactivation Assay

COS-7 cells were cultivated in 24-well plates and transfected with the pFACMV plasmids that encode the chimeric proteins containing the GAL4 DNA binding domain fused to the PPARγ LBD. The reporter plasmid for the foregoing constructions was pFR-Luc, which contains five repetitions of the GAL4-response element in front of a promoter that controls the transcription of the luciferase gene. Lipofectamine was used as a transfection agent. The plasmids of the chimeric receptors and the reporter gene were inserted in the cells by transitory transfection in COS-7 cells in culture. When the products were added to the culture for 48 h, the luciferase activity showed the effect of the PPAR activity modulation on the transcription of the reporter construction (Wright et al., $J.$ $Biol.$ $Chem.$ 2000, 275, 1873).

Cloning of Human PPARγ2

The human PPAR cDNA was amplified through RT-PCR. For hPPARγ2, RNA was obtained from human white adipose tissue. Each amplified fragment was cloned into pBluescript (Stratagene®) and sequenced. One clone for each construction was selected and used as template for further subcloning and PCR amplifications.

GST-Fused Protein Construction

To generate this chimeric protein, the complete cDNA of the human PPAR was cloned into pGEX4T2 (Amersham Biosciences). The fragment was obtained from the pBluescript-cDNAs clones digested with endonucleases. To assess the plasmid identity and to ensure the in-phase cloning of the proteins, pGEX construction was sequenced. GST-hPPARγ2 fusion protein was generated in *Escherichia coli* (BL21 strain DE3). Cells were cultured in LB medium to a density of A600=1.6 odu, and induced for overexpression by addition of isopropyl-1-thio-β-D-galactopyranoside (IPTG)-induced cultures to a final concentration of 0.5 mM. The IPTG-induced cultures were grown at room temperature o/n, before cells were harvested by centrifugation at 5000 g for 15 min. After sonication, the GST-fusion protein was purified from the cell pellet using glutathione-Sepharose beads, following the procedure recommended by the manufacturer (Amersham Pharmacia Biotech). Excess of gluthatione was removed o/n by dyalisis at 4° C. Receptor purity was visualized by SDS-PAGE and protein content was determined by Bradford method. Receptor aliquots were stored at −80° C. until use.

In Table 1, affinity and functional activity data of some of the compounds of the present invention are shown.

TABLE 1

| Example Number | Affinity PPARγ[1] | Functional activity PPARγ |
|---|---|---|
| I_121 | ++ | ANTAGONIST |
| I_128 | ++ | — |
| I_149 | + | — |
| I_178 | +++ | — |
| I_198 | ++ | PARTIAL AGONIST |
| I_262 | +++ | AGONIST |
| I_265 | +++ | AGONIST |
| I_280 | +++ | — |
| I_303 | +++ | — |
| I_375 | +++ | PARTIAL AGONIST |
| I_379 | ++ | — |
| I_391 | ++ | — |
| I_410 | +++ | ANTAGONIST |
| I_412 | +++ | — |
| I_418 | ++ | PARTIAL AGONIST |
| I_438 | ++ | — |
| I_440 | ++ | — |
| I_467 | +++ | — |
| I_469 | ++ | — |

[1]+++: Ki < 500 nM, ++: 500 nM < Ki < 1500 nM, +: Ki > 1500 nM

Additional objects, advantages and novel features of the invention will be set forth in part in the description, and in part will become apparent to those skilled in the art upon examination of the description or may be learned by practice of the invention. The present invention will be further illustrated by the following examples. The examples are given by way of illustration only and are not to be construed as limiting the scope of the invention.

The nomenclature of the different compounds used in the present document is based on the software AUTONOM (Automatic Nomenclature) from the Beilstein Institute, which uses the IUPAC systematic nomenclature.

LC-MS spectra have been performed using the following chromatographic equipment: Hewlett-Packard model 1100, equipped with a selective mass detector model 1100 VL, autosampler, ChemStation software and a laser printer (mass spectrometry ionization mode: Atmospheric pressure ionisation with positive ion detection) and using the following chromatographic methods:

Method A: Column Kromasil 100 C18, 40×4.0 mm, 3.5 μm, flow: 0.7 mL/min, eluent: A=0.1% formic acid in water, B=0.1% formic acid in acetonitrile, gradient: 0 min 5% B–8 min 90% B.

Method B: Column: Gemini 5u C18 110, 40×4.0 mm, flow: 0.7 mL/min, eluent: A=0.1% formic acid in water, B=0.1% formic acid in acetonitrile, gradient: 0 min 5% B–8 min 90% B.

$^1$H-NMR spectra of the compounds have been recorded using a VARIAN GEMINI-200 MHz and a VARIAN UNITY-300 MHz equipment and chemical shifts are expressed as ppm (δ) from the internal reference TMS. Mass spectra have been obtained with an Agilent 1100 VL mass spectrometer.

The following abbreviations have been used in the examples:
DEAD: diethyl azodicarboxylate
DMF: N,N-dimethylformamide
EDC: 1-(3-dimethylaminopropyl)-3-ethylcarbodiimide
eq: molar equivalent
EtOAc: ethyl acetate
HOBT: 1-hydroxybenzotriazol
LC-MS: liquid chromatography-mass spectrometry
rt: retention time
THF: tetrahydrofuran
TMS: trimethylsylane Intermediates IIIa and IIIb:

Compounds of formula IIIa and IIIb can be prepared following similar procedures to those described in Cobb et al., *J. Med. Chem.* 1998, 41, 5055-69.

IIIa_1: (S)-2-(2-Benzoylphenylamino)-3-(4-hydroxyphenyl)propionic acid methyl ester; rt: 7.357, MS [M+1]$^+$: 376.

IIIb_1: (R)-2-(2-Benzoylphenylamino)-3-(4-hydroxyphenyl)propionic acid methyl ester; rt: 7.357, MS [M+1]$^+$: 376.

Intermediates XIII:

Compounds of formula XIII shown in Table 2 were obtained starting from a phenol III and an amine derivative of formula XIVa or XIVb following one of the procedures A-D described below.

PROCEDURE A: A 0.5 M suspension-of phenol III (1 eq) in EtOAc containing anhydrous potassium carbonate (3 eq) and compound XIVa (1.3 eq) was refluxed for 18 h. Then, the suspension was allowed to cool down and the white solid was filtered. The solvent was distilled off under reduced pressure, and the obtained residue was purified by column chromatography.

PROCEDURE B: A 0.5 M suspension of phenol III (1 eq) in anhydrous DMF containing cesium carbonate (3 eq), compound XIVa (1.3 eq) and potassium iodide (catalythic amount) was heated at 80° C. for 18 h. Then, the suspension was allowed to cool down at room temperature, and treated with water and EtOAc. The organic layer was washed three times with brine, dried over anhydrous sodium sulfate and filtered. The solvent was distilled off under reduced pressure, and the obtained residue was purified by column chromatography.

PROCEDURE C: To a 0.1 M solution of phenol III (1 eq) in anhydrous DMF, containing a catalythic amount of potassium iodide, sodium hydride (60%, 1.1 eq) was added. The resulting suspension was stirred at room temperature for 1 hour and then compound XIVa (1.1 eq) was added. The reaction mixture was stirred at 80° C. for 18 h, and then allowed to cool down to room temperature. After treating with water and EtOAc, the organic layer was washed three times with brine, dried over anhydrous sodium sulfate and filtered. The solvent was distilled off under reduced pressure, and the obtained residue was purified by column chromatography.

PROCEDURE D: To a 0.2 M solution of phenol III (1 eq) in THF, containing compound XIVb (2.2 eq) and triphenylphosphine (2.2 eq), DEAD (2.2 eq) was added under inert atmosphere. The solution was stirred at room temperature for 18 h. Then, the solvent was distilled off under reduced pressure, and the obtained residue was purified by column chromatography.

TABLE 2

| Example Number | Starting product | Compound name | $^1$H-NMR/LC-MS | HPLC Method |
|---|---|---|---|---|
| XIII_1 | IIIa_1 | (S)-2-(2-Benzoylphenylamino)-3-(4-{2-[benzyl-(2,2,2-trifluoroacetyl)amino]-ethoxy}phenyl)propionic acid methyl ester | 8.86(d, 1H), 7.62-7.56(ca, 2H), 7.56-7.16(ca, 12H), 6.79(d, 2H), 6.68-6.55(ca, 2H), 4.80(s, 2H), 4.40(q, 1H), 4.10(t, 2H), 3.75-3.60(ca, 5H), 3.19(dd, 1H), 3.09(dd, 1H) | A |
| XIII_2 | IIIa_1 | (S)-2-(2-Benzoylphenylamino)-3-(4-{3-[benzyl-(2,2,2-trifluoroacetyl)amino]-propoxy}phenyl)propionic acid methyl ester | rt: 9.383 MS[M+1]$^+$: 619 | A |
| XIII_3 | IIIa_1 | (S)-2-(2-Benzoylphenylamino)-3-(4-{2-[cyclohexyl-(2,2,2-trifluoroacetyl)-amino]ethoxy}phenyl)propionic acid methyl ester | rt: 9.706 MS[M+1]$^+$: 597 | A |
| XIII_4 | IIIa_1 | (S)-2-(2-Benzoylphenylamino)-3-(4-{2-[tert-butyl-(2,2,2-trifluoroacetyl)amino]-ethoxy}phenyl)propionic acid methyl ester | rt: 9.287 MS[M+1]$^+$: 571 | A |
| XIII_5 | IIIa_1 | (S)-2-(2-Benzoylphenylamino)-3-(4-{2-[cyclopropylmethyl(2-nitrobenzenesulfonyl)amino]ethoxy}-phenyl)propionic acid methyl ester | rt: 8.969 MS[M+1]$^+$: 658 | A |
| XIII_6 | IIIa_1 | (S)-2-(2-Benzoylphenylamino)-3-(4-{3-[cyclopropylmethyl(2-nitrobenzenesulfonyl)amino]propoxy}-phenyl)propionic acid methyl ester | rt: 9.103 MS[M+1]$^+$: 672 | A |
| XIII_7 | IIIa_1 | (S)-2-(2-Benzoylphenylamino)-3-(4-{2-[(3-methylbenzyl)(2-nitrobenzenesulfonyl)amino]ethoxy}-phenyl)propionic acid methyl ester | rt: 9.323 MS[M+1]$^+$: — | A |
| XIII_8 | IIIa_1 | (S)-2-(2-Benzoylphenylamino)-3-(4-{3-[(3-methylbenzyl)(2-nitrobenzenesulfonyl)amino]propoxy}-phenyl)propionic acid methyl ester | rt: 9.449 MS[M+1]$^+$: — | A |
| XIII_9 | IIIa_1 | (S)-2-(2-Benzoylphenylamino)-3-(4-{2-[(2-nitrobenzenesulfonyl)propylamino]-ethoxy}phenyl)propionic acid methyl ester | rt: 8.948 MS[M+1]$^+$: 646 | A |
| XIII_10 | IIIa_1 | (S)-2-(2-Benzoylphenylamino)-3-(4-{2-[ethyl-(2-nitrobenzenesulfonyl)amino]-ethoxy}phenyl)propionic acid methyl ester | rt: 8.726 MS[M+1]$^+$: 632 | A |

Intermediates V:

Compounds of formula V shown in Table 3 were obtained starting from phenol III and an amine derivative of formula XVa following one of the procedures A-C described above or alternatively starting from compound XIII using procedures E-F described below.

PROCEDURE E: To a 0.1 M solution of compound XIII (1 eq) (PG=trifluoroacetyl) in a mixture of THF:methanol (3:1), a 1 M aqueous solution of lithium hydroxide (5 eq) was added. The solution was stirred for 18 h at room temperature, then diluted with a mixture of water/EtOAc, and then acidified to pH=5 with HCl 1 N. The organic layer was dried over anhydrous sodium sulfate and filtered. The solvent was distilled off under reduced pressure, and the obtained residue was redissolved in methanol to afford a 0.1 M solution, which was treated with thionyl chloride (3.2 eq). The solution was refluxed for 18 h, and then allowed to cool down to room temperature. The solvent was distilled off under reduced pressure. The obtained residue was purified by column chromatography.

PROCEDURE F: To a 0.1 M solution of compound XIII (PG=2-nitrobenzenesulfonyl, 1 eq) in DMF containing thiophenol (1 eq), KO$^t$Bu (2 eq) was added. The solution was stirred at room temperature for 6 h and then diluted with a mixture of water/EtOAc. The organic layer was washed three times with brine, dried over anhydrous sodium sulfate and filtered. The solvent was distilled off under reduced pressure, and the obtained residue was purified by column chromatography.

TABLE 3

| Example Number | Starting product | Compound name | $^1$H-NMR/LC-MS | HPLC Method |
|---|---|---|---|---|
| V_1 | XIII_1 | (S)-2-(2-Benzoylphenylamino)-3-[4-(2-benzylaminoethoxy)phenyl]-propionic acid methyl ester | 8.86(d, 1H), 7.62-7.56(ca, 2H), 7.56-7.40(ca, 6H), | A |

TABLE 3-continued

| Example Number | Starting product | Compound name | ¹H-NMR/LC-MS | HPLC Method |
|---|---|---|---|---|
| | | | 7.40-7.27(ca, 4H), 7.14(d, 2H), 6.83(d, 2H), 6.65-6.53(ca, 2H), 4.63(q, 1H), 4.13(t, 2H), 3.99(s, 2H), 3.68(s, 3H), 3.19(dd, 1H), 3.09(dd, 1H), 3.03(t, 2H) | |
| V_2 | XIII_2 | (S)-2-(2-Benzoylphenylamino)-3-[4-(3-benzylaminopropoxy)phenyl]-propionic acid methyl ester | rt: 6.385 MS[M+1]$^+$: 523 | A |
| V_3 | XIII_3 | (S)-2-(2-Benzoylphenylamino)-3-[4-(2-cyclohexylaminoethoxy)phenyl]-propionic acid methyl ester | rt: 6.495 MS[M+1]$^+$: 501 | A |
| V_4 | XIII_4 | (S)-2-(2-Benzoylphenylamino)-3-[4-(2-tert-butylaminoethoxy)phenyl]-propionic acid methyl ester | rt: 6.209 MS[M+1]$^+$: 475 | A |
| V_5 | XIII_5 | (S)-2-(2-Benzoylphenylamino)-3-{4-[2-cyclopropylmethylamino)ethoxy]-phenyl}propionic acid methyl ester | rt: 5.882 MS[M+1]$^+$: 473 | A |
| V_6 | XIII_6 | (S)-2-(2-Benzoylphenylamino)-3-{4-[3-(cyclopropylmethylamino)-propoxy]phenyl}propionic acid methyl ester | rt: 6.354 MS[M+1]$^+$: 487 | A |
| V_7 | XIII_7 | (S)-2-(2-Benzoylphenylamino)-3-{4-[2-(3-methylbenzylamino)ethoxy]-phenyl}propionic acid methyl ester | rt: 6.591 MS[M+1]$^+$: 523 | A |
| V_8 | XIII_8 | (S)-2-(2-Benzoylphenylamino)-3-{4-[3-(3-methylbenzylamino)propoxy]-phenyl}propionic acid methyl ester | rt: 6.758 MS[M+1]$^+$: 537 | A |
| V_9 | IIIa_1 | (S)-2-(2-Benzoylphenylamino)-3-[4-(2-phenylaminoethoxy)phenyl]-propionic acid methyl ester | rt: 8.96 MS[M+1]$^+$: 495 | A |
| V_10 | IIIa_1 | (S)-2-(2-Benzoylphenylamino)-3-[4-(3-phenylaminopropoxy)phenyl]-propionic acid methyl ester | rt: 8.993 MS[M+1]$^+$: 509 | A |
| V_11 | IIIa_1 | (S)-2-(2-Benzoylphenylamino)-3-{4-[2-(2-fluorophenylamino)ethoxy]-phenyl}propionic acid methyl ester | rt: 9.131 MS[M+1]$^+$: 513 | A |
| V_12 | IIIa_1 | (S)-2-(2-Benzoylphenylamino)-3-{4-[2-(3-fluorophenylamino)ethoxy]-phenyl}propionic acid methyl ester | rt: 9.013 MS[M+1]$^+$: 513 | A |
| V_13 | IIIa_1 | (S)-2-(2-Benzoylphenylamino)-3-{4-[2-(4-fluorophenylamino)ethoxy]-phenyl}propionic acid methyl ester | rt: 8.876 MS[M+1]$^+$: 513 | A |
| V_14 | IIIa_1 | (S)-2-(2-Benzoylphenylamino)-3-[4-(2-o-tolylaminoethoxy)phenyl]-propionic acid methyl ester | rt: 9.247 MS[M+1]$^+$: 509 | A |
| V_15 | IIIa_1 | (S)-2-(2-Benzoylphenylamino)-3-[4-(2-m-tolylaminoethoxy)phenyl]-propionic acid methyl ester | rt: 9.127 MS[M+1]$^+$: 509 | A |
| V_16 | IIIa_1 | (S)-2-(2-Benzoylphenylamino)-3-[4-(2-p-tolylaminoethoxy)phenyl]-propionic acid methyl ester | rt: 9.014 MS[M+1]$^+$: 509 | A |
| V_17 | IIIa_1 | (S)-2-(2-Benzoylphenylamino)-3-{4-[2-(2-chlorophenylamino)ethoxy]-phenyl}propionic acid methyl ester | rt: 9.431 MS[M, M+2]$^+$: 530, 532 | A |
| V_18 | IIIa_1 | (S)-2-(2-Benzoylphenylamino)-3-{4-[2-(3-chlorophenylamino)ethoxy]-phenyl}propionic acid methyl ester | rt: 9.293 MS[M, M+2]$^+$: 530, 532 | A |
| V_19 | IIIa_1 | (S)-2-(2-Benzoylphenylamino)-3-{4-[2-(4-chlorophenylamino)ethoxy]-phenyl}propionic acid methyl ester | rt: 9.265 MS[M, M+2]$^+$: 530, 532 | A |
| V_20 | IIIa_1 | (S)-2-(2-Benzoylphenylamino)-3-[4-(3-o-tolylaminopropoxy)phenyl]-propionic acid methyl ester | rt: 9.377 MS[M+1]$^+$: 523 | A |
| V_21 | IIIa_1 | (S)-2-(2-Benzoylphenylamino)-3-[4-(3-m-tolylaminopropoxy)phenyl]-propionic acid methyl ester | rt: 9.11 MS[M+1]$^+$: 523 | A |
| V_22 | IIIa_1 | (S)-2-(2-Benzoylphenylamino)-3-[4-(3-p-tolylaminopropoxy)phenyl]-propionic acid methyl ester | rt: 8.714 MS[M+1]$^+$: 523 | A |
| V_23 | IIIa_1 | (S)-2-(2-Benzoylphenylamino)-3-{4-[3-(2-chlorophenylamino)propoxy]-phenyl}propionic acid methyl ester | rt: 9.632 MS[M, M+2]$^+$: 543, 545 | A |

TABLE 3-continued

| Example Number | Starting product | Compound name | ¹H-NMR/LC-MS | HPLC Method |
|---|---|---|---|---|
| V_24 | IIIa_1 | (S)-2-(2-Benzoylphenylamino)-3-{4-[3-(3-chlorophenylamino)propoxy]-phenyl}propionic acid methyl ester | rt: 9.474 MS[M, M+2]⁺: 543, 545 | A |
| V_25 | IIIa_1 | (S)-2-(2-Benzoylphenylamino)-3-{4-[3-(4-chlorophenylamino)propoxy]-phenyl}propionic acid methyl ester | rt: 9.435 MS[M, M+2]⁺: 543, 545 | A |
| V_26 | IIIa_1 | (S)-2-(2-Benzoylphenylamino)-3-{4-[2-(naphthalen-1-ylamino)ethoxy]-phenyl}propionic acid methyl ester | rt: 10.202 MS[M+1]⁺: 545 | A |
| V_27 | IIIa_1 | (S)-2-(2-Benzoylphenylamino)-3-{4-[2-(3-methylsulfanylphenylamino)-ethoxy]phenyl}propionic acid methyl ester | rt: 9.189 MS[M+1]⁺: 541 | A |
| V_28 | IIIa_1 | (S)-2-(2-Benzoylphenylamino)-3-{4-[2-(4-methylsulfanylphenylamino)-ethoxy]phenyl}propionic acid methyl ester | rt: 9.178 MS[M+1]⁺: 541 | A |
| V_29 | IIIb_1 | (R)-2-(2-Benzoylphenylamino)-3-[4-(2-phenylaminoethoxy)phenyl]-propionic acid methyl ester | rt: 8.968 MS[M+1]⁺: 495 | A |
| V_30 | IIIa_1 | (S)-2-(2-Benzoylphenylamino)-3-{4-[2-(naphthalen-2-ylamino)ethoxy]-phenyl}propionic acid methyl ester | rt: 9.417 MS[M+1]⁺: 545 | A |
| V_31 | IIIa_1 | (S)-2-(2-Benzoylphenylamino)-3-{4-[3-(2-fluorophenylamino)propoxy]-phenyl}propionic acid methyl ester | rt: 9.369 MS[M+1]⁺: 527 | A |
| V_32 | IIIa_1 | (S)-2-(2-Benzoylphenylamino)-3-{4-[3-(3-fluorophenylamino)propoxy]-phenyl}propionic acid methyl ester | rt: 9.233 MS[M+1]⁺: 527 | A |
| V_33 | IIIa_1 | (S)-2-(2-Benzoylphenylamino)-3-{4-[3-(4-fluorophenylamino)propoxy]-phenyl}propionic acid methyl ester | rt: 8.992 MS[M+1]⁺: 527 | A |
| V_34 | IIIa_1 | (S)-2-(2-Benzoylphenylamino)-3-{4-[2-(2-methoxyphenylamino)ethoxy]-phenyl}propionic acid methyl ester | rt: 9.085 MS[M+1]⁺: 525 | A |
| V_35 | IIIa_1 | (S)-2-(2-Benzoylphenylamino)-3-{4-[2-(3-methoxyphenylamino)ethoxy]-phenyl}propionic acid methyl ester | rt: 8.850 MS[M+1]⁺: 525 | A |
| V_36 | XIII_10 | (S)-2-(2-Benzoylphenylamino)-3-[4-(2-ethylaminoethoxy)phenyl]-propionic acid methyl ester | rt: 5.889 MS[M+1]⁺: 447 | A |
| V_37 | IIIa_1 | (S)-2-(2-Benzoylphenylamino)-3-{4-[3-(2-methoxyphenylamino)propoxy]-phenyl}propionic acid methyl ester | rt: 9.097 MS[M+1]⁺: 539 | A |
| V_38 | IIIa_1 | (S)-2-(2-Benzoylphenylamino)-3-{4-[3-(3-methoxyphenylamino)propoxy]-phenyl}propionic acid methyl ester | rt: 8.923 MS[M+1]⁺: 539 | A |
| V_39 | XIII_9 | (S)-2-(2-Benzoylphenylamino)-3-[4-(2-propylaminoethoxy)phenyl]-propionic acid methyl ester | rt: 6.063 MS[M+1]⁺: 461 | A |

Intermediates II:

Compounds of formula II shown in Table 4 were obtained starting from phenol III and a compound of formula IVa or IVb following one of the procedures A-D described above.

TABLE 4

| Example Number | Starting product | Compound name | ¹H-NMR/LC-MS | HPLC Method |
|---|---|---|---|---|
| II_1 | IIIa_1 | (S)-2-(2-Benzoylphenylamino)-3-{4-[2-(benzylindan-5-ylamino)ethoxy]-phenyl}propionic acid methyl ester | rt: 10.561 MS[M+1]⁺: 625 | A |
| II_2 | IIIa_1 | (S)-2-(2-Benzoylphenylamino)-3-(4-{2-[benzyl(2,6-difluorophenyl)amino]-ethoxy}phenyl)propionic acid methyl ester | rt: 10.023 MS[M+1]⁺: 621 | A |
| II_3 | IIIa_1 | (S)-2-(2-Benzoylphenylamino)-3-(4-{2-[(2-chlorophenyl)-(2-fluorobenzyl)-amino]ethoxy}phenyl)propionic acid methyl ester | rt: 10.22 MS[M+1]⁺: 638 | A |

TABLE 4-continued

| Example Number | Starting product | Compound name | ¹H-NMR/LC-MS | HPLC Method |
|---|---|---|---|---|
| II_4 | IIIa_1 | (S)-2-(2-Benzoylphenylamino)-3-(4-{2-[benzyl-(2-fluorophenyl)amino]-ethoxy}phenyl)propionic acid methyl ester | rt: 9.977 MS[M+1]⁺: 603 | A |
| II_5 | IIIa_1 | (S)-2-(2-Benzoylphenylamino)-3-(4-{2-[(2-methylbenzyl)phenylamino]-ethoxy}phenyl)propionic acid methyl ester | rt: 10.123 MS[M+1]⁺: 599 | A |
| II_6 | IIIa_1 | (S)-2-(2-Benzoylphenylamino)-3-(4-{2-[(3-chlorophenyl)-(2-methoxybenzyl)amino]ethoxy}-phenyl)propionic acid methyl ester | rt: 10.204 MS[M+1]⁺: 650 | A |
| II_7 | IIIa_1 | (S)-2-(2-Benzoylphenylamino)-3-(4-{2-[(2-methoxybenzyl)-m-tolylamino]-ethoxy}phenyl)propionic acid methyl ester | rt: 10.134 MS[M+1]⁺: 629 | A |
| II_8 | IIIa_1 | (S)-2-(2-Benzoylphenylamino)-3-(4-{3-[(2-methoxybenzyl)phenylamino]-propoxy}phenyl)propionic acid methyl ester | rt: 10.014 MS[M+1]⁺: 629 | A |
| II_9 | IIIa_1 | (S)-2-(2-Benzoylphenylamino)-3-{4-[2-(benzyl-o-tolylamino)ethoxy]-phenyl}propionic acid methyl ester | rt: 10.25 MS[M+1]⁺: 599 | A |
| II_10 | IIIa_1 | (S)-2-(2-Benzoylphenylamino)-3-(4-{2-[benzyl-(3-ethylphenyl)amino]-ethoxy}phenyl)propionic acid methyl ester | rt: 10.356 MS[M+1]⁺: 613 | A |
| II_11 | IIIa_1 | (S)-2-(2-Benzoylphenylamino)-3-(4-{2-[benzyl-(3-fluorophenyl)amino]-ethoxy}phenyl)propionic acid methyl ester | rt: 9.864 MS[M+1]⁺: 603 | A |
| II_12 | IIIa_1 | (S)-2-(2-Benzoylphenylamino)-3-(4-{2-[(2-chlorophenyl)-(3-methoxybenzyl)amino]ethoxy}-phenyl)propionic acid methyl ester | rt: 10.119 MS[M+1]⁺: 650 | A |
| II_13 | IIIa_1 | (S)-2-(2-Benzoylphenylamino)-3-(4-{2-[(3-chlorophenyl)-(3-methoxybenzyl)amino]ethoxy}-phenyl)propionic acid methyl ester | rt: 10.012 MS[M+1]⁺: 650 | A |
| II_14 | IIIa_1 | (S)-2-(2-Benzoylphenylamino)-3-(4-{2-[(3-methoxybenzyl)-m-tolylamino]-ethoxy}phenyl)propionic acid methyl ester | rt: 10.004 MS[M+1]⁺: 629 | A |
| II_15 | IIIa_1 | (S)-2-(2-Benzoylphenylamino)-3-(4-{3-[(3-methoxybenzyl)phenylamino]-propoxy}phenyl)propionic acid methyl ester | rt: 9.931 MS[M+1]⁺: 629 | A |
| II_16 | IIIa_1 | (S)-2-(2-Benzoylphenylamino)-3-{4-[2-(benzyl-m-tolylamino)ethoxy]-phenyl}propionic acid methyl ester | rt: 10.127 MS[M+1]⁺: 599 | A |
| II_17 | IIIa_1 | (S)-2-(2-Benzoylphenylamino)-3-(4-{2-[benzyl-(4-chlorophenyl)amino]-ethoxy}phenyl)propionic acid methyl ester | rt: 10.164 MS[M+1]⁺: 619 | A |
| II_18 | IIIa_1 | (S)-2-(2-Benzoylphenylamino)-3-(4-{2-[benzyl-(4-fluorophenyl)amino]-ethoxy}phenyl)propionic acid methyl ester | rt: 9.863 MS[M+1]⁺: 603 | A |
| II_19 | IIIa_1 | (S)-2-(2-Benzoylphenylamino)-3-(4-{2-[(4-methylbenzyl)phenylamino]-ethoxy}phenyl)propionic acid methyl ester | rt: 10.172 MS[M+1]⁺: 599 | A |
| II_20 | IIIa_1 | (S)-2-(2-Benzoylphenylamino)-3-(4-{3-[(4-methoxybenzyl)phenylamino]-propoxy}phenyl)propionic acid methyl ester | rt: 9.879 MS[M+1]⁺: 629 | A |
| II_21 | IIIa_1 | (S)-2-(Benzoylphenylamino)-3-{4-[2-(di-p-tolylamino)ethoxy]phenyl}-propionic acid methyl ester | rt: 10.592 MS[M+1]⁺: 599 | A |
| II_22 | IIIa_1 | (S)-2-(2-Benzoylphenylamino)-3-{4-[2-(benzyl-p-tolylamino)ethoxy]-phenyl}propionic acid methyl ester | rt: 10.174 MS[M+1]⁺: 599 | A |
| II_23 | IIIa_1 | (S)-2-(2-Benzoylphenylamino)-3-{4-[3-(benzylindan-5-ylamino)propoxy]-phenyl}propionic acid methyl ester | rt: 10.601 MS[M+1]⁺: 639 | A |

TABLE 4-continued

| Example Number | Starting product | Compound name | $^1$H-NMR/LC-MS | HPLC Method |
|---|---|---|---|---|
| II_24 | IIIa_1 | (S)-2-(2-Benzoylphenylamino)-3-(4-{3-[benzyl-(3-ethylphenyl)amino]-propoxy}phenyl)propionic acid methyl ester | rt: 10.507 MS[M+1]$^+$: 627 | A |
| II_25 | IIIa_1 | (S)-2-(2-Benzoylphenylamino)-3-{4-[3-(benzyl-m-tolylamino)propoxy]-phenyl}propionic acid methyl ester | rt: 10.261 MS[M+1]$^+$: 613 | A |
| II_26 | IIIa_1 | (S)-2-(2-Benzoylphenylamino)-3-{4-[3-(benzyl-p-tolylamino)propoxy]-phenyl}propionic acid methyl ester | rt: 10.27 MS[M+1]$^+$: 613 | A |
| II_27 | IIIa_1 | (S)-2-(2-Benzoylphenylamino)-3-{4-[3-(benzylcyclohexylamino)propoxy]-phenyl}propionic acid methyl ester | rt: 7.251 MS[M+1]$^+$: 605 | A |
| II_28 | IIIa_1 | (S)-2-(2-Benzoylphenylamino)-3-{4-[3-(benzylphenylamino)propoxy]-phenyl}propionic acid methyl ester | 8.92(d, 1H), 7.60(d, 2H), 7.60-7.15(ca, 17H), 6.85-6.55(ca, 4H), 4.55(s, 2H), 4.39(q, 1H), 3.97(t, 2H), 3.69(s, 3H), 3.62(t, 2H), 3.22(dd, 1H), 3.13(dd, 1H), 2.20-2.00(ca, 2H) | A |
| II_29 | IIIa_1 | (S)-2-(2-Benzoylphenylamino)-3-(4-{2-[(2-fluorophenyl)isobutylamino]-ethoxy}phenyl)propionic acid methyl ester | rt: 10.281 MS[M+1]$^+$: 569 | A |
| II_30 | IIIa_1 | (S)-2-(2-Benzoylphenylamino)-3-{4-[2-(isobutyl-o-tolylamino)ethoxy]-phenyl}propionic acid methyl ester | rt: 10.614 MS[M+1]$^+$: 565 | A |
| II_31 | IIIa_1 | (S)-2-(2-Benzoylphenylamino)-3-{4-[3-(isobutyl-o-tolylamino)propoxy]-phenyl}propionic acid methyl ester | rt: 10.455 MS[M+1]$^+$: 579 | A |
| II_32 | IIIa_1 | (S)-2-(2-Benzoylphenylamino)-3-(4-{2-[(3-fluorophenyl)isobutylamino]-ethoxy}phenyl)propionic acid methyl ester | rt: 10.109 MS[M+1]$^+$: 569 | A |
| II_33 | IIIa_1 | (S)-2-(2-Benzoylphenylamino)-3-(4-{2-[isobutyl-m-tolylamino]ethoxy}-phenyl)propionic acid methyl ester | rt: 10.397 MS[M+1]$^+$: 565 | A |
| II_34 | IIIa_1 | (S)-2-(2-Benzoylphenylamino)-3-{4-[3-(isobutyl-m-tolylamino)propoxy]-phenyl}propionic acid methyl ester | rt: 10.412 MS[M+1]$^+$: 579 | A |
| II_35 | IIIa_1 | (S)-2-(2-Benzoylphenylamino)-3-{4-[2-(benzylphenethylamino)ethoxy]-phenyl}propionic acid methyl ester | rt: 7.539 MS[M+1]$^+$: 613 | A |
| II_36 | IIIa_1 | (S)-2-(2-Benzoylphenylamino)-3-{4-[2-(cyclobutylmethyl-o-tolylamino)-ethoxy]phenyl}propionic acid methyl ester | rt: 10.223 MS[M+1]$^+$: 577 | A |
| II_37 | IIIa_1 | (S)-2-(2-Benzoylphenylamino)-3-{4-[2-(benzylcyclopentylamino)ethoxy]-phenyl}propionic acid methyl ester | rt: 7.03 MS[M+1]$^+$: 577 | A |
| II_38 | IIIa_1 | (S)-2-(2-Benzoylphenylamino)-3-{4-[3-(cyclopentylphenylamino)-propoxy]phenyl}propionic acid methyl ester | rt: 7.811 MS[M+1]$^+$: 577 | A |
| II_39 | IIIa_1 | (S)-2-(2-Benzoylphenylamino)-3-(4-{2-[cyclopentylmethyl-(2-fluorophenyl)amino]ethoxy}phenyl)-propionic acid methyl ester | rt: 10.786 MS[M+1]$^+$: 595 | A |
| II_40 | IIIa_1 | (S)-2-(2-Benzoylphenylamino)-3-{4-[2-(cyclopentymethylphenylamino)-ethoxy]phenyl}propionic acid methyl ester | rt: 10.602 MS[M+1]$^+$: 577 | A |
| II_41 | IIIa_1 | (S)-2-(2-Benzoylphenylamino)-3-{4-[2-(benzylcyclopropylmethylamino)-ethoxy]phenyl}propionic acid methyl ester | rt: 6.954 MS[M+1]$^+$: 563 | A |
| II_42 | IIIa_1 | (S)-2-(2-Benzoylphenylamino)-3-{4-[3-(benzylcyclopropylmethylamino)-propoxy]phenyl}propionic acid methyl ester | rt: 7.052 MS[M+1]$^+$: 577 | A |
| II_43 | IIIa_1 | (S)-2-(2-Benzoylphenylamino)-3-(4-{2-[(2-methoxybenzyl)phenylamino]-ethoxy}phenyl)propionic acid methyl ester | rt: 9.936 MS[M+1]$^+$: 615 | A |

TABLE 4-continued

| Example Number | Starting product | Compound name | $^1$H-NMR/LC-MS | HPLC Method |
|---|---|---|---|---|
| II_44 | IIIa_1 | (S)-2-(2-Benzoylphenylamino)-3-(4-{2-[(3-methoxybenzyl)phenylamino]-ethoxy}phenyl)propionic acid methyl ester | rt: 9.8<br>MS[M+1]$^+$: 615 | A |
| II_45 | IIIa_1 | (S)-2-(2-Benzoylphenylamino)-3-(4-{2-[(3-methoxyphenyl)phenylamino]-ethoxy}phenyl)propionic acid methyl ester | rt: 9.831<br>MS[M+1]$^+$: 601 | A |
| II_46 | IIIa_1 | (S)-2-(2-Benzoylphenylamino)-3-(4-{2-[(4-methoxybenzyl)phenylamino]-ethoxy}phenyl)propionic acid methyl ester | rt: 9.788<br>MS[M+1]$^+$: 615 | A |
| II_47 | IIIa_1 | (S)-2-(2-Benzoylphenylamino)-3-(4-{2-[(4-tert-butylbenzyl)phenylamino]-ethoxy}phenyl)propionic acid methyl ester | rt: —<br>MS[M+1]$^+$: 641 | A |
| II_48 | IIIa_1 | (S)-2-(2-Benzoylphenylamino)-3-{4-[2-(benzylphenylamino)ethoxy]-phenyl}propionic acid methyl ester | 8.89(d, 1H), 7.59(d, 2H), 7.55-7.40(ca, 4H), 7.40-7.15(ca, 11H), 6.85-6.55(ca, 8H), 4.67(s, 2H), 4.42(m, 1H), 4.18(t, 2H), 3.85(t, 2H), 3.71(s, 3H), 3.30-3.10(ca, 2H) | A |
| II_49 | IIIa_1 | (S)-2-(2-Benzoylphenylamino)-3-{4-[2-(cyclobutylmethylphenylamino)-ethoxy]phenyl}propionic acid methyl ester | rt: 10.206<br>MS[M+1]$^+$: 563 | A |
| II_50 | IIIa_1 | (S)-2-(2-Benzoylphenylamino)-3-{4-[2-(cyclohexylphenylamino)ethoxy]-phenyl}propionic acid methyl ester | rt: 10.01<br>MS[M+1]$^+$: 577 | A |
| II_51 | IIIa_1 | (S)-2-(2-Benzoylphenylamino)-3-{4-[2-(cyclohexylmethylphenylamino)-ethoxy]phenyl}propionic acid methyl ester | rt: —<br>MS[M+1]$^+$: 589 | A |
| II_52 | IIIa_1 | (S)-2-(2-Benzoylphenylamino)-3-{4-[2-(cyclopentylphenylamino)ethoxy]-phenyl}propionic acid methyl ester | rt: 8.769<br>MS[M+1]$^+$: 563 | A |
| II_53 | IIIa_1 | (S)-2-(2-Benzoylphenylamino)-3-{4-[2-(cyclopropylmethylphenylamino)-ethoxy]phenyl}propionic acid methyl ester | rt: 9.696<br>MS[M+1]$^+$: 549 | A |
| II_54 | IIIa_1 | (S)-2-(2-Benzoylphenylamino)-3-{4-[2-(diphenylamino)ethoxy]phenyl}-propionic acid methyl ester | 8.98(d, 1H), 7.70-7.60(ca, 2H), 7.60-7.45(ca, 3H), 7.45-7.15(ca, 8H), 7.15-6.95(ca, 6H), 6.85(d, 2H), 6.75-6.60(ca, 2H), 4.44(q, 1H), 4.17(s, 4H), 3.72(s, 3H), 3.30-3.10(ca, 2H). | A |
| II_55 | IIIa_1 | (S)-2-(2-Benzoylphenylamino)-3-(4-{2-[cyclohexylmethyl-(2-fluorophenyl)amino]ethoxy}phenyl)-propionic acid methyl ester | rt: __<br>MS[M+1]$^+$: __ | A |
| II_56 | IIIa_1 | (S)-2-(2-Benzoylphenylamino)-3-(4-{2-[(3-chlorophenyl)-cyclopentylmethylamino]ethoxy}-phenyl)propionic acid methyl ester | rt: __<br>MS[M+1]$^+$: __ | A |
| II_57 | IIIa_1 | (S)-2-(2-Benzoylphenylamino)-3-(4-{3-[cyclobutylmethyl-(3-fluorophenyl)amino]propoxy}phenyl)-propionic acid methyl ester | rt: 10.527<br>MS[M+1]$^+$: 595 | A |
| II_58 | IIIa_1 | (S)-2-(2-Benzoylphenylamino)-3-{4-[3-(cyclobutylmethyl-m-tolylamino)-propoxy]phenyl}propionic acid methyl ester | rt: 9.994<br>MS[M+1]$^+$: 591 | A |
| II_59 | IIIb_1 | (R)-2-(2-Benzoylphenylamino)-3-{4-[2-(benzylphenylamino)ethoxy]-phenyl}propionic acid methyl ester | rt: 9.945<br>MS[M+1]$^+$: 585 | A |
| II_60 | IIIa_1 | (S)-2-(2-Benzoylphenylamino)-3-(4-{2-[(2-chlorophenyl)-cyclopentylmethylamino]ethoxy}-phenyl)propionic acid methyl ester | rt: __<br>MS[M+1]$^+$: __ | A |

TABLE 4-continued

| Example Number | Starting product | Compound name | ¹H-NMR/LC-MS | HPLC Method |
|---|---|---|---|---|
| II_61 | IIIa_1 | (S)-2-(2-Benzoylphenylamino)-3-(4-{2-[(2-fluorophenyl)thiophen-2-ylmethylamino]ethoxy}phenyl)-propionic acid methyl ester | rt: 9.831 MS[M+1]$^+$: 609 | A |
| II_62 | IIIa_1 | (S)-2-(2-Benzoylphenylamino)-3-(4-{3-[(2-fluorophenyl)isobutylamino]-propoxy}phenyl)propionic acid methyl ester | rt: 10.561 MS[M+1]$^+$: 583 | A |
| II_63 | IIIa_1 | (S)-2-(2-Benzoylphenylamino)-3-(4-{3-[cyclopentylmethyl-(2-fluorophenyl)amino]propoxy}phenyl)-propionic acid methyl ester | rt: __ MS[M+1]$^+$: __ | A |
| II_64 | IIIa_1 | (S)-2-(2-Benzoylphenylamino)-3-{4-[3-(cyclobutylmethyl-o-tolylamino)-propoxy]phenyl}propionic acid methyl ester | rt: 9.655 MS[M+1]$^+$: 591 | A |
| II_65 | IIIa_1 | (S)-2-(2-Benzoylphenylamino)-3-(4-{2-[(3-fluorophenyl)thiophen-2-ylmethylamino]ethoxy}phenyl)-propionic acid methyl ester | rt: 9.752 MS[M+1]$^+$: 609 | A |
| II_66 | IIIa_1 | (S)-2-(2-Benzoylphenylamino)-3-{4-[2-(thiophen-2-ylmethyl-m-tolylamino)ethoxy]phenyl}propionic acid methyl ester | rt: 9.996 MS[M+1]$^+$: 605 | A |
| II_67 | IIIa_1 | (S)-2-(2-Benzoylphenylamino)-3-{4-[3-(thiophen-3-ylmethyl-m-tolylamino)propoxy]phenyl}propionic acid methyl ester | rt: 10.131 MS[M+1]$^+$: 316 | A |
| II_68 | IIIa_1 | (S)-2-(2-Benzoylphenylamino)-3-{4-[3-(furan-2-ylmethyl-m-tolylamino)-propoxy]phenyl}propionic acid methyl ester | rt: 9.929 MS[M+1]$^+$: 603 | A |
| II_69 | IIIa_I | (S)-2-(2-Benzoylphenylamino)-3-(4-{2-[(4-fluorophenyl)thiophen-2-ylmethylamino]ethoxy}phenyl)-propionic acid methyl ester | rt: 9.744 MS[M+1]$^+$: 609 | A |
| II_70 | IIIa_1 | (S)-2-(2-Benzoylphenylamino)-3-{4-[2-(phenylthiophen-2-ylmethylamino)ethoxy]phenyl}-propionic acid methyl ester | rt: 9.795 MS[M+1]$^+$: 591 | A |
| II_71 | IIIa_1 | (S)-2-(2-Benzoylphenylamino)-3-{4-[3-(phenylthiophen-2-ylmethylamino)propoxy]phenyl}-propionic acid methyl ester | rt: 9.933 MS[M+1]$^+$: 605 | A |

Intermediates IIa:

Compounds of formula IIa shown in Table 5 were obtained starting from a compound Va and a compound of formula VIa or VIb, following one of the procedures G-H described below.

PROCEDURE G: To a 0.2 M solution of compound Va (1 eq) in dichloromethane or EtOAc, triethylamine (3 eq) and a solution of an acyl chloride VIa (1.2 eq) were added. After stirring for 18 h, the crude was treated with 5% NaHCO$_3$. The organic layer was washed twice with 5% NaHCO$_3$ and once with brine. The organic layer was dried over anhydrous sodium sulfate and filtered. The solvent was distilled off under reduced pressure. The obtained residue was purified by column chromatography.

PROCEDURE H: To a 0.3 M suspension of compound Va (1 eq) in EtOAc containing HOBT (1.5 eq) and EDC (1.5 eq), triethylamine (3 eq) was added. Then, carboxylic acid VIb (1 eq) was added and stirred for 18 h. The reaction mixture was treated with water, the organic layer was separated and the aqueous layer was extracted once with EtOAc. The combined organic layers were washed once with 5% NaHCO$_3$ and once with brine, dried over anhydrous sodium sulfate, and filtered. The solvent was distilled off under reduced pressure, and the obtained residue was purified by column chromatography.

TABLE 5

| Example Number | Starting product | Compound name | ¹H-NMR/LC-MS | HPLC Method |
|---|---|---|---|---|
| IIa_1 | V_17 | (S)-2-(2-Benzoylphenylamino)-3-(4-{2-[(2-(2-chlorophenyl)-(2-methylacryloyl)amino]ethoxy}-phenyl)propionic acid methyl ester | rt: 9.069 MS[M+1]$^+$: 597 | A |
| IIa_2 | V_23 | (S)-2-(2-Benzoylphenylamino)-3-(4-{3-[(2-chlorophenyl-(2- | rt: 9.926 MS[M, M+2]$^+$: 611, | B |

TABLE 5-continued

| Example Number | Starting product | Compound name | ¹H-NMR/LC-MS | HPLC Method |
|---|---|---|---|---|
| | | methylacryloyl)amino]propoxy}-phenyl)propionic acid methyl ester | 613 | |
| IIa_3 | V_17 | (S)-2-(2-Benzoylphenylamino)-3-(4-{2-[but-2-(E)-enoyl-(2-chlorophenyl)-amino]ethoxy}phenyl)propionic acid methyl ester | rt: 9.034 MS[M, M+2]⁺: 597, 599 | A |
| IIa_4 | V_17 | (S)-2-(2-Benzoylphenylamino)-3-(4-{2-[(2-chlorophenyl)-(3-methylbutyryl)amino]ethoxy}phenyl)-propionic acid methyl ester | rt: 9.532 MS[M, M+2]⁺: 613, 615 | A |
| IIa_5 | V_17 | (S)-2-(2-Benzoylphenylamino)-3-(4-{2-[(2-chlorophenyl)-cyclobutanecarbonylamino]ethoxy}-phenyl)propionic acid methyl ester | rt: 9.427 MS[M, M+2]⁺: 611, 613 | A |
| IIa_6 | V_17 | (S)-2-(2-Benzoylphenylamino)-3-(4-{2-[(2-chlorophenyl)-cyclopentanecarbonylamino]ethoxy}-phenyl)propionic acid methyl ester | rt: 9.657 MS[M, M+2]⁺: 625, 627 | A |
| IIa_7 | V_17 | (S)-2-(2-Benzoylphenylamino)-3-(4-{2-[(2-chlorophenyl)-cyclopropanecarbonylamino]ethoxy}-phenyl)propionic acid methyl ester | rt: 9.094 MS[M, M+2]⁺: 597, 599 | A |
| IIa_8 | V_23 | (S)-2-(2-Benzoylphenylamino)-3-(4-{3-[(2-chlorophenyl)-cyclopropanecarbonylamino]-propoxy}phenyl)propionic acid methyl ester | rt: 9.28 MS[M, M+2]⁺: 611, 613 | A |
| IIa_9 | V_17 | (S)-2-(2-Benzoylphenylamino)-3-(4-{2-[(2-chlorophenyl)propionylamino]-ethoxy}phenyl)propionic acid methyl ester | rt: 9.049 MS[M, M+2]⁺: 585, 587 | A |
| IIa_10 | V_23 | (S)-2-(2-Benzoylphenylamino)-3-(4-{3-[(2-chlorophenyl)propionylamino]-propoxy}phenyl)propionic acid methyl ester | rt: 9.247 MS[M, M+2]⁺: 599, 601 | A |
| IIa_11 | V_17 | (S)-2-(2-Benzoylphenylamino)-3-(4-{2-[(2-chlorophenyl)isobutyrylamino]-ethoxy}phenyl)propionic acid methyl ester | rt: 9.28 MS[M, M+2]⁺: 599, 601 | A |
| IIa_12 | V_23 | (S)-2-(2-Benzoylphenylamino)-3-(4-{3-[(2-chlorophenyl)isobutyrylamino]-propoxy}phenyl)propionic acid methyl ester | rt: 10.126 MS[M, M+2]⁺: 613, 615 | B |
| IIa_13 | V_17 | (S)-2-(2-Benzoylphenylamino)-3-(4-{2-[butyryl-(2-chlorophenyl)amino]-ethoxy}phenyl)propionic acid methyl ester | rt: 9.069 MS[M, M+2]⁺: 597, 599 | A |
| IIa_14 | V_23 | (S)-2-(2-Benzoylphenylamino)-3-(4-{3-[butyryl-(2-chlorophenyl)amino]-propoxy}phenyl)propionic acid methyl ester | rt: 10.148 MS[M, M+2]⁺: 613, 615 | B |
| IIa_15 | V_23 | (S)-3-(4-{3-[Acryloyl-(2-chlorophenyl)amino]propoxy}-phenyl)-2-(2-benzoylphenylamino)-propionic acid methyl ester | rt: 9.102 MS[M, M+2]⁺: 597, 599 | A |
| IIa_16 | V_11 | (S)-2-(2-Benzoylphenylamino)-3-(4-{2-[(2-fluorophenyl)-(thiophene-2-carbonyl)amino]ethoxy}phenyl)-propionic acid methyl ester | rt: 8.961 MS[M+1]⁺: 623 | A |
| IIa_17 | V_11 | (S)-2-(2-Benzoylphenylamino)-3-(4-{2-[(2-fluorophenyl)-(2-methylacryloyl)amino]ethoxy}-phenyl)propionic acid methyl ester | rt: 8.857 MS[M+1]⁺: 581 | A |
| IIa_18 | V_11 | (S)-2-(2-Benzoylphenylamino)-3-(4-{2-[(2-fluorophenyl)-(3-methylbutyryl)amino]ethoxy}phenyl)-propionic acid methyl ester | rt: 9.282 MS[M+1]⁺: 597 | A |
| IIa_19 | V_11 | (S)-2-(2-Benzoylphenylamino)-3-(4-{2-[cyclobutanecarbonyl-(2-fluorophenyl)amino]ethoxy}phenyl)-propionic acid methyl ester | rt: 9.185 MS[M+1]⁺: 595 | A |
| IIa_20 | V_11 | (S)-2-(2-Benzoylphenylamino)-3-(4-{2-[cyclopentanecarbonyl-(2-fluorophenyl)amino]ethoxy}phenyl)-propionic acid methyl ester | rt: 9.412 MS[M+1]⁺: 609 | A |

TABLE 5-continued

| Example Number | Starting product | Compound name | $^1$H-NMR/LC-MS | HPLC Method |
|---|---|---|---|---|
| IIa_21 | V_11 | (S)-2-(2-Benzoylphenylamino)-3-(4-{2-[cyclopropanecarbonyl-(2-fluorophenyl)amino]ethoxy}phenyl)-propionic acid methyl ester | rt: 8.865<br>MS[M+1]$^+$: 581 | A |
| IIa_22 | V_11 | (S)-2-(2-Benzoylphenylamino)-3-(4-{2-[(2-fluorophenyl)propionylamino]-ethoxy}phenyl)propionic acid methyl ester | rt: 8.796<br>MS[M+1]$^+$: 569 | A |
| IIa_23 | V_11 | (S)-2-(2-Benzoylphenylamino)-3-(4-{2-[(2-fluorophenyl)isobutyrylamino]-ethoxy}phenyl)propionic acid methyl ester | rt: 9.04<br>MS[M+1]$^+$: 583 | A |
| IIa_24 | V_11 | (S)-2-(2-Benzoylphenylamino)-3-(4-{2-[butyryl-(2-fluorophenyl)amino]-ethoxy}phenyl)propionic acid methyl ester | rt: 9.05<br>MS[M+1]$^+$: 583 | A |
| IIa_25 | V_17 | (S)-2-(2-Benzoylphenylamino)-3-(4-{2-[(2,2-dimethylpropionyl)-(2-fluorophenyl)amino]ethoxy}phenyl)-propionic acid methyl ester | rt: 9.408<br>MS[M+1]$^+$: 597 | A |
| IIa_26 | V_20 | (S)-2-(2-Benzoylphenylamino)-3-(4-{3-[(2-methylacryloyl)-o-tolylamino]-propoxy}phenyl)propionic acid methyl ester | rt: 9.828<br>MS[M+1]$^+$: 591 | B |
| IIa_27 | V_14 | (S)-2-(2-Benzoylphenylamino)-3-(4-{2-[(2-ethylbutyryl)-o-tolylamino]-ethoxy}phenyl)propionic acid methyl ester | rt: 9.684<br>MS[M+1]$^+$: 607 | A |
| IIa_28 | V_20 | (S)-2-(2-Benzoylphenylamino)-3-(4-{3-[(3-methylbut-2-(E)-enoyl)-o-tolylamino]propoxy}phenyl)propionic acid methyl ester | rt: 10.165<br>MS[M+1]$^+$: 605 | B |
| IIa_29 | V_20 | (S)-2-(2-Benzoylphenylamino)-3-{4-[3-(but-2-(E)-enoyl-o-tolylamino)-propoxy]phenyl}propionic acid methyl ester | rt: 9.911<br>MS[M+1]$^+$: 591 | B |
| IIa_30 | V_14 | (S)-2-(2-Benzoylphenylamino)-3-(4-{2-[(3,3-dimethylbutyryl)-o-tolylamino]ethoxy}phenyl)propionic acid methyl ester | rt: 9.788<br>MS[M+1]$^+$: 607 | A |
| IIa_31 | V_14 | (S)-2-(2-Benzoylphenylamino)-3-(4-{2-[(3-methylbutyryl)-o-tolylamino]-ethoxy}phenyl)propionic acid methyl ester | rt: 9.465<br>MS[M+1]$^+$: 593 | A |
| IIa_32 | V_20 | (S)-2-(2-Benzoylphenylamino)-3-(4-{3-[(3-methylbutyryl)-o-tolylamino]-propoxy}phenyl)propionic acid methyl ester | rt: 10.331<br>MS[M+1]$^+$: 607 | B |
| IIa_33 | V_20 | (S)-2-(2-Benzoylphenylamino)-3-{4-[3-(o-tolylpent-4-enoylamino)-propoxy]phenyl}propionic acid methyl ester | rt: 10.129<br>MS[M+1]$^+$: 605 | B |
| IIa_34 | V_14 | (S)-2-(2-Benzoylphenylamino)-3-{4-[2-(cyclobutanecarbonyl-o-tolylamino)ethoxy]phenyl}propionic acid methyl ester | rt: 9.378<br>MS[M+1]$^+$: 591 | A |
| IIa_35 | V_14 | (S)-2-(2-Benzoylphenylamino)-3-{4-[2-(cyclopentanecarbonyl-o-tolylamino)ethoxy]phenyl}propionic acid methyl ester | rt: 9.607<br>MS[M+1]$^+$: 605 | A |
| IIa_36 | V_20 | (S)-2-(2-Benzoylphenylamino)-3-{4-[3-(propionyl-o-tolylamino)propoxy]-phenyl}propionic acid methyl ester | rt: 9.849<br>MS[M+1]$^+$: 579 | B |
| IIa_37 | V_14 | (S)-2-(2-Benzoylphenylamino)-3-{4-[2-(isobutyryl-o-tolylamino)ethoxy]-phenyl}propionic acid methyl ester | rt: 9.22<br>MS[M+1]$^+$: 579 | A |
| IIa_38 | V_20 | (S)-2-(2-Benzoylphenylamino)-3-{4-[3-(isobutyryl-o-tolylamino)propoxy]-phenyl}propionic acid methyl ester | rt: 10.08<br>MS[M+1]$^+$: 593 | B |
| IIa_39 | V_20 | (S)-2-(2-Benzoylphenylamino)-3-{4-[3-(pentanoyl-o-tolylamino)propoxy]-phenyl}propionic acid methyl ester | rt: 10.348<br>MS[M+1]$^+$: 607 | B |
| IIa_40 | V_14 | (S)-2-(2-Benzoylphenylamino)-3-{4-[2-(butyryl-o-tolylamino)ethoxy]-phenyl}propionic acid methyl ester | rt: 9.233<br>MS[M+1]$^+$: 579 | A |

TABLE 5-continued

| Example Number | Starting product | Compound name | ¹H-NMR/LC-MS | HPLC Method |
|---|---|---|---|---|
| IIa_41 | V_20 | (S)-2-(2-Benzoylphenylamino)-3-{4-[3-(butyryl-o-tolylamino)propoxy]-phenyl}propionic acid methyl ester | rt: 10.094<br>MS[M+1]⁺: 593 | B |
| IIa_42 | V_14 | (S)-2-(2-Benzoylphenylamino)-3-{4-[2-(benzoyl-o-tolylamino)ethoxy]-phenyl}propionic acid methyl ester | rt: 9.077<br>MS[M+1]⁺: 613 | A |
| IIa_43 | V_14 | (S)-2-(2-Benzoylphenylamino)-3-(4-{2-[(2,2-dimethylpropionyl)-o-tolylamino]ethoxy}phenyl)propionic acid methyl ester | rt: 9.597<br>MS[M+1]⁺: 593 | A |
| IIa_44 | V_20 | (S)-2-(2-Benzoylphenylamino)-3-(4-{3-[(2,2-dimethylpropionyl)-o-tolylamino]propoxy}phenyl)propionic acid methyl ester | rt: 10.435<br>MS[M+1]⁺: 607 | B |
| IIa_45 | V_20 | (S)-3-{4-[3-(Acryloyl-o-tolylamino)-propoxy]phenyl}-2-(2-benzoylphenylamino)propionic acid methyl ester | rt: 9.781<br>MS[M+1]⁺: 577 | B |
| IIa_46 | V_18 | (S)-2-(2-Benzoylphenylamino)-3-(4-{2-[(3-chlorophenyl)-(2-methylacryloyl)amino]ethoxy}-phenyl)propionic acid methyl ester | rt: 9.126<br>MS[M, M+2]⁺: 597, 599 | A |
| IIa_47 | V_18 | (S)-2-(2-Benzoylphenylamino)-3-(4-{2-[but-2-(E)-enoyl-(3-chlorophenyl)-amino]ethoxy}phenyl}propionic acid methyl ester | rt: 9.184<br>MS[M, M+2]⁺: 597, 599 | A |
| IIa_48 | V_24 | (S)-2-(2-Benzoylphenylamino)-3-(4-{3-[but-2-(E)-enoyl-(3-chlorophenyl)-amino]propoxy}phenyl)propionic acid methyl ester | rt: 9.348<br>MS[M, M+2]⁺: 611, 613 | A |
| IIa_49 | V_18 | (S)-2-(2-Benzoylphenylamino)-3-(4-{2-[(3-chlorophenyl)-(3-methylbutyryl)amino]ethoxy}phenyl)-propionic acid methyl ester | rt: 9.557<br>MS[M, M+2]⁺: 613, 615 | A |
| IIa_50 | V_18 | (S)-2-(2-Benzoylphenylamino)-3-(4-{2-[(3-chlorophenyl)-pent-4-enoylamino]ethoxy}phenyl)propionic acid methyl ester | rt: 9.375<br>MS[M, M+2]⁺: 611, 613 | A |
| IIa_51 | V_18 | (S)-2-(2-Benzoylphenylamino)-3-(4-{2-[(3-chlorophenyl)-cyclobutanecarbonylamino]ethoxy}-phenyl)propionic acid methyl ester | rt: 9.488<br>MS[M, M+2]⁺: 611, 613 | A |
| IIa_52 | V_18 | (S)-2-(2-Benzoylphenylamino)-3-(4-{2-[(3-chlorophenyl)-cyclopentanecarbonylamino]ethoxy}-phenyl)propionic acid methyl ester | rt: 9.708<br>MS[M, M+2]⁺: 625, 627 | A |
| IIa_53 | V_18 | (S)-2-(2-Benzoylphenylamino)-3-(4-{2-[(3-chlorophenyl)-cyclopropanecarbonylamino]ethoxy}-phenyl)propionic acid methyl ester | rt: 9.217<br>MS[M, M+2]⁺: 597, 599 | A |
| IIa_54 | V_24 | (S)-2-(2-Benzoylphenylamino)-3-(4-{3-[(3-chlorophenyl)-cyclopropanecarbonylamino]-propoxy}phenyl)propionic acid methyl ester | rt: 9.401<br>MS[M, M+2]⁺: 611, 613 | A |
| IIa_55 | V_18 | (S)-2-(2-Benzoylphenylamino)-3-(4-{2-[(3-chlorophenyl)propionylamino]-ethoxy}phenyl)propionic acid methyl ester | rt: 9.097<br>MS[M, M+2]⁺: 585, 587 | A |
| IIa_56 | V_24 | (S)-2-(2-Benzoylphenylamino)-3-(4-{3-[(3-chlorophenyl)propionylamino]-propoxy}phenyl)propionic acid methyl ester | rt: 9.279<br>MS[M, M+2]⁺: 599, 601 | A |
| IIa_57 | V_18 | (S)-2-(2-Benzoylphenylamino)-3-(4-{2-[(3-chlorophenyl)isobutyrylamino]-ethoxy}phenyl)propionic acid methyl ester | rt: 9.332<br>MS[M, M+2]⁺: 599, 601 | A |
| IIa_58 | V_24 | (S)-2-(2-Benzoylphenylamino)-3-(4-{3-[(3-chlorophenyl)isobutyrylamino]-propoxy}phenyl)propionic acid methyl ester | rt: 9.502<br>MS[M, M+2]⁺: 613, 615 | A |
| IIa_59 | V_18 | (S)-2-(2-Benzoylphenylamino)-3-(4-{2-[butyryl-(3-chlorophenyl)amino]-ethoxy}phenyl)propionic acid methyl ester | rt: 9.339<br>MS[M, M+2]⁺: 599, 601 | A |

TABLE 5-continued

| Example Number | Starting product | Compound name | ¹H-NMR/LC-MS | HPLC Method |
|---|---|---|---|---|
| IIa_60 | V_24 | (S)-2-(2-Benzoylphenylamino)-3-(4-{3-[butyryl-(3-chlorophenyl)amino]-propoxy}phenyl)propionic acid methyl ester | rt: 9.508 MS[M, M+2]⁺: 613, 615 | A |
| IIa_61 | V_18 | (S)-2-(2-Benzoylphenylamino)-3-(4-{2-[(3-chlorophenyl)-(2,2-dimethylpropionyl)amino]ethoxy}-phenyl)propionic acid methyl ester | rt: 9.669 MS[M, M+2]⁺: 613, 615 | A |
| IIa_62 | V_24 | (S)-3-(4-{3-[Acryloyl-(3-chlorophenyl)amino]propoxy}-phenyl)-2-(2-benzoylphenylamino)-propionic acid methyl ester | rt: 9.202 MS[M, M+2]⁺: 597, 599 | A |
| IIa_63 | V_12 | (S)-2-(2-Benzoylphenylamino)-3-(4-{2-[(3-fluorophenyl)-(thiophene-2-carbonyl)amino]ethoxy}phenyl)-propionic acid methyl ester | rt: 9.016 MS[M+1]⁺: 623 | A |
| IIa_64 | V_12 | (S)-2-(2-Benzoylphenylamino)-3-(4-{2-[(3-fluorophenyl)-(2-methylacryloyl)amino]ethoxy}-phenyl)propionic acid methyl ester | rt: 8.86 MS[M+1]⁺: 581 | A |
| IIa_65 | V_12 | (S)-2-(2-Benzoylphenylamino)-3-(4-{2-[(3-fluorophenyl)-(3-methylbutyryl)amino]ethoxy}phenyl)-propionic acid methyl ester | rt: 9.284 MS[M+1]⁺: 597 | A |
| IIa_66 | V_12 | (S)-2-(2-Benzoylphenylamino)-3-(4-{2-[cyclobutanecarbonyl-(3-fluorophenyl)amino]ethoxy}phenyl)-propionic acid methyl ester | rt: 9.198 MS[M+1]⁺: 595 | A |
| IIa_67 | V_12 | (S)-2-(2-Benzoylphenylamino)-3-(4-{2-[cyclopentanecarbonyl-(3-fluorophenyl)amino]ethoxy}phenyl)-propionic acid methyl ester | rt: 9.424 MS[M+1]⁺: 609 | A |
| IIa_68 | V_12 | (S)-2-(2-Benzoylphenylamino)-3-(4-{2-[cyclopropanecarbonyl-(3-fluorophenyl)amino]ethoxy}phenyl)-propionic acid methyl ester | rt: 8.93 MS[M+1]⁺: 581 | A |
| IIa_69 | V_12 | (S)-2-(2-Benzoylphenylamino)-3-(4-{2-[(3-fluorophenyl)propionylamino]-ethoxy}phenyl)propionic acid methyl ester | rt: 8.805 MS[M+1]⁺: 569 | A |
| IIa_70 | V_12 | (S)-2-(2-Benzoylphenylamino)-3-(4-{2-[(3-fluorophenyl)isobutyrylamino]-ethoxy}phenyl)propionic acid methyl ester | rt: 9.047 MS[M+1]⁺: 583 | A |
| IIa_71 | V_12 | (S)-2-(2-Benzoylphenylamino)-3-(4-{2-[butyryl-(3-fluorophenyl)amino]-ethoxy}phenyl)propionic acid methyl ester | rt: 9.057 MS[M+1]⁺: 583 | A |
| IIa_72 | V_12 | (S)-2-(2-Benzoylphenylamino)-3-(4-{2-[(2,2-dimethylpropionyl)-(3-fluorophenyl)amino]ethoxy}phenyl)-propionic acid methyl ester | rt: 9.393 MS[M+1]⁺: 597 | A |
| IIa_73 | V_8 | (S)-2-(2-Benzoylphenylamino)-3-(4-{3-[(2-methylacryloyl)-(3-methylbenzyl)amino]propoxy}-phenyl)propionic acid methyl ester | rt: 9.199 MS[M+1]⁺: 605 | A |
| IIa_74 | V_7 | (S)-2-(2-Benzoylphenylamino)-3-(4-{2-[(2-ethylbutyryl)-(3-methylbenzyl)-amino]ethoxy}phenyl)propionic acid methyl ester | rt: 9.678 MS[M+1]⁺: 621 | A |
| IIa_75 | V_8 | (S)-2-(2-Benzoylphenylamino)-3-(4-{3-[(3-methylbenzyl)-(3-methylbut-2-(E)-enoyl)amino]propoxy}phenyl)-propionic acid methyl ester | rt: 9.382 MS[M+1]⁺: 619 | A |
| IIa_76 | V_8 | (S)-2-(2-Benzoylphenylamino)-3-(4-{3-[but-2-(E)-enoyl-(3-methylbenzyl)-amino]propoxy}phenyl)propionic acid methyl ester | rt: 9.153 MS[M+1]⁺: 605 | A |
| IIa_77 | V_7 | (S)-2-(2-Benzoylphenylamino)-3-(4-{2-[(3,3-dimethylbutyryl)-(3-methylbenzyl)amino]ethoxy}phenyl)-propionic acid methyl ester | rt: 9.728 MS[M+1]⁺: 621 | A |
| IIa_78 | V_7 | (S)-2-(2-Benzoylphenylamino)-3-(4-{2-[(3-methylbenzyl)-(3-methylbutyryl)amino]ethoxy}phenyl)-propionic acid methyl ester | rt: 9.471 MS[M+1]⁺: 607 | A |

TABLE 5-continued

| Example Number | Starting product | Compound name | $^1$H-NMR/LC-MS | HPLC Method |
|---|---|---|---|---|
| IIa_79 | V_8 | (S)-2-(2-Benzoylphenylamino)-3-(4-{3-[(3-methylbenzyl)-(3-methylbutyryl)amino]propoxy}-phenyl)propionic acid methyl ester | rt: 9.549 MS[M+1]$^+$: 621 | A |
| IIa_80 | V_7 | (S)-2-(2-Benzoylphenylamino)-3-(4-{2-[cyclobutanecarbonyl-(3-methylbenzyl)amino]ethoxy}phenyl)-propionic acid methyl ester | rt: 9.389 MS[M+1]$^+$: 605 | A |
| IIa_81 | V_8 | (S)-2-(2-Benzoylphenylamino)-3-(4-{3-[cyclobutanecarbonyl-(3-methylbenzyl)amino]propoxy}-phenyl)propionic acid methyl ester | rt: 9.464 MS[M+1]$^+$: 619 | A |
| IIa_82 | V_7 | (S)-2-(2-Benzoylphenylamino)-3-(4-{2-[cyclopentanecarbonyl-(3-methylbenzyl)amino]ethoxy}phenyl)-propionic acid methyl ester | rt: 9.588 MS[M+1]$^+$: 619 | A |
| IIa_83 | V_8 | (S)-2-(2-Benzoylphenylamino)-3-(4-{3-[cyclopropanecarbonyl-(3-methylbenzyl)amino]propoxy}-phenyl)propionic acid methyl ester | rt: 9.194 MS[M+1]$^+$: 605 | A |
| IIa_84 | V_8 | (S)-2-(2-Benzoylphenylamino)-3-(4-{3-[(3-methylbenzyl)propionylamino]-propoxy}phenyl)propionic acid methyl ester | rt: 9.095 MS[M+1]$^+$: 593 | A |
| IIa_85 | V_7 | (S)-2-(2-Benzoylphenylamino)-3-(4-{2-[isobutyryl-(3-methylbenzyl)-amino]ethoxy}phenyl)propionic acid methyl ester | rt: 9.23 MS[M+1]$^+$: 593 | A |
| IIa_86 | V_8 | (S)-2-(2-Benzoylphenylamino)-3-(4-{3-[isobutyryl-(3-methylbenzyl)-amino]propoxy}phenyl)propionic acid methyl ester | rt: 9.319 MS[M+1]$^+$: 607 | A |
| IIa_87 | V_7 | (S)-2-(2-Benzoylphenylamino)-3-(4-{2-[butyryl-(3-methylbenzyl)amino]-ethoxy}phenyl)propionic acid methyl ester | rt: 9.247 MS[M+1]$^+$: 593 | A |
| IIa_88 | V_8 | (S)-2-(2-Benzoylphenylamino)-3-(4-{3-[butyryl-(3-methylbenzyl)amino]-propoxy}phenyl)propionic acid methyl ester | rt: 9.328 MS[M+1]$^+$: 607 | A |
| IIa_89 | V_7 | (S)-3-(4-{2-[Benzoyl-(3-methylbenzyl)amino]ethoxy}phenyl)-2-(2-benzoylphenylamino)propionic acid methyl ester | rt: 9.28 MS[M+1]$^+$: 627 | A |
| IIa_90 | V_7 | (S)-2-(2-Benzoylphenylamino)-3-(4-{2-[(2,2-dimethylpropionyl)-(3-methylbenzyl)amino]ethoxy}phenyl)-propionic acid methyl ester | rt: 9.602 MS[M+1]$^+$: 607 | A |
| IIa_91 | V_8 | (S)-2-(2-Benzoylphenylamino)-3-(4-{3-[(2,2-dimethylpropionyl)-(3-methylbenzyl)amino]propoxy}-phenyl)propionic acid methyl ester | rt: 9.635 MS[M+1]$^+$: 621 | A |
| IIa_92 | V_21 | (S)-2-(2-Benzoylphenylamino)-3-(4-{3-[(2-methylacryloyl)-m-tolylamino]-propoxy}phenyl)propionic acid methyl ester | rt: 9.906 MS[M+1]$^+$: 591 | B |
| IIa_93 | V_15 | (S)-2-(2-Benzoylphenylamino)-3-(4-{2-[(2-ethylbutyryl)-m-tolylamino]-ethoxy}phenyl)propionic acid methyl ester | rt: 9.75 MS[M+1]$^+$: 607 | A |
| IIa_94 | V_21 | (S)-2-(2-Benzoylphenylamino)-3-(4-{3-[(3-methylbut-2-(E)-enoyl)-m-tolylamino]propoxy}phenyl)propionic acid methyl ester | rt: 10.231 MS[M+1]$^+$: 605 | B |
| IIa_95 | V_21 | (S)-2-(2-Benzoylphenylamino)-3-{4-[3-(but-2-(E)-enoyl-m-tolylamino)-propoxy]phenyl}propionic acid methyl ester | rt: 9.985 MS[M+1]$^+$: 591 | B |
| IIa_96 | V_15 | (S)-2-(2-Benzoylphenylamino)-3-(4-{2-[(3,3-dimethylbutyryl)-m-tolylamino]ethoxy}phenyl)propionic acid methyl ester | rt: 9.826 MS[M+1]$^+$: 607 | A |
| IIa_97 | V_15 | (S)-2-(2-Benzoylphenylamino)-3-(4-{2-[(3-methylbutyryl)-m-tolylamino]-ethoxy}phenyl)propionic acid methyl ester | rt: 9.518 MS[M+1]$^+$: 593 | A |

TABLE 5-continued

| Example Number | Starting product | Compound name | ¹H-NMR/LC-MS | HPLC Method |
|---|---|---|---|---|
| IIa_98 | V_15 | (S)-2-(2-Benzoylphenylamino)-3-{4-[2-(cyclobutanecarbonyl-m-tolylamino)ethoxy]phenyl}propionic acid methyl ester | rt: 9.46<br>MS[M+1]$^+$: 591 | A |
| IIa_99 | V_15 | (S)-2-(2-Benzoylphenylamino)-3-{4-[2-(cyclopentanecarbonyl-m-tolylamino)ethoxy]phenyl}propionic acid methyl ester | rt: 9.671<br>MS[M+1]$^+$: 605 | A |
| IIa_100 | V_21 | (S)-2-(2-Benzoylphenylamino)-3-{4-[3-(cyclopropanecarbonyl-m-tolylamino)propoxy]phenyl}propionic acid methyl ester | rt: 10.041<br>MS[M+1]$^+$: 591 | B |
| IIa_101 | V_21 | (S)-2-(2-Benzoylphenylamino)-3-{4-[3-(propionyl-m-tolylamino)propoxy]-phenyl}propionic acid methyl ester | rt: 9.915<br>MS[M+1]$^+$: 579 | B |
| IIa_102 | V_15 | (S)-2-(2-Benzoylphenylamino)-3-{4-[2-(isobutyryl-m-tolylamino)ethoxy]-phenyl}propionic acid methyl ester | rt: 9.287<br>MS[M+1]$^+$: 579 | A |
| IIa_103 | V_21 | (S)-2-(2-Benzoylphenylamino)-3-{4-[3-(isobutyryl-m-tolylamino)propoxy]-phenyl}propionic acid methyl ester | rt: 10.134<br>MS[M+1]$^+$: 593 | B |
| IIa_104 | V_21 | (S)-2-(2-Benzoylphenylamino)-3-{4-[3-(pentanoyl-m-tolylamino)propoxy]-phenyl}propionic acid methyl ester | rt: 10.398<br>MS[M+1]$^+$: 607 | B |
| IIa_105 | V_15 | (S)-2-(2-Benzoylphenylamino)-3-{4-[2-(butyryl-m-tolylamino)ethoxy]-phenyl}propionic acid methyl ester | rt: 9.296<br>MS[M+1]$^+$: 579 | A |
| IIa_106 | V_21 | (S)-2-(2-Benzoylphenylamino)-3-{4-[3-(butyryl-m-tolylamino)propoxy]-phenyl}propionic acid methyl ester | rt: 10.146<br>MS[M+1]$^+$: 593 | B |
| IIa_107 | V_15 | (S)-2-(2-Benzoylphenylamino)-3-{4-[2-(benzoyl-m-tolylamino)ethoxy]-phenyl}propionic acid methyl ester | rt: 9.176<br>MS[M+1]$^+$: 613 | A |
| IIa_108 | V_15 | (S)-2-(2-Benzoylphenylamino)-3-(4-{2-[(2,2-dimethylpropionyl)-m-tolylamino]ethoxy}phenyl)propionic acid methyl ester | rt: 9.659<br>MS[M+1]$^+$: 593 | A |
| IIa_109 | V_21 | (S)-2-(2-Benzoylphenylamino)-3-(4-{3-[(2,2-dimethylpropionyl)-m-tolylamino]propoxy}phenyl)propionic acid methyl ester | rt: 10.508<br>MS[M+1]$^+$: 607 | B |
| IIa_110 | V_21 | (S)-3-{4-[3-(Acryloyl-m-tolylamino)-propoxy]phenyl}-2-(2-benzoylphenylamino)propionic acid methyl ester | rt: 9.85<br>MS[M+1]$^+$: 577 | B |
| IIa_111 | V_19 | (S)-2-(2-Benzoylphenylamino)-3-(4-{2-[(4-chlorophenyl)-(2-methylacryloyl)amino]ethoxy}-phenyl)propionic acid methyl ester | rt: 9.173<br>MS[M, M+2]$^+$: 597, 599 | A |
| IIa_112 | V_19 | (S)-2-(2-Benzoylphenylamino)-3-(4-{2-[but-2-(E)-enoyl-(4-chlorophenyl)-amino]ethoxy}phenyl)propionic acid methyl ester | rt: 9.242<br>MS[M, M+2]$^+$: 597, 599 | A |
| IIa_113 | V_19 | (S)-2-(2-Benzoylphenylamino)-3-(4-{2-[(4-chlorophenyl)-(3-methylbutyryl)amino]ethoxy}phenyl)-propionic acid methyl ester | rt: 9.615<br>MS[M, M+2]$^+$: 613, 615 | A |
| IIa_114 | V_19 | (S)-2-(2-Benzoylphenylamino)-3-(4-{2-[(4-chlorophenyl)-pent-4-enoylamino]ethoxy}phenyl)propionic acid methyl ester | rt: 9.428<br>MS[M, M+2]$^+$: 611, 613 | A |
| IIa_115 | V_19 | (S)-2-(2-Benzoylphenylamino)-3-(4-{2-[(4-chlorophenyl)-cyclobutanecarbonylamino]ethoxy}-phenyl)propionic acid methyl ester | rt: 9.532<br>MS[M, M+2]$^+$: 611, 613 | A |
| IIa_116 | V_19 | (S)-2-(2-Benzoylphenylamino)-3-(4-{2-[(4-chlorophenyl)-cyclopentanecarbonylamino]ethoxy}-phenyl)propionic acid methyl ester | rt: 9.763<br>MS[M, M+2]$^+$: 625, 627 | A |
| IIa_117 | V_19 | (S)-2-(2-Benzoylphenylamino)-3-(4-{2-[(4-chlorophenyl)-cyclopropanecarbonylamino]ethoxy}-phenyl)propionic acid methyl ester | rt: 9.263<br>MS[M, M+2]$^+$: 597, 599 | A |
| IIa_118 | V_25 | (S)-2-(2-Benzoylphenylamino)-3-(4-{3-[(4-chlorophenyl)-cyclopropanecarbonylamino]- | rt: 9.442<br>MS[M, M+2]$^+$: 611, 613 | A |

TABLE 5-continued

| Example Number | Starting product | Compound name | ¹H-NMR/LC-MS | HPLC Method |
|---|---|---|---|---|
| | | propoxy}phenyl)propionic acid methyl ester | | |
| IIa_119 | V_19 | (S)-2-(2-Benzoylphenylamino)-3-(4-{2-[(4-chlorophenyl)propionylamino]-ethoxy}phenyl)propionic acid methyl ester | rt: 9.146 MS[M, M+2]⁺: 585, 587 | A |
| IIa_120 | V_25 | (S)-2-(2-Benzoylphenylamino)-3-(4-{3-[(4-chlorophenyl)propionylamino]-propoxy}phenyl)propionic acid methyl ester | rt: 9.323 MS[M, M+2]⁺: 599, 601 | A |
| IIa_121 | V_19 | (S)-2-(2-Benzoylphenylamino)-3-(4-{2-[(4-chlorophenyl)isobutyrylamino]-ethoxy}phenyl)propionic acid methyl ester | rt: 9.393 MS[M, M+2]⁺: 599, 601 | A |
| IIa_122 | V_25 | (S)-2-(2-Benzoylphenylamino)-3-(4-{3-[(4-chlorophenyl)isobutyrylamino]-propoxy}phenyl)propionic acid methyl ester | rt: 9.558 MS[M, M+2]⁺: 613, 615 | A |
| IIa_123 | V_19 | (S)-2-(2-Benzoylphenylamino)-3-(4-{2-[butyryl-(4-chlorophenyl)amino]-ethoxy}phenyl)propionic acid methyl ester | rt: 9.393 MS[M, M+2]⁺: 599, 601 | A |
| IIa_124 | V_25 | (S)-2-(2-Benzoylphenylamino)-3-(4-{3-[butyryl-(4-chlorophenyl)amino]-propoxy}phenyl)propionic acid methyl ester | rt: 9.558 MS[M, M+2]⁺: 613, 615 | A |
| IIa_125 | V_19 | (S)-2-(2-Benzoylphenylamino)-3-(4-{2-[(4-chlorophenyl)-(2,2-dimethylpropionyl)amino]ethoxy}-phenyl)propionic acid methyl ester | rt: 9.71 MS[M, M+2]⁺: 613, 615 | A |
| IIa_126 | V_25 | (S)-3-(4-{3-[Acryloyl-(4-chlorophenyl)amino]propoxy}-phenyl)-2-(2-benzoylphenylamino)-propionic acid methyl ester | rt: 9.246 MS[M, M+2]⁺: 597, 599 | A |
| IIa_127 | V_13 | (S)-2-(2-Benzoylphenylamino)-3-(4-{2-[(4-fluorophenyl)-(thiophene-2-carbonyl)amino]ethoxy}phenyl)-propionic acid methyl ester | rt: 9.015 MS[M+1]⁺: 623 | A |
| IIa_128 | V_13 | (S)-2-(2-Benzoylphenylamino)-3-(4-{2-[(4-fluorophenyl)-(2-methylacryloyl)amino]ethoxy}phenyl)propionic acid methyl ester | rt: 8.828 MS[M+1]⁺: 581 | A |
| IIa_129 | V_13 | (S)-2-(2-Benzoylphenylamino)-3-(4-{2-[(4-fluorophenyl)-(3-methylbut-2-(E)-enoyl)amino]ethoxy}phenyl)-propionic acid methyl ester | rt: 9.141 MS[M+1]⁺: 595 | A |
| IIa_130 | V_13 | (S)-2-(2-Benzoylphenylamino)-3-(4-{2-[(4-fluorophenyl)-(3-methylbutyryl)amino]ethoxy}phenyl)-propionic acid methyl ester | rt: 9.278 MS[M+1]⁺: 597 | A |
| IIa_131 | V_13 | (S)-2-(2-Benzoylphenylamino)-3-(4-{2-[cyclobutanecarbonyl-(4-fluorophenyl)amino]ethoxy}phenyl)-propionic acid methyl ester | rt: 9.184 MS[M+1]⁺: 595 | A |
| IIa_132 | V_13 | (S)-2-(2-Benzoylphenylamino)-3-(4-{2-[cyclopentanecarbonyl-(4-fluorophenyl)amino]ethoxy}phenyl)-propionic acid methyl ester | rt: 9.413 MS[M+1]⁺: 609 | A |
| IIa_133 | V_13 | (S)-2-(2-Benzoylphenylamino)-3-(4-{2-[cyclopropanecarbonyl-(4-fluorophenyl)amino]ethoxy}phenyl)-propionic acid methyl ester | rt: 8.913 MS[M+1]⁺: 581 | A |
| IIa_134 | V_13 | (S)-2-(2-Benzoylphenylamino)-3-(4-{2-[(4-fluorophenyl)propionylamino]-ethoxy}phenyl)propionic acid methyl ester | rt: 8.794 MS[M+1]⁺: 569 | A |
| IIa_135 | V_13 | (S)-2-(2-Benzoylphenylamino)-3-(4-{2-[(4-fluorophenyl)isobutyrylamino]-ethoxy}phenyl)propionic acid methyl ester | rt: 9.038 MS[M+1]⁺: 583 | A |
| IIa_136 | V_13 | (S)-2-(2-Benzoylphenylamino)-3-(4-{2-[butyryl-(4-fluorophenyl)amino]-ethoxy}phenyl)propionic acid methyl ester | rt: 9.046 MS[M+1]⁺: 583 | A |
| IIa_137 | V_13 | (S)-2-(2-Benzoylphenylamino)-3-(4-{2-[(2,2-dimethylpropionyl)-(4- | rt: 9.384 MS[M+1]⁺: 597 | A |

TABLE 5-continued

| Example Number | Starting product | Compound name | $^1$H-NMR/LC-MS | HPLC Method |
|---|---|---|---|---|
| | | fluorophenyl)amino]ethoxy}phenyl)-propionic acid methyl ester | | |
| IIa_138 | V_22 | (S)-2-(2-Benzoylphenylamino)-3-(4-{3-[(2-methylacryloyl)-p-tolylamino]-propoxy}phenyl)propionic acid methyl ester | rt: 9.202 MS[M+1]$^+$: 591 | A |
| IIa_139 | V_16 | (S)-2-(2-Benzoylphenylamino)-3-(4-{2-[(2-ethylbutyryl)-p-tolylamino]-ethoxy}phenyl)propionic acid methyl ester | rt: 9.775 MS[M+1]$^+$: 607 | A |
| IIa_140 | V_16 | (S)-2-(2-Benzoylphenylamino)-3-(4-{2-[(3,3-dimethylbutyryl)-p-tolylamino]ethoxy}phenyl)propionic acid methyl ester | rt: 9.851 MS[M+1]$^+$: 607 | A |
| IIa_141 | V_16 | (S)-2-(2-Benzoylphenylamino)-3-(4-{2-[(3-methylbutyryl)-p-tolylamino]-ethoxy}phenyl)propionic acid methyl ester | rt: 9.541 MS[M+1]$^+$: 593 | A |
| IIa_142 | V_22 | (S)-2-(2-Benzoylphenylamino)-3-(4-{3-[(3-methylbutyryl)-p-tolylamino]-propoxy}phenyl)propionic acid methyl ester | rt: 9.674 MS[M+1]$^+$: 607 | A |
| IIa_143 | V_16 | (S)-2-(2-Benzoylphenylamino)-3-{4-[2-(cyclobutanecarbonyl-p-tolylamino)ethoxy]phenyl}propionic acid methyl ester | rt: 9.472 MS[M+1]$^+$: 591 | A |
| IIa_144 | V_22 | (S)-2-(2-Benzoylphenylamino)-3-{4-[3-(cyclobutanecarbonyl-p-tolylamino)propoxy]phenyl}propionic acid methyl ester | rt: 9.605 MS[M+1]$^+$: 605 | A |
| IIa_145 | V_16 | (S)-2-(2-Benzoylphenylamino)-3-{4-[2-(cyclopentanecarbonyl-p-tolylamino)ethoxy]phenyl}propionic acid methyl ester | rt: 9.693 MS[M+1]$^+$: 605 | A |
| IIa_146 | V_22 | (S)-2-(2-Benzoylphenylamino)-3-{4-[3-(propionyl-p-tolylamino)propoxy]-phenyl}propionic acid methyl ester | rt: 9.208 MS[M+1]$^+$: 579 | A |
| IIa_147 | V_16 | (S)-2-(2-Benzoylphenylamino)-3-{4-[2-(isobutyryl-p-tolylamino)ethoxy]-phenyl}propionic acid methyl ester | rt: 9.307 MS[M+1]$^+$: 579 | A |
| IIa_148 | V_22 | (S)-2-(2-Benzoylphenylamino)-3-{4-[3-(isobutyryl-p-tolylamino)propoxy]-phenyl}propionic acid methyl ester | rt: 9.443 MS[M+1]$^+$: 593 | A |
| IIa_149 | V_16 | (S)-2-(2-Benzoylphenylamino)-3-{4-[2-(butyryl-p-tolylamino)ethoxy]-phenyl}propionic acid methyl ester | rt: 9.313 MS[M+1]$^+$: 579 | A |
| IIa_150 | V_16 | (S)-2-(2-Benzoylphenylamino)-3-{4-[2-(benzoyl-p-tolylamino)ethoxy]-phenyl}propionic acid methyl ester | rt: 9.169 MS[M+1]$^+$: 613 | A |
| IIa_151 | V_16 | (S)-2-(2-Benzoylphenylamino)-3-(4-{2-[(2,2-dimethylpropionyl)-p-tolylamino]ethoxy}phenyl)propionic acid methyl ester | rt: 9.671 MS[M+1]$^+$: 593 | A |
| IIa_152 | V_22 | (S)-2-(2-Benzoylphenylamino)-3-(4-{3-[(2,2-dimethylpropionyl)-p-tolylamino]propoxy}phenyl)propionic acid methyl ester | rt: 9.772 MS[M+1]$^+$: 607 | A |
| IIa_153 | V_1 | (S)-2-(2-Benzoylphenylamino)-3-(4-{2-[benzyl(naphthalene-1-carbonyl)-amino]ethoxy}phenyl)propionic acid methyl ester | rt: 9.4 MS[M+1]$^+$: 663 | A |
| IIa_154 | V_1 | (S)-2-(2-Benzoylphenylamino)-3-(4-{2-[benzyl(naphthalene-2-carbonyl)-amino]ethoxy}phenyl)propionic acid methyl ester | rt: 9.42 MS[M+1]$^+$: 663 | A |
| IIa_155 | V_1 | (S)-2-(2-Benzoylphenylamino)-3-(4-{2-[benzyl(pyrazine-2-carbonyl)-amino]ethoxy}phenyl)propionic acid methyl ester | rt: 8.532 MS[M+1]$^+$: 615 | A |
| IIa_156 | V_2 | (S)-2-(2-Benzoylphenylamino)-3-(4-{3-[benzyl(pyrazine-2-carbonyl)-amino]propoxy}phenyl)propionic acid methyl ester | rt: 8.642 MS[M+1]$^+$: 629 | A |

TABLE 5-continued

| Example Number | Starting product | Compound name | ¹H-NMR/LC-MS | HPLC Method |
|---|---|---|---|---|
| IIa_157 | V_1 | (S)-2-(2-Benzoylphenylamino)-3-(4-{2-[benzyl(pyridine-2-carbonyl)-amino]ethoxy}phenyl)propionic acid methyl ester | rt: 8.693<br>MS[M+1]⁺: 614 | A |
| IIa_158 | V_2 | (S)-2-(2-Benzoylphenylamino)-3-(4-{3-[benzyl(pyridine-2-carbonyl)-amino]propoxy}phenyl)propionic acid methyl ester | 8.90(d, 1H), 8.55, 8.45(2×d, 1H, rotamers mixture), 7.77-7.12(ca, 17H), 6.81-6.55(ca, 4H), 4.80, 4.69(2×s, 2H, rotamers mixture), 4.39(q, 1H), 3.39, 3.76(2×t, 2H, rotamers mixture), 3.70, 3.69(2×s, 3H, rotamers mixture), 3.62, 3.58(2×t, 2H, rotamers mixture), 3.20(dd, 1H), 3.10(m, 1H), 2.15-1.97(ca, 2H) | A |
| IIa_159 | V_1 | (S)-2-(2-Benzoylphenylamino)-3-(4-{2-[benzyl(quinoline-2-carbonyl)-amino]ethoxy}phenyl)propionic acid methyl ester | rt: 9.294<br>MS[M+1]⁺: 664 | A |
| IIa_160 | V_2 | (S)-2-(2-Benzoylphenylamino)-3-(4-{3-[benzyl(quinoline-2-carbonyl)-amino]propoxy}phenyl)propionic acid methyl ester | 8.90(t, 1H), 8.21, 8.13(2×d, 1H, rotamers mixture), 8.04, 7.80(2×t, 2H, rotamers mixture), 7.73-7.25(ca, 14H), 7.18, 7.06(2×d, 2H, rotamers mixture), 6.82, 6.47(2×d, 2H, rotamers mixture), 6.70-6.55(ca, 2H), 4.86, 4.79(2×s, 2H, rotamers mixture), 4.37(q, 1H), 4.02, 3.77(2×t, 2H, rotamers mixture), 3.69-3.64(ca, 5H), 3.25-3.05(ca, 2H), 2.20-2.04(ca, 2H) | A |
| IIa_161 | V_1 | (S)-2-(2-Benzoylphenylamino)-3-(4-{2-[benzyl(quinoxaline-2-carbonyl)-amino]ethoxy}phenyl)propionic acid methyl ester | rt: 9.119<br>MS[M+1]⁺: 665 | A |
| IIa_162 | V_2 | (S)-2-(2-Benzoylphenylamino)-3-(4-{3-[benzyl(quinoxaline-2-carbonyl)-amino]propoxy}phenyl)propionic acid methyl ester | rt: 9.211<br>MS[M+1]⁺: 679 | A |
| IIa_163 | V_1 | (S)-2-(2-Benzoylphenylamino)-3-(4-{2-[benzyl(thiophene-2-carbonyl)-amino]ethoxy}phenyl)propionic acid methyl ester | rt: 9.07<br>MS[M+1]⁺: 619 | A |
| IIa_164 | V_2 | (S)-2-(2-Benzoylphenylamino)-3-(4-{3-[benzyl(thiophene-2-carbonyl)-amino]propoxy}phenyl)propionic acid methyl ester | rt: 9.193<br>MS[M+1]⁺: 633 | A |
| IIa_165 | V_1 | (S)-2-(2-Benzoylphenylamino)-3-(4-{2-[benzyl(furan-3-carbonyl)amino]-ethoxy}phenyl)propionic acid methyl ester | rt: 8.815<br>MS[M+1]⁺: 603 | A |
| IIa_166 | V_2 | (S)-2-(2-Benzoylphenylamino)-3-(4-{3-[benzyl(furan-3-carbonyl)amino]-propoxy}phenyl)propionic acid methyl ester | rt: 8.907<br>MS[M+1]⁺: 617 | A |
| IIa_167 | V_1 | (S)-2-(2-Benzoylphenylamino)-3-(4-{2-[benzyl(isoquinoline-3-carbonyl)-amino]ethoxy}phenyl)propionic acid methyl ester | rt: 9.1<br>MS[M+1]⁺: 664 | A |
| IIa_168 | V_2 | (S)-2-(2-Benzoylphenylamino)-3-(4-{3-[benzyl(isoquinoline-3-carbonyl)-amino]propoxy}phenyl)propionic acid methyl ester | 9.19, 9.10(2×s, 1H, rotamers mixture), 8.90(t, 1H), 8.07, 7.99(2×s, 1H, rotamers mixture), | A |

TABLE 5-continued

| Example Number | Starting product | Compound name | ¹H-NMR/LC-MS | HPLC Method |
|---|---|---|---|---|
| | | | 7.64-7.25(ca, 16H), 7.18, 7.05(2×d, 2H, rotamers mixture), 6.82, 6.50(2×d, 2H, rotamers mixture), 6.65-6.55(ca, 2H), 4.86, 4.76(2×s, 2H, rotamers mixture), 4.37(m, 1H), 4.02, 3.77(2×t, 2H, rotamers mixture), 3.69-3.60(ca, 5H), 3.25-3.05(ca, 2H), 2.20-2.04(ca, 2H) | |
| IIa_169 | V_1 | (S)-2-(2-Benzoylphenylamino)-3-(4-{2-benzyl(pyridine-3-carbonyl)-amino]ethoxy}phenyl)propionic acid methyl ester | 8.90(d, 1H), 8.78-8.62(ca, 2H), 7.83-7.73(m 1H), 7.59(d, 2H), 7.51-7.41(ca, 4H), 7.37-7.20(m, 9H), 6.85-6.72(ca, 2H), 6.65-6.56(ca, 2H), 4.87, 4.69(2×s, 2H, rotamers mixture), 4.40(q, 1H), 4.25-3.58(ca, 7H), 3.25(dd, 1H), 3.10(dd, 1H) | A |
| IIa_170 | V_2 | (S)-2-(2-Benzoylphenylamino)-3-(4-{3-[benzyl(pyridine-3-carbonyl)-amino]propoxy}phenyl)propionic acid methyl ester | 8.90(d, 1H), 8.67-8.59(ca, 2H), 7.67-7.10(m 16H), 6.81-6.55(ca, 4H), 4.80, 4.51(2×s, 2H, rotamers mixture), 4.39(q, 1H), 4.02-3.39(ca, 7H), 3.25(dd, 1H), 3.10(dd, 1H), 1.92-1.71(ca, 2H) | A |
| IIa_171 | V_1 | (S)-2-(2-Benzoylphenylamino)-3-{4-[2-(benzylphenylacetylamino)-ethoxy]phenyl}propionic acid methyl ester | 8.91(d, 1H), 7.59(d, 2H), 7.51-7.41(ca, 4H), 7.33-7.09(ca, 13H), 6.78-6.70(ca, 2H), 6.65-6.55(ca, 2H), 4.71, 4.67(2×s, 2H, rotamers mixture), 4.39(q, 1H), 4.14, 3.88(2×t, 2H, rotamers mixture), 3.92-3.60(ca, 7H), 3.26-3.08(ca, 2H) | A |
| IIa_172 | V_2 | (S)-2-(2-Benzoylphenylamino)-3-{4-[3-(benzylphenylacetylamino)-propoxy]phenyl}propionic acid methyl ester | rt: 9.26 MS[M+1]⁺: 641 | A |
| IIa_173 | V_1 | (S)-2-(2-Benzoylphenylamino)-3-(4-{2-[benzyl-(2-methylacryloyl)amino]-ethoxy}phenyl)propionic acid methyl ester | rt: 8.865 MS[M+1]⁺: 577 | A |
| IIa_174 | V_2 | (S)-2-(2-Benzoylphenylamino)-3-(4-{3-[benzyl-(2-methylacryloyl)amino]-propoxy}phenyl)propionic acid methyl ester | rt: 8.948 MS[M+1]⁺: 591 | A |
| IIa_175 | V_1 | (S)-2-(2-Benzoylphenylamino)-3-(4-{2-[benzyl-(3-phenylpropynoyl)-amino]ethoxy}phenyl)propionic acid methyl ester | rt: 9.367 MS[M+1]⁺: 637 | A |
| IIa_176 | V_2 | (S)-2-(2-Benzoylphenylamino)-3-(4-{3-[benzyl-(3-phenylpropynoyl)-amino]propoxy}phenyl)propionic acid methyl ester | rt: 9.454 MS[M+1]⁺: 651 | A |
| IIa_177 | V_1 | (S)-2-(2-Benzoylphenylamino)-3-(4-{2-[benzyl-(2-ethylbutyryl)amino]-ethoxy}phenyl)propionic acid methyl ester | rt: 9.45 MS[M+1]⁺: 607 | A |
| IIa_178 | V_2 | (S)-2-(2-Benzoylphenylamino)-3-(4-{3-[benzyl-(2-ethylbutyryl)amino]-propoxy}phenyl)propionic acid methyl ester | rt: 9.511 MS[M+1]⁺: 621 | A |
| IIa_179 | V_1 | (S)-2-(2-Benzoylphenylamino)-3-(4-{2-[benzyl-(3-methylbut-2-(E)-enoyl)- | rt: 9.087 MS[M+1]⁺: 591 | A |

TABLE 5-continued

| Example Number | Starting product | Compound name | ¹H-NMR/LC-MS | HPLC Method |
|---|---|---|---|---|
| | | amino]ethoxy}phenyl)propionic acid methyl ester | | |
| IIa_180 | V_2 | (S)-2-(2-Benzoylphenylamino)-3-(4-{3-[benzyl-(3-methylbut-2-(E)-enoyl)-amino]propoxy}phenyl)propionic acid methyl ester | rt: 9.187<br>MS[M+1]⁺: 605 | A |
| IIa_181 | V_1 | (S)-2-(2-Benzoylphenylamino)-3-(4-{2-[benzyl-(3-furan-2-ylacryloyl)-amino]ethoxy}phenyl)propionic acid methyl ester | rt: 9.027<br>MS[M+1]⁺: 629 | A |
| IIa_182 | V_2 | (S)-2-(2-Benzoylphenylamino)-3-(4-{3-[benzyl-(3-furan-2-ylacryloyl)-amino]propoxy}phenyl)propionic acid methyl ester | rt: 9.12<br>MS[M+1]⁺: 643 | A |
| IIa_183 | V_1 | (S)-2-(2-Benzoylphenylamino)-3-(4-{2-[benzyl-(3-thiophen-2-ylacryloyl)-amino]ethoxy}phenyl)propionic acid methyl ester | rt: 9.19<br>MS[M+1]⁺: 645 | A |
| IIa_184 | V_2 | (S)-2-(2-Benzoylphenylamino)-3-(4-{3-[benzyl-(3-thiophen-2-ylacryloyl)-amino]propoxy}phenyl)propionic acid methyl ester | rt: 9.304<br>MS[M+1]⁺: 659 | A |
| IIa_185 | V_1 | (S)-2-(2-Benzoylphenylamino)-3-(4-{2-[benzyl-(3-furan-3-yl-(E)-acryloyl)-amino]ethoxy}phenyl)propionic acid methyl ester | rt: 8.889<br>MS[M+1]⁺: 629 | A |
| IIa_186 | V_2 | (S)-2-(2-Benzoylphenylamino)-3-(4-{3-[benzyl-(3-furan-3-yl-(E)-acryloyl)-amino]propoxy}phenyl)propionic acid methyl ester | rt: 9.005<br>MS[M+1]⁺: 643 | A |
| IIa_187 | V_1 | (S)-2-(2-Benzoylphenylamino)-3-(4-{2-[benzyl-(3-pyridin-3-yl-(E)-acryloyl)amino]ethoxy}phenyl)-propionic acid methyl ester | rt: 8.097<br>MS[M+1]⁺: 640 | A |
| IIa_188 | V_2 | (S)-2-(2-Benzoylphenylamino)-3-(4-{3-[benzyl-(3-pyridin-3-yl-(E)-acryloyl)amino]propoxy}phenyl)-propionic acid methyl ester | rt: 8.245<br>MS[M+1]⁺: 654 | A |
| IIa_189 | V_1 | (S)-2-(2-Benzoylphenylamino)-3-(4-{2-[benzyl-(3-thiophen-3-yl-(E)-acryloyl)amino]ethoxy}phenyl)-propionic acid methyl ester | rt: 9.105<br>MS[M+1]⁺: 645 | A |
| IIa_190 | V_2 | (S)-2-(2-Benzoylphenylamino)-3-(4-{3-[benzyl-(3-thiophen-3-yl-(E)-acryloyl)amino]propoxy}phenyl)-propionic acid methyl ester | rt: 9.214<br>MS[M+1]⁺: 659 | A |
| IIa_191 | V_1 | (S)-2-(2-Benzoylphenylamino)-3-{4-[2-(benzylbut-2-(E)-enoylamino)-ethoxy]phenyl}propionic acid methyl ester | rt: 8.808<br>MS[M+1]⁺: 577 | A |
| IIa_192 | V_2 | (S)-2-(2-Benzoylphenylamino)-3-{4-[3-(benzylbut-2-(E)-enoylamino)-propoxy]phenyl}propionic acid methyl ester | rt: 9.336<br>MS[M+1]⁺: 607 | A |
| IIa_193 | V_1 | (S)-2-(2-Benzoylphenylamino)-3-(4-{2-[benzyl-(2-thiophen-2-ylacetyl)-amino]ethoxy}phenyl)propionic acid methyl ester | rt: 9.093<br>MS[M+1]⁺: 633 | A |
| IIa_194 | V_2 | (S)-2-(2-Benzoylphenylamino)-3-(4-{3-[benzyl-(2-thiophen-2-ylacetyl)-amino]propoxy}phenyl)propionic acid methyl ester | 8.90(d, 1H), 7.59(d, 2H), 7.50-7.43(m 4H), 7.36-7.10(m, 9H), 6.91-6.74(ca, 4H), 6.64-6.58(ca, 2H), 4.63, 4.56(2×s, 2H, rotamers mixture), 4.38(q, 1H), 3.98, 3.86(2×s, 2H, rotamers mixture), 3.92-3.85(ca, 2H), 3.69(s, 3H), 3.56, 3.47(2×t, 2H, rotamers mixture), 3.25-3.06(ca, 2H), 2.06-1.90(ca, 2H) | A |
| IIa_195 | V_1 | (S)-2-(2-Benzoylphenylamino)-3-(4-{2-[benzyl-(2-pyridin-3-ylacetyl)- | 8.90(d, 1H), 8.52-8.34(ca, 2H), 7.61-7.14(m | A |

TABLE 5-continued

| Example Number | Starting product | Compound name | ¹H-NMR/LC-MS | HPLC Method |
|---|---|---|---|---|
| | | amino]ethoxy}phenyl)propionic acid methyl ester | 16H), 6.83-6.74(ca, 2H), 6.65-6.56(ca, 2H), 4.74, 4.70(2×s, 2H, rotamers mixture), 4.40(q, 1H), 4.15, 3.98(2×t, 2H, rotamers mixture), 3.93-3.66(ca, 7H), 3.26-3.00(ca, 2H) | |
| IIa_196 | V_2 | (S)-2-(2-Benzoylphenylamino)-3-(4-{3-[benzyl-(2-pyridin-3-ylacetyl)-amino]propoxy}phenyl)propionic acid methyl ester | 8.90(d, 1H), 8.48-8.37(ca, 2H), 7.61-7.13(m 16H), 6.81-6.74(ca, 2H), 6.64-6.55(ca, 2H), 4.63, 4.57(2×s, 2H, rotamers mixture), 4.38(q, 1H), 3.92-3.88(ca, 2H), 3.78-3.65(ca, 5H), 3.58, 3.48(2×t, 2H, rotamers mixture), 3.25-3.06(ca, 2H), 2.06-1.94(ca, 2H) | A |
| IIa_197 | V_1 | (S)-2-(2-Benzoylphenylamino)-3-(4-{2-[benzyl-(2-thiophen-3-ylacetyl)-amino]ethoxy}phenyl)propionic acid methyl ester | rt: 9.076 MS[M+1]⁺: 633 | A |
| IIa_198 | V_2 | (S)-2-(2-Benzoylphenylamino)-3-(4-{3-[benzyl-(2-thiophen-3-ylacetyl)-amino]propoxy}phenyl)propionic acid methyl ester | 8.90(d, 1H), 7.59(d, 2H), 7.51-7.43(m 4H), 7.36-6.97(ca, 11H), 6.79-6.73(ca, 2H), 6.64-6.55(ca, 2H), 4.62, 4.52(2×s, 2H, rotamers mixture), 4.38(q, 1H), 3.91-3.85(ca, 2H), 3.80-3.69(ca, 5H), 3.54, 3.45(2×t, 2H, rotamers mixture), 3.25-3.12(ca, 2H), 2.05-1.89(ca, 2H) | A |
| IIa_199 | V_1 | (S)-2-(2-Benzoylphenylamino)-3-(4-{2-[benzyl-(3,3-dimethylbutyryl)-amino]ethoxy}phenyl)propionic acid methyl ester | rt: 9.502 MS[M+1]⁺: 607 | A |
| IIa_200 | V_2 | (S)-2-(2-Benzoylphenylamino)-3-(4-{3-[benzyl-(3,3-dimethylbutyryl)-amino]propoxy}phenyl)propionic acid methyl ester | rt: 9.594 MS[M+1]⁺: 621 | A |
| IIa_201 | V_1 | (S)-2-(2-Benzoylphenylamino)-3-(4-{2-[benzyl-(3-methylbutyryl)-amino]-ethoxy}phenyl)propionic acid methyl ester | rt: 9.243 MS[M+1]⁺: 593 | A |
| IIa_202 | V_2 | (S)-2-(2-Benzoylphenylamino)-3-(4-{3-[benzyl-(3-methylbutyryl)amino]-propoxy}phenyl)propionic acid methyl ester | rt: 9.324 MS[M+1]⁺: 607 | A |
| IIa_203 | V_1 | (S)-2-(2-Benzoylphenylamino)-3-(4-{2-[benzyl-(3-pyridin-3-ylpropionyl)-amino]ethoxy}phenyl)propionic acid methyl ester | 8.90(d, 1H), 8.58-8.39(ca, 2H), 7.59(d, 2H), 7.49-7.05(ca, 14H), 6.79-6.56(ca, 4H), 4.68, 4.63(2×s, 2H, rotamers mixture), 4.39(q, 1H), 4.11, 3.90(2×t, 2H, rotamers mixture), 3.75-3.57(ca, 5H), 3.21(dd, 1H), 3.10(m, 1H), 3.96, 2.95(2×t, 2H, rotamers mixture), 2.84, 2.62(2×t, 2H, rotamers mixture) | A |
| IIa_204 | V_2 | (S)-2-(2-Benzoylphenylamino)-3-(4-{3-[benzyl-(3-pyridin-3-ylpropionyl)-amino]propoxy}phenyl)propionic acid methyl ester | rt: 7.131 MS[M+1]⁺: 656 | A |

TABLE 5-continued

| Example Number | Starting product | Compound name | $^1$H-NMR/LC-MS | HPLC Method |
|---|---|---|---|---|
| IIa_205 | V_1 | (S)-2-(2-Benzoylphenylamino)-3-{4-[2-(benzylpent-4-enoylamino)-ethoxy]phenyl}propionic acid methyl ester | rt: 9.064<br>MS[M+1]$^+$: 591 | A |
| IIa_206 | V_2 | (S)-2-(2-Benzoylphenylamino)-3-{4-[3-(benzylpent-4-enoylamino)-propoxy]phenyl}propionic acid methyl ester | rt: 9.159<br>MS[M+1]$^+$: 605 | A |
| IIa_207 | V_1 | (S)-2-(2-Benzoylphenylamino)-3-(4-{2-[benzyl-(3-phenylpropionyl)-amino]ethoxy}phenyl)propionic acid methyl ester | rt: 9.368<br>MS[M+1]$^+$: 641 | A |
| IIa_208 | V_2 | (S)-2-(2-Benzoylphenylamino)-3-(4-{3-[benzyl-(3-phenylpropionyl)-amino]propoxy}phenyl)propionic acid methyl ester | 8.90(d, 1H), 7.59(d, 2H), 7.50-7.04(ca, 14H), 6.78-6.71(ca, 2H), 6.64-6.55(ca, 2H), 4.61, 4.43(2×s, 2H, rotamers mixture), 4.38(q, 1H), 3.88, 3.82(2×t, 2H, rotamers mixture), 3.69(s, 3H), 3.52, 3.36(2×t, 2H, rotamers mixture), 3.21(dd, 1H), 3.10(dd, 1H), 3.02-2.90(ca, 2H), 2.72, 2.61(2×t, 2H, rotamers mixture), 2.03, 1.88(2×t, 2H, rotamers mixture) | A |
| IIa_209 | V_1 | (S)-2-(2-Benzoylphenylamino)-3-{4-[2-(benzylcyclobutanecarbonylamino)-ethoxy]phenyl}propionic acid methyl ester | rt: 9.19<br>MS[M+1]$^+$: 591 | A |
| IIa_210 | V_2 | (S)-2-(2-Benzoylphenylamino)-3-{4-[3-(benzylcyclobutanecarbonylamino)-propoxy]phenyl}propionic acid methyl ester | rt: 9.596<br>MS[M+1]$^+$: 621 | A |
| IIa_211 | V_1 | (S)-2-(2-Benzoylphenylamino)-3-{4-[2-(benzylcyclohexanecarbonylamino)-ethoxy]phenyl}propionic acid methyl ester | rt: 9.536<br>MS[M+1]$^+$: 619 | A |
| IIa_212 | V_2 | (S)-2-(2-Benzoylphenylamino)-3-{4-[3-(benzylcyclohexanecarbonylamino)-propoxy]phenyl}propionic acid methyl ester | rt: 9.624<br>MS[M+1]$^+$: 633 | A |
| IIa_213 | V_1 | (S)-2-(2-Benzoylphenylamino)-3-(4-{2-[benzyl-(3-cyclohexylpropionyl)-amino]ethoxy}phenyl)propionic acid methyl ester | rt: 10.056<br>MS[M+1]$^+$: 647 | A |
| IIa_214 | V_2 | (S)-2-(2-Benzoylphenylamino)-3-(4-{3-[benzyl-(3-cyclohexylpropionyl)-amino]propoxy}phenyl)propionic acid methyl ester | 8.90(d, 1H), 7.59(d, 2H), 7.51-7.41(ca, 4H), 7.31-7.13(ca, 8H), 6.78(d, 2H), 6.64-6.55(ca, 2H), 4.60, 4.52(2×s, 2H, rotamers mixture), 4.38(q, 1H), 3.93-3.86(ca, 2H), 3.69(s, 3H), 3.52, 3.42(2×t, 2H, rotamers mixture), 3.25-3.08(ca, 2H), 2.43-2.29(ca, 2H), 2.04-1.92(ca, 2H), 1.69-1.48(ca, 13H) | A |
| IIa_215 | V_1 | (S)-2-(2-Benzoylphenylamino)-3-(4-{2-[benzyl-(2-cyclohexylacetyl)-amino]ethoxy}phenyl)propionic acid methyl ester | rt: 9.828<br>MS[M+1]$^+$: 633 | A |
| IIa_216 | V_2 | (S)-2-(2-Benzoylphenylamino)-3-(4-{3-[benzyl-(2-cyclohexylacetyl)- | 8.90(d, 1H), 7.59(d, 2H), 7.51-7.41(ca, | A |

TABLE 5-continued

| Example Number | Starting product | Compound name | $^1$H-NMR/LC-MS | HPLC Method |
|---|---|---|---|---|
| | | amino]propoxy}phenyl)propionic acid methyl ester | 4H), 7.33-7.12(ca, 8H), 6.77(d, 2H), 6.64-6.55(ca, 2H), 4.61, 4.53(2×s, 2H, rotamers mixture), 4.38(q, 1H), 3.93-3.85(ca, 2H), 3.69(s, 3H), 3.51, 3.44(2×t, 2H, rotamers mixture), 3.25-3.08(ca, 2H), 2.26, 2.18(2×d, 2H, rotamers mixture), 2.04-1.92(ca, 3H), 1.80-1.64(ca, 10H) | |
| IIa_217 | V_1 | (S)-2-(2-Benzoylphenylamino)-3-{4-[2-(benzylcyclopentanecarbonylamino)-ethoxy]phenyl}propionic acid methyl ester | 8.90(d, 1H), 7.59(d, 2H), 7.51-7.44(ca, 4H), 7.36-7.14(ca, 8H), 6.79-6.73(ca, 2H), 6.64-6.55(ca, 2H), 4.75, 4.69(2×s, 2H, rotamers mixture), 4.38(q, 1H), 4.11, 3.96(2×t, 2H, rotamers mixture), 3.75-3.65(ca, 5H), 3.24-3.08(ca, 2H), 2.75(m, 1H), 1.87-1.74(ca, 8H) | A |
| IIa_218 | V_2 | (S)-2-(2-Benzoylphenylamino)-3-{4-[3-(benzylcyclopentanecarbonylamino)-propoxy]phenyl}propionic acid methyl ester | 8.90(d, 1H), 7.59(d, 2H), 7.51-7.41(ca, 4H), 7.33-7.13(ca, 8H), 6.77(d, 2H), 6.64-6.55(ca, 2H), 4.61, 4.59(2×s, 2H, rotamers mixture), 4.38(q, 1H), 3.93-3.87(ca, 2H), 3.69(s, 3H), 3.53-3.44(ca, 2H), 3.25-3.10(ca, 2H), 2.75(m, 1H), 1.99-1.74(ca, 10H) | A |
| IIa_219 | V_1 | (S)-2-(2-Benzoylphenylamino)-3-(4-{2-[benzyl-(3-cyclopentylpropionyl)-amino]ethoxy}phenyl)propionic acid methyl ester | rt: 9.814 MS[M+1]$^+$: 633 | A |
| IIa_220 | V_2 | (S)-2-(2-Benzoylphenylamino)-3-(4-{3-[benzyl-(3-cyclopentylpropionyl)-amino]propoxy}phenyl)propionic acid methyl ester | rt: 9.246 MS[M+1]$^+$: 605 | A |
| IIa_221 | V_1 | (S)-2-(2-Benzoylphenylamino)-3-{4-[2-(benzylcyclopropanecarbonylamino)-ethoxy]phenyl}propionic acid methyl ester | rt: 8.885 MS[M+1]$^+$: 577 | A |
| IIa_222 | V_2 | (S)-2-(2-Benzoylphenylamino)-3-{4-[3-(benzylcyclopropanecarbonylamino)-propoxy]phenyl}propionic acid methyl ester | rt: 8.969 MS[M+1]$^+$: 591 | A |
| IIa_223 | V_1 | (S)-2-(2-Benzoylphenylamino)-3-{4-[2-(benzylpropionylamino)ethoxy]-phenyl}propionic acid methyl ester | rt: 8.784 MS[M+1]$^+$: 565 | A |
| IIa_224 | V_2 | (S)-2-(2-Benzoylphenylamino)-3-{4-[3-(benzylpropionylamino)propoxy]-phenyl}propionic acid methyl ester | rt: 8.858 MS[M+1]$^+$: 579 | A |
| IIa_225 | V_1 | (S)-2-(2-Benzoylphenylamino)-3-{4-[2-(benzylisobutyrylamino)ethoxy]-phenyl}propionic acid methyl ester | rt: 9.02 MS[M+1]$^+$: 579 | A |
| IIa_226 | V_2 | (S)-2-(2-Benzoylphenylamino)-3-{4-[3-(benzylisobutyrylamino)propoxy]-phenyl}propionic acid methyl ester | rt: 9.091 MS[M+1]$^+$: 593 | A |
| IIa_227 | V_1 | (S)-2-(2-Benzoylphenylamino)-3-{4-[2-(benzylhexanoylamino)ethoxy]-phenyl}propionic acid methyl ester | rt: 9.511 MS[M+1]$^+$: 607 | A |

TABLE 5-continued

| Example Number | Starting product | Compound name | ¹H-NMR/LC-MS | HPLC Method |
|---|---|---|---|---|
| IIa_228 | V_2 | (S)-2-(2-Benzoylphenylamino)-3-{4-[3-(benzylhexanoylamino)propoxy]phenyl}propionic acid methyl ester | rt: 9.108<br>MS[M+]⁺: 593 | A |
| IIa_229 | V_1 | (S)-2-(2-Benzoylphenylamino)-3-{4-[2-(benzylpentanoylamino)ethoxy]phenyl}propionic acid methyl ester | rt: 9.261<br>MS[M+1]⁺: 593 | A |
| IIa_230 | V_2 | (S)-2-(2-Benzoylphenylamino)-3-{4-[3-(benzylpentanoylamino)propoxy]phenyl}propionic acid methyl ester | rt: 9.337<br>MS[M+1]⁺: 607 | A |
| IIa_231 | V_1 | (S)-2-(2-Benzoylphenylamino)-3-{4-[2-(benzyloctanoylamino)ethoxy]phenyl}propionic acid methyl ester | rt: 10.027<br>MS[M+1]⁺: 635 | A |
| IIa_232 | V_2 | (S)-2-(2-Benzoylphenylamino)-3-{4-[3-(benzyloctanoylamino)propoxy]phenyl}propionic acid methyl ester | rt: 10.092<br>MS[M+1]⁺: 649 | A |
| IIa_233 | V_1 | (S)-2-(2-Benzoylphenylamino)-3-{4-[2-(benzylheptanoylamino)ethoxy]phenyl}propionic acid methyl ester | rt: 9.763<br>MS[M+1]⁺: 621 | A |
| IIa_234 | V_2 | (S)-2-(2-Benzoylphenylamino)-3-{4-[3-(benzylheptanoylamino)propoxy]phenyl}propionic acid methyl ester | rt: 9.829<br>MS[M+1]⁺: 635 | A |
| IIa_235 | V_1 | (S)-2-(2-Benzoylphenylamino)-3-{4-[2-(benzylnonanoylamino)ethoxy]phenyl}propionic acid methyl ester | rt: 10.341<br>MS[M+1]⁺: 649 | A |
| IIa_236 | V_2 | (S)-2-(2-Benzoylphenylamino)-3-{4-[3-(benzylnonanoylamino)propoxy]phenyl}propionic acid methyl ester | rt: 10.403<br>MS[M+1]⁺: 663 | A |
| IIa_237 | V_1 | (S)-2-(2-Benzoylphenylamino)-3-{4-[2-(benzylbutyrylamino)ethoxy]phenyl}propionic acid methyl ester | rt: 9.045<br>MS[M+1]⁺: 579 | A |
| IIa_238 | V_2 | (S)-2-(2-Benzoylphenylamino)-3-{4-[3-(benzylbutyrylamino)propoxy]phenyl}propionic acid methyl ester | rt: 9.873<br>MS[M+1]⁺: 647 | A |
| IIa_239 | V_1 | (S)-3-{4-[2-(Benzoylbenzylamino)ethoxy]phenyl}-2-(2-benzoylphenylamino)propionic acid methyl ester | 8.90(d, 1H), 7.59(d, 2H), 7.51-7.15(ca, 17H), 6.85-6.56(ca, 4H), 4.87, 4.67(2×s, 2H, rotamers mixture), 4.39(q, 1H), 4.24-3.56(ca, 7H), 3.25-3.08(ca, 2H) | A |
| IIa_240 | V_2 | (S)-3-{4-[3-(Benzoylbenzylamino)propoxy]phenyl}-2-(2-benzoylphenylamino)propionic acid methyl ester | 8.90(bs, 1H), 7.59(d, 2H), 7.51-7.14(ca, 17H), 6.83-6.55(ca, 4H), 4.80, 4.51(2×s, 2H, rotamers mixture), 4.38(m, 1H), 4.00-3.38(ca, 7H), 3.23(dd, 1H), 3.11(dd, 1H) | A |
| IIa_241 | V_1 | (S)-2-(2-Benzoylphenylamino)-3-(4-{2-[benzyl-(3-phenylacryloyl)amino]ethoxy}phenyl)propionic acid methyl ester | 8.90(d, 1H), 7.77(m, 1H), 7.59(d, 2H), 7.50-7.05(ca, 18H), 6.85-6.73(ca, 2H), 6.64-6.55(ca, 2H), 4.86, 4.81(2×s, 2H, rotamers mixture), 4.38(q, 1H), 4.20, 4.03(2×t, 2H, rotamers mixture), 3.85-3.68(ca, 5H), 3.23-3.08(ca, 2H) | A |
| IIa_242 | V_2 | (S)-2-(2-Benzoylphenylamino)-3-(4-{3-[benzyl-(3-phenylactyloyl)amino]propoxy}phenyl)propionic acid methyl ester | 8.91(d, 1H), 7.75(m, 1H), 7.59-7.16(ca, 19H), 7.03-6.79(ca, 2H), 6.64-6.55(ca, 2H), 4.73, 4.69(2×s, 2H, rotamers mixture), 4.38(q, 1H), 3.98-3.91(ca, 2H), 3.69-3.59(ca, 5H), 3.23-3.08(ca, 2H), 2.12-2.01(ca, 2H) | A |
| IIa_243 | V_1 | (S)-2-(2-Benzoylphenylamino)-3-(4-{2-[benzyl-(2,2-dimethylpropionyl)amino]ethoxy}phenyl)propionic acid methyl ester | rt: 9.363<br>MS[M+1]⁺: 593 | A |

TABLE 5-continued

| Example Number | Starting product | Compound name | $^1$H-NMR/LC-MS | HPLC Method |
|---|---|---|---|---|
| IIa_244 | V_2 | (S)-2-(2-Benzoylphenylamino)-3-(4-{3-[benzyl-(2,2-dimethylpropionyl)-amino]propoxy}phenyl)propionic acid methyl ester | rt: 9.411<br>MS[M+1]$^+$: 607 | A |
| IIa_245 | V_3 | (S)-2-(2-Benzoylphenylamino)-3-(4-{2-[cyclohexyl-(3-furan-2-ylacryloyl)-amino]ethoxy}phenyl)propionic acid methyl ester | rt: 9.408<br>MS[M+1]$^+$: 621 | A |
| IIa_246 | V_3 | (S)-2-(2-Benzoylphenylamino)-3-{4-[2-(cyclobutanecarbonylcyclohexylamino)ethoxy]phenyl}propionic acid methyl ester | rt: 9.655<br>MS[M+1]$^+$: 583 | A |
| IIa_247 | V_3 | (S)-2-(2-Benzoylphenylamino)-3-(4-{2-[cyclohexyl-(3-cyclopentylpropionyl)amino]ethoxy}-phenyl)propionic acid methyl ester | rt: 10.336<br>MS[M+1]$^+$: 625 | A |
| IIa_248 | V_3 | (S)-2-(2-Benzoylphenylamino)-3-{4-[2-(butyrylcyclohexylamino)ethoxy]-phenyl}propionic acid methyl ester | rt: 9.459<br>MS[M+1]$^+$: 571 | A |
| IIa_249 | V_5 | (S)-2-(2-Benzoylphenylamino)-3-(4-{2-[cyclopropylmethyl(naphthalene-2-carbonyl)amino]ethoxy}phenyl)-propionic acid methyl ester | rt: 9.272<br>MS[M+1]$^+$: 627 | A |
| IIa_250 | V_6 | (S)-2-(2-Benzoylphenylamino)-3-(4-{3-[cyclopropylmethyl(naphthalene-2-carbonyl)amino]propoxy}phenyl)-propionic acid methyl ester | rt: 9.351<br>MS[M+1]$^+$: 641 | A |
| IIa_251 | V_5 | (S)-2-(2-Benzoylphenylamino)-3-(4-{2-[cyclopropylmethyl(quinoline-2-carbonyl)amino]ethoxy}phenyl)-propionic acid methyl ester | rt: 9.005<br>MS[M+1]$^+$: 628 | A |
| IIa_252 | V_6 | (S)-2-(2-Benzoylphenylamino)-3-(4-{3-[cyclopropylmethyl(quinoline-2-carbonyl)amino]propoxy}phenyl)-propionic acid methyl ester | rt: 9.065<br>MS[M+1]$^+$: 642 | A |
| IIa_253 | V_5 | (S)-2-(2-Benzoylphenylamino)-3-(4-{2-[cyclopropylmethyl(quinoxaline-2-carbonyl)amino]ethoxy}phenyl)-propionic acid methyl ester | rt: 8.896<br>MS[M+1]$^+$: 629 | A |
| IIa_254 | V_6 | (S)-2-(2-Benzoylphenylamino)-3-(4-{3-[cyclopropylmethyl(quinoxaline-2-carbonyl)amino]propoxy}phenyl)-propionic acid methyl ester | rt: 9.003<br>MS[M+1]$^+$: 643 | A |
| IIa_255 | V_5 | (S)-2-(2-Benzoylphenylamino)-3-(4-{2-[cyclopropylmethyl(thiophene-2-carbonyl)amino]ethoxy}phenyl)-propionic acid methyl ester | rt: 8.871<br>MS[M+1]$^+$: 583 | A |
| IIa_256 | V_6 | (S)-2-(2-Benzoylphenylamino)-3-(4-{3-[cyclopropylmethyl(thiophene-2-carbonyl)amino]propoxy}phenyl)-propionic acid methyl ester | rt: 9.976<br>MS[M+1]$^+$: 597 | A |
| IIa_257 | V_5 | (S)-2-(2-Benzoylphenylamino)-3-(4-{2-[cyclopropylmethyl(pyridine-3-carbonyl)amino]ethoxy}phenyl)-propionic acid methyl ester | rt: 7.92<br>MS[M+1]$^+$: 578 | A |
| IIa_258 | V_6 | (S)-2-(2-Benzoylphenylamino)-3-(4-{3-[cyclopropylmethyl(pyridine-3-carbonyl)amino]propoxy}phenyl)-propionic acid methyl ester | rt: 8.062<br>MS[M+1]$^+$: 592 | A |
| IIa_259 | V_5 | (S)-2-(2-Benzoylphenylamino)-3-{4-[2-(cyclopropylmethylphenylacetylamino)ethoxy]phenyl}propionic acid methyl ester | rt: 8.958<br>MS[M+1]$^+$: 591 | A |
| IIa_260 | V_6 | (S)-2-(2-Benzoylphenylamino)-3-{4-[3-(cyclopropylmethylphenylacetylamino)propoxy]phenyl}propionic acid methyl ester | rt: 9.053<br>MS[M+1]$^+$: 605 | A |
| IIa_261 | V_5 | (S)-2-(2-Benzoylphenylamino)-3-(4-{2-[cyclopropylmethyl-(3-furan-2-ylacryloyl)amino]ethoxy}phenyl)-propionic acid methyl ester | rt: 8.833<br>MS[M+1]$^+$: 593 | A |
| IIa_262 | V_6 | (S)-2-(2-Benzoylphenylamino)-3-(4-{3-[cyclopropylmethyl-(3-furan-2- | rt: 8.934<br>MS[M+1]$^+$: 607 | A |

TABLE 5-continued

| Example Number | Starting product | Compound name | $^1$H-NMR/LC-MS | HPLC Method |
|---|---|---|---|---|
| | | ylacryloyl)amino]propoxy}phenyl)-propionic acid methyl ester | | |
| IIa_263 | V_5 | (S)-2-(2-Benzoylphenylamino)-3-(4-{2-[cyclopropylmethyl-(3-thiophen-2-ylacryloyl)amino]ethoxy}phenyl)-propionic acid methyl ester | rt: 9.003<br>MS[M+1]$^+$: 609 | A |
| IIa_264 | V_6 | (S)-2-(2-Benzoylphenylamino)-3-(4-{3-[cyclopropylmethyl-(3-thiophen-2-ylacryloyl)amino]propoxy}phenyl)-propionic acid methyl ester | rt: 9.11<br>MS[M+1]$^+$: 623 | A |
| IIa_265 | V_5 | (S)-2-(2-Benzoylphenylamino)-3-(4-{2-[cyclopropylmethyl-(2-thiophen-2-ylacetyl)amino]ethoxy}phenyl)-propionic acid methyl ester | rt: 8.864<br>MS[M+1]$^+$: 597 | A |
| IIa_266 | V_6 | (S)-2-(2-Benzoylphenylamino)-3-(4-{3-[cyclopropylmethyl-(2-thiophen-2-ylacetyl)amino]propoxy}phenyl)-propionic acid methyl ester | rt: 8.96<br>MS[M+1]$^+$: 611 | A |
| IIa_267 | V_5 | (S)-2-(2-Benzoylphenylamino)-3-(4-{2-[cyclopropylmethyl-(2-thiophen-3-ylacetyl)amino]ethoxy}phenyl)-propionic acid methyl ester | rt: 8.836<br>MS[M+1]$^+$: 597 | A |
| IIa_268 | V_6 | (S)-2-(2-Benzoylphenylamino)-3-(4-{3-[cyclopropylmethyl-(2-thiophen-3-ylacetyl)amino]propoxy}phenyl)-propionic acid methyl ester | rt: 8.929<br>MS[M+1]$^+$: 611 | A |
| IIa_269 | V_5 | (S)-2-(2-Benzoylphenylamino)-3-(4-{2-[cyclopropylmethyl-(3-pyridin-3-ylpropionyl)amino]ethoxy}phenyl)-propionic acid methyl ester | rt: 6.894<br>MS[M+1]$^+$: 606 | A |
| IIa_270 | V_6 | (S)-2-(2-Benzoylphenylamino)-3-(4-{3-[cyclopropylmethyl-(3-pyridin-3-ylpropionyl)amino]propoxy}phenyl)-propionic acid methyl ester | rt: 6.961<br>MS[M+1]$^+$: 620 | A |
| IIa_271 | V_5 | (S)-2-(2-Benzoylphenylamino)-3-(4-{2-[cyclopropylmethyl-(3-phenylpropionyl)amino]ethoxy}-phenyl)propionic acid methyl ester | rt: 9.169<br>MS[M+1]$^+$: 605 | A |
| IIa_272 | V_6 | (S)-2-(2-Benzoylphenylamino)-3-(4-{3-[cyclopropylmethyl-(3-phenylpropionyl)amino]propoxy}-phenyl)propionic acid methyl ester | rt: 9.244<br>MS[M+1]$^+$: 619 | A |
| IIa_273 | V_5 | (S)-2-(2-Benzoylphenylamino)-3-{4-[2-(cyclobutanecarbonylcyclopropylmethylamino)ethoxy]phenyl}propionic acid methyl ester | rt: 8.977<br>MS[M+1]$^+$: 555 | A |
| IIa_274 | V_6 | (S)-2-(2-Benzoylphenylamino)-3-{4-[3-(cyclobutanecarbonylcyclopropylmethylamino)propoxy]phenyl}propionic acid methyl ester | rt: 9.059<br>MS[M+1]$^+$: 569 | A |
| IIa_275 | V_5 | (S)-2-(2-Benzoylphenylamino)-3-(4-{2-[(2-cyclohexylacetyl)-cyclopropylmethylamino]ethoxy}-phenyl)propionic acid methyl ester | rt: 9.641<br>MS[M+1]$^+$: 597 | A |
| IIa_276 | V_6 | (S)-2-(2-Benzoylphenylamino)-3-(4-{3-[(2-cyclohexylacetyl)-cyclopropylmethylamino]propoxy}-phenyl)propionic acid methyl ester | rt: 9.707<br>MS[M+1]$^+$: 611 | A |
| IIa_277 | V_5 | (S)-2-(2-Benzoylphenylamino)-3-{4-[2-(cyclopentanecarbonylcyclopropylmethylamino)ethoxy]phenyl}propionic acid methyl ester | rt: 9.201<br>MS[M+1]$^+$: 569 | A |
| IIa_278 | V_6 | (S)-2-(2-Benzoylphenylamino)-3-{4-[3-(cyclopentanecarbonylcyclopropylmethylamino)propoxy]phenyl}propionic acid methyl ester | rt: 9.285<br>MS[M+1]$^+$: 583 | A |
| IIa_279 | V_5 | (S)-2-(2-Benzoylphenylamino)-3-{4-[2-(cyclopropanecarbonylcyclopropylmethylamino)ethoxy]phenyl}propaonic acid methyl ester | rt: 8.641<br>MS[M+1]$^+$: 541 | A |

TABLE 5-continued

| Example Number | Starting product | Compound name | $^1$H-NMR/LC-MS | HPLC Method |
|---|---|---|---|---|
| IIa_280 | V_6 | (S)-2-(2-Benzoylphenylamino)-3-{4-[3-(cyclopropanecarbonylcyclopropylmethylamino)propoxy]phenyl}propaonic acid methyl ester | rt: 8.747<br>MS[M+1]$^+$: 555 | A |
| IIa_281 | V_5 | (S)-2-(2-Benzoylphenylamino)-3-{4-[2-(cyclopropylmethylpropionylamino)-ethoxy]phenyl}propionic acid methyl ester | rt: 8.525<br>MS[M+1]$^+$: 529 | A |
| IIa_282 | V_6 | (S)-2-(2-Benzoylphenylamino)-3-{4-[3-(cyclopropylmethylpropionylamino)-propoxy]phenyl}propionic acid methyl ester | rt: 8.626<br>MS[M+1]$^+$: 543 | A |
| IIa_283 | V_5 | (S)-2-(2-Benzoylphenylamino)-3-{4-[2-(cyclopropylmethylisobutyrylamino)-ethoxy]phenyh}propionic acid methyl ester | rt: 8.791<br>MS[M+1]$^+$: 543 | A |
| IIa_284 | V_6 | (S)-2-(2-Benzoylphenylamino)-3-{4-[3(cyclopropylmethylisobutyrylamino)-propoxy]phenyl}propionic acid methyl ester | rt: 8.895<br>MS[M+1]$^+$: 557 | A |
| IIa_285 | V_5 | (S)-2-(2-Benzoylphenylamino)-3-{4-[2-(butyrylcyclopropylmethylamino)-ethoxy]phenyl}propionic acid methyl ester | rt: 8.813<br>MS[M+1]$^+$: 543 | A |
| IIa_286 | V_6 | (S)-2-(2-Benzoylphenylamino)-3-{4-[3-(butyrylcyclopropylmethylamino)-propoxy]phenyl}propionic acid methyl ester | rt: 8.903<br>MS[M+1]$^+$: 557 | A |
| IIa_287 | V_5 | (S)-3-{4-[2-(Benzoylcyclopropylmethylamino)-ethoxy]phenyl}-2-(2-benzoylphenylamino)propionic acid methyl ester | rt: 8.858<br>MS[M+1]$^+$: 577 | A |
| IIa_288 | V_6 | (S)-3-{4-[3-(Benzoylcyclopropylmethylamino)-propoxy]phenyl}-2-(2-benzoylphenylamino)propionic acid methyl ester | rt: 8.958<br>MS[M+1]$^+$: 591 | A |
| IIa_289 | V_5 | (S)-2-(2-Benzoylphenylamino)-3-(4-{2-[cyclopropylmethyl-(3-phenylacryloyl)amino]ethoxy}-phenyl)propionic acid methyl ester | rt: 9.085<br>MS[M+1]$^+$: 602 | A |
| IIa_290 | V_6 | (S)-2-(2-Benzoylphenylamino)-3-(4-{3-[cyclopropylmethyl-(3-phenylacryloyl)amino]propoxy}-phenyl)propionic acid methyl ester | rt: 9.182<br>MS[M+1]$^+$: 617 | A |
| IIa_291 | V_9 | (S)-2-(2-Benzoylphenylamino)-3-(4-{2-[(naphthalene-1-carbonyl)-phenylamino]ethoxy}phenyl)-propionic acid methyl ester | rt: 9.13<br>MS[M+1]$^+$: 649 | A |
| IIa_292 | V_10 | (S)-2-(2-Benzoylphenylamino)-3-(4-{3-[(naphthalene-1-carbonyl)-phenylamino]propoxy}phenyl)-propionic acid methyl ester | rt: 9.283<br>MS[M+1]$^+$: 663 | A |
| IIa_293 | V_9 | (S)-2-(2-Benzoylphenylamino)-3-(4-{2-[(naphthalene-2-carbonyl)-phenylamino]ethoxy}phenyl)-propionic acid methyl ester | rt: 9.315<br>MS[M+1]$^+$: 649 | A |
| IIa_294 | V_10 | (S)-2-(2-Benzoylphenylamino)-3-(4-{3-[(naphthalene-2-carbonyl)-phenylamino]propoxy}phenyl)-propionic acid methyl ester | rt: 9.429<br>MS[M+1]$^+$: 663 | A |
| IIa_295 | V_9 | (S)-2-(2-Benzoylphenylamino)-3-(4-{2-[phenyl(quinoline-2-carbonyl)-amino]ethoxy}phenyl)propionic acid methyl ester | rt: 8.904<br>MS[M+1]$^+$: 650 | A |
| IIa_296 | V_10 | (S)-2-(2-Benzoylphenylamino)-3-(4-{3-[phenyl(quinoline-2-carbonyl)-amino]propoxy}phenyl)propionic acid methyl ester | rt: 9.023<br>MS[M+1]$^+$: 664 | A |

TABLE 5-continued

| Example Number | Starting product | Compound name | ¹H-NMR/LC-MS | HPLC Method |
|---|---|---|---|---|
| IIa_297 | V_9 | (S)-2-(2-Benzoylphenylamino)-3-(4-{2-[phenyl(quinoxaline-2-carbonyl)-amino]ethoxy}phenyl)propionic acid methyl ester | rt: 8.817<br>MS[M+1]⁺: 651 | A |
| IIa_298 | V_10 | (S)-2-(2-Benzoylphenylamino)-3-(4-{3-[phenyl(quinoxaline-2-carbonyl)-amino]propoxy}phenyl)propionic acid methyl ester | rt: 8.976<br>MS[M+1]⁺: 665 | A |
| IIa_299 | V_9 | (S)-2-(2-Benzoylphenylamino)-3-(4-{2-[phenyl(thiophene-2-carbonyl)-amino]ethoxy}phenyl)propionic acid methyl ester | rt: 9.049<br>MS[M+1]⁺: 605 | A |
| IIa_300 | V_10 | (S)-2-(2-Benzoylphenylamino)-3-(4-{3-[phenyl(thiophene-2-carbonyl)-amino]propoxy}phenyl)propionic acid methyl ester | rt: 9.155<br>MS[M+1]⁺: 619 | A |
| IIa_301 | V_9 | (S)-2-(2-Benzoylphenylamino)-3-(4-{2-[(isoquinoline-3-carbonyl)-phenylamino]ethoxy}phenyl)-propionic acid methyl ester | rt: 8.746<br>MS[M+1]⁺: 650 | A |
| IIa_302 | V_9 | (S)-2-(2-Benzoylphenylamino)-3-(4-{2-[phenyl(pyridine-3-carbonyl)-amino]ethoxy}phenyl)propionic acid methyl ester | rt: 8.086<br>MS[M+1]⁺: 600 | A |
| IIa_303 | V_10 | (S)-2-(2-Benzoylphenylamino)-3-(4-{3-[phenyl(pyridine-3-carbonyl)-amino]propoxy}phenyl)propionic acid methyl ester | rt: 8.264<br>MS[M+1]⁺: 614 | A |
| IIa_304 | V_9 | (S)-2-(2-Benzoylphenylamino)-3-(4-{2-[phenyl(pyridine-4-carbonyl)-amino]ethoxy}phenyl)propionic acid methyl ester | rt: 7.934<br>MS[M+1]⁺: 600 | A |
| IIa_305 | V_10 | (S)-2-(2-Benzoylphenylamino)-3-(4-{3-[phenyl(pyridine-4-carbonyl)-amino]propoxy}phenyl)propionic acid methyl ester | rt: 8.124<br>MS[M+1]⁺: 614 | A |
| IIa_306 | V_9 | (S)-2-(2-Benzoylphenylamino)-3-{4-[2-(phenylphenylacetylamino)-ethoxy]phenyl}propionic acid methyl ester | rt: 9.22<br>MS[M+1]⁺: 613 | A |
| IIa_307 | V_10 | (S)-2-(2-Benzoylphenylamino)-3-{4-[3-(phenylphenylacetylamino)-propoxy]phenyl}propionic acid methyl ester | rt: 9.363<br>MS[M+1]⁺: 627 | A |
| IIa_308 | V_9 | (S)-2-(2-Benzoylphenylamino)-3-(4-{2-[(2-methylacryloyl)phenylamino]-ethoxy}phenyl)propionic acid methyl ester | rt: 8.799<br>MS[M+1]⁺: 563 | A |
| IIa_309 | V_10 | (S)-2-(2-Benzoylphenylamino)-3-(4-{3-[(2-methylacryloyl)phenylamino]-propoxy}phenyl)propionic acid methyl ester | rt: 8.943<br>MS[M+1]⁺: 577 | A |
| IIa_310 | V_9 | (S)-2-(2-Benzoylphenylamino)-3-(4-{2-[phenyl-(3-phenylpropynoyl)-amino]ethoxy}phenyl)propionic acid methyl ester | rt: 9.245<br>MS[M+1]⁺: 615 | A |
| IIa_311 | V_9 | (S)-2-(2-Benzoylphenylamino)-3-(4-{2-[(2-ethylbutyryl)phenylamino]-ethoxy}phenyl)propionic acid methyl ester | rt: 9.5<br>MS[M+1]⁺: 593 | A |
| IIa_312 | V_10 | (S)-2-(2-Benzoylphenylamino)-3-(4-{3-[(2-ethylbutyryl)phenylamino]-propoxy}phenyl)propionic acid methyl ester | rt: 9.628<br>MS[M+1]⁺: 607 | A |
| IIa_313 | V_9 | (S)-2-(2-Benzoylphenylamino)-3-(4-{2-[(3-furan-2-ylacryloyl)-phenylamino]ethoxy}phenyl)-propionic acid methyl ester | rt: 9.025<br>MS[M+1]⁺: 615 | A |
| IIa_314 | V_10 | (S)-2-(2-Benzoylphenylamino)-3-(4-{3-[(3-furan-2-ylacryloyl)-phenylamino]propoxy}phenyl)-propionic acid methyl ester | rt: 9.164<br>MS[M+1]⁺: 629 | A |
| IIa_315 | V_9 | (S)-2-(2-Benzoylphenylamino)-3-(4-{2-[phenyl-(3-thiophen-2-ylacryloyl)-amino]ethoxy}phenyl)propionic acid methyl ester | rt: 9.267<br>MS[M+1]⁺: 631 | A |

TABLE 5-continued

| Example Number | Starting product | Compound name | ¹H-NMR/LC-MS | HPLC Method |
|---|---|---|---|---|
| IIa_316 | V_10 | (S)-2-(2-Benzoylphenylamino)-3-(4-{3-[phenyl-(3-thiophen-2-ylacryloyl)-amino]propoxy}phenyl)propionic acid methyl ester | rt: 9.394<br>MS[M+1]⁺: 645 | A |
| IIa_317 | V_9 | (S)-2-(2-Benzoylphenylamino)-3-(4-{2-[(3-furan-3-yl-(E)-acryloyl)-phenylamino]ethoxy}phenyl)-propionic acid methyl ester | rt: 8.954<br>MS[M+1]⁺: 615 | A |
| IIa_318 | V_10 | (S)-2-(2-Benzoylphenylamino)-3-(4-{3-[(3-furan-3-yl-(E)-acryloyl)-phenylamino]propoxy}-phenyl)-propionic acid methyl ester | rt: 9.091<br>MS[M+1]⁺: 629 | A |
| IIa_319 | V_9 | (S)-2-(2-Benzoylphenylamino)-3-(4-{2-[phenyl-(3-pyridin-3-yl-(E)-acryloyl)amino]ethoxy}phenyl)-propionic acid methyl ester | rt: 8.103<br>MS[M+1]⁺: 626 | A |
| IIa_320 | V_10 | (S)-2-(2-Benzoylphenylamino)-3-(4-{3-[phenyl-(3-pyridin-3-yl-(E)-acryloyl)amino]propoxy}phenyl)-propionic acid methyl ester | rt: 8.293<br>MS[M+1]⁺: 640 | A |
| IIa_321 | V_9 | (S)-2-(2-Benzoylphenylamino)-3-(4-{2-[phenyl-(3-thiophen-3-yl-(E)-acryloyl)amino]ethoxy}phenyl)-propionic acid methyl ester | rt: 9.213<br>MS[M+1]⁺: 631 | A |
| IIa_322 | V_10 | (S)-2-(2-Benzoylphenylamino)-3-(4-{3-[phenyl-(3-thiophen-3-yl-(E)-acryloyl)amino]propoxy}phenyl)-propionic acid methyl ester | rt: 9.334<br>MS[M+1]⁺: 645 | A |
| IIa_323 | V_10 | (S)-2-(2-Benzoylphenylamino)-3-{4-[3-(but-2-(E)-enoylphenylamino)-propoxy]phenyl}propionic acid methyl ester | rt: 9<br>MS[M+1]⁺: 577 | A |
| IIa_324 | V_9 | (S)-2-(2-Benzoylphenylamino)-3-(4-{2-[phenyl-(2-thiophen-2-ylacetyl)-amino]ethoxy}phenyl)propionic acid methyl ester | rt: 9.132<br>MS[M+1]⁺: 619 | A |
| IIa_325 | V_10 | (S)-2-(2-Benzoylphenylamino)-3-(4-{3-[phenyl-(2-thiophen-2-ylacetyl)-amino]propoxy}phenyl)propionic acid methyl ester | rt: 9.295<br>MS[M+1]⁺: 633 | A |
| IIa_326 | V_10 | (S)-2-(2-Benzoylphenylamino)-3-(4-{3-[phenyl-(2-thiophen-3-ylacetyl)-amino]propoxy}phenyl)propionic acid methyl ester | rt: 9.23<br>MS[M+1]⁺: 633 | A |
| IIa_327 | V_9 | (S)-2-(2-Benzoylphenylamino)-3-(4-{2-[(3,3-dimethylbutyryl)-phenylamino]ethoxy}phenyl)-propionic acid methyl ester | rt: 9.587<br>MS[M+1]⁺: 593 | A |
| IIa_328 | V_10 | (S)-2-(2-Benzoylphenylamino)-3-(4-{3[(3,3-dimethylbutryl)-phenylamino]propoxy}phenyl)-propionic acid methyl ester | rt: 9.706<br>MS[M+1]⁺: 607 | A |
| IIa_329 | V_9 | (S)-2-(2-Benzoylphenylamino)-3-(4-{2-[(3-methylbutyryl)phenylamino]-ethoxy}phenyl)propionic acid methyl ester | rt: 9.271<br>MS[M+1]⁺: 579 | A |
| IIa_330 | V_10 | (S)-2-(2-Benzoylphenylamino)-3-(4-{3-[(3-methylbutyryl)phenylamino]-propoxy}phenyl)propionic acid methyl ester | rt: 9.401<br>MS[M+1]⁺: 593 | A |
| IIa_331 | V_9 | (S)-2-(2-Benzoylphenylamino)-3-(4-{2-[phenyl-(3-pyridin-3-ylpropionyl)-amino]ethoxy}phenyl)propionic acid methyl ester | rt: 7.038<br>MS[M+1]⁺: 627 | A |
| IIa_332 | V_10 | (S)-2-(2-Benzoylphenylamino)-3-(4-{3-[phenyl-(3-pyridin-3-ylpropionyl)-amino]propoxy}phenyl)propionic acid methyl ester | rt: 7.229<br>MS[M+1]⁺: 641 | A |
| IIa_333 | V_9 | (S)-2-(2-Benzoylphenylamino)-3-{4-[2-(pent-4-enoylphenylamino)-ethoxy]phenyl}propionic acid methyl ester | rt: 9.078<br>MS[M+1]⁺: 577 | A |
| IIa_334 | V_10 | (S)-2-(2-Benzoylphenylamino)-3-{4-[3-(pent-4-enoylphenylamino)-propoxy]phenyl}propionic acid methyl ester | rt: 9.212<br>MS[M+1]⁺: 591 | A |

TABLE 5-continued

| Example Number | Starting product | Compound name | ¹H-NMR/LC-MS | HPLC Method |
|---|---|---|---|---|
| IIa_335 | V_9 | (S)-2-(2-Benzoylphenylamino)-3-(4-{2-[phenyl-(3-phenylpropionyl)-amino]ethoxy}phenyl)propionic acid methyl ester | rt: 9.369<br>MS[M+1]⁺: 627 | A |
| IIa_336 | V_10 | (S)-2-(2-Benzoylphenylamino)-3-(4-{3-[phenyl-(3-phenylpropionyl)-amino]propoxy}phenyl)propionic acid methyl ester | rt: 9.494<br>MS[M+1]⁺: 641 | A |
| IIa_337 | V_9 | (S)-2-(2-Benzoylphenylamino)-3-{4-[2-(cyclobutanecarbonylphenylamino)-ethoxy]phenyl}propionic acid methyl ester | rt: 9.203<br>MS[M+1]⁺: 577 | A |
| IIa_338 | V_10 | (S)-2-(2-Benzoylphenylamino)-3-{4-[3-(cyclobutanecarbonylphenylamino)-propoxy]phenyl}propionic acid methyl ester | rt: 9.333<br>MS[M+1]⁺: 591 | A |
| IIa_339 | V_9 | (S)-2-(2-Benzoylphenylamino)-3-{4-[2-(cyclohexanecarbonylphenylamino)-ethoxy]phenyl}propionic acid methyl ester | rt: 9.602<br>MS[M+1]⁺: 605 | A |
| IIa_340 | V_10 | (S)-2-(2-Benzoylphenylamino)-3-{4-[3-(cyclohexanecarbonylphenylamino)-propoxy]phenyl}propionic acid methyl ester | rt: 9.708<br>MS[M+1]⁺: 619 | A |
| IIa_341 | V_9 | (S)-2-(2-Benzoylphenylamino)-3-(4-{2-[(3-cyclohexylpropionyl)-phenylamino]ethoxy}phenyl)-propionic acid methyl ester | rt: 10.166<br>MS[M+1]⁺: 633 | A |
| IIa_342 | V_10 | (S)-2-(2-Benzoylphenylamino)-3-(4-{3-[(3-cyclohexylpropionyl)-phenylamino]propoxy}phenyl)-propionic acid methyl ester | rt: 10.282<br>MS[M+1]⁺: 647 | A |
| IIa_343 | V_9 | (S)-2-(2-Benzoylphenylamino)-3-(4-{2-[(2-cyclohexylacetyl)-phenylamino]ethoxy}phenyl)-propionic acid methyl ester | rt: 9.883<br>MS[M+1]⁺: 619 | A |
| IIa_344 | V_10 | (S)-2-(2-Benzoylphenylamino)-3-(4-{3-[(2-cyclohexylacetyl)-phenylamino]propoxy}phenyl)-propionic acid methyl ester | rt: 10<br>MS[M+1]⁺: 633 | A |
| IIa_345 | V_9 | (S)-2-(2-Benzoylphenylamino)-3-{4-[2-(cyclopentanecarbonylphenylamino)-ethoxy]phenyl}propionic acid methyl ester | rt: 9.463<br>MS[M+1]⁺: 591 | A |
| IIa_346 | V_10 | (S)-2-(2-Benzoylphenylamino)-3-{4-[3-(cyclopentanecarbonylphenylamino)-propoxy]phenyl}propionic acid methyl ester | rt: 9.582<br>MS[M+1]⁺: 605 | A |
| IIa_347 | V_9 | (S)-2-(2-Benzoylphenylamino)-3-(4-{2-[(3-cyclopentylpropionyl)-phenylamino]ethoxy}phenyl)-propionic acid methyl ester | rt: 9.87<br>MS[M+1]⁺: 619 | A |
| IIa_348 | V_10 | (S)-2-(2-Benzoylphenylamino)-3-(4-{3-[(3-cyclopentylpropionyl)-phenylamino]propoxy}phenyl)-propionic acid methyl ester | rt: 9.98<br>MS[M+1]⁺: 633 | A |
| IIa_349 | V_9 | (S)-2-(2-Benzoylphenylamino)-3-{4-[2-(cyclopropanecarbonylphenylamino)-ethoxy]phenyl}propionic acid methyl ester | rt: 8.91<br>MS[M+1]⁺: 563 | A |
| IIa_350 | V_10 | (S)-2-(2-Benzoylphenylamino)-3-{4-[3-(cyclopropanecarbonylphenylamino)-propoxy]phenyl}propionic acid methyl ester | rt: 9.06<br>MS[M+1]⁺: 577 | A |
| IIa_351 | V_9 | (S)-2-(2-Benzoylphenylamino)-3-{4-[2-(phenylpropionylamino)ethoxy]-phenyl}propionic acid methyl ester | rt: 8.78<br>MS[M+1]⁺: 551 | A |

TABLE 5-continued

| Example Number | Starting product | Compound name | $^1$H-NMR/LC-MS | HPLC Method |
|---|---|---|---|---|
| IIa_352 | V_10 | (S)-2-(2-Benzoylphenylamino)-3-{4-[3-(phenylpropionylamino)propoxy]-phenyl}propionic acid methyl ester | rt: 8.925<br>MS[M+1]$^+$: 565 | A |
| IIa_353 | V_9 | (S)-2-(2-Benzoylphenylamino)-3-{4-[2-(isobutyrylphenylamino)ethoxy]-phenyl}propionic acid methyl ester | rt: 9.033<br>MS[M+1]$^+$: 565 | A |
| IIa_354 | V_10 | (S)-2-(2-Benzoylphenylamino)-3-{4-[3-(isobutyrylphenylamino)propoxy]-phenyl}propionic acid methyl ester | rt: 9.168<br>MS[M+1]$^+$: 579 | A |
| IIa_355 | V_9 | (S)-2-(2-Benzoylphenylamino)-3-{4-[2-(hexanoylphenylamino)ethoxy]-phenyl}propionic acid methyl ester | rt: 9.56<br>MS[M+1]$^+$: 593 | A |
| IIa_356 | V_10 | (S)-2-(2-Benzoylphenylamino)-3-{4-[3-(hexanoylphenylamino)propoxy]-phenyl}propionic acid methyl ester | rt: 9.671<br>MS[M+1]$^+$: 607 | A |
| IIa_357 | V_9 | (S)-2-(2-Benzoylphenylamino)-3-{4-[2-(pentanoylphenylamino)ethoxy]-phenyl}propionic acid methyl ester | rt: 9.298<br>MS[M+1]$^+$: 579 | A |
| IIa_358 | V_10 | (S)-2-(2-Benzoylphenylamino)-3-{4-[3-(pentanoylphenylamino)propoxy]-phenyl}propionic acid methyl ester | rt: 9.421<br>MS[M+1]$^+$: 593 | A |
| IIa_359 | V_9 | (S)-2-(2-Benzoylphenylamino)-3-{4-[2-(octanoylphenylamino)ethoxy]-phenyl}propionic acid methyl ester | rt: 10.11<br>MS[M+1]$^+$: 621 | A |
| IIa_360 | V_10 | (S)-2-(2-Benzoylphenylamino)-3-{4-[3-(octanoylphenylamino)propoxy]-phenyl}propionic acid methyl ester | rt: 10.224<br>MS[M+1]$^+$: 635 | A |
| IIa_361 | V_9 | (S)-2-(2-Benzoylphenylamino)-3-{4-[2-(heptanoylphenylamino)ethoxy]-phenyl}propionic acid methyl ester | rt: 9.825<br>MS[M+1]$^+$: 607 | A |
| IIa_362 | V_10 | (S)-2-(2-Benzoylphenylamino)-3-{4-[3-(heptanoylphenylamino)propoxy]-phenyl}propionic acid methyl ester | rt: 9.933<br>MS[M+1]$^+$: 621 | A |
| IIa_363 | V_9 | (S)-2-(2-Benzoylphenylamino)-3-{4-[2-(nonanoylphenylamino)ethoxy]-phenyl}propionic acid methyl ester | rt: 10.455<br>MS[M+1]$^+$: 635 | A |
| IIa_364 | V_10 | (S)-2-(2-Benzoylphenylamino)-3-{4-[3-(nonanoylphenylamino)propoxy]-phenyl}propionic acid methyl ester | rt: 10.588<br>MS[M+1]$^+$: 649 | A |
| IIa_365 | V_9 | (S)-2-(2-Benzoylphenylamino)-3-{4-[2-(butyrylphenylamino)ethoxy]-phenyl}propionic acid methyl ester | rt: 9.043<br>MS[M+1]$^+$: 565 | A |
| IIa_366 | V_10 | (S)-2-(2-Benzoylphenylamino)-3-{4-[3-(butyrylphenylamino)propoxy]-phenyl}propionic acid methyl ester | rt: 9.18<br>MS[M+1]$^+$: 579 | A |
| IIa_367 | V_9 | (S)-2-(2-Benzoylphenylamino)-3-{4-[2-(benzoylphenylamino)ethoxy]-phenyl}propionic acid methyl ester | rt: 8.97<br>MS[M+1]$^+$: 599 | A |
| IIa_368 | V_10 | (S)-2-(2-Benzoylphenylamino)-3-{4-[3-(benzoylphenylamino)propoxy]-phenyl}propionic acid methyl ester | rt: 9.121<br>MS[M+1]$^+$: 613 | A |
| IIa_369 | V_9 | (S)-2-(2-Benzoylphenylamino)-3-(4-{2-[phenyl-(3-phenylacryloyl)amino]-ethoxy}phenyl)propionic acid methyl ester | rt: 9.383<br>MS[M+1]$^+$: 625 | A |
| IIa_370 | V_10 | (S)-2-(2-Benzoylphenylamino)-3-(4-{3-[phenyl-(3-phenylacryloyl)amino]-propoxy}phenyl)propionic acid methyl ester | rt: 9.51<br>MS[M+1]$^+$: 639 | A |
| IIa_371 | V_9 | (S)-2-(2-Benzoylphenylamino)-3-(4-{2-[(2,2-dimethylpropionyl)-phenylamino]ethoxy}phenyl)-propionic acid methyl ester | rt: 9.402<br>MS[M+1]$^+$: 579 | A |
| IIa_372 | V_10 | (S)-2-(2-Benzoylphenylamino)-3-(4-{3-[(2,2-dimethylpropionyl)-phenylamino]propoxy}phenyl)-propionic acid methyl ester | rt: 9.5<br>MS[M+1]$^+$: 593 | A |
| IIa_373 | V_4 | (S)-2-(2-Benzoylphenylamino)-3-{4-[2-(tert-butylcyclobutanecarbonylamino)-ethoxy]phenyl}propionic acid methyl ester | rt: 9.256<br>MS[M+1]$^+$: 557 | A |
| IIa_374 | V_4 | (S)-2-(2-Benzoylphenylamino)-3-(4-{2-[tert-butyl-(3-cyclopentylpropionyl)amino]ethoxy}-phenyl)propionic acid methyl ester | rt: 9.917<br>MS[M+1]$^+$: 599 | A |

TABLE 5-continued

| Example Number | Starting product | Compound name | ¹H-NMR/LC-MS | HPLC Method |
|---|---|---|---|---|
| IIa_375 | V_26 | (S)-2-(2-Benzoylphenylamino)-3-(4-{2-[(2-methylacryloyl)naphthalen-1-ylamino]ethoxy}phenyl)propionic acid methyl ester | rt: 9.214 MS[M+1]⁺: 613 | A |
| IIa_376 | V_26 | (S)-2-(2-Benzoylphenylamino)-3-{4-[2-(but-2-(E)-enoylnaphthalen-1-ylamino)ethoxy]phenyl}propionic acid methyl ester | rt: 9.276 MS[M+1]⁺: 613 | A |
| IIa_377 | V_26 | (S)-2-(2-Benzoylphenylamino)-3-{4-[2-(cyclopropanecarbonylnaphthalen-1-ylamino)ethoxy]phenyl}propionic acid methyl ester | rt: 9.336 MS[M+1]⁺: 613 | A |
| IIa_378 | V_26 | (S)-2-(2-Benzoylphenylamino)-3-{4-[2-(naphthalen-1-ylpropionylamino)-ethoxy]phenyl}propionic acid methyl ester | rt: 9.273 MS[M+1]⁺: 601 | A |
| IIa_379 | V_30 | (S)-2-(2-Benzoylphenylamino)-3-(4-{2-[(2-methylacryloyl)naphthalen-2-ylamino]ethoxy}phenyl)propionic acid methyl ester | rt: 9.261 MS[M+1]⁺: 613 | A |
| IIa_380 | V_30 | (S)-2-(2-Benzoylphenylamino)-3-{4-[2-(but-2-(E)-enoylnaphthalen-2-ylamino)ethoxy]phenyl}propionic acid methyl ester | rt: 9.355 MS[M+1]⁺: 613 | A |
| IIa_381 | V_30 | (S)-2-(2-Benzoylphenylamino)-3-{4-[2-(naphthalen-2-ylpropionylamino)-ethoxy]phenyl}propionic acid methyl ester | rt: 9.269 MS[M+1]⁺: 601 | A |
| IIa_382 | V_30 | (S)-3-{4-[2-(Acetylnaphthalen-2-ylamino)ethoxy]phenyl}-2-(2-benzoylphenylamino)propionic acid methyl ester | rt: 8.914 MS[M+1]⁺: 587 | A |
| IIa_383 | V_27 | (S)-2-(2-Benzoylphenylamino)-3-(4-{2-[(2-methylacryloyl)-(3-methylsulfanylphenyl)amino]ethoxy}-phenyl)propionic acid methyl ester | rt: 9.054 MS[M+1]⁺: 609 | A |
| IIa_384 | V_27 | (S)-2-(2-Benzoylphenylamino)-3-(4-{2-[but-2-(E)-enoyl-(3-methylsulfanylphenyl)amino]ethoxy}-phenyl)propionic acid methyl ester | rt: 9.126 MS[M+1]⁺: 609 | A |
| IIa_385 | V_27 | (S)-2-(2-Benzoylphenylamino)-3-(4-{2-[butyryl-(3-methylsulfanylphenyl)-amino]ethoxy}phenyl)propionic acid methyl ester | rt: 9.28 MS[M+1]⁺: 611 | A |
| IIa_386 | V_28 | (S)-2-(2-Benzoylphenylamino)-3-(4-{2-[(2-methylacryloyl)-(4-methylsulfanylphenyl)amino]ethoxy}-phenyl)propionic acid methyl ester | rt: 9.051 MS[M+1]⁺: 609 | A |
| IIa_387 | V_28 | (S)-2-(2-Benzoylphenylamino)-3-(4-{2-[but-2-(E)-enoyl-(4-methylsulfanylphenyl)amino]ethoxy}-phenyl)propionic acid methyl ester | rt: 9.134 MS[M+1]⁺: 609 | A |
| IIa_388 | V_28 | (S)-2-(2-Benzoylphenylamino)-3-(4-{2-[isobutyryl-(4-methylsulfanylphenyl)amino]ethoxy}-phenyl)propionic acid methyl ester | rt: 9.284 MS[M+1]⁺: 611 | A |
| IIa_389 | V_28 | (S)-2-(2-Benzoylphenylamino)-3-(4-{2-[butyryl-(4-methylsulfanylphenyl)-amino]ethoxy}phenyl)propionic acid methyl ester | rt: 9.284 MS[M+1]⁺: 611 | A |
| IIa_390 | V_26 | (S)-3-{4-[2-(Acetylnaphthalen-1-ylamino)ethoxy]phenyl}-2-(2-benzoylphenylamino)propionic acid methyl ester | rt: 8.903 MS[M+1]⁺: 587 | A |
| IIa_391 | V_30 | (S)-2-(2-Benzoylphenylamino)-3-{4-[2-(cyclopropanecarbonylnaphthalen-2-ylamino)ethoxy]phenyl}propionic acid methyl ester | rt: 9.387 MS[M+1]⁺: 613 | A |
| IIa_392 | V_31 | (S)-2-(2-Benzoylphenylamino)-3-(4-{3-[butyryl-(2-fluorophenyl)amino]-propoxy}phenyl)propionic acid methyl ester | rt: 9.23 MS[M+1]⁺: 597 | A |
| IIa_393 | V_31 | (S)-2-(2-Benzoylphenylamino)-3-(4-{3-[cyclobutanecarbonyl-(2- | rt: 9.355 MS[M+1]⁺: 609 | A |

TABLE 5-continued

| Example Number | Starting product | Compound name | $^1$H-NMR/LC-MS | HPLC Method |
|---|---|---|---|---|
| | | fluorophenyl)amino]propoxy}phenyl)-propionic acid methyl ester | | |
| IIa_394 | V_31 | (S)-2-(2-Benzoylphenylamino)-3-(4-{3-[cyclopropanecarbonyl-(2-fluorophenyl)amino]propoxy}phenyl)-propionic acid methyl ester | rt: 9.056 MS[M+1]$^+$: 595 | A |
| IIa_395 | V_31 | (S)-2-(2-Benzoylphenylamino)-3-(4-{3-[(2-fluorophenyl)isobutyrylamino]-propoxy}phenyl)propionic acid methyl ester | rt: 9.219 MS[M+1]$^+$: 597 | A |
| IIa_396 | V_1 | (S)-3-{4-[2-(Acryloylbenzylamino)-ethoxy]phenyl}-2-(2-benzoylphenylamino)propionic acid methyl ester | rt: 8.639 MS[M+1]$^+$: 563 | A |
| IIa_397 | V_2 | (S)-3-{4-[3-(Acryloylbenzylamino)-propoxy]phenyl}-2-(2-benzoylphenylamino)propionic acid methyl ester | rt: 8.747 MS[M+1]$^+$: 577 | A |
| IIa_398 | V_9 | (S)-3-{4-[2-(Acryloylphenylamino)-ethoxy]phenyl}-2-(2-benzoylphenylamino)propionic acid methyl ester | rt: 8.693 MS[M+1]$^+$: 549 | A |
| IIa_399 | V_10 | (S)-3-{4-[2-(Acryloylphenylamino)-propoxy]phenyl}-2-(2-benzoylphenylamino)propionic acid methyl ester | rt: 8.842 MS[M+1]$^+$: 563 | A |
| IIa_400 | V_31 | (S)-2-(2-Benzoylphenylamino)-3-(4-{3-[(2-fluorophenyl)propionylamino]-propoxy}phenyl)propionic acid methyl ester | rt: 8.986 MS[M+1]$^+$: 583 | A |
| IIa_401 | V_31 | (S)-2-(2-Benzoylphenylamino)-3-(4-{3-[(2-fluorophenyl)pent-4-enoylamino]propoxy}phenyl)-propionic acid methyl ester | rt: 9.279 MS[M+1]$^+$: 609 | A |
| IIa_402 | V_31 | (S)-3-(4-{3-[Acryloyl-(2-fluorophenyl)amino]propoxy}phenyl)-2-(2-benzoylphenylamino)propionic acid methyl ester | rt: 8.87 MS[M+1]$^+$: 581 | A |
| IIa_403 | V_31 | (S)-2-(2-Benzoylphenylamino)-3-(4-{3-[but-2-(E)-enoyl-(2-fluorophenyl)-amino]propoxy}phenyl)propionic acid methyl ester | rt: 9.009 MS[M+1]$^+$: 595 | A |
| IIa_404 | V_31 | (S)-2-(2-Benzoylphenylamino)-3-(4-{3-[(2-fluorophenyl)-(3-methylbutyryl)amino]propoxy}-phenyl)propionic acid methyl ester | rt: 9.45 MS[M+1]$^+$: 611 | A |
| IIa_405 | V_29 | (R)-2-(2-Benzoylphenylamino)-3-(4-{2-[phenyl(thiophene-2-carbonyl)-amino]ethoxy}phenyl)propionic acid methyl ester | rt: 9.023 MS[M+1]$^+$: 605 | A |
| IIa_406 | V_31 | (S)-2-(2-Benzoylphenylamino)-3-(4-{3-[(2-fluorophenyl)-(2-methylacryloyl)amino]propoxy}-phenyl)propionic acid methyl ester | rt: 9.048 MS[M+1]$^+$: 595 | A |
| IIa_407 | V_32 | (S)-2-(2-Benzoylphenylamino)-3-(4-{3-[(3-fluorophenyl)-(2-methylacryloyl)amino]propoxy}-phenyl)propionic acid methyl ester | rt: 9.025 MS[M+1]$^+$: 595 | A |
| IIa_408 | V_34 | (S)-2-(2-Benzoylphenylamino)-3-(4-{2-[but-2-(E)-enoyl-(2-methoxyphenyl)amino]ethoxy}-phenyl)propionic acid methyl ester | rt: 8.84 MS[M+1]$^+$: 593 | A |
| IIa_409 | V_35 | (S)-2-(2-Benzoylphenylamino)-3-(4-{2-[but-2-(E)-enoyl-(3-methoxyphenyl)amino]ethoxy}-phenyl)propionic acid methyl ester | rt: 8.852 MS[M+1]$^+$: 593 | A |
| IIa_410 | V_34 | (S)-2-(2-Benzoylphenylamino)-3-(4-{2-[(2-methoxyphenyl)-(3-methylbutyryl)amino]ethoxy}phenyl)-propionic acid methyl ester | rt: 9.303 MS[M+1]$^+$: 609 | A |
| IIa_411 | V_32 | (S)-2-(2-Benzoylphenylamino)-3-(4-{3-[(3-fluorophenyl)-(3-methylbutyryl)amino]propoxy}-phenyl)propionic acid methyl ester | rt: 9.436 MS[M+1]$^+$: 611 | A |
| IIa_412 | V_35 | (S)-2-(2-Benzoylphenylamino)-3-(4-{2-[(3-methoxyphenyl)-(3- | rt: 9.243 MS[M+1]$^+$: 609 | A |

TABLE 5-continued

| Example Number | Starting product | Compound name | ¹H-NMR/LC-MS | HPLC Method |
|---|---|---|---|---|
| | | methylbutyryl)amino]ethoxy}phenyl)-propionic acid methyl ester | | |
| IIa_413 | V_32 | (S)-2-(2-Benzoylphenylamino)-3-(4-{3-[(3-fluorophenyl)pent-4-enoylamino]propoxy}phenyl)-propionic acid methyl ester | rt: 9.262 MS[M+1]⁺: 609 | A |
| IIa_414 | V_32 | (S)-2-(2-Benzoylphenylamino)-3-(4-{3-[cyclobutanecarbonyl-(3-fluorophenyl)amino]propoxy}phenyl)-propionic acid methyl ester | rt: 9.353 MS[M+1]⁺: 609 | A |
| IIa_415 | V_33 | (S)-2-(2-Benzoylphenylamino)-3-(4-{3-[cyclobutanecarbonyl-(4-fluorophenyl)amino]propoxy}phenyl)-propionic acid methyl ester | rt: 9.338 MS[M+1]⁺: 609 | A |
| IIa_416 | V_29 | (R)-2-(2-Benzoylphenylamino)-3-{4-[2-(cyclobutanecarbonylphenylamino)-ethoxy]phenyl}propionic acid methyl ester | rt: 9.207 MS[M+1]⁺: 577 | A |
| IIa_417 | V_34 | (S)-2-(2-Benzoylphenylamino)-3-(4-{2-[cyclopropanecarbonyl-(2-methoxyphenyl)amino]ethoxy}-phenyl)propionic acid methyl ester | rt: 8.891 MS[M+1]⁺: 593 | A |
| IIa_418 | V_32 | (S)-2-(2-Benzoylphenylamino)-3-(4-{3-[cyclopropanecarbonyl-(3-fluorophenyl)amino]propoxy}phenyl)-propionic acid methyl ester | rt: 9.103 MS[M+1]⁺: 595 | A |
| IIa_419 | V_33 | (S)-2-(2-Benzoylphenylamino)-3-(4-{3-[cyclopropanecarbonyl-(4-fluorophenyl)amino]propoxy}phenyl)-propionic acid methyl ester | rt: 9.082 MS[M+1]⁺: 595 | A |
| IIa_420 | V_34 | (S)-2-(2-Benzoylphenylamino)-3-(4-{2-[(2-methoxyphenyl)-propionylamino]ethoxy}phenyl)-propionic acid methyl ester | rt: 8.817 MS[M+1]⁺: 581 | A |
| IIa_421 | V_32 | (S)-2-(2-Benzoylphenylamino)-3-(4-{3-[(3-fluorophenyl)propionylamino]-propoxy}phenyl)propionic acid methyl ester | rt: 8.976 MS[M+1]⁺: 583 | A |
| IIa_422 | V_35 | (S)-2-(2-Benzoylphenylamino)-3-(4-{2-[(3-methoxyphenyl)-propionylamino]ethoxy}phenyl)-propionic acid methyl ester | rt: 8.766 MS[M+1]⁺: 581 | A |
| IIa_423 | V_33 | (S)-2-(2-Benzoylphenylamino)-3-(4-{3-[(4-fluorophenyl)propionylamino]-propoxy}phenyl)propionic acid methyl ester | rt: 8.958 MS[M+1]⁺: 583 | A |
| IIa_424 | V_29 | (R)-2-(2-Benzoylphenylamino)-3-{4-[2-(phenylpropionylamino)ethoxy]-phenyl}propionic acid methyl ester | rt: 8.783 MS[M+1]⁺: 551 | A |
| IIa_425 | V_32 | (S)-2-(2-Benzoylphenylamino)-3-(4-{3-[(3-fluorophenyl)isobutyrylamino]-propoxy}phenyl)propionic acid methyl ester | rt: 9.206 MS[M+1]⁺: 597 | A |
| IIa_426 | V_35 | (S)-2-(2-Benzoylphenylamino)-3-(4-{2-[isobutyryl-(3-methoxyphenyl)-amino]ethoxy}phenyl)propionic acid methyl ester | rt: 9.011 MS[M+1]⁺: 595 | A |
| IIa_427 | V_33 | (S)-2-(2-Benzoylphenylamino)-3-(4-{3-[(4-fluorophenyl)isobutyrylamino]-propoxy}phenyl)propionic acid methyl ester | rt: 9.187 MS[M+1]⁺: 597 | A |
| IIa_428 | V_31 | (S)-2-(2-Benzoylphenylamino)-3-(4-{3-[(2-fluorophenyl)pentanoylamino]-propoxy}phenyl)propionic acid methyl ester | rt: 9.473 MS[M+1]⁺: 611 | A |
| IIa_429 | V_32 | (S)-2-(2-Benzoylphenylamino)-3-(4-{3-[(3-fluorophenyl)pentanoylamino]-propoxy}phenyl)propionic acid methyl ester | rt: 9.455 MS[M+1]⁺: 611 | A |
| IIa_430 | V_34 | (S)-2-(2-Benzoylphenylamino)-3-(4-{2-[butyryl-(2-methoxyphenyl)amino]-ethoxy}phenyl)propionic acid methyl ester | rt: 9.069 MS[M+1]⁺: 595 | A |
| IIa_431 | V_32 | (S)-2-(2-Benzoylphenylamino)-3-(4-{3-[butyryl-(3-fluorophenyl)amino]- | rt: 9.227 MS[M+1]⁺: 597 | A |

TABLE 5-continued

| Example Number | Starting product | Compound name | $^1$H-NMR/LC-MS | HPLC Method |
|---|---|---|---|---|
| IIa_432 | V_35 | propoxy}phenyl)propionic acid methyl ester (S)-2-(2-Benzoylphenylamino)-3-(4-{2-[butyryl-(3-methoxyphenyl)amino]-ethoxy}phenyl)propionic acid methyl ester | rt: 9.014 MS[M+1]$^+$: 595 | A |
| IIa_433 | V_33 | (S)-2-(2-Benzoylphenylamino)-3-(4-{3-[butyryl-(4-fluorophenyl)amino]-propoxy}phenyl)propionic acid methyl ester | rt: 9.202 MS[M+1]$^+$: 597 | A |
| IIa_434 | V_31 | (S)-2-(2-Benzoylphenylamino)-3-(4-{3-[(2,2-dimethylpropionyl)-(2-fluorophenyl)amino]propoxy}phenyl)-propionic acid methyl ester | rt: 9.539 MS[M+1]$^+$: 611 | A |
| IIa_435 | V_34 | (S)-2-(2-Benzoylphenylamino)-3-(4-{2-[(2,2-dimethylpropionyl)-(2-methoxyphenyl)amino]ethoxy}-phenyl)propionic acid methyl ester | rt: 9.411 MS[M+1]$^+$: 609 | A |
| IIa_436 | V_32 | (S)-2-(2-Benzoylphenylamino)-3-(4-{3-[(2,2-dimethylpropionyl)-(3-fluorophenyl)amino]propoxy}phenyl)-propionic acid methyl ester | rt: 9.518 MS[M+1]$^+$: 611 | A |
| IIa_437 | V_35 | (S)-2-(2-Benzoylphenylamino)-3-(4-{2-[(2,2-dimethylpropionyl)-(3-methoxyphenyl)amino]ethoxy}-phenyl)propionic acid methyl ester | rt: 9.367 MS[M+1]$^+$: 609 | A |
| IIa_438 | V_27 | (S)-2-(2-Benzoylphenylamino)-3-(4-{2-[isobutyryl-(3-methylsulfanylphenyl)amino]ethoxy}-phenyl)propionic acid methyl ester | rt: 9.277 MS[M+1]$^+$: 611 | A |
| IIa_439 | V_37 | (S)-2-(2-Benzoylphenylamino)-3-(4-{3-[(2-methoxyphenyl)-propionylamino]propoxy}phenyl)-propionic acid methyl ester | rt: 8.92 MS[M+1]$^+$: 595 | A |
| IIa_440 | V_37 | (S)-2-(2-Benzoylphenylamino)-3-(4-{3-[cyclopropanecarbonyl-(2-methoxyphenyl)amino]propoxy}-phenyl)propionic acid methyl ester | rt: 9.154 MS[M+1]$^+$: 609 | A |
| IIa_441 | V_37 | (S)-2-(2-Benzoylphenylamino)-3-(4-{3-[isobutyryl-(2-methoxyphenyl)-amino]propoxy}phenyl)propionic acid methyl ester | rt: 8.999 MS[M+1]$^+$: 607 | A |
| IIa_442 | V_37 | (S)-2-(2-Benzoylphenylamino)-3-(4-{3-[but-2-(E)-(enoyl-(2-methoxyphenyl)amino]propoxy)-phenyl)propionic acid methyl ester | rt: 8.942 MS[M+1]$^+$: 607 | A |
| IIa_443 | V_37 | (S)-2-(2-Benzoylphenylamino)-3-(4-{3-[(2-methoxyphenyl)-(2-methylacryloyl)amino]propoxy)-phenyl)propionic acid methyl ester | rt: 8.954 MS[M+1]$^+$: 607 | A |
| IIa_444 | V_37 | (S)-3-(4-{3-[Acryloyl-(2-methoxyphenyl)amino]propoxy}-phenyl)-2-(2-benzoylphenylamino)-propionic acid methyl ester | rt: 8.82 MS[M+1]$^+$: 593 | A |
| IIa_445 | V_37 | (S)-2-(2-Benzoylphenylamino)-3-(4-{3-[butyryl-(2-methoxyphenyl)amino]-propoxy}phenyl)propionic acid methyl ester | rt: 9.161 MS[M+1]$^+$: 609 | A |
| IIa_446 | V_38 | (S)-2-(2-Benzoylphenylamino)-3-(4-{3-[(3-methoxyphenyl)-propionylamino]propoxy}phenyl)-propionic acid methyl ester | rt: 8.904 MS[M+1]$^+$: 595 | A |
| IIa_447 | V_38 | (S)-2-(2-Benzoylphenylamino)-3-(4-{3-[cyclopropanecarbonyl-(3-methoxyphenyl)amino]propoxy}-phenyl)propionic acid methyl ester | rt: 9.029 MS[M+1]$^+$: 607 | A |
| IIa_448 | V_38 | (S)-2-(2-Benzoylphenylamino)-3-(4-{3-[isobutyryl-(3-methoxyphenyl)-amino]propoxy}phenyl)propionic acid methyl ester | rt: 9.137 MS[M+1]$^+$: 609 | A |
| IIa_449 | V_38 | (S)-2-(2-Benzoylphenylamino)-3-(4-{3-[but-2-(E)-enoyl-(3-methoxyphenyl)amino]propoxy}-phenyl)propionic acid methyl ester | rt: 8.98 MS[M+1]$^+$: 607 | A |
| IIa_450 | V_38 | (S)-2-(2-Benzoylphenylamino)-3-(4-{3-[(3-methoxyphenyl)-(2- | rt: 8.923 MS[M+1]$^+$: 607 | A |

TABLE 5-continued

| Example Number | Starting product | Compound name | ¹H-NMR/LC-MS | HPLC Method |
|---|---|---|---|---|
| | | methylacryloyl)amino]propoxy}-phenyl)propionic acid methyl ester | | |
| IIa_451 | V_38 | (S)-3-(4-{3-[Acryloyl-(3-methoxyphenyl)amino]propoxy}-phenyl)-2-(2-benzoylphenylamino)-propionic acid methyl ester | rt: 8.845 MS[M+1]⁺: 593 | A |
| IIa_452 | V_38 | (S)-2-(2-Benzoylphenylamino)-3-(4-{3-[butyryl-(3-methoxyphenyl)amino]-propoxy}phenyl)propionic acid methyl ester | rt: 9.143 MS[M+1]⁺: 609 | A |
| IIa_453 | V_34 | (S)-2-(2-Benzoylphenylamino)-3-(4-{2-[cyclobutanecarbonyl-(2-methoxyphenyl)amino]ethoxy}-phenyl)propionic acid methyl ester | rt: 9.202 MS[M+1]⁺: 607 | A |
| IIa_454 | V_34 | (S)-2-(2-Benzoylphenylamino)-3-(4-{2-[isobutyryl-(2-methoxyphenyl)-amino]ethoxy}phenyl)propionic acid methyl ester | rt: 9.066 MS[M+1]⁺: 595 | A |
| IIa_455 | V_26 | (S)-3-{4-[2-(Acryloylnaphthalen-1-ylamino)ethoxy]phenyl}-2-(2-benzoylphenylamino)propionic acid methyl ester | rt: 9.145 MS[M+1]⁺: 599 | A |
| IIa_456 | V_30 | (S)-3-{4-[2-(Acryloylnaphthalen-2-ylamino)ethoxy]phenyl}-2-(2-benzoylphenylamino)propionic acid methyl ester | rt: 9.201 MS[M+1]⁺: 599 | A |
| IIa_457 | V_27 | (S)-3-(4-{2-[Acryloyl-(3-methylsulfanylphenyl)amino]ethoxy}-phenyl)-2-(2-benzoylphenylamino)-propionic acid methyl ester | rt: 8.979 MS[M+1]⁺: 595 | A |
| IIa_458 | V_28 | (S)-3-(4-{2-[Acryloyl-(4-methylsulfanylphenyl)amino]ethoxy}-phenyl)-2-(2-benzoylphenylamino)-propionic acid methyl ester | rt: 8.982 MS[M+1]⁺: 595 | A |
| IIa_459 | V_32 | (S)-3-(4-{3-[Acryloyl-(3-fluorophenyl)amino]propoxy}phenyl)-2-(2-benzoylphenylamino)propionic acid methyl ester | rt: 8.908 MS[M+1]⁺: 581 | A |
| IIa_460 | V_32 | (S)-2-(2-Benzoylphenylamino)-3-(4-{3-[but-2-(E)-enoyl-(3-fluorophenyl)-amino]propoxy}phenyl)propionic acid methyl ester | rt: 9.06 MS[M+1]⁺: 595 | A |
| IIa_461 | V_34 | (S)-3-(4-{2-[Acryloyl-(2-methoxyphenyl)amino]ethoxy}-phenyl)-2-(2-benzoylphenylamino)-propionic acid methyl ester | rt: 8.709 MS[M+1]⁺: 579 | A |
| IIa_462 | V_34 | (S)-2-(2-Benzoylphenylamino)-3-(4-{2-[(2-methoxyphenyl)-(2-methylacryloyl)amino]ethoxy}-phenyl)propionic acid methyl ester | rt: 8.85 MS[M+1]⁺: 593 | A |
| IIa_463 | V_35 | (S)-2-(2-Benzoylphenylamino)-3-(4-{2-[cyclopropanecarbonyl-(3-methoxyphenyl)amino]ethoxy}-phenyl)propionic acid methyl ester | rt: 8.887 MS[M+1]⁺: 593 | A |
| IIa_464 | V_35 | (S)-2-(2-Benzoylphenylamino)-3-(4-{2-[cyclobutanecarbonyl-(3-methoxyphenyl)amino]ethoxy}-phenyl)propionic acid methyl ester | rt: 9.164 MS[M+1]⁺: 607 | A |
| IIa_465 | V_35 | (S)-3-(4-{2-[Acryloyl-(3-methoxyphenyl)amino]ethoxy}-phenyl)-2-(2-benzoylphenylamino)-propionic acid methyl ester | rt: 8.703 MS[M+1]⁺: 579 | A |
| IIa_466 | V_35 | (S)-2-(2-Benzoylphenylamino)-3-(4-{2-[(3-methoxyphenyl)-(2-methylacryloyl)amino]ethoxy}-phenyl)propionic acid methyl ester | rt: 8.786 MS[M+1]⁺: 593 | A |
| IIa_467 | V_36 | (S)-2-(2-Benzoylphenylamino)-3-(4-{2-[ethyl(naphthalene-2-carbonyl)-amino]ethoxy}phenyl)propionic acid methyl ester | rt: 9.001 MS[M+1]⁺: 601 | A |
| IIa_468 | V_39 | (S)-2-(2-Benzoylphenylamino)-3-(4-{2-[(naphthalene-2-carbonyl)-propylamino]ethoxy}phenyl)propionic acid methyl ester | rt: 9.244 MS[M+1]⁺: 615 | A |
| IIa_469 | V_36 | (S)-2-(2-Benzoylphenylamino)-3-(4-{2-[ethyl(quinoline-2-carbonyl)- | rt: 8.712 MS[M+1]⁺: 602 | A |

TABLE 5-continued

| Example Number | Starting product | Compound name | ¹H-NMR/LC-MS | HPLC Method |
|---|---|---|---|---|
| | | amino]ethoxy}phenyl)propionic acid methyl ester | | |
| IIa_470 | V_39 | (S)-2-(2-Benzoylphenylamino)-3-(4-{2-[propyl(quinoline-2-carbonyl)-amino]ethoxy}phenyl)propionic acid methyl ester | rt: 8.999<br>MS[M+1]$^+$: 616 | A |
| IIa_471 | V_36 | (S)-2-(2-Benzoylphenylamino)-3-(4-{2-[ethyl(quinoxaline-2-carbonyl)-amino]ethoxy}phenyl)propionic acid methyl ester | rt: 8.595<br>MS[M+1]$^+$: 603 | A |
| IIa_472 | V_39 | (S)-2-(2-Benzoylphenylamino)-3-(4-{2-[propyl(quinoxaline-2-carbonyl)-amino]ethoxy}phenyl)propionic acid methyl ester | rt: 8.888<br>MS[M+1]$^+$: 617 | A |
| IIa_473 | V_36 | (S)-2-(2-Benzoylphenylamino)-3-(4-{2-[ethyl(thiophene-2-carbonyl)-amino]ethoxy}phenyl)propionic acid methyl ester | rt: 8.558<br>MS[M+1]$^+$: 557 | A |
| IIa_474 | V_39 | (S)-2-(2-Benzoylphenylamino)-3-(4-{2-[propyl(thiophene-2-carbonyl)-amino]ethoxy}phenyl)propionic acid methyl ester | rt: 8.841<br>MS[M+1]$^+$: 571 | A |
| IIa_475 | V_36 | (S)-2-(2-Benzoylphenylamino)-3-(4-{2-[ethyl(pyridine-3-carbonyl)amino]-ethoxy}phenyl)propionic acid methyl ester | rt: 7.545<br>MS[M+1]$^+$: 552 | A |
| IIa_476 | V_39 | (S)-2-(2-Benzoylphenylamino)-3-(4-{2-[propyl(pyridine-3-carbonyl)-amino]ethoxy}phenyl)propionic acid methyl ester | rt: 7.863<br>MS[M+1]$^+$: 566 | A |
| IIa_477 | V_36 | (S)-2-(2-Benzoylphenylamino)-3-(4-{2-[ethyl-(3-thiophen-2-ylacryloyl)-amino]ethoxy}phenyl)propionic acid methyl ester | rt: 8.711<br>MS[M+1]$^+$: 583 | A |
| IIa_478 | V_39 | (S)-2-(2-Benzoylphenylamino)-3-(4-{2-[propyl-(3-thiophen-2-ylacryloyl)-amino]ethoxy}phenyl)propionic acid methyl ester | rt: 8.993<br>MS[M+1]$^+$: 597 | A |
| IIa_479 | V_39 | (S)-2-(2-Benzoylphenylamino)-3-(4-{2-[(3,3-dimethylbutyryl)-propylamino]ethoxy}phenyl)propionic acid methyl ester | rt: 9.34<br>MS[M+1]$^+$: 559 | A |
| IIa_480 | V_36 | (S)-2-(2-Benzoylphenylamino)-3-(4-{2-[ethyl-(3-pyridin-3-ylpropionyl)-amino]ethoxy}phenyl)propionic acid methyl ester | rt: 6.512<br>MS[M+1]$^+$: 580 | A |
| IIa_481 | V_39 | (S)-2-(2-Benzoylphenylamino)-3-(4-{2-[propyl-(3-pyridin-3-ylpropionyl)-amino]ethoxy}phenyl)propionic acid methyl ester | rt: 6.767<br>MS[M+1]$^+$: 594 | A |
| IIa_482 | V_39 | (S)-2-(2-Benzoylphenylamino)-3-{4-[2-(cyclobutanecarbonylpropylamino)-ethoxy]phenyl}propionic acid methyl ester | rt: 8.955<br>MS[M+1]$^+$: 543 | A |
| IIa_483 | V_39 | (S)-2-(2-Benzoylphenylamino)-3-{4-[2-(isobutyrylpropylamino)ethoxy]-phenyl}propionic acid methyl ester | rt: 8.789<br>MS[M+1]$^+$: 531 | A |
| IIa_484 | V_39 | (S)-2-(2-Benzoylphenylamino)-3-{4-[2-(butyrylpropylamino)ethoxy]-phenyl}propionic acid methyl ester | rt: 8.775<br>MS[M+1]$^+$: 531 | A |
| IIa_485 | V_36 | (S)-3-{4-[2-(Benzoylethylamino)-ethoxy]phenyl}-2-(2-benzoylphenylamino)propionic acid methyl ester | rt: 8.547<br>MS[M+1]$^+$: 551 | A |
| IIa_486 | V_39 | (S)-2-(2-Benzoylphenylamino)-3-{4-[2-(benzoylpropylamino)ethoxy]-phenyl}propionic acid methyl ester | rt: 8.829<br>MS[M+1]$^+$: 565 | A |
| IIa_487 | V_36 | (S)-2-(2-Benzoylphenylamino)-3-(4-{2-[ethyl-(3-phenylacryloyl)amino]-ethoxy}phenyl)propionic acid methyl ester | rt: 8.806<br>MS[M+1]$^+$: 577 | A |
| IIa_488 | V_36 | (S)-2-(2-Benzoylphenylamino)-3-(4-{2-[(2,2-dimethylpropionyl)-ethylamino]ethoxy}phenyl)propionic acid methyl ester | rt: 8.931<br>MS[M+1]$^+$: 531 | A |

TABLE 5-continued

| Example Number | Starting product | Compound name | ¹H-NMR/LC-MS | HPLC Method |
|---|---|---|---|---|
| IIa_489 | V_39 | (S)-2-(2-Benzoylphenylamino)-3-(4-{2-[(2,2-dimethylpropionyl)-propylamino]ethoxy}phenyl)propionic acid methyl ester | rt: 9.233 MS[M+1]⁺: 545 | A |
| IIa_490 | V_24 | (S)-2-(2-Benzoylphenylamino)-3-(4-{3-[(3-chlorophenyl)-(2-methylacryloyl)amino]propoxy}-phenyl)propionic acid methyl ester | rt: 9.298 MS[M, M+2]⁺: 611, 613 | A |
| IIa_491 | V_25 | (S)-2-(2-Benzoylphenylamino)-3-(4-{3-[(3-chlorophenyl)-(2-methylacryloyl)amino]propoxy}-phenyl)propionic acid methyl ester | rt: 9.347 MS[M, M+2]⁺: 611, 613 | A |

Compounds I:

Compounds I described shown in Table 6 were obtained starting from the corresponding ester derivative of formula II following any of the procedures J or K described below.

PROCEDURE J: To a 0.02 M solution of compound II (1 eq) in a mixture of THF:methanol (3:1) or THF, a 1 M aqueous solution of lithium hydroxide (1.5 eq) was added. The resulting mixture was stirred at room temperature for 18 h, then treated with HCl 1 N until pH=56, and extracted twice with EtOAc. The organic layers were dried over anhydrous sodium sulfate and filtered. The solvent was distilled off under reduced pressure.

PROCEDURE K: To a solution 0.03 M of compound II (1 eq) in methanol, potassium hydroxide (10 eq) was added. The resulting solution was stirred at room temperature for 18 h, then treated with HCl 1 N until acid pH=4-5. To the resulting suspension, water and EtOAc were added. The organic layer was separated and the aqueous layer was extracted once with EtOAc. The combined organic layers were dried over anhydrous sodium sulfate and filtered. The solvent was distilled off under reduced pressure.

TABLE 6

| Example Number | Starting product | Compound name | ¹H-NMR/LC-MS | HPLC Method |
|---|---|---|---|---|
| I_1 | IIa_1 | (S)-2-(2-Benzoylphenylamino)-3-(4-{2-[(2-chlorophenyl)-(2-methylacryloyl)amino]ethoxy}phenyl)-propionic acid | rt: 8.327 MS[M, M+2]⁺: 583, 585 | A |
| I_2 | IIa_2 | (S)-2-(2-Benzoylphenylamino)-3-(4-{3-[(2-chlorophenyl)-(2-methylacryloyl)amino]propoxy}-phenyl)propionic acid | rt: 8.476 MS[M, M+2]⁺: 597, 599 | A |
| I_3 | IIa_3 | (S)-2-(2-Benzoylphenylamino)-3-(4-{2-[but-2-(E)-enoyl-(2-chlorophenyl)-amino]ethoxy}phenyl)propionic acid | rt: 8.295 MS[M, M+2]⁺: 583, 585 | A |
| I_4 | IIa_4 | (S)-2-(2-Benzoylphenylamino)-3-(4-{2-[(2-chlorophenyl)-(3-methylbutyryl)-amino]ethoxy}phenyl)propionic acid | rt: 8.855 MS[M, M+2]⁺: 599, 601 | A |
| I_5 | IIa_5 | (S)-2-(2-Benzoylphenylamino)-3-(4-{2-[(2-chlorophenyl)-cyclobutanecarbonylamino]ethoxy}-phenyl)propionic acid | rt: 8.728 MS[M, M+2]⁺: 597, 599 | A |
| I_6 | IIa_6 | (S)-2-(2-Benzoylphenylamino)-3-(4-{2-[(2-chlorophenyl)-cyclopentanecarbonylamino]ethoxy}-phenyl)propionic acid | rt: 8.989 MS[M, M+2]⁺: 611, 613 | A |
| I_7 | IIa_7 | (S)-2-(2-Benzoylphenylamino)-3-(4-{2-[(2-chlorophenyl)-cyclopropanecarbonylamino]ethoxy}-phenyl)propionic acid | rt: 8.353; MS[M, M+2]⁺: 583, 585 | A |
| I_8 | IIa_8 | (S)-2-(2-Benzoylphenylamino)-3-(4-{3-[(2-chlorophenyl)-cyclopropanecarbonylamino]propoxy}-phenyl)propionic acid | rt: 8.508 MS[M, M+2]⁺: 597, 599 | A |
| I_9 | IIa_9 | (S)-2-(2-Benzoylphenylamino)-3-(4-{2-[(2-chlorophenyl)propionylamino]-ethoxy}phenyl)propionic acid | rt: 8.298 MS[M, M+2]⁺: 571, 573 | A |
| I_10 | IIa_10 | (S)-2-(2-Benzoylphenylamino)-3-(4-{3-[(2-chlorophenyl)propionylamino]-propoxy}phenyl)propionic acid | rt: 8.446 MS[M, M+2]⁺: 585, 587 | A |
| I_11 | IIa_11 | (S)-2-(2-Benzoylphenylamino)-3-(4-{2-[(2-chlorophenyl)isobutyrylamino]-ethoxy}phenyl)propionic acid | rt: 8.561 MS[M, M+2]⁺: 585, 587 | A |

TABLE 6-continued

| Example Number | Starting product | Compound name | $^1$H-NMR/LC-MS | HPLC Method |
|---|---|---|---|---|
| I_12 | IIa_12 | (S)-2-(2-Benzoylphenylamino)-3-(4-{3-[(2-chlorophenyl)isobutyrylamino]-propoxy}phenyl)propionic acid | rt: 8.701<br>MS[M, M+2]$^+$: 599, 601 | A |
| I_13 | IIa_13 | (S)-2-(2-Benzoylphenylamino)-3-(4-{2-[butyryl-(2-chlorophenyl)amino]-ethoxy}phenyl)propionic acid | rt: 8.588<br>MS[M, M+2]$^+$: 585, 587 | A |
| I_14 | IIa_14 | (S)-2-(2-Benzoylphenylamino)-3-(4-{3-[butyryl-(2-chlorophenyl)amino]-propoxy}phenyl)propionic acid | rt: 8.726<br>MS[M, M+2]$^+$: 599, 601 | A |
| I_15 | IIa_15 | (S)-3-(4-{3-[Acryloyl-(2-chlorophenyl)-amino]propoxy}phenyl)-2-(2-benzoylphenylamino)propionic acid | rt: 8.293<br>MS[M, M+2]$^+$: 583, 585 | A |
| I_16 | IIa_16 | (S)-2-(2-Benzoylphenylamino)-3-(4-{2-[(2-fluorophenyl)-(thiophene-2-carbonyl)amino]ethoxy}phenyl)-propionic acid | rt: 8.19<br>MS[M+1]$^+$: 609 | A |
| I_17 | IIa_17 | (S)-2-(2-Benzoylphenylamino)-3-(4-{2-[(2-fluorophenyl)-(2-methylacryloyl)amino]ethoxy}phenyl)-propionic acid | rt: 8.054<br>MS[M+1]$^+$: 567 | A |
| I_18 | IIa_18 | (S)-2-(2-Benzoylphenylamino)-3-(4-{2-[(2-fluorophenyl)-(3-methylbutyryl)-amino]ethoxy}phenyl)propionic acid | rt: 8.534<br>MS[M+1]$^+$: 583 | A |
| I_19 | IIa_19 | (S)-2-(2-Benzoylphenylamino)-3-(4-{2-[cyclobutanecarbonyl-(2-fluorophenyl)amino]ethoxy}phenyl)-propionic acid | rt: 8.414<br>MS[M+1]$^+$: 581 | A |
| I_20 | IIa_20 | (S)-2-(2-Benzoylphenylamino)-3-(4-{2-[cyclopentanecarbonyl-(2-fluorophenyl)amino]ethoxy}phenyl)-propionic acid | rt: 8.674<br>MS[M+1]$^+$: 595 | A |
| I_21 | IIa_21 | (S)-2-(2-Benzoylphenylamino)-3-(4-{2-[cyclopropanecarbonyl-(2-fluorophenyl)amino]ethoxy}phenyl)-propionic acid | rt: 8.061<br>MS[M+1]$^+$: 567 | A |
| I_22 | IIa_22 | (S)-2-(2-Benzoylphenylamino)-3-(4-{2-[(2-fluorophenyl)propionylamino]-ethoxy}phenyl)propionic acid | rt: 7.981<br>MS[M+1]$^+$: 555 | A |
| I_23 | IIa_23 | (S)-2-(2-Benzoylphenylamino)-3-(4-{2-[(2-fluorophenyl)isobutyrylamino]-ethoxy}phenyl)propionic acid | rt: 8.256<br>MS[M+1]$^+$: 569 | A |
| I_24 | IIa_24 | (S)-2-(2-Benzoylphenylamino)-3-(4-{2-[butyryl-(2-fluorophenyl)amino]-ethoxy}phenyl)propionic acid | rt: 8.269<br>MS[M+1]$^+$: 569 | A |
| I_25 | IIa_25 | (S)-2-(2-Benzoylphenylamino)-3-(4-{2-[(2,2-dimethylpropionyl)-(2-fluorophenyl)amino]ethoxy}phenyl)-propionic acid | rt: 8.665<br>MS[M+1]$^+$: 583 | A |
| I_26 | IIa_26 | (S)-2-(2-Benzoylphenylamino)-3-(4-{3-[(2-methylacryloyl)-o-tolylamino]-propoxy}phenyl)propionic acid | rt: 8.369<br>MS[M+1]$^+$: 577 | A |
| I_27 | IIa_27 | (S)-2-(2-Benzoylphenylamino)-3-(4-{2-[(2-ethylbutyryl)-o-tolylamino]-ethoxy}phenyl)propionic acid | rt: 8.99<br>MS[M+1]$^+$: 593 | A |
| I_28 | IIa_28 | (S)-2-(2-Benzoylphenylamino)-3-(4-{3-[(3-methylbut-2-(E)-enoyl)-o-tolylamino]propoxy}phenyl)propionic acid | rt: 8.758<br>MS[M+1]$^+$: 591 | A |
| I_29 | IIa_29 | (S)-2-(2-Benzoylphenylamino)-3-{4-[3-(but-2-(E)-enoyl-o-tolylamino)-propoxy]phenyl}propionic acid | rt: 8.471<br>MS[M+1]$^+$: 577 | A |
| I_30 | IIa_30 | (S)-2-(2-Benzoylphenylamino)-3-(4-{2-[(3,3-dimethylbutyryl)-o-tolylamino]-ethoxy}phenyl)propionic acid | rt: 9.101<br>MS[M+1]$^+$: 593 | A |
| I_31 | IIa_31 | (S)-2-(2-Benzoylphenylamino)-3-(4-{2-[(3-methylbutyryl)-o-tolylamino]-ethoxy}phenyl)propionic acid | rt: 8.75<br>MS[M+1]$^+$: 579 | A |
| I_32 | IIa_32 | (S)-2-(2-Benzoylphenylamino)-3-(4-{3-[(3-methylbutyryl)-o-tolylamino]-propoxy}phenyl)propionic acid | rt: 8.945<br>MS[M+1]$^+$: 593 | A |
| I_33 | IIa_33 | (S)-2-(2-Benzoylphenylamino)-3-{4-[3-(o-tolylpent-4-enoylamino)propoxy]-phenyl}propionic acid | rt: 8.742<br>MS[M+1]$^+$: 591 | A |
| I_34 | IIa_34 | (S)-2-(2-Benzoylphenylamino)-3-{4-[2-(cyclobutanecarbonyl-o-tolylamino)-ethoxy]phenyl}propionic acid | rt: 8.634<br>MS[M+1]$^+$: 577 | A |

TABLE 6-continued

| Example Number | Starting product | Compound name | ¹H-NMR/LC-MS | HPLC Method |
|---|---|---|---|---|
| I_35 | IIa_35 | (S)-2-(2-Benzoylphenylamino)-3-{4-[2-(cyclopentanecarbonyl-o-tolylamino)-ethoxy]phenyl}propionic acid | rt: 8.898<br>MS[M+1]⁺: 591 | A |
| I_36 | IIa_36 | (S)-2-(2-Benzoylphenylamino)-3-{4-[3-(propionyl-o-tolylamino)propoxy]-phenyl}propionic acid | rt: 8.387<br>MS[M+1]⁺: 565 | A |
| I_37 | IIa_37 | (S)-2-(2-Benzoylphenylamino)-3-{4-[2-(isobutyryl-o-tolylamino)ethoxy]-phenyl}propionic acid | rt: 8.458<br>MS[M+1]⁺: 565 | A |
| I_38 | IIa_38 | (S)-2-(2-Benzoylphenylamino)-3-{4-[3-(isobutyryl-o-tolylamino)propoxy]-phenyl}propionic acid | rt: 8.66<br>MS[M+1]⁺: 579 | A |
| I_39 | IIa_39 | (S)-2-(2-Benzoylphenylamino)-3-{4-[3-(pentanoyl-o-tolylamino)propoxy]-phenyl}propionic acid | rt: 8.968<br>MS[M+1]⁺: 593 | A |
| I_40 | IIa_40 | (S)-2-(2-Benzoylphenylamino)-3-{4-[2-(butyryl-o-tolylamino)ethoxy]phenyl}-propionic acid | rt: 8.474<br>MS[M+1]⁺: 565 | A |
| I_41 | IIa_41 | (S)-2-(2-Benzoylphenylamino)-3-{4-[3-(butyryl-o-tolylamino)propoxy]phenyl)-propionic acid | rt: 8.677<br>MS[M+1]⁺: 579 | A |
| I_42 | IIa_42 | (S)-2-(2-Benzoylphenylamino)-3-{4-[2-(benzoyl-o-tolylamino)ethoxy]phenyl}-propionic acid | rt: 8.324<br>MS[M+1]⁺: 599 | A |
| I_43 | IIa_43 | (S)-2-(2-Benzoylphenylamino)-3-(4-{2-[(2,2-dimethylpropionyl)-o-tolylamino]ethoxy}phenyl)propionic acid | rt: 8.884<br>MS[M+1]⁺: 579 | A |
| I_44 | IIa_44 | (S)-2-(2-Benzoylphenylamino)-3-(4-{3-[(2,2-dimethylpropionyl)-o-tolylamino]propoxy}phenyl)propionic acid | rt: 9.028<br>MS[M+1]⁺: 593 | A |
| I_45 | IIa_45 | (S)-3-{4-[3-(Acryloyl-o-tolylamino)-propoxy]phenyl}-2-(2-benzoylphenylamino)propionic acid | rt: 8.31<br>MS[M+1]⁺: 563 | A |
| I_46 | IIa_46 | (S)-2-(2-Benzoylphenylamino)-3-(4-{2-[(3-chlorophenyl)-(2-methylacryloyl)amino]ethoxy}phenyl)-propionic acid | rt: 8.385<br>MS[M, M+2]⁺: 583, 586 | A |
| I_47 | IIa_490 | (S)-2-(2-Benzoylphenylamino)-3-(4-{3-[(3-chlorophenyl)-(2-methylacryloyl)amino]propoxy}-phenyl)propionic acid | rt: 8.54<br>MS[M, M+2]⁺: 597, 599 | A |
| I_48 | IIa_47 | (S)-2-(2-Benzoylphenylamino)-3-(4-{2-[but-2-(E)-enoyl-(3-chlorophenyl)-amino]ethoxy}phenyl)propionic acid | rt: 8.45<br>MS[M, M+2]⁺: 583, 585 | A |
| I_49 | IIa_48 | (S)-2-(2-Benzoylphenylamino)-3-(4-{3-[but-2-(E)-enoyl-(3-chlorophenyl)-amino]propoxy}phenyl)propionic acid | rt: 8.596<br>MS[M, M+2]⁺: 597, 599 | A |
| I_50 | IIa_49 | (S)-2-(2-Benzoylphenylamino)-3-(4-{2-[(3-chlorophenyl)-(3-methylbutyryl)-amino]ethoxy}phenyl)propionic acid | rt: 8.877<br>MS[M, M+2]⁺: 599, 601 | A |
| I_51 | IIa_50 | (S)-2-(2-Benzoylphenylamino)-3-(4-{2-[(3-chlorophenyl)-pent-4-enoylamino]ethoxy}phenyl)propionic acid | rt: 8.68<br>MS[M, M+2]⁺: 597, 599 | A |
| I_52 | IIa_51 | (S)-2-(2-Benzoylphenylamino)-3-(4-{2-[(3-chlorophenyl)-cyclobutanecarbonylamino]ethoxy}-phenyl)propionic acid | rt: 8.787<br>MS[M, M+2]⁺: 597, 599 | A |
| I_53 | IIa_52 | (S)-2-(2-Benzoylphenylamino)-3-(4-{2-[(3-chlorophenyl)-cyclopentanecarbonylamino]ethoxy}-phenyl)propionic acid | rt: 9.040<br>MS[M, M+2]⁺: 611, 613 | A |
| I_54 | IIa_53 | (S)-2-(2-Benzoylphenylamino)-3-(4-{2-[(3-chlorophenyl)-cyclopropanecarbonylamino]ethoxy}-phenyl)propionic acid | rt: 8.481<br>MS[M, M+2]⁺: 583, 585 | A |
| I_55 | IIa_54 | (S)-2-(2-Benzoylphenylamino)-3-(4-{3-[(3-chlorophenyl)-cyclopropanecarbonylamino]propoxy}-phenyl)propionic acid | rt: 8.645; MS[M, M+2]⁺: 597, 599 | A |
| I_56 | IIa_55 | (S)-2-(2-Benzoylphenylamino)-3-(4-{2-[(3-chlorophenyl)propioylamino]-ethoxy}phenyl)propionic acid | rt: 8.345<br>MS[M, M+2]⁺: 571, 573 | A |

TABLE 6-continued

| Example Number | Starting product | Compound name | ¹H-NMR/LC-MS | HPLC Method |
|---|---|---|---|---|
| I_57 | IIa_56 | (S)-2-(2-Benzoylphenylamino)-3-(4-{3-[(3-chlorophenyl)propionylamino]-propoxy}phenyl)propionic acid | rt: 8.509<br>MS[M, M+2]$^+$: 585, 587 | A |
| I_58 | IIa_57 | (S)-2-(2-Benzoylphenylamino)-3-(4-{2-[(3-chlorophenyl)isobutyrylamino]-ethoxy}phenyl)propionic acid | rt: 8.613<br>MS[M, M+2]$^+$: 585, 587 | A |
| I_59 | IIa_58 | (S)-2-(2-Benzoylphenylamino)-3-(4-{3-[(3-chlorophenyl)isobutyrylamino]-propoxy}phenyl)propionic acid | rt: 8.768<br>MS[M, M+2]$^+$: 599, 601 | A |
| I_60 | IIa_59 | (S)-2-(2-Benzoylphenylamino)-3-(4-{2-[butyryl-(3-chlorophenyl)amino]-ethoxy}phenyl)propionic acid | rt: 8.623<br>MS[M, M+2]$^+$: 585, 587 | A |
| I_61 | IIa_60 | (S)-2-(2-Benzoylphenylamino)-3-(4-{3-[butyryl-(3-chlorophenyl)amino]-propoxy}phenyl)propionic acid | rt: 8.779; MS[M, M+2]$^+$: 599, 601 | A |
| I_62 | IIa_61 | (S)-2-(2-Benzoylphenylamino)-3-(4-{2-[(3-chlorophenyl)-(2,2-dimethylpropionyl)amino]ethoxy}-phenyl)propionic acid | rt: 8.995<br>MS[M, M+2]$^+$: 599, 601 | A |
| I_63 | IIa_62 | (S)-3-(4-{3-[Acryloyl-(3-chlorophenyl)-amino]propoxy}phenyl)-2-(2-benzoylphenylamino)propionic acid | rt: 8.419<br>MS[M, M+2]$^+$: 583, 585 | A |
| I_64 | IIa_63 | (S)-2-(2-Benzoylphenylamino)-3-(4-{2-[(3-fluorophenyl)-(thiophene-2-carbonyl)amino]ethoxy}phenyl)-propionic acid | rt: 8.250<br>MS[M+1]$^+$: 609 | A |
| I_65 | IIa_64 | (S)-2-(2-Benzoylphenylamino)-3-(4-{2-[(3-fluorophenyl)-(2-methylacryloyl)amino]ethoxy}phenyl)-propionic acid | rt: 8.062<br>MS[M+1]$^+$: 567 | A |
| I_66 | IIa_65 | (S)-2-(2-Benzoylphenylamino)-3-(4-{2-[(3-fluorophenyl)-(3-methylbutyryl)-amino]ethoxy}phenyl)propionic acid | rt: 8.538<br>MS[M+1]$^+$: 583 | A |
| I_67 | IIa_66 | (S)-2-(2-Benzoylphenylamino)-3-(4-{2-[cyclobutanecarbonyl-(3-fluorophenyl)amino]ethoxy}phenyl)-propionic acid | rt: 8.431<br>MS[M+1]$^+$: 581 | A |
| I_68 | IIa_67 | (S)-2-(2-Benzoylphenylamino)-3-(4-{2-[cyclopentanecarbonyl-(3-fluorophenyl)amino]ethoxy}phenyl)-propionic acid | rt: 8.688<br>MS[M+1]$^+$: 595 | A |
| I_69 | IIa_68 | (S)-2-(2-Benzoylphenylamino)-3-(4-{2-[cyclopropanecarbonyl-(3-fluorophenyl)amino]ethoxy}phenyl)-propionic acid | rt: 8.134<br>MS[M+1]$^+$: 567 | A |
| I_70 | IIa_69 | (S)-2-(2-Benzoylphenylamino)-3-(4-{2-[(3-fluorophenyl)propionylamino]-ethoxy}phenyl)propionic acid | rt: 7.998<br>MS[M+1]$^+$: 555 | A |
| I_71 | IIa_70 | (S)-2-(2-Benzoylphenylamino)-3-(4-{2-[(3-fluorophenyl)isobutyrylamino]-ethoxy}phenyl)propionic acid | rt: 8.267<br>MS[M+1]$^+$: 569 | A |
| I_72 | IIa_71 | (S)-2-(2-Benzoylphenylamino)-3-(4-{2-[butyryl-(3-fluorophenyl)amino]-ethoxy}phenyl)propionic acid | rt: 8.278<br>MS[M+1]$^+$: 569 | A |
| I_73 | IIa_72 | (S)-2-(2-Benzoylphenylamino)-3-(4-{2-[(2,2-dimethylpropionyl)-(3-fluorophenyl)amino]ethoxy}phenyl)-propionic acid | rt: 8.65<br>MS[M+1]$^+$: 583 | A |
| I_74 | IIa_73 | (S)-2-(2-Benzoylphenylamino)-3-(4-{3-[(2-methylacryloyl)-(3-methylbenzyl)amino]propoxy}phenyl)-propionic acid | rt: 8.439<br>MS[M+1]$^+$: 591 | A |
| I_75 | IIa_74 | (S)-2-(2-Benzoylphenylamino)-3-(4-{2-[(2-ethylbutyryl)-(3-methylbenzyl)-amino]ethoxy}phenyl)propionic acid | rt: 8.973<br>MS[M+1]$^+$: 607 | A |
| I_76 | IIa_75 | (S)-2-(2-Benzoylphenylamino)-3-(4-{3-[(3-methylbenzyl)-(3-methylbut-2-(E)-enoyl)amino]propoxy}phenyl)-propionic acid | rt: 8.634<br>MS[M+1]$^+$: 605 | A |
| I_77 | IIa_76 | (S)-2-(2-Benzoylphenylamino)-3-(4-{3-[but-2-(E)-enoyl-(3-methylbenzyl)-amino]propoxy}phenyl)propionic acid | rt: 8.381<br>MS[M+1]$^+$: 591 | A |
| I_78 | IIa_77 | (S)-2-(2-Benzoylphenylamino)-3-(4-{2-[(3,3-dimethylbutyryl)-(3-methylbenzyl)amino]ethoxy}phenyl)-propionic acid | rt: 9.041<br>MS[M+1]$^+$: 607 | A |

TABLE 6-continued

| Example Number | Starting product | Compound name | $^1$H-NMR/LC-MS | HPLC Method |
|---|---|---|---|---|
| I_79 | IIa_78 | (S)-2-(2-Benzoylphenylamino)-3-(4-{2-[(3-methylbenzyl)-(3-methylbutyryl)amino]ethoxy}phenyl)-propionic acid | rt: 8.745<br>MS[M+1]$^+$: 593 | A |
| I_80 | IIa_79 | (S)-2-(2-Benzoylphenylamino)-3-(4-{3-[(3-methylbenzyl)-(3-methylbutyryl)amino]propoxy}phenyl)-propionic acid | rt: 8.828<br>MS[M+1]$^+$: 607 | A |
| I_81 | IIa_80 | (S)-2-(2-Benzoylphenylamino)-3-(4-{2-[cyclobutanecarbonyl-(3-methylbenzyl)amino]ethoxy}phenyl)-propionic acid | rt: 8.645<br>MS[M+1]$^+$: 591 | A |
| I_82 | IIa_81 | (S)-2-(2-Benzoylphenylamino)-3-(4-{3-[cyclobutanecarbonyl-(3-methylbenzyl)amino]propoxy}phenyl)-propionic acid | rt: 8.722<br>MS[M+1]$^+$: 605 | A |
| I_83 | IIa_82 | (S)-2-(2-Benzoylphenylamino)-3-(4-{2-[cyclopentanecarbonyl-(3-methylbenzyl)amino]ethoxy}phenyl)-propionic acid | rt: 8.874<br>MS[M+1]$^+$: 605 | A |
| I_84 | IIa_83 | (S)-2-(2-Benzoylphenylamino)-3-(4-{3[cyclopropanecarbonyl-(3-methylbenzyl)amino]propoxy}phenyl)-propionic acid | rt: 8.422<br>MS[M+1]$^+$: 591 | A |
| I_85 | IIa_84 | (S)-2-(2-Benzoylphenylamino)-3-(4-{3-[(3-methylbenzyl)propionylamino]-propoxy}phenyl)propionic acid | rt: 8.31<br>MS[M+1]$^+$: 579 | A |
| I_86 | IIa_85 | (S)-2-(2-Benzoylphenylamino)-3-(4-{2-[isobutyryl-(3-methylbenzyl)amino]-ethoxy}phenyl)propionic acid | rt: 8.468<br>MS[M+1]$^+$: 579 | A |
| I_87 | IIa_86 | (S)-2-(2-Benzoylphenylamino)-3-(4-{3-[isobutyryl-(3-methylbenzyl)amino]-propoxy}phenyl)propionic acid | rt: 8.56<br>MS[M+1]$^+$: 593 | A |
| I_88 | IIa_87 | (S)-2-(2-Benzoylphenylamino)-3-(4-{2-[butyryl-(3-methylbenzyl)amino]-ethoxy}phenyl)propionic acid | rt: 8.489<br>MS[M+1]$^+$: 579 | A |
| I_89 | IIa_88 | (S)-2-(2-Benzoylphenylamino)-3-(4-{3-[butyryl-(3-methylbenzl)amino]-propoxy}phenyl)propionic acid | rt: 8.574<br>MS[M+1]$^+$: 593 | A |
| I_90 | IIa_89 | (S)-3-(4-{2-[Benzoyl-(3-methylbenzyl)-amino]ethoxy}phenyl)-2-(2-benzoylphenylamino)propionic acid | rt: 8.545<br>MS[M+1]$^+$: 613 | A |
| I_91 | IIa_90 | (S)-2-(2-Benzoylphenylamino)-3-(4-{2-[(2,2-dimethylpropionyl)-(3-methylbenzyl)amino]ethoxy}phenyl)-propionic acid | rt: 8.886<br>MS[M+1]$^+$: 593 | A |
| I_92 | IIa_91 | (S)-2-(2-Benzoylphenylamino)-3-(4-{3-[(2,2-dimethylpropionyl)-(3-methylbenzyl)amino]propoxy}phenyl)-propionic acid | rt: 8.909<br>MS[M+1]$^+$: 607 | A |
| I_93 | IIa_92 | (S)-2-(2-Benzoylphenylamino)-3-(4-{3-[(2-methylacryloyl)-m-tolylamino]-propoxy}phenyl)propionic acid | rt: 8.472<br>MS[M+1]$^+$: 577 | A |
| I_94 | IIa_93 | (S)-2-(2-Benzoylphenylamino)-3-(4-{2-[(2-ethylbutyryl)-m-tolylamino]-ethoxy}phenyl)propionic acid | rt: 9.062<br>MS[M+1]$^+$: 593 | A |
| I_95 | IIa_94 | (S)-2-(2-Benzoylphenylamino)-3-(4-{3-[(3-methylbut-2-(E)-enoyl)-m-tolylamino]propoxy}phenyl)propionic acid | rt: 8.826<br>MS[M+1]$^+$: 591 | A |
| I_96 | IIa_95 | (S)-2-(2-Benzoylphenylamino)-3-{4-[3-(but-2-(E)-enoyl-m-tolylamino)-propoxy]phenyl}propionic acid | rt: 8.554<br>MS[M+1]$^+$: 577 | A |
| I_97 | IIa_96 | (S)-2-(2-Benzoylphenylamino)-3-(4-{2-[(3,3-dimethylbutyryl)-m-tolylamino]ethoxy}phenyl)propionic acid | rt: 9.152<br>MS[M+1]$^+$: 593 | A |
| I_98 | IIa_97 | (S)-2-(2-Benzoylphenylamino)-3-(4-{2-[(3-methylbutyryl)-m-tolylamino]-ethoxy}phenyl)propionic acid | rt: 8.802<br>MS[M+1]$^+$: 579 | A |
| I_99 | IIa_98 | (S)-2-(2-Benzoylphenylamino)-3-{4-[2-(cyclobutanecarbonyl-m-tolyamino)-ethoxy]phenyl}propionic acid | rt: 8.724<br>MS[M+1]$^+$: 577 | A |
| I_100 | IIa_99 | (S)-2-(2-Benzoylphenylamino)-3-{4-[2-(cyclopentanecabonyl-m-tolyamino)-ethoxy]phenyl}propionic acid | rt: 8.958<br>MS[M+1]$^+$: 591 | A |

TABLE 6-continued

| Example Number | Starting product | Compound name | $^1$H-NMR/LC-MS | HPLC Method |
|---|---|---|---|---|
| I_101 | IIa_100 | (S)-2-(2-Benzoylphenylamino)-3-{4-[3-(cyclopropanecarbonyl-m-tolylamino)-propoxy]phenyl}propionic acid | rt: 8.607<br>MS[M+1]$^+$: 577 | A |
| I_102 | IIa_101 | (S)-2-(2-Benzoylphenylamino)-3-{4-[3-(propionyl-m-tolylamino)propoxy]-phenyl}propionic acid | rt: 8.468<br>MS[M+1]$^+$: 565 | A |
| I_103 | IIa_102 | (S)-2-(2-Benzoylphenylamino)-3-{4-[2-(isobutyryl-m-tolylamino)ethoxy]-phenyl}propionic acid | rt: 8.532<br>MS[M+1]$^+$: 565 | A |
| I_104 | IIa_103 | (S)-2-(2-Benzoylphenylamino)-3-{4-[3-(isobutyryl-m-tolylamino)propoxy]-phenyl}propionic acid | rt: 8.731<br>MS[M+1]$^+$: 579 | A |
| I_105 | IIa_104 | (S)-2-(2-Benzoylphenylamino)-3-{4-[3-(pentanoyl-m-tolylamino)propoxy]-phenyl}propionic acid | rt: 9.025<br>MS[M+1]$^+$: 593 | A |
| I_106 | IIa_105 | (S)-2-(2-Benzoylphenylamino)-3-{4-[2-(butyryl-m-tolylamino)ethoxy]phenyl}-propionic acid | rt: 8.543<br>MS[M+1]$^+$: 565 | A |
| I_107 | IIa_106 | (S)-2-(2-Benzoylphenylamino)-3-{4-[3-(butyryl-m-tolylamino)propoxy]-phenyl}propionic acid | rt: 8.741<br>MS[M+1]$^+$: 579 | A |
| I_108 | IIa_107 | (S)-2-(2-Benzoylphenylamino)-3-{4-[2-(benzoyl-m-tolylamino)ethoxy]phenyl}-propionic acid | rt: 8.436<br>MS[M+1]$^+$: 599 | A |
| I_109 | IIa_108 | (S)-2-(2-Benzoylphenylamino)-3-(4-{2-[(2,2-dimethylpropionyl)-m-tolylamino]ethoxy}phenyl)propionic acid | rt: 8.953<br>MS[M+1]$^+$: 579 | A |
| I_110 | IIa_109 | (S)-2-(2-Benzoylphenylamino)-3-(4-{3-[(2,2-dimethylpropionyl)-m-tolylamino]propoxy}phenyl)propionic acid | rt: 9.109<br>MS[M+1]$^+$: 593 | A |
| I_111 | IIa_110 | (S)-3-{4-[3-(Acryloyl-m-tolylamino)-propoxy]phenyl}-2-(2-benzoylphenylamino)propionic acid | rt: 8.388<br>MS[M+1]$^+$: 563 | A |
| I_112 | IIa_111 | (S)-2-(2-Benzoylphenylamino)-3-(4-{2-[(4-chlorophenyl)-(2-methylacryloyl)amino]ethoxy}phenyl)-propionic acid | rt: 8.437<br>MS[M, M+2]$^+$: 583, 586 | A |
| I_113 | IIa_491 | (S)-2-(2-Benzoylphenylamino)-3-(4-{3-[(4-chlorophenyl)-(2-methylacryloyl)amino]propoxy}-phenyl)propionic acid | rt: 8.595<br>MS[M, M+2]$^+$: 597, 599 | A |
| I_114 | IIa_112 | (S)-2-(2-Benzoylphenyamino)-3-(4-{2-[but-2-(E)-enoyl-(4-chlorophenyl)-amino]ethoxy}phenyl)propionic acid | rt: 8.517<br>MS[M, M+2]$^+$: 583, 585 | A |
| I_115 | IIa_113 | (S)-2-(2-Benzoylphenylamino)-3-(4-{2-[(4-chlorophenyl)-(3-methylbutyryl)-amino]ethoxy}phenyl)propionic acid | rt: 8.942<br>MS[M, M+2]$^+$: 599, 601 | A |
| I_116 | IIa_114 | (S)-2-(2-Benzoylphenylamino)-3-(4-{2-[(4-chlorophenyl)-pent-4-enoylamino]ethoxy}phenyl)propionic acid | rt: 8.739<br>MS[M, M+2]$^+$: 597, 599 | A |
| I_117 | IIa_115 | (S)-2-(2-Benzoylphenylamino)-3-(4-{2-[(4-chlorophenyl)-cyclobutanecarbonylamino]ethoxy}-phenyl)propionic acid | rt: 8.839<br>MS[M, M+2]$^+$: 597, 599 | A |
| I_118 | IIa_116 | (S)-2-(2-Benzoylphenylamino)-3-(4-{2-[(4-chlorophenyl)-cyclopentanecarbonylamino]ethoxy}-phenyl)propionic acid | rt: 9.103<br>MS[M, M+2]$^+$: 611, 613 | A |
| I_119 | IIa_117 | (S)-2-(2-Benzoylphenylamino)-3-(4-{2-[(4-chlorophenyl)-cyclopropanecarbonylamino]ethoxy}-phenyl)propionic acid | rt: 8.533<br>MS[M, M+2]$^+$: 583, 585 | A |
| I_120 | IIa_118 | (S)-2-(2-Benzoylphenylamino)-3-(4-{3-[(4-chlorophenyl)-cyclopropanecarbonylamino]propoxy}-phenyl)propionic acid | rt: 9.696<br>MS[M, M+2]$^+$: 597, 599 | A |
| I_121 | IIa_119 | (S)-2-(2-Benzoylphenylamino)-3-(4-{2-[(4-chlorophenyl)propionylamino]-ethoxy}phenyl)propionic acid | rt: 8.399<br>MS[M, M+2]$^+$: 571, 573 | A |
| I_122 | IIa_120 | (S)-2-(2-Benzoylphenylamino)-3-(4-{3-[(4-chlorophenyl)propionylamino]-propoxy}phenyl)propionic acid | rt: 8.562<br>MS[M, M+2]$^+$: 585, 587 | A |

TABLE 6-continued

| Example Number | Starting product | Compound name | ¹H-NMR/LC-MS | HPLC Method |
|---|---|---|---|---|
| I_123 | IIa_121 | (S)-2-(2-Benzoylphenylamino)-3-(4-{2-[(4-chlorophenyl)isobutyrylamino]-ethoxy}phenyl)propionic acid | rt: 8.682<br>MS[M, M+2]$^+$: 585, 587 | A |
| I_124 | IIa_122 | (S)-2-(2-Benzoylphenylamino)-3-(4-{3-[(4-chlorophenyl)isobutyrylamino]-propoxy}phenyl)propionic acid | rt: 8.835<br>MS[M, M+2]$^+$: 599, 601 | A |
| I_125 | IIa_123 | (S)-2-(2-Benzoylphenylamino)-3-(4-{2-[butyryl-(4-chlorophenyl)amino]-ethoxy}phenyl)propionic acid | rt: 8.684<br>MS[M, M+2]$^+$: 585, 587 | A |
| I_126 | IIa_124 | (S)-2-(2-Benzoylphenylamino)-3-(4-{3-[butyryl-(4-chlorophenyl)amino]-propoxy}phenyl)propionic acid | rt: 8.836<br>MS[M, M+2]$^+$: 599, 601 | A |
| I_127 | IIa_125 | (S)-2-(2-Benzoylphenylamino)-3-(4-{2-[(4-chlorophenyl)-(2,2-dimethylpropionyl)amino]ethoxy}-phenyl)propionic acid | rt: 9.043<br>MS[M, M+2]$^+$: 599, 601 | A |
| I_128 | IIa_126 | (S)-3-(4-{3-[Acryloyl-(4-chlorophenyl)-amino]propoxy}phenyl)-2-(2-benzoylphenylamino)propionic acid | rt: 8.475<br>MS[M, M+2]$^+$: 583, 585 | A |
| I_129 | IIa_127 | (S)-2-(2-Benzoylphenylamino)-3-(4-{2-[(4-fluorophenyl)-(thiophene-2-carbonyl)amino]ethoxy}phenyl)-propionic acid | rt: 8.247<br>MS[M+1]$^+$: 609 | A |
| I_130 | IIa_128 | (S)-2-(2-Benzoylphenylamino)-3-(4-{2-[(4-fluorophenyl)-(2-methylacryloyl)amino]ethoxy}phenyl)-propionic acid | rt: 8.026<br>MS[M+1]$^+$: 567 | A |
| I_131 | IIa_129 | (S)-2-(2-Benzoylphenylamino)-3-(4-{2-[(4-fluorophenyl)-(3-methylbut-2-(E)-enoyl)amino]ethoxy}phenyl)-propionic acid | rt: 8.365<br>MS[M+1]$^+$: 581 | A |
| I_132 | IIa_130 | (S)-2-(2-Benzoylphenylamino)-3-(4-{2-[(4-fluorophenyl)-(3-methylbutyryl)-amino]ethoxy}phenyl)propionic acid | rt: 8.528<br>MS[M+1]$^+$: 583 | A |
| I_133 | IIa_131 | (S)-2-(2-Benzoylphenylamino)-3-(4-{2-[cyclobutanecarbonyl-(4-fluorophenyl)amino]ethoxy}phenyl)-propionic acid | rt: 8.421<br>MS[M+1]$^+$: 581 | A |
| I_134 | IIa_132 | (S)-2-(2-Benzoylphenylamino)-3-(4-{2-[cyclopentanecarbonyl-(4-fluorophenyl)amino]ethoxy}phenyl)-propionic acid | rt: 8.675<br>MS[M+1]$^+$: 595 | A |
| I_135 | IIa_133 | (S)-2-(2-Benzoylphenylamino)-3-(4-{2-[cyclopropanecarbonyl-(4-fluorophenyl)amino]ethoxy}phenyl)-propionic acid | rt: 8.117<br>MS[M+1]$^+$: 567 | A |
| I_136 | IIa_134 | (S)-2-(2-Benzoylphenylamino)-3-(4-{2-[(4-fluorophenyl)propionylamino]-ethoxy}phenyl)propionic acid | rt: 7.987<br>MS[M+1]$^+$: 555 | A |
| I_137 | IIa_135 | (S)-2-(2-Benzoylphenylamino)-3-(4-{2-[(4-fluorophenyl)isobutyrylamino]-ethoxy}phenyl)propionic acid | rt: 8.253<br>MS[M+1]$^+$: 569 | A |
| I_138 | IIa_136 | (S)-2-(2-Benzoylphenylamino)-3-(4-{2-[butyryl-(4-fluorophenyl)amino]-ethoxy}phenyl)propionic acid | rt: 8.266<br>MS[M+1]$^+$: 569 | A |
| I_139 | IIa_137 | (S)-2-(2-Benzoylphenylamino)-3-(4-{2-[(2,2-dimethylpropionyl)-(4-fluorophenyl)amino]ethoxy}phenyl)-propionic acid | rt: 8.64<br>MS[M+1]$^+$: 583 | A |
| I_140 | IIa_138 | (S)-2-(2-Benzoylphenylamino)-3-(4-{3-[(2-methylacryloyl)-p-tolylamino]-propoxy}phenyl)propionic acid | rt: 8.483<br>MS[M+1]$^+$: 577 | A |
| I_141 | IIa_139 | (S)-2-(2-Benzoylphenylamino)-3-(4-{2-[(2-ethylbutyryl)-p-tolylamino]-ethoxy}phenyl)propionic acid | rt: 9.088<br>MS[M+1]$^+$: 593 | A |
| I_142 | IIa_140 | (S)-2-(2-Benzoylphenylamino)-3-(4-{2-[(3,3-dimethylbutyryl)-p-tolylamino]-ethoxy}phenyl)propionic acid | rt: 9.178<br>MS[M+1]$^+$: 593 | A |
| I_143 | IIa_141 | (S)-2-(2-Benzoylphenylamino)-3-(4-{2-[(3-methylbutyryl)-p-tolylamino]-ethoxy}phenyl)propionic acid | rt: 8.827<br>MS[M+1]$^+$: 579 | A |
| I_144 | IIa_142 | (S)-2-(2-Benzoylphenylamino)-3-(4-{3-[(3-methylbutyryl)-p-tolylamino]-propoxy}phenyl)propionic acid | rt: 9.025<br>MS[M+1]$^+$: 593 | A |

TABLE 6-continued

| Example Number | Starting product | Compound name | $^1$H-NMR/LC-MS | HPLC Method |
|---|---|---|---|---|
| I_145 | IIa_143 | (S)-2-(2-Benzoylphenylamino)-3-{4-[2-(cyclobutanecarbonyl-p-tolylamino)-ethoxy]phenyl}propionic acid | rt: 8.737<br>MS[M+1]$^+$: 577 | A |
| I_146 | IIa_144 | (S)-2-(2-Benzoylphenylamino)-3-{4-[3-(cyclobutanecarbonyl-p-tolylamino)-propoxy]phenyl}propionic acid | rt: 8.936<br>MS[M+1]$^+$: 591 | A |
| I_147 | IIa_145 | (S)-2-(2-Benzoylphenylamino)-3-{4-[2-(cyclopentanecarbonyl-p-tolylamino)-ethoxy]phenyl}propionic acid | rt: 8.992<br>MS[M+1]$^+$: 591 | A |
| I_148 | IIa_146 | (S)-2-(2-Benzoylphenylamino)-3-{4-[3-(propionyl-p-tolylamino)propoxy]-phenyl}propionic acid | rt: 8.486<br>MS[M+1]$^+$: 565 | A |
| I_149 | IIa_147 | (S)-2-(2-Benzoylphenylamino)-3-{4-[2-(isobutyryl-p-tolylamino)ethoxy]-phenyl}propionic acid | rt: 8.554<br>MS[M+1]$^+$: 565 | A |
| I_150 | IIa_148 | (S)-2-(2-Benzoylphenylamino)-3-{4-[3-(isobutyryl-p-tolylamino)propoxy]-phenyl}propionic acid | rt: 8.758<br>MS[M+1]$^+$: 579 | A |
| I_151 | IIa_149 | (S)-2-(2-Benzoylphenylamino)-3-{4-[2-(butyryl-p-tolylamino)ethoxy]phenyl}-propionic acid | rt: 8.561<br>MS[M+1]$^+$: 565 | A |
| I_152 | IIa_150 | (S)-2-(2-Benzoylphenylamino)-3-{4-[2-(benzoyl-p-tolylamino)ethoxy]phenyl}-propionic acid | rt: 8.431<br>MS[M+1]$^+$: 599 | A |
| I_153 | IIa_151 | (S)-2-(2-Benzoylphenylamino)-3-(4-{2-[(2,2-dimethylpropionyl)-p-tolylamino]ethoxy}phenyl)propionic acid | rt: 8.967<br>MS[M+1]$^+$: 579 | A |
| I_154 | IIa_152 | (S)-2-(2-Benzoylphenylamino)-3-(4-{3-[(2,2-dimethylpropionyl)-p-tolylamino]propoxy}phenyl)propionic acid | rt: 9.126<br>MS[M+1]$^+$: 593 | A |
| I_155 | IIa_153 | (S)-2-(2-Benzoylphenylamino)-3-(4-{2-[benzyl(naphthalene-1-carbonyl)-amino]ethoxy}phenyl)propionic acid | rt: 8.702<br>MS[M+1]$^+$: 649 | A |
| I_156 | IIa_154 | (S)-2-(2-Benzoylphenylamino)-3-(4-{2-[benzyl(naphthalene-2-carbonyl)-amino]ethoxy}phenyl)propionic acid | rt: 8.744<br>MS[M+1]$^+$: 649 | A |
| I_157 | IIa_155 | (S)-2-(2-Benzoylphenylamino)-3-(4-{2-[benzyl(pyrazine-2-carbonyl)-amino]ethoxy}phenyl)propionic acid | rt: 7.713<br>MS[M+1]$^+$: 601 | A |
| I_158 | IIa_156 | (S)-2-(2-Benzoylphenylamino)-3-(4-{3-[benzyl(pyrazine-2-carbonyl)-amino]propoxy}phenyl)propionic acid | rt: 7.813<br>MS[M+1]$^+$: 615 | A |
| I_159 | IIa_157 | (S)-2-(2-Benzoylphenylamino)-3-(4-{2-[benzyl(pyridine-2-carbonyl)amino]-ethoxy}phenyl)propionic acid | rt: 7.866<br>MS[M+1]$^+$: 600 | A |
| I_160 | IIa_158 | (S)-2-(2-Benzoylphenylamino)-3-(4-{3-[benzyl(pyridine-2-carbonyl)amino]-propoxy}phenyl)propionic acid | rt: 7.978<br>MS[M+1]$^+$: 614 | A |
| I_161 | IIa_159 | (S)-2-(2-Benzoylphenylamino)-3-(4-{2-[benzyl(quinoline-2-carbonyl)-amino]ethoxy}phenyl)propionic acid | rt: 8.538<br>MS[M+1]$^+$: 650 | A |
| I_162 | IIa_160 | (S)-2-(2-Benzoylphenylamino)-3-(4-{3-[benzyl(quinoline-2-carbonyl)-amino]propoxy}phenyl)propionic acid | rt: 8.602<br>MS[M+1]$^+$: 664 | A |
| I_163 | IIa_161 | (S)-2-(2-Benzoylphenylamino)-3-(4-{2-[benzyl(quinoxaline-2-carbonyl)-amino]ethoxy}phenyl)propionic acid | rt: 8.374<br>MS[M+1]$^+$: 651 | A |
| I_164 | IIa_162 | (S)-2-(2-Benzoylphenylamino)-3-(4-{3-[benzyl(quinoxaline-2-carbonyl)-amino]propoxy}phenyl)propionic acid | rt: 8.455<br>MS[M+1]$^+$: 665 | A |
| I_165 | IIa_163 | (S)-2-(2-Benzoylphenylamino)-3-(4-{2-[benzyl(thiophene-2-carbonyl)-amino]ethoxy}phenyl)propionic acid | rt: 8.331<br>MS[M+1]$^+$: 605 | A |
| I_166 | IIa_164 | (S)-2-(2-Benzoylphenylamino)-3-(4-{3-[benzyl(thiophene-2-carbonyl)-amino]propoxy}phenyl)propionic acid | rt: 8.415<br>MS[M+1]$^+$: 619 | A |
| I_167 | IIa_165 | (S)-2-(2-Benzoylphenylamino)-3-(4-{2-[benzyl(furan-3-carbonyl)amino]-ethoxy}phenyl)propionic acid | rt: 8.026<br>MS[M+1]$^+$: 589 | A |
| I_168 | IIa_166 | (S)-2-(2-Benzoylphenylamino)-3-(4-{3-[benzyl(furan-3-carbonyl)amino]-propoxy}phenyl)propionic acid | rt: 8.105<br>MS[M+1]$^+$: 603 | A |

TABLE 6-continued

| Example Number | Starting product | Compound name | $^1$H-NMR/LC-MS | HPLC Method |
|---|---|---|---|---|
| I_169 | IIa_167 | (S)-2-(2-Benzoylphenylamino)-3-(4-{2-[benzyl(isoquinoline-3-carbonyl)-amino]ethoxy}phenyl)propionic acid | rt: 8.318<br>MS[M+1]$^+$: 650 | A |
| I_170 | IIa_168 | (S)-2-(2-Benzoylphenylamino)-3-(4-{3-[benzyl(isoquinoline-3-carbonyl)-amino]propoxy}phenyl)propionic acid | rt: 8.383<br>MS[M+1]$^+$: 664 | A |
| I_171 | IIa_169 | (S)-2-(2-Benzoylphenylamino)-3-(4-{2-[benzyl(pyridine-3-carbonyl)amino]-ethoxy}phenyl)propionic acid | rt: 7.448<br>MS[M+1]$^+$: 600 | A |
| I_172 | IIa_170 | (S)-2-(2-Benzoylphenylamino)-3-(4-{3-[benzyl(pyridine-3-carbonyl)amino]-propoxy}phenyl)propionic acid | rt: 7.584<br>MS[M+1]$^+$: 614 | A |
| I_173 | IIa_171 | (S)-2-(2-Benzoylphenylamino)-3-{4-[2-(benzylphenylacetylamino)ethoxy]-phenyl}propionic acid | rt: 8.461<br>MS[M+1]$^+$: 613 | A |
| I_174 | IIa_172 | (S)-2-(2-Benzoylphenylamino)-3-{4-[3-(benzylphenylacetylamino)propoxy]-phenyl}propionic acid | rt: 8.489<br>MS[M+1]$^+$: 627 | A |
| I_175 | IIa_173 | (S)-2.(2-Benzoylphenylamino)-3-(4-{2-[benzyl-(2-methylacryloyl)amino]-ethoxy}phenyl)propionic acid | rt: 8.057<br>MS[M+1]$^+$: 563 | A |
| I_176 | IIa_174 | (S)-2-(2-Benzoylphenylamino)-3-(4-{3-[benzyl-(2-methylacryloyl)amino]-propoxy}phenyl)propionic acid | rt: 8.14<br>MS[M+1]$^+$: 577 | A |
| I_177 | IIa_175 | (S)-2-(2-Benzoylphenylamino)-3-(4-{2-[benzyl-(3-phenylpropynoyl)amino]-ethoxy}phenyl)propionic acid | rt: 8.675<br>MS[M+1]$^+$: 623 | A |
| I_178 | IIa_176 | (S)-2-(2-Benzoylphenylamino)-3-(4-{3-[benzyl-(3-phenylpropynoyl)amino]-propoxy}phenyl)propionic acid | rt: 8.762<br>MS[M+1]$^+$: 637 | A |
| I_179 | IIa_177 | (S)-2-(2-Benzoylphenylamino)-3-(4-{2-[benzyl-(2-ethylbutyryl)amino]-ethoxy}phenyl)propionic acid | rt: 8.711<br>MS[M+1]$^+$: 593 | A |
| I_180 | IIa_178 | (S)-2-(2-Benzoylphenylamino)-3-(4-{3-[benzyl-(2-ethylbutyryl)amino]-propoxy}phenyl)propionic acid | rt: 8.766<br>MS[M+1]$^+$: 607 | A |
| I_181 | IIa_179 | (S)-2-(2-Benzoylphenylamino)-3-(4-{2-[benzyl-(3-methylbut-2-(E)-enoyl)-amino]ethoxy}phenyl)propionic acid | rt: 8.278<br>MS[M+1]$^+$: 577 | A |
| I_182 | IIa_180 | (S)-2-(2-Benzoylphenylamino)-3-(4-{3-[benzyl-(3-methylbut-2-(E)-enoyl)-amino]propoxy}phenyl)propionic acid | rt: 8.381<br>MS[M+1]$^+$: 591 | A |
| I_183 | IIa_181 | (S)-2-(2-Benzoylphenylamino)-3-(4-{2-[benzyl-(3-furan-2-ylacryloyl)-amino]ethoxy}phenyl)propionic acid | rt: 8.279<br>MS[M+1]$^+$: 615 | A |
| I_184 | IIa_182 | (S)-2-(2-Benzoylphenylamino)-3-(4-{3-[benzyl-(3-furan-2-ylacryloyl)-amino]propoxy}phenyl)propionic acid | rt: 8.386<br>MS[M+1]$^+$: 629 | A |
| I_185 | IIa_183 | (S)-2-(2-Benzoylphenylamino)-3-(4-{2-[benzyl-(3-thiophen-2-ylacryloyl)-amino]ethoxy}phenyl)propionic acid | rt: 8.436<br>MS[M+1]$^+$: 631 | A |
| I_186 | IIa_184 | (S)-2-(2-Benzoylphenylamino)-3-(4-{3-[benzyl-(3-thiophen-2-ylacryloyl)-amino]propoxy}phenyl)propionic acid | rt: 8.551<br>MS[M+1]$^+$: 645 | A |
| I_187 | IIa_185 | (S)-2-(2-Benzoylphenylamino)-3-(4-{2-[benzyl-(3-furan-3-yl-(E)-acryloyl)-amino]ethoxy}phenyl)propionic acid | rt: 8.158<br>MS[M+1]$^+$: 615 | A |
| I_188 | IIa_186 | (S)-2-(2-Benzoylphenylamino)-3-(4-{3-[beznyl-(3-furan-3-yl-(E)-acryloyl)-amino]propoxy}phenyl)propionic acid | rt: 8.266<br>MS[M+1]$^+$: 629 | A |
| I_189 | IIa_187 | (S)-2-(2-Benzoylphenylamino)-3-(4-{2-[benzyl-(3-pyridin-3-yl-(E)-acryloyl)-amino]ethoxy}phenyl)propionic acid | rt: 7.303<br>MS[M+1]$^+$: 626 | A |
| I_190 | IIa_188 | (S)-2-(2-Benzoylphenylamino)-3-(4-{3-[benzyl-(3-pyridin-3-yl-(E)-acryloyl)-amino]propoxy}phenyl)propionic acid | rt: 7.428<br>MS[M+1]$^+$: 640 | A |
| I_191 | IIa_189 | (S)-2-(2-Benzoylphenylamino)-3-(4-{2-[benzyl-(3-thiophen-3-yl-(E)-acryloyl)amino]ethoxy}phenyl)-propionic acid | rt: 8.388<br>MS[M+1]$^+$: 631 | A |
| I_192 | IIa_190 | (S)-2-(2-Benzoylphenylamino)-3-(4-{3-[benzyl-(3-thiophen-3-yl-(E)-acryloyl)amino]propoxy}phenyl)-propionic acid | rt: 8.489<br>MS[M+1]$^+$: 645 | A |

TABLE 6-continued

| Example Number | Starting product | Compound name | ¹H-NMR/LC-MS | HPLC Method |
|---|---|---|---|---|
| I_193 | IIa_191 | (S)-2-(2-Benzoylphenylamino)-3-{4-[2-(benzylbut-2-(E)-enoylamino)ethoxy]-phenyl}propionic acid | rt: 8.008<br>MS[M+1]⁺: 563 | A |
| I_194 | IIa_192 | (S)-2-(2-Benzoylphenylamino)-3-{4-[3-(benzylbut-2-(E)-enoylamino)-propoxy]phenyl}propionic acid | rt: 8.114<br>MS[M+1]⁺: 577 | A |
| I_195 | IIa_193 | (S)-2-(2-Benzoylphenylamino)-3-(4-{2-[benzyl-(2-thiophen-2-ylacetyl)-amino]ethoxy}phenyl)propionic acid | rt: 8.325<br>MS[M+1]⁺: 619 | A |
| I_196 | IIa_194 | (S)-2-(2-Benzoylphenylamino)-3-(4-{3-[benzyl-(2-thiophe-2-ylacetyl)-amino]propoxy}phenyl)propionic acid | rt: 8.441<br>MS[M+1]⁺: 633 | A |
| I_197 | IIa_195 | (S)-2-(2-Benzoylphenylamino)-3-(4-{2-[benzyl-(2-pyridin-3-ylacetyl)-amino]ethoxy}phenyl)propionic acid | rt: 6.546<br>MS[M+1]⁺: 614 | A |
| I_198 | IIa_196 | (S)-2-(2-Benzoylphenylamino)-3-(4-{3-[benzyl-(2-pyridin-3-ylacetyl)-amino]propoxy}phenyl)propionic acid | rt: 6.683<br>MS[M+1]⁺: 628 | A |
| I_199 | IIa_197 | (S)-2-(2-Benzoylphenylamino)-3-(4-{2-[benzyl-(2-thiophen-3-ylacetyl)-amino]ethoxy}phenyl)propionic acid | rt: 8.32<br>MS[M+1]⁺: 619 | A |
| I_200 | IIa_198 | (S)-2-(2-Benzoylphenylamino)-3-(4-{3-[benzyl-(2-thiophen-3-ylacetyl)-amino]propoxy}phenyl)propionic acid | rt: 8.417<br>MS[M+1]⁺: 633 | A |
| I_201 | IIa_199 | (S)-2-(2-Benzoylphenylamino)-3-(4-{2-[benzyl(3,3-dimethylbutyryl)amino]-ethoxy}phenyl)propionic acid | rt: 8.803<br>MS[M+1]⁺: 593 | A |
| I_202 | IIa_200 | (S)-2-(2-Benzoylphenylamino)-3-(4-{3-[benzyl(3,3-dimethylbutyryl)amino]-propoxy}phenyl)propionic acid | rt: 8.88<br>MS[M+1]⁺: 607 | A |
| I_203 | IIa_201 | (S)-2-(2-Benzoylphenylamino)-3-(4-{2-[benzyl-(3-methylbutyryl)amino]-ethoxy}phenyl)propionic acid | rt: 8.483<br>MS[M+1]⁺: 579 | A |
| I_204 | IIa_202 | (S)-2-(2-Benzoylphenylamino)-3-(4-{3-[benzyl-(3-methylbutyryl)amino]-propoxy}phenyl)propionic acid | rt: 8.562<br>MS[M+1]⁺: 593 | A |
| I_205 | IIa_203 | (S)-2-(2-Benzoylphenylamino)-3-(4-{2-[benzyl-(3-pyridin-3-ylpropionyl)-amino]ethoxy}phenyl)propionic acid | rt: 6.329<br>MS[M+1]⁺: 628 | A |
| I_206 | IIa_204 | (S)-2-(2-Benzoylphenylamino)-3-(4-{3-[benzyl-(3-pyridin-3-ylpropionyl)-amino]propoxy}phenyl)propionic acid | rt: 6.584<br>MS[M+1]⁺: 642 | A |
| I_207 | IIa_205 | (S)-2-(2-Benzoylphenylamino)-3-{4-[2-(benzylpent-4-enoylamino)ethoxy]-phenyl}propionic acid | rt: 8.32<br>MS[M+1]⁺: 577 | A |
| I_208 | IIa_206 | (S)-2-(2-Benzoylphenylamino)-3-{4-[3-(benzylpent-4-enoylamino)propoxy]-phenyl}propionic acid | rt: 8.401<br>MS[M+1]⁺: 591 | A |
| I_209 | IIa_207 | (S)-2-(2-Benzoylphenylamino)-3-(4-{2-[benzyl-(3-phenylpropionyl)amino]-ethoxy}phenyl)propionic acid | rt: 8.628<br>MS[M+1]⁺: 627 | A |
| I_210 | IIa_208 | (S)-2-(2-Benzoylphenylamino)-3-(4-{3-[benzyl-(3-phenylpropionyl)amino]-propoxy}phenyl)propionic acid | rt: 8.732<br>MS[M+1]⁺: 641 | A |
| I_211 | IIa_209 | (S)-2-(2-Benzoylphenylamino)-3-{4-[2-(benzylcyclobutanecarbonylamino)-ethoxy]phenyl}propionic acid | rt: 8.41<br>MS[M+1]⁺: 577 | A |
| I_212 | IIa_210 | (S)-2-(2-Benzoylphenylamino)-3-{4-[3-(benzylcyclobutanecarbonylamino)-propoxy]phenyl}propionic acid | rt: 8.481<br>MS[M+1]⁺: 591 | A |
| I_213 | IIa_211 | (S)-2-(2-Benzoylphenylamino)-3-{4-[2-(benzylcyclohexanecarbonylamino)-ethoxy]phenyl}propionic acid | rt: 8.786<br>MS[M+1]⁺: 605 | A |
| I_214 | IIa_212 | (S)-2-(2-Benzoylphenylamino)-3-{4-[3-(benzylcyclohexanecarbonylamino)-propoxy]phenyl}propionic acid | rt: 8.865<br>MS[M+1]⁺: 619 | A |
| I_215 | IIa_213 | (S)-2-(2-Benzoylphenylamino)-3-(4-{2-[benzyl-(3-cyclohexylpropionyl)-amino]ethoxy}phenyl)propionic acid | rt: 9.382<br>MS[M+1]⁺: 633 | A |
| I_216 | IIa_214 | (S)-2-(2-Benzoylphenylamino)-3-(4-{3-[benzyl-(3-cyclohexylpropionyl)-amino]propoxy}phenyl)propionic acid | rt: 9.479<br>MS[M+1]⁺: 647 | A |
| I_217 | IIa_215 | (S)-2-(2-Benzoylphenylamino)-3-(4-{2-[benzyl-(2-cyclohexylacetyl)amino]-ethoxy}phenyl)propionic acid | rt: 9.109<br>MS[M+1]⁺: 619 | A |

TABLE 6-continued

| Example Number | Starting product | Compound name | $^1$H-NMR/LC-MS | HPLC Method |
|---|---|---|---|---|
| I_218 | IIa_216 | (S)-2-(2-Benzoylphenylamino)-3-(4-{3-[benzyl-(2-cyclohexylacetyl)amino]-propoxy}phenyl)propionic acid | rt: 9.207<br>MS[M+1]$^+$: 633 | A |
| I_219 | IIa_217 | (S)-2-(2-Benzoylphenylamino)-3-{4-[2-(benzylcyclopentanecarbonylamino)-ethoxy]phenyl}propionic acid | rt: 8.663<br>MS[M+1]$^+$: 591 | A |
| I_220 | IIa_218 | (S)-2-(2-Benzoylphenylamino)-3-{4-[3-benzylcyclopentanecarbonylamino)-propoxy}phenyl}propionic acid | rt: 8.84<br>MS[M+1]$^+$: 605 | A |
| I_221 | IIa_219 | (S)-2-(2-Benzoylphenylamino)-3-(4-{2-[benzyl-(3-cyclopentylpropionyl)-amino]ethoxy}phenyl)propionic acid | rt: 9.16<br>MS[M+1]$^+$: 619 | A |
| I_222 | IIa_220 | (S)-2-(2-Benzoylphenylamino)-3-(4-{3-[benzyl-(3-cyclopentylpropionyl)-amino]propoxy}phenyl)propionic acid | rt: 9.208<br>MS[M+1]$^+$: 633 | A |
| I_223 | IIa_221 | (S)-2-(2-Benzoylphenylamino)-3-{4-[2-(benzylcyclopropanecarbonylamino)-ethoxy]phenyl}propionic acid | rt: 8.08<br>MS[M+1]$^+$: 563 | A |
| I_224 | IIa_222 | (S)-2-(2-Benzoylphenylamino)-3-{4-[3-(benzylcyclopropanecarbonylamino)-propoxy]phenyl}propionic acid | rt: 8.181<br>MS[M+1]$^+$: 577 | A |
| I_225 | IIa_223 | (S)-2-(2-Benzoylphenylamino)-3-{4-[2-(benzylpropionylamino)ethoxy-phenyl}propionic acid | rt: 7.968<br>MS[M+1]$^+$: 551 | A |
| I_226 | IIa_224 | (S)-2-(2-Benzoylphenylamino)-3-{4-[3-(benzylpropionylamino)propoxy]-phenyl}propionic acid | rt: 8.054<br>MS[M+1]$^+$: 565 | A |
| I_227 | IIa_225 | (S)-2-(2-Benzoylphenylamino)-3-{4-[2-(benzylisobutyrylamino)ethoxy]-phenyl}propionic acid | rt: 8.225<br>MS[M+1]$^+$: 565 | A |
| I_228 | IIa_226 | (S)-2-(2-Benzoylphenylamino)-3-{4-[3-(benzylisobutyrylamino)propoxy]-phenyl}propionic acid | rt: 8.311<br>MS[M+1]$^+$: 579 | A |
| I_229 | IIa_227 | (S)-2-(2-Benzoylphenylamino)-3-{4-[2-(benzylhexanoylamino)ethoxy]-phenyl}propionic acid | rt: 8.843<br>MS[M+1]$^+$: 593 | A |
| I_230 | IIa_228 | (S)-2-(2-Benzoylphenylamino)-3-{4-[3-(benzylhexanoylamino)propoxy]-phenyl}propionic acid | rt: 8.898<br>MS[M+1]$^+$: 607 | A |
| I_231 | IIa_229 | (S)-2-(2-Benzoylphenylamino)-3-{4-[2-(benzylpentanoylamino)ethoxy]-phenyl}propionic acid | rt: 8.507<br>MS[M+1]$^+$: 579 | A |
| I_232 | IIa_230 | (S)-2-(2-Benzoylphenylamino)-3-{4-[3-(benzylpentanoylamino)propoxy]-phenyl}propionic acid | rt: 8.581<br>MS[M+1]$^+$: 593 | A |
| I_233 | IIa_231 | (S)-2-(2-Benzoylphenylamino)-3-{4-[2-(benzyloctanoylamino)ethoxy]phenyl}-propionic acid | rt: 9.396<br>MS[M+1]$^+$: 621 | A |
| I_234 | IIa_232 | (S)-2-(2-Benzoylphenylamino)-3-{4-[3-(benzyloctanoylamino)propoxy]-phenyl}propionic acid | rt: 9.432<br>MS[M+1]$^+$: 635 | A |
| I_235 | IIa_233 | (S)-2-(2-Benzoylphenylamino)-3-{4-[2-(benzylheptanoylamino)ethoxy]-phenyl}propionic acid | rt: 9.112<br>MS[M+1]$^+$: 607 | A |
| I_236 | IIa_234 | (S)-2-(2-Benzoylphenylamino)-3-{4-[3-(benzylheptanoylamino)propoxy]-phenyl}propionic acid | rt: 9.158<br>MS[M+1]$^+$: 621 | A |
| I_237 | IIa_235 | (S)-2-(2-Benzoylphenylamino)-3-{4-[2-(benzylnonanoylamino)ethoxy]-phenyl}propionic acid | rt: 9.653<br>MS[M+1]$^+$: 635 | A |
| I_238 | IIa_236 | (S)-2-(2-Benzoylphenylamino)-3-{4-[3-(benzylnonanoylamino)propoxy]-phenyl}propionic acid | rt: 9.69<br>MS[M+1]$^+$: 649 | A |
| I_239 | IIa_237 | (S)-2-(2-Benzoylphenylamino)-3-{4-[2-(benzylbutyrylamino)ethoxy]phenyl}-propionic acid | rt: 8.256<br>MS[M+1]$^+$: 565 | A |
| I_240 | IIa_238 | (S)-2-(2-Benzoylphenylamino)-3-{4-[3-(benzylbutyrylamino)propoxy]phenyl}-propionic acid | rt: 8.332<br>MS[M+1]$^+$: 579 | A |
| I_241 | IIa_239 | (S)-3-{4-[2-(Benzoylbenzylamino)-ethoxy]phenyl}-2-(2-(benzoylphenylamino)propionic acid | rt: 8.333<br>MS[M+1]$^+$: 599 | A |
| I_242 | IIa_240 | (S)-3-{4-[3-(Benzoylbenzylamino)-propoxy]phenyl}-2-(2-benzoylphenylamino)propionic acid | rt: 8.378<br>MS[M+1]$^+$: 613 | A |

TABLE 6-continued

| Example Number | Starting product | Compound name | $^1$H-NMR/LC-MS | HPLC Method |
|---|---|---|---|---|
| I_243 | IIa_241 | (S)-2-(2-Benzoylphenylamino)-3-(4-{2-[benzyl-(3-phenylacryloyl)amino]-ethoxy}phenyl)propionic acid | rt: 8.579<br>MS[M+1]$^+$: 625 | A |
| I_244 | IIa_242 | (S)-2-(2-Benzoylphenylamino)-3-(4-{3-[benzyl-(3-phenylacryloyl)amino]-propoxy}phenyl)propionic acid | rt: 8.68<br>MS[M+1]$^+$: 639 | A |
| I_245 | IIa_243 | (S)-2-(2-Benzoylphenylamino)-3-(4-{2-[benzyl-(2,2-dimethylpropionyl)-amino]ethoxy}phenyl)propionic acid | rt: 8.628<br>MS[M+1]$^+$: 579 | A |
| I_246 | IIa_244 | (S)-2-(2-Benzoylphenylamino)-3-(4-{3-[benzyl-(2,2-dimethylpropionyl)-amino]propoxy}phenyl)propionic acid | rt: 8.656<br>MS[M+1]$^+$: 593 | A |
| I_247 | IIa_245 | (S)-2-(2-Benzoylphenylamino)-3-(4-{2-[cyclohexyl-(3-furan-2-ylacryloyl)-amino]ethoxy}phenyl)propionic acid | rt: 8.676<br>MS[M+1]$^+$: 607 | A |
| I_248 | IIa_246 | (S)-2-(2-Benzoylphenylamino)-3-{4-[2-(cyclobutanecarbonylcyclohexylamino)ethoxy]phenyl}propionic acid | rt: 8.913<br>MS[M+1]$^+$: 569 | A |
| I_249 | IIa_247 | (S)-2-(2-Benzoylphenylamino)-3-(4-{2-[cyclohexyl-(3-cyclopentylpropionyl)amino]ethoxy}-phenyl)propionic acid | rt: 9.607<br>MS[M+1]$^+$: 611 | A |
| I_250 | IIa_248 | (S)-2-(2-Benzoylphenylamino)-3-{4-[2-(butyrylcyclohexylamino)ethoxy]-phenyl}propionic acid | rt: 8.691<br>MS[M+1]$^+$: 557 | A |
| I_251 | IIa_249 | (S)-2-(2-Benzoylphenylamino)-3-(4-{2-[cyclopropylmethyl(naphthalene-2-carbonyl)amino]ethoxy}phenyl)-propionic acid | rt: 8.536<br>MS[M+1]$^+$: 613 | A |
| I_252 | IIa_250 | (S)-2-(2-Benzoylphenylamino)-3-(4-{3-[cyclopropylmethyl(naphthalene-2-carbonyl)amino]propoxy}phenyl)-propionic acid | rt: 8.609<br>MS[M+1]$^+$: 627 | A |
| I_253 | IIa_251 | (S)-2-(2-Benzoylphenylamino)-3-(4-{2-[cyclopropylmethyl(quinoline-2-carbonyl)amino]ethoxy}phenyl)-propionic acid | rt: 8.206<br>MS[M+1]$^+$: 614 | A |
| I_254 | IIa_252 | (S)-2-(2-Benzoylphenylamino)-3-(4-{3-[cyclopropylmethyl(quinoline-2-carbonyl)amino]propoxy}phenyl)-propionic acid | rt: 8.267<br>MS[M+1]$^+$: 628 | A |
| I_255 | IIa_253 | (S)-2-(2-Benzoylphenylamino)-3-(4-{2-[cyclopropylmethyl(quinoxaline-2-carbonyl)amino]ethoxy}phenyl)-propionic acid | rt: 8.084<br>MS[M+1]$^+$: 615 | A |
| I_256 | IIa_254 | (S)-2-(2-Benzoylphenylamino)-3-(4-{3-[cyclopropylmethy(quinoxaline-2-carbonyl)amino]propoxy}phenyl)-propionic acid | rt: 8.192<br>MS[M+1]$^+$: 629 | A |
| I_257 | IIa_255 | (S)-2-(2-Benzoylphenylamino)-3-(4-{2-[cyclopropylmethyl(thiophene-2-carbonyl)amino]ethoxy}phenyl)-propionic acid | rt: 8.068<br>MS[M+1]$^+$: 569 | A |
| I_258 | IIa_256 | (S)-2-(2-Benzoylphenylamino)-3-(4-{3-[cyclopropylmethyl(thiophene-2-carbonyl)amino]propoxy}phenyl)-propionic acid | rt: 8.17<br>MS[M+1]$^+$: 583 | A |
| I_259 | IIa_257 | (S)-2-(2-Benzoylphenylamino)-3-(4-{2-[cyclopropylmethyl(pyridine-3-carbonyl)amino]ethoxy}phenyl)-propionic acid | rt: 7.1<br>MS[M+1]$^+$: 564 | A |
| I_260 | IIa_258 | (S)-2-(2-Benzoylphenylamino)-3-(4-{3-[cyclopropylmethyl(pyridine-3-carbonyl)amino]propoxy}phenyl)-propionic acid | rt: 7.299<br>MS[M+1]$^+$: 578 | A |
| I_261 | IIa_259 | (S)-2-(2-Benzoylphenylamino)-3-{4-[2-(cyclopropylmethylphenylacetylamino)ethoxy]phenyl}propionic acid | rt: 8.179<br>MS[M+1]$^+$: 577 | A |
| I_262 | IIa_260 | (S)-2-(2-Benzoylphenylamino)-3-{4-[3-(cyclopropylmethylphenylacetylamino)propoxy]phenyl}propionic acid | rt: 8.268<br>MS[M+1]$^+$: 591 | A |
| I_263 | IIa_261 | (S)-2-(2-Benzoylphenylamino)-3-(4-{2-[cyclopropylmethyl-(3-furan-2-ylacryloyl)amino]ethoxy}phenyl)-propionic acid | rt: 8.056<br>MS[M+1]$^+$: 579 | A |

TABLE 6-continued

| Example Number | Starting product | Compound name | ¹H-NMR/LC-MS | HPLC Method |
|---|---|---|---|---|
| I_264 | IIa_262 | (S)-2-(2-Benzoylphenylamino)-3-(4-{3-[cyclopropylmethyl-(3-furan-2-ylacryloyl)amino]propoxy}phenyl)-propionic acid | rt: 8.149<br>MS[M+1]⁺: 593 | A |
| I_265 | IIa_263 | (S)-2-(2-Benzoylphenylamino)-3-(4-{2-[cyclopropylmethyl-(3-thiophen-2-ylacryloyl)amino]ethoxy}phenyl)-propionic acid | rt: 8.239<br>MS[M+1]⁺: 595 | A |
| I_266 | IIa_264 | (S)-2-(2-Benzoylphenylamino)-3-(4-{3-[cyclopropylmethyl-(3-thiophen-2-ylacryloyl)amino]propoxy}phenyl)-propionic acid | rt: 8.342<br>MS[M+1]⁺: 609 | A |
| I_267 | IIa_265 | (S)-2-(2-Benzoylphenylamino)-3-(4-{2-[cyclopropylmethyl-(2-thiophen-2-ylacetyl)amino]ethoxy}phenyl)-propionic acid | rt: 8.085<br>MS[M+1]⁺: 583 | A |
| I_268 | IIa_266 | (S)-2-(2-Benzoylphenylamino)-3-(4-{3-[cyclopropylmethyl-(2-thiophen-2-ylacetyl)amino]propoxy}phenyl)-propionic acid | rt: 8.175<br>MS[M+1]⁺: 597 | A |
| I_269 | IIa_267 | (S)-2-(2-Benzoylphenylamino)-3-(4-{2-[cyclopropylmethyl-(2-thiophen-3-ylacetyl)amino]ethoxy}phenyl)-propionic acid | rt: 8.056<br>MS[M+1]⁺: 583 | A |
| I_270 | IIa_268 | (S)-2-(2-Benzoylphenylamino)-3-(4-{3-[cyclopropylmethyl-(2-thiophen-3-ylacetyl)amino]propoxy}phenyl)-propionic acid | rt: 8.142<br>MS[M+1]⁺: 597 | A |
| I_271 | IIa_269 | (S)-2-(2-Benzoylphenylamino)-3-(4-{2-[cyclopropylmethyl-(3-pyridin-3-ylpropionyl)amino]ethoxy}phenyl)-propionic acid | rt: 6.234<br>MS[M+1]⁺: 592 | A |
| I_272 | IIa_270 | (S)-2-(2-Benzoylphenylamino)-3-(4-{3-[cyclopropylmethyl-(3-pyridin-3-ylpropionyl)amino]propoxy}phenyl)-popionic acid | rt: 6.385<br>MS[M+1]⁺: 606 | A |
| I_273 | IIa_271 | (S)-2-(2-Benzoylphenylamino)-3-(4-{2-[cyclopropylmethyl-(3-phenylpropionyl)amino]ethoxy}-phenyl)propionic acid | rt: 8.413<br>MS[M+1]⁺: 591 | A |
| I_274 | IIa_272 | (S)-2-(2-Benzoylphenylamino)-3-(4-{3-[cyclopropylmethyl-(3-phenylpropionyl)amino]propoxy}-phenyl)propionic acid | rt: 8.488<br>MS[M+1]⁺: 605 | A |
| I_275 | IIa_273 | (S)-2-(2-Benzoylphenylamino)-3-{4-[2-(cyclobutanecarbonylcyclopropylmethylamino)ethoxy]phenyl}propionic acid | rt: 8.16<br>MS[M+1]⁺: 541 | A |
| I_276 | IIa_274 | (S)-2-(2-Benzoylphenylamino)-3-{4-[3-(cyclobutanecarbonylcyclopropylmethylamino)propoxy]phenyl}propionic acid | rt: 8.24<br>MS[M+1]⁺: 555 | A |
| I_277 | IIa_275 | (S)-2-(2-Benzoylphenylamino)-3-(4-{2-[(2-cyclohexylacetyl)-cyclopropylmethylamino]ethoxy}-phenyl)propionic acid | rt: 9.907<br>MS[M+1]⁺: 583 | A |
| I_278 | IIa_276 | (S)-2-(2-Benzoylphenylamino)-3-(4-{3-[(2-cyclohexylacetyl)-cyclopropylmethylamino]propoxy}-phenyl)propionic acid | rt: 8.975<br>MS[M+1]⁺: 597 | A |
| I_279 | IIa_277 | (S)-2-(2-Benzoylphenylamino)-3-{4-[2-(cyclopentanecarbonylcyclopropylmethylamino)ethoxy]phenyl}propionic acid | rt: 8.405<br>MS[M+1]⁺: 555 | A |
| I_280 | IIa_278 | (S)-2-(2-Benzoylphenylamino)-3-{4-[3-(cyclopentanecarbonylcyclopropylmethylamino)propoxy]phenyl}propionic acid | rt: 8.486<br>MS[M+1]⁺: 569 | A |
| I_281 | IIa_279 | (S)-2-(2-Benzoylphenylamino)-3-{4-[2-(cyclopropanecarbonylcyclopropylmethylamino)ethoxy]phenyl}propionic acid | rt: 7.808<br>MS[M+1]⁺: 527 | A |
| I_282 | IIa_280 | (S)-2-(2-Benzoylphenylamino)-3-{4-[3-(cyclopropanecarbonylcyclopropylmethylamino)propoxy]phenyl}propionic acid | rt: 7.905<br>MS[M+1]⁺: 541 | A |

TABLE 6-continued

| Example Number | Starting product | Compound name | $^1$H-NMR/LC-MS | HPLC Method |
|---|---|---|---|---|
| I_283 | IIa_281 | (S)-2-(2-Benzoylphenylamino)-3-{4-[2-(cyclopropylmethylpropionylamino)-ethoxy]phenyl}propionic acid | rt: 7.682<br>MS[M+1]$^+$: 515 | A |
| I_284 | IIa_282 | (S)-2-(2-Benzoylphenylamino)-3-{4-[3-(cyclopropylmethylpropionylamino)-propoxy]phenyl}propionic acid | rt: 7.776<br>MS[M+1]$^+$: 529 | A |
| I_285 | IIa_283 | (S)-2-(2-Benzoylphenylamino)-3-{4-[2-(cyclopropylmethylisobutyrylamino)-ethoxy]phenyl}propionic acid | rt: 7.966<br>MS[M+1]$^+$: 529 | A |
| I_286 | IIa_284 | (S)-2-(2-Benzoylphenylamino)-3-{4-[3-(cyclopropylmethylisobutyrylamino)-propoxy]phenyl}propionic acid | rt: 8.056<br>MS[M+1]$^+$: 543 | A |
| I_287 | IIa_285 | (S)-2-(2-Benzoylphenylamino)-3-{4-[2-(butyrylcyclopropylmethylamino)-ethoxy]phenyl}propionic acid | rt: 7.99<br>MS[M+1]$^+$: 529 | A |
| I_288 | IIa_286 | (S)-2-(2-Benzoylphenylamino)-3-{4-[3-(butyrylcyclopropylmethylamino)-propoxy]phenyl}propionic acid | rt: 8.071<br>MS[M+1]$^+$: 543 | A |
| I_289 | IIa_287 | (S)-3-{4-[2-(Benzoylcyclopropylmethylamino)-ethoxy]phenyl}-2-(2-benzoylphenylamino)propionic acid | rt: 8.06<br>MS[M+1]$^+$: 563 | A |
| I_290 | IIa_288 | (S)-3-{4-[3-(Benzoylcyclopropylmethylamino)-propoxy]phenyl}-2-(2-benzoylphenylamino)propionic acid | rt: 8.161<br>MS[M+1]$^+$: 577 | A |
| I_291 | IIa_289 | (S)-2-(2-Benzoylphenylamino)-3-(4-{2-[cyclopropylmethyl-(3-phenylacryloyl)amino]ethoxy}phenyl)-propionic acid | rt: 8.338<br>MS[M+1]$^+$: 589 | A |
| I_292 | IIa_290 | (S)-2-(2-Benzoylphenylamino)-3-(4-{3-[cyclopropylmethyl-(3-phenylacryloyl)amino]propoxy}-phenyl)propionic acid | rt: 8.424<br>MS[M+1]$^+$: 603 | A |
| I_293 | IIa_291 | (S)-2-(2-Benzoylphenylamino)-3-(4-{2-[(naphthalene-1-carbonyl)-phenylamino]ethoxy}phenyl)propionic acid | rt: 8.404<br>MS[M+1]$^+$: 635 | A |
| I_294 | IIa_292 | (S)-2-(2-Benzoylphenylamino)-3-(4-{3-[(naphthalene-1-carbonyl)-phenylamino]propoxy}phenyl)-propionic acid | rt: 8.588<br>MS[M+1]$^+$: 649 | A |
| I_295 | IIa_293 | (S)-2-(2-Benzoylphenylamino)-3-(4-{2-[(naphthalene-2-carbonyl)-phenylamino]ethoxy}phenyl)propionic acid | rt: 8.618<br>MS[M+1]$^+$: 635 | A |
| I_296 | IIa_294 | (S)-2-(2-Benzoylphenylamino)-3-(4-{3-[(naphthalene-2-carbonyl)-phenylamino]propoxy}phenyl)-propionic acid | rt: 8.762<br>MS[M+1]$^+$: 649 | A |
| I_297 | IIa_295 | (S)-2-(2-Benzoylphenylamino)-3-(4-{2-[(quinoline-2-carbonyl)-phenylamino]ethoxy}phenyl)propionic acid | rt: 8.095<br>MS[M+1]$^+$: 636 | A |
| I_298 | IIa_296 | (S)-2-(2-Benzoylphenylamino)-3-(4-{3-[phenyl(quinoline-2-carbonyl)-amino]propoxy}phenyl)propionic acid | rt: 8.241<br>MS[M+1]$^+$: 650 | A |
| I_299 | IIa_297 | (S)-2-(2-Benzoylphenylamino)-3-(4-{2-[phenyl(quinoxaline-2-carbonyl)-amino]ethoxy}phenyl)propionic acid | rt: __<br>MS[M+1]$^+$: 637 | A |
| I_300 | IIa_298 | (S)-2-(2-Benzoylphenylamino)-3-(4-{3-[phenyl(quinoxaline-2-carbonyl)-amino]propoxy}phenyl)propionic acid | rt: 8.214<br>MS[M+1]$^+$: 651 | A |
| I_301 | IIa_299 | (S)-2-(2-Benzoylphenylamino)-3-(4-{2-[phenyl(thiophene-2-carbonyl)-amino]ethoxy}phenyl)propionic acid | rt: 8.259<br>MS[M+1]$^+$: 591 | A |
| I_302 | IIa_300 | (S)-2-(2-Benzoylphenylamino)-3-(4-{3-[phenyl(thiophene-2-carbonyl)-amino]propoxy}phenyl)propionic acid | rt: 8.416<br>MS[M+1]$^+$: 605 | A |
| I_303 | IIa_301 | (S)-2-(2-Benzoylphenylamino)-3-(4-{2-[(isoquinoline-3-carbonyl)-phenylamino]ethoxy}phenyl)propionic acid | rt: 7.925<br>MS[M+1]$^+$: 636 | A |
| I_304 | IIa_302 | (S)-2-(2-Benzoylphenylamino)-3-(4-{2-[phenyl(pyridine-3-carbonyl)amino]-ethoxy}phenyl)propionic acid | rt: 7.253<br>MS[M+1]$^+$: 586 | A |

TABLE 6-continued

| Example Number | Starting product | Compound name | ¹H-NMR/LC-MS | HPLC Method |
|---|---|---|---|---|
| I_305 | IIa_303 | (S)-2-(2-Benzoylphenylamino)-3-(4-{3-[phenyl(pyridine-3-carbonyl)amino]-propoxy}phenyl)propionic acid | rt: 7.434<br>MS[M+1]⁺: 600 | A |
| I_306 | IIa_304 | (S)-2-(2-Benzoylphenylamino)-3-(4-{2-[phenyl(pyridine-4-carbonyl)amino]-ethoxy}phenyl)propionic acid | rt: 7.061<br>MS[M+1]⁺: 586 | A |
| I_307 | IIa_305 | (S)-2-(2-Benzoylphenylamino)-3-(4-{3-[phenyl(pyridine-4-carbonyl)amino]-propoxy}phenyl)propionic acid | rt: 7.261<br>MS[M+1]⁺: 600 | A |
| I_308 | IIa_306 | (S)-2-(2-Benzoylphenylamino)-3-{4-[2-(phenylphenylacetylamino)ethoxy]-phenyl}propionic acid | rt: 8.439<br>MS[M+1]⁺: 599 | A |
| I_309 | IIa_307 | (S)-2-(2-Benzoylphenylamino)-3-{4-[3-(phenylphenylacetylamino)propoxy]-phenyl}propionic acid | rt: 8.619<br>MS[M+1]⁺: 613 | A |
| I_310 | IIa_308 | (S)-2-(2-Benzoylphenylamino)-3-(4-{2-[(2-methylacryloyl)phenylamino]-ethoxy}phenyl)propionic acid | rt: 7.98<br>MS[M+1]⁺: 549 | A |
| I_311 | IIa_309 | (S)-2-(2-Benzoylphenylamino)-3-(4-{2-[(2-methylacryloyl)phenylamino]-propoxy}phenyl)propionic acid | rt: 8.146<br>MS[M+1]⁺: 563 | A |
| I_312 | IIa_310 | (S)-2-(2-Benzoylphenylamino)-3-(4-{2-[phenyl-(3-phenylpropynoyl)amino]-ethoxy}phenyl)propionic acid | rt: 8.511<br>MS[M+1]⁺: 609 | A |
| I_313 | IIa_311 | (S)-2-(2-Benzoylphenylamino)-3-(4-{2-[(2-ethylbutyryl)phenylamino]-ethoxy}phenyl)propionic acid | rt: 8.759<br>MS[M+1]⁺: 579 | A |
| I_314 | IIa_312 | (S)-2-(2-Benzoylphenylamino)-3-(4-{3-[(2-ethylbutyryl)phenylamino]-propoxy}phenyl)propionic acid | rt: 8.917<br>MS[M+1]⁺: 593 | A |
| I_315 | IIa_313 | (S)-2-(2-Benzoylphenylamino)-3-(4-{2-[(3-furan-2-ylacryloyl)phenylamino]-ethoxy}phenyl)propionic acid | rt: 8.259<br>MS[M+1]⁺: 601 | A |
| I_316 | IIa_314 | (S)-2-(2-Benzoylphenylamino)-3-(4-{3-[(3-furan-2-ylacryloyl)phenylamino]-propoxy}phenyl)propionic acid | rt: 8.422<br>MS[M+1]⁺: 615 | A |
| I_317 | IIa_315 | (S)-2-(2-Benzoylphenylamino)-3-(4-{2-[phenyl-(3-thiophen-2-ylacryloyl)-amino]ethoxy}phenyl)propionic acid | rt: 8.521<br>MS[M+1]⁺: 617 | A |
| I_318 | IIa_316 | (S)-2-(2-Benzoylphenylamino)-3-(4-{3-[phenyl-(3-thiophen-2-ylacryloyl)-amino]propoxy}phenyl)propionic acid | rt: 8.677<br>MS[M+1]⁺: 631 | A |
| I_319 | IIa_317 | (S)-2-(2-Benzoylphenylamino)-3-(4-{2-[(3-furan-3-yl-(E)-acryloyl)-phenylamino]ethoxy}phenyl)propionic acid | rt: 8.191<br>MS[M+1]⁺: 601 | A |
| I_320 | IIa_318 | (S)-2-(2-Benzoylphenylamino)-3-(4-{3-[(3-furan-3-yl-(E)-acryloyl)-phenylamino]propoxy}phenyl)-propionic acid | rt: 8.348<br>MS[M+1]⁺: 615 | A |
| I_321 | IIa_319 | (S)-2-(2-Benzoylphenylamino)-3-(4-{2-[phenyl-(3-pyridin-3-yl-(E)-acryloyl)-amino]ethoxy}phenyl)propionic acid | rt: 7.217<br>MS[M+1]⁺: 612 | A |
| I_322 | IIa_320 | (S)-2-(2-Benzoylphenylamino)-3-(4-{3-[phenyl-(3-pyridin-3-yl-(E)-acryloyl)-amino]propoxy}phenyl)propionic acid | rt: 7.417<br>MS[M+1]⁺: 626 | A |
| I_323 | IIa_321 | (S)-2-(2-Benzoylphenylamino)-3-(4-{2-[phenyl-(3-thiophen-3-yl-(E)-acryloyl)amino]ethoxy}phenyl)-propionic acid | rt: 8.471<br>MS[M+1]⁺: 617 | A |
| I_324 | IIa_322 | (S)-2-(2-Benzoylphenylamino)-3-(4-{3-[phenyl-(3-thiophen-3-yl-(E)-acryloyl)amino]propoxy}phenyl)-propionic acid | rt: 8.616<br>MS[M+1]⁺: 631 | A |
| I_325 | IIa_323 | (S)-2-(2-Benzoylphenylamino)-3-{4-[3-(but-2-(E)-enoylphenylamino)-propoxy]phenyl}propionic acid | rt: 8.213<br>MS[M+1]⁺: 563 | A |
| I_326 | IIa_324 | (S)-2-(2-Benzoylphenylamino)-3-(4-{2-[phenyl-(2-thiophen-2-ylacetyl)-amino]ethoxy}phenyl)propionic acid | rt: 8.348<br>MS[M+1]⁺: __ | A |
| I_327 | IIa_325 | (S)-2-(2-Benzoylphenylamino)-3-(4-{3-[phenyl-(2-thiophen-2-ylacetyl)-amino]propoxy}phenyl)propionic acid | rt: 8.506<br>MS[M+1]⁺: 619 | A |
| I_328 | IIa_326 | (S)-2-(2-Benzoylphenylamino)-3-(4-{3-[phenyl-(2-thiophen-3-ylacetyl)-amino]propoxy}phenyl)propionic acid | rt: 8.478<br>MS[M+1]⁺: 619 | A |

TABLE 6-continued

| Example Number | Starting product | Compound name | ¹H-NMR/LC-MS | HPLC Method |
|---|---|---|---|---|
| I_329 | IIa_327 | (S)-2-(2-Benzoylphenylamino)-3-(4-{2-[(3,3-dimethylbutyryl)phenylamino]-ethoxy}phenyl)propionic acid | rt: 8.882<br>MS[M+1]⁺: 579 | A |
| I_330 | IIa_328 | (S)-2-(2-Benzoylphenylamino)-3-(4-{3-[(3,3-dimethylbutyryl)phenylamino]-propoxy}phenyl)propionic acid | rt: 9.037<br>MS[M+1]⁺: 593 | A |
| I_331 | IIa_329 | (S)-2-(2-Benzoylphenylamino)-3-(4-{2-[(3-methylbutyryl)phenylamino]-ethoxy}phenyl)propionic acid | rt: 8.503<br>MS[M+1]⁺: 565 | A |
| I_332 | IIa_330 | (S)-2-(2-Benzoylphenylamino)-3-(4-{3-[(3-methylbutyryl)phenylamino]-propoxy}phenyl)propionic acid | rt: 8.663<br>MS[M+1]⁺: 579 | A |
| I_333 | IIa_331 | (S)-2-(2-Benzoylphenylamino)-3-(4-{2-[phenyl-(3-pyridin-3-ylpropionyl)-amino]ethoxy}phenyl)propionic acid | rt: 6.373<br>MS[M+1]⁺: 614 | A |
| I_334 | IIa_332 | (S)-2-(2-Benzoylphenylamino)-3-(4-{3-[phenyl-(3-pyridin-3-ylpropionyl)-amino]propoxy}phenyl)propionic acid | rt: 6.561<br>MS[M+1]⁺: 628 | A |
| I_335 | IIa_333 | (S)-2-(2-Benzoylphenylamino)-3-{4-[2-(pent-4-enoylphenylamino)ethoxy]-phenyl}propionic acid | rt: 8.317<br>MS[M+1]⁺: 563 | A |
| I_336 | IIa_334 | (S)-2-(2-Benzoylphenylamino)-3-{4-[3-(pent-4-enoylphenylamino)propoxy]-phenyl}propionic acid | rt: 8.482<br>MS[M+1]⁺: 577 | A |
| I_337 | IIa_335 | (S)-2-(2-Benzoylphenylamino)-3-(4-{2-[phenyl-(3-phenylpropionyl)amino]-ethoxy}phenyl)propionic acid | rt: 8.631<br>MS[M+1]⁺: 613 | A |
| I_338 | IIa_336 | (S)-2-(2-Benzoylphenylamino)-3-(4-{3-[phenyl-(3-phenylpropionyl)amino]-propoxy}phenyl)propionic acid | rt: 8.791<br>MS[M+1]⁺: 627 | A |
| I_339 | IIa_337 | (S)-2-(2-Benzoylphenylamino)-3-{4-[2-(cyclobutanecarbonylphenylamino)-ethoxy]phenyl}propionic acid | rt: 8.432<br>MS[M+1]⁺: 563 | A |
| I_340 | IIa_338 | (S)-2-(2-Benzoylphenylamino)-3-{4-[3-(cyclobutanecarbonylphenylamino)-propoxy]phenyl}propionic acid | rt: 8.594<br>MS[M+1]⁺: 577 | A |
| I_341 | IIa_339 | (S)-2-(2-Benzoylphenylamino)-3-{4-[2-(cyclohexanecarbonylphenylamino)-ethoxy]phenyl}propionic acid | rt: __<br>MS[M+1]⁺: __ | A |
| I_342 | IIa_340 | (S)-2-(2-Benzoylphenylamino)-3-{4-[3-(cyclohexanecarbonylphenylamino)-propoxy]phenyl}propionic acid | rt: 8.986<br>MS[M+1]⁺: 605 | A |
| I_343 | IIa_341 | (S)-2-(2-Benzoylphenylamino)-3-(4-{2-[(3-cyclohexylpropionyl)-phenylamino]ethoxy}phenyl)propionic acid | rt: 9.466<br>MS[M+1]⁺: 619 | A |
| I_344 | IIa_342 | (S)-2-(2-Benzoylphenylamino)-3-(4-{3-[(3-cyclohexylpropionyl)-phenylamino]propoxy}phenyl)-propionic acid | rt: 9.587<br>MS[M+1]⁺: 633 | A |
| I_345 | IIa_343 | (S)-2-(2-Benzoylphenylamino)-3-(4-{2-[(2-cyclohexylacetyl)phenylamino]-ethoxy}phenyl)propionic | rt: 9.175<br>MS[M+1]⁺: 605 | A |
| I_346 | IIa_344 | (S)-2-(2-Benzoylphenylamino)-3-(4-{3-[(2-cyclohexylacetyl)phenylamino]-propoxy}phenyl)propionic acid | rt: 9.316<br>MS[M+1]⁺: 619 | A |
| I_347 | IIa_345 | (S)-2-(2-Benzoylphenylamino)-3-{4-[2-(cyclopentanecarbonylphenylamino)-ethoxy]phenyl}propionic acid | rt: 8.68<br>MS[M+1]⁺: 577 | A |
| I_348 | IIa_346 | (S)-2-(2-Benzoylphenylamino)-3-{4-[3-(cyclopentanecarbonylphenylamino)-propoxy]phenyl}propionic acid | rt: 8.839<br>MS[M+1]⁺: 591 | A |
| I_349 | IIa_347 | (S)-2-(2-Benzoylphenylamino)-3-(4-{2-[(3-cyclopentylpropionyl)-phenylamino]ethoxy}phenyl)propionic acid | rt: 9.207<br>MS[M+1]⁺: 605 | A |
| I_350 | IIa_348 | (S)-2-(2-Benzoylphenylamino)-3-(4-{3-[(3-cyclopentylpropionyl)-phenylamino]propoxy}phenyl)-propionic acid | rt: 9.339<br>MS[M+1]⁺: 619 | A |
| I_351 | IIa_349 | (S)-2-(2-Benzoylphenylamino)-3-{4-[2-(cyclopropanecarbonylphenylamino)-ethoxy]phenyl}propionic acid | rt: 8.11<br>MS[M+1]⁺: 549 | A |
| I_352 | IIa_350 | (S)-2-(2-Benzoylphenylamino)-3-{4-[3-(cyclopropanecarbonylphenylamino)-propoxy]phenyl}propionic acid | rt: 8.284<br>MS[M+1]⁺: 563 | A |

TABLE 6-continued

| Example Number | Starting product | Compound name | ¹H-NMR/LC-MS | HPLC Method |
|---|---|---|---|---|
| I_353 | IIa_351 | (S)-2-(2-Benzoylphenylamino)-3-{4-[2-(phenylpropionylamino)ethoxy]-phenyl}propionic acid | rt: 7.965<br>MS[M+1]⁺: 537 | A |
| I_354 | IIa_352 | (S)-2-(2-Benzoylphenylamino)-3-{4-[3-(phenylpropionylamino)propoxy]-phenyl}propionic acid | rt: 8.138<br>MS[M+1]⁺: 551 | A |
| I_355 | IIa_353 | (S)-2-(2-Benzoylphenylamino)-3-{4-[2-(isobutyrylphenylamino)ethoxy]-phenyl}propionic acid | rt: 8.246<br>MS[M+1]⁺: 551 | A |
| I_356 | IIa_354 | (S)-2-(2-Benzoylphenylamino)-3-{4-[3-(isobutyrylphenylamino)propoxy]-phenyl}propionic acid | rt: 8.411<br>MS[M+1]⁺: 656 | A |
| I_357 | IIa_355 | (S)-2-(2-Benzoylphenylamino)-3-{4-[2-(hexanoylphenylamino)ethoxy]-phenyl}propionic acid | rt: 8.850<br>MS[M+1]⁺: 579 | A |
| I_358 | IIa_356 | (S)-2-(2-Benzoylphenylamino)-3-{4-[3-(hexanoylphenylamino)propoxy]-phenyl}propionic acid | rt: 8.996<br>MS[M+1]⁺: 593 | A |
| I_359 | IIa_357 | (S)-2-(2-Benzoylphenylamino)-3-{4-[2-(pentanoylphenylamino)ethoxy]-phenyl}propionic acid | rt: 8.535<br>MS[M+1]⁺: 565 | A |
| I_360 | IIa_358 | (S)-2-(2-Benzoylphenylamino)-3-{4-[3-(pentanoylphenylamino)propoxy]-phenyl}propionic acid | rt: 8.691<br>MS[M+1]⁺: 579 | A |
| I_361 | IIa_359 | (S)-2-(2-Benzoylphenylamino)-3-{4-[2-(octanoylphenylamino)ethoxy]phenyl}-propionic acid | rt: 9.465<br>MS[M+1]⁺: 607 | A |
| I_362 | IIa_360 | (S)-2-(2-Benzoylphenylamino)-3-{4-[3-(octanoylphenylamino)propoxy]-phenyl}propionic acid | rt: 9.587<br>MS[M+1]⁺: 621 | A |
| I_363 | IIa_361 | (S)-2-(2-Benzoylphenylamino)-3-{4-[2-(heptanoylphenylamino)ethoxy]-phenyl}propionic acid | rt: 9.168<br>MS[M+1]⁺: 593 | A |
| I_364 | IIa_362 | (S)-2-(2-Benzoylphenylamino)-3-{4-[3-(heptanoylphenylamino)propoxy]-phenyl}propionic acid | rt: 9.302<br>MS[M+1]⁺: 607 | A |
| I_365 | IIa_363 | (S)-2-(2-Benzoylphenylamino)-3-{4-[2-(nonanoylphenylamino)ethoxy]-phenyl}propionic acid | rt: 9.736<br>MS[M+1]⁺: 621 | A |
| I_366 | IIa_364 | (S)-2-(2-Benzoylphenylamino)-3-{4-[3-(nonanoylphenylamino)propoxy]-phenyl}propionic acid | rt: 9.85<br>MS[M+1]⁺: 635 | A |
| I_367 | IIa_365 | (S)-2-(2-Benzoylphenylamino)-3-{4-[2-(butyrylphenylamino)ethoxy]phenyl}-propionic acid | rt: 8.259<br>MS[M+1]⁺: 551 | A |
| I_368 | IIa_366 | (S)-2-(2-Benzoylphenylamino)-3-{4-[3-(butylylphenylamino)propoxy]phenyl}-propionic acid | rt: 8.426<br>MS[M+1]⁺: 565 | A |
| I_369 | IIa_367 | (S)-2-(2-Benzoylphenylamino)-3-{4-[2-(benzoylphenylamino)ethoxy]phenyl}-propionic acid | rt: 8.172<br>MS[M+1]⁺: 585 | A |
| I_370 | IIa_368 | (S)-2-(2-Benzoylphenylamino)-3-{4-[3-(benzoylphenylamino)propoxy]-phenyl}propionic acid | rt: 8.348<br>MS[M+1]⁺: 599 | A |
| I_371 | IIa_369 | (S)-2-(2-Benzoylphenylamino)-3-(4-{2-[phenyl-(3-phenylacryloyl)amino]-ethoxy}phenyl)propionic acid | rt: 8.647<br>MS[M+1]⁺: 611 | A |
| I_372 | IIa_370 | (S)-2-(2-Benzoylphenylamino)-3-(4-{3-[phenyl-(3-phenylacryloyl)amino]-propoxy}phenyl)propionic acid | rt: 8.81<br>MS[M+1]⁺: 625 | A |
| I_373 | IIa_371 | (S)-2-(2-Benzoylphenylamino)-3-(4-{2-[(2,2-dimethylpropionyl)-phenylamino]ethoxy}phenyl)propionic acid | rt: 8.661<br>MS[M+1]⁺: 565 | A |
| I_374 | IIa_372 | (S)-2-(2-Benzoylphenylamino)-3-(4-{3-[(2,2-dimethylpropionyl)-phenylamino]propoxy}phenyl)-propionic acid | rt: 8.79<br>MS[M+1]⁺: 579 | A |
| I_375 | IIa_373 | (S)-2-(2-Benzoylphenylamino)-3-{4-[2-(tert-butylcyclobutanecarbonylamino)-ethoxy]phenyl}propionic acid | rt: 8.443<br>MS[M+1]⁺: 543 | A |
| I_376 | IIa_374 | (S)-2-(2-Benzoylphenylamino)-3-(4-{2-[tert-butyl-(3-cyclopentylpropionyl)-amino]ethoxy}phenyl)propionic acid | rt: 9.194<br>MS[M+1]⁺: 585 | A |
| I_377 | II_1 | (S)-2-(2-Benzoylphenylamino)-3-{4-[2-(benzylindan-5-ylamino)ethoxy]- | 8.98(bs, 1H), 7.56(d, 2H), 7.45-7.37(ca, 5H), | A |

TABLE 6-continued

| Example Number | Starting product | Compound name | ¹H-NMR/LC-MS | HPLC Method |
|---|---|---|---|---|
| | | phenyl}propionic acid | 7.27-7.19(ca, 8H), 7.01(t, 1H), 6.71-6.65(ca, 3H), 6.54-6.41(ca, 2H), 4.60(s, 2H), 4.27(m, 1H), 4.07(t, 2H), 3.76(t, 2H), 3.27(dd, 1H), 3.08(m, 1H), 2.80(ca, 4H), 2.01(ca, 2H) | |
| I_378 | II_2 | (S)-2-(2-Benzoylphenylamino)-3-(4-{2-[benzyl(2,6-difluorophenyl)amino]-ethoxy}phenyl)propionic acid | rt: 9.342 MS[M+1]⁺: 607 | A |
| I_379 | II_3 | (S)-2-(2-Benzoylphenylamino)-3-(4-{2-[(2-chlorophenyl)-(2-fluorobenzyl)-amino]ethoxy}phenyl)propionic acid | rt: 9.516 MS[M+1]⁺: 624 | A |
| I_380 | II_4 | (S)-2-(2-Benzoylphenylamino)-3-(4-{2-[benzyl-(2-fluorophenyl)amino]-ethoxy}phenyl)propionic acid | 8.98(bs, 1H), 7.56(d, 2H), 7.46-7.37(ca, 5H), 7.32-7.18(m, 9H), 6.98-6.91(ca, 2H), 6.70-6.65(ca, 3H), 6.44(t, 1H), 4.46(s, 2H), 4.27(m, 1H), 3.99(t, 2H), 3.56(t, 2H), 3.27(m, 1H), 3.08(m, 1H) | A |
| I_381 | II_5 | (S)-2-(2-Benzoylphenylamino)-3-(4-{2-[(2-methylbenzyl)phenylamino]-ethoxy}phenyl)propionic acid | 8.88(bs, 1H), 7.57(d, 2H), 7.55-7.32(ca, 6H), 7.24-7.09(ca, 8H), 6.75-6.64(ca, 5H), 6.58(t, 1H), 4.55(s, 2H), 4.33(m, 1H), 4.11(t, 2H), 3.80(t, 2H), 3.25(m, 1H), 3.09(m, 1H), 2.34(s, 3H) | A |
| I_382 | II_6 | (S)-2-(2-Benzoylphenylamino)-3-(4-{2-[(3-chlorophenyl)-(2-methoxybenzyl)amino]ethoxy}phenyl)-propionic acid | rt: 9.546 MS[M+1]⁺: 636 | A |
| I_383 | II_7 | (S)-2-(2-Benzoylphenylamino)-3-(4-{2-[(2-methoxybenzyl)-m-tolylamino]-ethoxy}phenyl)propionic acid | rt: 9.461 MS[M+1]⁺: 615 | A |
| I_384 | II_8 | (S)-2-(2-Benzoylphenylamino)-3-(4-{3-[(2-methoxybenzyl)phenylamino]-propoxy}phenyl)propionic acid | rt: 9.292 MS[M+1]⁺: 615 | A |
| I_385 | II_9 | (S)-2-(2-Benzoylphenylamino)-3-{4-[2-(benzyl-o-tolylamino)ethoxy]phenyl}-propionic acid | rt: 9.523 MS[M+1]⁺: 585 | A |
| I_386 | II_10 | (S)-2-(2-Benzoylphenylamino)-3-(4-{2-[benzyl-(3-ethylphenyl)amino]-ethoxy}phenyl)propionic acid | 8.98(bs, 1H), 7.56(d, 2H), 7.45-7.37(ca, 5H), 7.28-7.20(m, 9H), 7.08(t, 1H), 6.70(d, 2H), 6.58-6.52(ca, 2H), 6.43(t, 1H), 4.62(s, 2H), 4.27(m, 1H), 4.09(t, 2H), 3.78(t, 2H), 3.27(m, 1H), 3.08(m, 1H), 2.53(q, 2H), 1.14(t, 3H) | A |
| I_387 | II_11 | (S)-2-(2-Benzoylphenylamino)-3-(4-{2-[benzyl-(3-fluorophenyl)amino]-ethoxy}phenyl)propionic acid | 8.98(bs, 1H), 7.56(d, 2H), 7.46-7.37(ca, 5H), 7.31-7.17(ca, 8H), 7.08(m, 1H), 6.70(ca, 3H), 6.48-6.32(ca, 3H), 4.62(s, 2H), 4.27(m, 1H), 4.08(t, 2H), 3.78(t, 2H), 3.27(dd, 1H), 3.08(m, 1H) | A |
| I_388 | II_12 | (S)-2-(2-Benzoylphenylamino)-3-(4-{2-[(2-chlorophenyl)-(3-methoxybenzyl)amino]ethoxy}phenyl)-propionic acid | rt: 9.428 MS[M+1]⁺: 636 | A |
| I_389 | II_13 | (S)-2-(2-Benzoylphenylamino)-3-(4-{2-[(3-chlorophenyl)-(3-methoxybenzyl)amino]ethoxy}phenyl)-propionic acid | rt: 9.375 MS[M+1]⁺: 636 | A |
| I_390 | II_14 | (S)-2-(2-Benzoylphenylamino)-3-(4-{2-[(3-methoxybenzyl)-m-tolylamino]-ethoxy}phenyl)propionic acid | rt: 9.354 MS[M+1]⁺: 615 | A |

TABLE 6-continued

| Example Number | Starting product | Compound name | ¹H-NMR/LC-MS | HPLC Method |
|---|---|---|---|---|
| I_391 | II_15 | (S)-2-(2-Benzoylphenylamino)-3-(4-{3-[(3-methoxybenzyl)phenylamino]-propoxy}phenyl)propionic acid | rt: 9.259<br>MS[M+1]⁺: 615 | A |
| I_392 | II_16 | (S)-2-(2-Benzoylphenylamino)-3-{4-[2-(benzyl-m-tolylamino)ethoxy]phenyl}-propionic acid | 8.98(bs, 1H), 7.56(d, 2H), 7.45-7.37(ca, 5H), 7.27-7.19(ca, 7H), 7.05(t, 1H), 6.71-6.68(ca, 3H), 6.56-6.42(ca, 4H), 4.61(s, 2H), 4.28(m, 1H), 4.07(t, 2H), 3.77(t, 2H), 3.26(dd, 1H), 3.06(m, 1H), 2.25(s, 3H) | A |
| I_393 | II_17 | (S)-2-(2-Benzoylphenylamino)-3-(4-{2-[benzyl-(4-chlorophenyl)amino]-ethoxy}phenyl)propionic acid | 8.98(bs, 1H), 7.56(d, 2H), 7.47-7.39(ca, 5H), 7.30-7.16(ca, 8H), 7.08(d, 2H), 6.72-6.61(ca, 4H), 6.44(t, 1H), 4.60(s, 2H), 4.27(m, 1H), 4.07(t, 2H), 3.77(t, 2H), 3.26(dd, 1H), 3.08(m, 1H) | A |
| I_394 | II_18 | (S)-2-(2-Benzoylphenylamino)-3-(4-{2-[benzyl-(4-fluorophenyl)amino]-ethoxy}phenyl)propionic acid | 8.98(bs, 1H), 7.56(d, 2H), 7.46-7.37(ca, 5H), 7.32-7.19(ca, 8H), 6.89-6.84(ca, 2H), 6.72-6.61(ca, 4H), 6.44(t, 1H), 4.57(s, 2H), 4.28(m, 1H), 4.06(t, 2H), 3.75(t, 2H), 3.27(dd, 1H), 3.08(m, 1H) | A |
| I_395 | II_19 | (S)-2-(2-Benzoylphenylamino)-3-(4-{2-[(4-methylbenzyl)phenylamino]-ethoxy}phenyl)propionic acid | 8.96(bs, 1H), 7.55(d, 2H), 7.46-7.37(ca, 5H), 7.24-7.09(m, 9H), 6.72-6.64(ca, 5H), 6.45(t, 1H), 4.58(s, 2H), 4.27(m, 1H), 4.06(t, 2H), 3.77(t, 2H), 3.27(dd, 1H), 3.08(m, 1H), 2.30(s, 3H) | A |
| I_396 | II_20 | (S)-2-(2-Benzoylphenylamino)-3-(4-{3-[(4-methoxybenzyl)phenylamino]-propoxy}phenyl)propionic acid | rt: 9.178<br>MS[M+1]⁺: 615 | A |
| I_397 | II_21 | (S)-2-(Benzoylphenylamino)-3-{4-[2-(di-p-tolylamino)ethoxy]phenyl}-propionic acid | 8.96(bs, 1H), 7.53(d, 2H), 7.48-7.35(ca, 5H), 7.22-7.15(m, 9H), 7.03(d, 1H), 6.89(d, 1H), 6.69-6.65(ca, 3H), 6.43(t, 1H), 4.23(m, 1H), 4.02(bs, 4H), 3.25(m, 1H), 3.05(m, 1H), 2.27(s, 6H).. | A |
| I_398 | II_22 | (S)-2-(2-Benzoylphenylamino)-3-{4-[2-(benzyl-p-tolylamino)ethoxy]phenyl}-propionic acid | 8.83(bs, 1H), 7.50-6.93(ca, 17H), 6.60-6.55(ca, 4H), 6.34(t, 1H), 4.53(s, 2H), 4.21(m, 1H), 3.93(t, 2H), 3.62(t, 2H), 3.17(dd, 1H), 2.98(m, 1H), 2.19(s, 3H) | A |
| I_399 | II_23 | (S)-2-(2-Benzoylphenylamino)-3-{4-[3-(benzylindan-5-ylamino)propoxy]-phenyl}propionic acid | rt: 9.736<br>MS[M+1]⁺: 625 | A |
| I_400 | II_24 | (S)-2-(2-Benzoylphenylamino)-3-(4-{3-[benzyl-(3-ethylphenyl)amino]-propoxy}phenyl)propionic acid | rt: 9.747<br>MS[M+1]⁺: 613 | A |
| I_401 | II_25 | (S)-2-(2-Benzoylphenylamino)-3-{4-[3-(benzyl-m-tolylamino)propoxy]-phenyl}propionic acid | rt: 9.549<br>MS[M+1]⁺: 599 | A |
| I_402 | II_26 | (S)-2-(2-Benzoylphenylamino)-3-{4-[3-(benzyl-p-tolylamino)propoxy]phenyl}-propionic acid | rt: 9.526<br>MS[M+1]⁺: 599 | A |
| I_403 | II_27 | (S)-2-(2-Benzoylphenylamino)-3-{4-[3-(benzylcyclohexylamino)propoxy]-phenyl}propionic acid methyl ester | rt: 6.67<br>MS[M+1]⁺: 591 | A |

TABLE 6-continued

| Example Number | Starting product | Compound name | $^1$H-NMR/LC-MS | HPLC Method |
|---|---|---|---|---|
| I_404 | II_28 | (S)-2-(2-Benzoylphenylamino)-3-{4-[3-(benzyphenylamino)propoxy]phenyl}-propionic acid | 8.92(bs, 1H), 7.56(d, 2H), 7.46-7.37(ca, 5H), 7.30-7.10(ca, 10H), 6.76-6.61(ca, 5H), 6.44(t, 1H), 4.53(s, 2H), 4.28(m, 1H), 3.92(t, 2H), 3.62(t, 2H), 3.22(dd, 1H), 3.10(m, 1H), 2.09-1.98(ca, 2H) | A |
| I_405 | II_29 | (S)-2-(2-Benzoylphenylamino)-3-(4-{2-[(2-fluorophenyl)isobutylamino]-ethoxy}phenyl)propionic acid | rt: 9.565 MS[M+1]$^+$: 555 | A |
| I_406 | II_30 | (S)-2-(2-Benzoylphenylamino)-3-{4-[2-(isobutyl-o-tolylamino)ethoxy]phenyl}-propionic acid | rt: 9.729 MS[M+1]$^+$: 551 | A |
| I_407 | II_31 | (S)-2-(2-Benzoylphenylamino)-3-{4-[3-(isobutyl-o-tolylamino)propoxy]-phenyl}propionic acid | rt: 9.443 MS[M+1]$^+$: 565 | A |
| I_408 | II_32 | (S)-2-(2-Benzoylphenylamino)-3-(4-{2-[(3-fluorophenyl)isobutylamino]-ethoxy}phenyl)propionic acid | rt: 9.445 MS[M+1]$^+$: 555 | A |
| I_409 | II_33 | (S)-2-(2-Benzoylphenylamino)-3-(4-{2-[isobutyl-m-tolylamino]ethoxy}-phenyl)propionic acid | rt: 9.65 MS[M+1]$^+$: 551 | A |
| I_410 | II_34 | (S)-2-(2-Benzoylphenylamino)-3-(4-{3-[isobutyl-m-tolylamino]propoxy}-phenyl)propionic acid | rt: 9.573 MS[M+1]$^+$: 565 | A |
| I_411 | II_35 | (S)-2-(2-Benzoylphenylamino)-3-{4-[2-(benzylphenethylamino)ethoxy]-phenyl}propionic acid | 8.99(bs, 1H), 7.57(d, 2H), 7.46-7.36(ca, 4H), 7.32-7.21(ca, 11H), 7.13(d, 2H), 6.73-6.69(ca, 3H), 6.44(t, 1H), 4.23(m, 1H), 3.94(t, 2H), 3.76(s, 2H), 3.27(m, 1H), 3.07(m, 1H), 2.93(t, 2H), 2.81(bs, 4H) | A |
| I_412 | II_36 | (S)-2-(2-Benzoylphenylamino)-3-{4-[2-(cyclobutylmethyl-o-tolylamino)-ethoxy]phenyl}propionic acid | rt: 9.089 MS[M+1]$^+$: 563 | A |
| I_413 | II_37 | (S)-2-(2-Benzoylphenylamino)-3-{4-[2-(benzylcyclopentylamino)ethoxy]-phenyl}propionic acid | rt: 6.418 MS[M+1]$^+$: 563 | A |
| I_414 | II_38 | (S)-2-(2-Benzoylphenylamino)-3-{4-[3-(cyclopentylphenylamino)propoxy]-phenyl}propionic acid | rt: 6.97 MS[M+1]$^+$: 563 | A |
| I_415 | II_39 | (S)-2-(2-Benzoylphenylamino)-3-(4-{2-[cyclopentylmethyl-(2-fluorophenyl)amino]ethoxy}phenyl)-propionic acid | rt: 9.937 MS[M+1]$^+$: 581 | A |
| I_416 | II_40 | (S)-2-(2-Benzoylphenylamino)-3-{4-[2-(cyclopentylmethylphenylamino)-ethoxy]phenyl}propionic acid | 8.84(bs, 1H), 7.57-7.41(ca, 7H), 7.22-7.16(ca, 4H), 6.75-6.55(ca, 7H), 4.31(ca, 3H), 3.98(t, 1H), 3.71(t, 2H), 3.30-3.20(ca, 3H), 3.09(m, 1H), 2.29(m, 1H), 1.75-1.54(ca, 8H) | A |
| I_417 | II_41 | (S)-2-(2-Benzoylphenylamino)-3-{4-[2-(benzylcyclopropylmethylamino)-ethoxy]phenyl}propionic acid | rt: 6.432 MS[M+1]$^+$: 549 | A |
| I_418 | II_42 | (S)-2-(2-Benzoylphenylamino)-3-{4-[3-(benzylcyclopropylmethylamino)-propoxy]phenyl}propionic acid | rt: 6.47 MS[M+1]$^+$: 563 | A |
| I_419 | II_43 | (S)-2-(2-Benzoylphenylamino)-3-(4-{2-[(2-methoxybenzyl)phenylamino]-ethoxy}phenyl)propionic acid | 8.98(bs, 1H), 7.57(d, 2H), 7.48-7.39(ca, 5H), 7.27-7.13(ca, 6H), 7.05(d, 1H), 6.88-6.80(ca, 2H), 6.73-6.60(ca, 5H), 6.44(t, 1H), 4.59(s, 2H), 4.27(m, 1H), 4.10(t, 2H), 3.85(s, 3H), 3.79(t, 2H), 3.27(dd, 1H), 3.08(m, 1H) | A |
| I_420 | II_44 | (S)-2-(2-Benzoylphenylamino)-3-(4-{2-[(3-methoxybenzyl)phenylamino]- | 8.98(bs, 1H), 7.57(d, 2H), 7.48-7.39(ca, 5H), | A |

TABLE 6-continued

| Example Number | Starting product | Compound name | $^1$H-NMR/LC-MS | HPLC Method |
|---|---|---|---|---|
| | | ethoxy}phenyl)propionic acid | 7.27-7.13(ca, 6H), 6.85-6.62(ca, 8H), 6.44(t, 1H), 4.60(s, 2H), 4.27(m, 1H), 4.10(t, 2H), 3.85(s, 3H), 3.79(t, 2H), 3.27(m, 1H), 3.08(m, 1H) | |
| I_421 | II_45 | (S)-2-(2-Benzoylphenylamino)-3-(4-{2-[(3-methoxyphenyl)phenylamino]-ethoxy}phenyl)propionic acid | 8.97(bs, 1H), 7.55-7.3(ca, 6H), 7.28-6.95(ca, 11H), 6.68-6.40(ca, 5H), 4.23(m, 1H), 4.05(bs, 4H), 3.71(s, 3H), 3.25(m, 1H), 3.05(m, 1H) | A |
| I_422 | II_46 | (S)-2-(2-Benzoylphenylamino)-3-(4-{2-[(4-methoxybenzoyl)phenylamino]-ethoxy}phenyl)propionic acid | 8.98(bs, 1H), 7.57(d, 2H), 7.48-7.39(ca, 5H), 7.27-7.13(ca, 7H), 6.85(d, 2H), 6.75-6.60(ca, 5H), 6.42(t, 1H), 4.59(s, 2H), 4.27(m, 1H), 4.10(t, 2H), 3.79(ca, 2H), 3.76(s, 3H), 3.27(m, 1H), 3.08(m, 1H) | A |
| I_423 | II_47 | (S)-2-(2-Benzoylphenylamino)-3-(4-{2-[(4-tert-butylbenzyl)phenylamino]-ethoxy}phenyl)propionic acid | t: 9.939 MS[M+1]$^+$: 627 | A |
| I_424 | II_48 | (S)-2-(2-Benzoylphenylamino)-3-{4-[2-(benzylphenylamino)ethoxy]phenyl}-propionic acid | 8.70(d, 1H), 7.60-7.40(ca, 4H), 7.40-7.10(m, 9H), 7.10-7.00(ca, 4H), 6.80-6.60(ca, 4H), 7.60-7.45(ca, 2H), 4.60(s, 2H), 4.31(bs, 1H) 4.07(t, 2H), 3.77(t, 2H), 3.13(dd, 1H), 2.96(dd, 1H). | A |
| I_425 | II_49 | (S)-2-(2-Benzoylphenylamino)-3-{4-[2-(cyclobutylmethylphenylamino)-ethoxy]phenyl}propionic acid | 8.98(d, 1H), 7.56(d, 2H), 7.46-7.38(ca, 4H), 7.21-7.15(ca, 5H), 6.73-6.63(ca, 6H), 6.45(t, 1H), 4.27(m, 1H), 3.97(t, 2H), 3.68(t, 2H), 3.37(d, 2H), 3.26(dd, 1H), 2.68(m, 1H), 2.03-1.70(ca, 6H) | A |
| I_426 | II_50 | (S)-2-(2-Benzoylphenylamino)-3-{4-[2-(cyclohexylphenylamino)ethoxy]-phenyl}propionic acid | rt: 9.029 MS[M+1]$^+$: 563 | A |
| I_427 | II_51 | (S)-2-(2-Benzoylphenylamino)-3-{4-[2-(cyclohexylmethylphenylamino)-ethoxy]phenyl}propionic acid | 8.98(d, 1H), 7.57(d, 2H), 7.46-7.38(ca, 4H), 7.21-7.15(ca, 6H), 6.67-6.63(ca, 5H), 6.44(t, 1H), 4.27(m, 1H), 3.98(t, 2H), 3.70(t, 2H), 3.26(dd, 1H), 3.17(d, 2H), 3.06(m, 1H), 1.80-1.50(ca, 11H) | A |
| I_428 | II_52 | (S)-2-(2-Benzoylphenylamino)-3-{4-[2-(cyclopentylphenylamino)ethoxy]-phenyl}propionic acid | rt: 7.669 MS[M+1]$^+$: 549 | A |
| I_429 | II_53 | (S)-2-(2-Benzoylphenylamino)-3-{4-[2-(cyclopropylmethylphenylamino)-ethoxy]phenyl}propionic acid | 8.98(bs, 1H), 7.56(d, 2H), 7.44-7.40(ca, 4H), 7.23-7.18(ca, 6H), 6.78-6.66(ca, 5H), 6.44(t, 1H), 4.27(m, 1H), 4.04(t, 2H), 3.76(t, 2H), 3.29-3.24(ca, 3H), 3.06(m, 1H), 1.00-0.80(m, 1H), 0.54-0.40(ca, 2H), 0.26-0.21(ca, 2H) | A |
| I_430 | II_54 | (S)-2-(2-Benzoylphenylamino)-3-{4-[2-(diphenylamino)ethoxy]phenyl}-propionic acid | 8.62(d, 1H), 7.60-7.44(ca, 4H), 7.38(t, 1H), 7.32(dd, 2H), 7.24(td, 4H), 7.07(d, 2H), 6.99(d, 4H), 6.91(t, 2H), 6.82(d, 1H), 6.73(d, 2H), 6.57(t, 1H), | A |

TABLE 6-continued

| Example Number | Starting product | Compound name | $^1$H-NMR/LC-MS | HPLC Method |
|---|---|---|---|---|
| | | | 4.50(m, 1H), 4.05(s, 4H), 3.25-2.95(ca, 2H). | |
| I_431 | IIa_375 | (S)-2-(2-Benzoylphenylamino)-3-(4-{2-[(2-methylacryloyl)naphthalen-1-ylamino]ethoxy}phenyl)propionic acid | rt: 8.502 MS[M+1]$^+$: 599 | A |
| I_432 | IIa_376 | (S)-2-(2-Benzoylphenylamino)-3-{4-[2-(but-2-(E)-enoylnaphthalen-1-ylamino)ethoxy]phenyl}propionic acid | rt: 8.432 MS[M+1]$^+$: 599 | A |
| I_433 | IIa_377 | (S)-2-(2-Benzoylphenylamino)-3-{4-[2-(cyclopropanecarbonylnaphthalen-1-ylamino)ethoxy]phenyl}propionic acid | rt: 8.485 MS[M+1]$^+$: 587 | A |
| I_434 | IIa_378 | (S)-2-(2-Benzoylphenylamino)-3-{4-[2-(naphthalen-1-ylpropionylamino)-ethoxy]phenyl}propionic acid | rt: 8.563 MS[M+1]$^+$: 599 | A |
| I_435 | IIa_379 | (S)-2-(2-Benzoylphenylamino)-3-(4-{2-[(2-methylacryloyl)naphthalen-2-ylamino]ethoxy}phenyl)propionic acid | rt: 8.599 MS[M+1]$^+$: 599 | A |
| I_436 | IIa_380 | (S)-2-(2-Benzoylphenylamino)-3-{4-[2-(but-2-(E)-enoylnaphthalen-2-ylamino)ethoxy]phenyl}propionic acid | rt: 8.491 MS[M+1]$^+$: 599 | A |
| I_437 | IIa_381 | (S)-2-(2-Benzoylphenylamino)-3-{4-[2-(naphthalen-2-ylpropionylamino)-ethoxy]phenyl}propionic acid | rt: 8.494 MS[M+1]$^+$: 587 | A |
| I_438 | IIa_382 | (S)-3-{4-[2-(Acetylnaphthalen-2-ylamino)ethoxy]phenyl}-2-(2-benzoylphenylamino)propionic acid | rt: 8.099 MS[M+1]$^+$: 573 | A |
| I_439 | IIa_383 | (S)-2-(2-Benzoylphenylamino)-3-(4-{2-[(2-methylacryloyl)-(3-methylsulfanylphenyl)amino]ethoxy}-phenyl)propionic acid | rt: 8.343 MS[M+1]$^+$: 595 | A |
| I_440 | IIa_334 | (S)-2-(2-Benzoylphenylamino)-3-(4-{2-[but-2-(E)-enoyl-(3-methylsulfanylphenyl)amino]ethoxy}-phenyl)propionic acid | rt: 8.261 MS[M+1]$^+$: 595 | A |
| I_441 | IIa_385 | (S)-2-(2-Benzoylphenylamino)-3-(4-{2-[butyryl-(3-methylsulfanylphenyl)-amino]ethoxy}phenyl)propionic acid | rt: 8.51 MS[M+1]$^+$: 597 | A |
| I_442 | IIa_386 | (S)-2-(2-Benzoylphenylamino)-3-(4-{2-[(2-methylacryloyl)-(4-methylsulfanylphenyl)amino]ethoxy}-phenyl)propionic acid | rt: 8.36 MS[M+1]$^+$: 595 | A |
| I_443 | IIa_387 | (S)-2-(2-Benzoylphenylamino)-3-(4-{2-[but-2-(E)-enoyl-(4-methylsulfanylphenyl)amino]ethoxy}-phenyl)propionic acid | rt: 8.262 MS[M+1]$^+$: 595 | A |
| I_444 | IIa_388 | (S)-2-(2-Benzoylphenylamino)-3-(4-{2-[isobutyryl-(4-methylsulfanylphenyl)amino]ethoxy}-phenyl)propionic acid | rt: 8.519 MS[M+1]$^+$: 597 | A |
| I_445 | IIa_389 | (S)-2-(2-Benzoylphenylamino)-3-(4-{2-[butyryl-(4-methylsulfanylphenyl)-amino]ethoxy}phenyl)propionic acid | rt: 8.522 MS[M+1]$^+$: 597 | A |
| I_446 | IIa_390 | (S)-3-{4-[2-Acetylnaphthalen-1-ylamino)ethoxy]phenyl}-2-(2-benzoylphenylamino)propionic acid | rt: 8.599 MS[M+1]$^+$: __ | A |
| I_447 | IIa_391 | (S)-2-(2-Benzoylphenylamino)-3-{4-[2-(cyclopropanecarbonylnaphthalen-2-ylamino)ethoxy]phenyl}propionic acid | rt: 8.627 MS[M+1]$^+$: __ | A |
| I_448 | IIa_392 | (S)-2-(2-Benzoylphenylamino)-3-(4-{3-[butyryl-(2-fluorophenyl)amino]-propoxy}phenyl)propionic acid | rt: 8.464 MS[M+1]$^+$: 583 | A |
| I_449 | IIa_393 | (S)-2-(2-Benzoylphenylamino)-3-(4-{3-[cyclobutanecarbonyl-(2-fluorophenyl)amino]propoxy}phenyl)-propionic acid | rt: 8.603 MS[M+1]$^+$: 595 | A |
| I_450 | IIa_394 | (S)-2-(2-Benzoylphenylamino)-3-(4-{3-[cyclopropanecarbonyl-(2-fluorophenyl)amino]propoxy}phenyl)-propionic acid | rt: 8.269 MS[M+1]$^+$: 581 | A |
| I_451 | IIa_395 | (S)-2-(2-Benzoylphenylamino)-3-(4-{3-[(2-fluorophenyl)isobutyrylamino]-propoxy}phenyl)propionic acid | rt: 8.451 MS[M+1]$^+$: 583 | A |
| I_452 | II_55 | (S)-2-(2-Benzoylphenylamino)-3-(4-{2-[cyclohexylmethyl-(2-fluorophenyl)-amino]ethoxy}phenyl)propionic acid | rt: 10.216 MS[M+1]$^+$: 595 | A |

TABLE 6-continued

| Example Number | Starting product | Compound name | ¹H-NMR/LC-MS | HPLC Method |
|---|---|---|---|---|
| I_453 | II_56 | (S)-2-(2-Benzoylphenylamino)-3-(4-{2-[(3-chlorophenyl)-cyclopentylmethylamino]ethoxy}-phenyl)propionic acid | rt: 10.146<br>MS[M+1]⁺: 597, 599 | A |
| I_454 | II_57 | (S)-2-(2-Benzoylphenylamino)-3-(4-{3-[cyclobutylmethyl-(3-fluorophenyl)-amino]propoxy}phenyl)propionic acid | rt: 9.757<br>MS[M+1]⁺: 581 | A |
| I_455 | II_58 | (S)-2-(2-Benzoylphenylamino)-3-{4-[3-(cyclobutylmethyl-m-tolylamino)-propoxy]phenyl}propionic acid | rt: 8.973<br>MS[M+1]⁺: 577 | A |
| I_456 | II_59 | (R)-2-(2-Benzoylphenylamino)-3-{4-[2-(benzylphenylamino)ethoxy]-phenyl}propionic acid | rt: 9.268<br>MS[M+1]⁺: 571 | A |
| I_457 | II_60 | (S)-2-(2-Benzoylphenylamino)-3-(4-{2-[(2-chlorophenyl)-cyclopentylmethylamino]ethoxy}-phenyl)propionic acid | rt: 10.276<br>MS[M+1]⁺: 597, 599 | A |
| I_458 | II_61 | (S)-2-(2-Benzoylphenylamino)-3-(4-{2-[(2-fluorophenyl)thiophen-2-ylmethylamino]ethoxy}phenyl)-propionic acid | rt: 9.166<br>MS[M+1]⁺: 595 | A |
| I_459 | II_62 | (S)-2-(2-Benzoylphenylamino)-3-(4-{3-[(2-fluorophenyl)isobutylamino]-propoxy}phenyl)propionic acid | rt: 9.755<br>MS[M+1]⁺: 569 | A |
| I_460 | II_63 | (S)-2-(2-Benzoylphenylamino)-3-(4-{3-[cyclopentylmethyl-(2-fluorophenyl)amino]propoxy}phenyl)-propionic acid | rt: 10.09<br>MS[M+1]⁺: 595 | A |
| I_461 | II_64 | (S)-2-(2-Benzoylphenylamino)-3-{4-[3-(cyclobutylmethyl-o-tolylamino)-propoxy]phenyl}propionic acid | rt: 8.508<br>MS[M+1]⁺: 577 | A |
| I_462 | II_65 | (S)-2-(2-Benzoylphenylamino)-3-(4-{2-[(3-fluorophenyl)thiophen-2-ylmethylamino]ethoxy}phenyl)-propionic acid | rt: 9.089<br>MS[M+1]⁺: 595 | A |
| I_463 | II_66 | (S)-2-(2-Benzoylphenylamino)-3-{4-[2-(thiophen-2-ylmethyl-m-tolylamino)-ethoxy]phenyl}propionic acid | rt: 9.325<br>MS[M+1]⁺: 591 | A |
| I_464 | II_67 | (S)-2-(2-Benzoylphenylamino)-3-{4-[3-(thiophen-3-ylmethyl-m-tolylamino)-propoxy]phenyl}propionic acid methyl ester | rt: 9.412<br>MS[M+1]⁺: 605 | A |
| I_465 | II_68 | (S)-2-(2-Benzoylphenylamino)-3-{4-[3-(furan-2-ylmethyl-m-tolylamino)-propoxy]pheny}propionic acid | rt: 9.242<br>MS[M+1]⁺: 589 | A |
| I_466 | II_69 | (S)-2-(2-Benzoylphenylamino)-3-(4-{2-[(4-fluorophenyl)thiophen-2-ylmethylamino]ethoxy}phenyl)-propionic acid | rt: 9.077<br>MS[M+1]⁺: 595 | A |
| I_467 | II_70 | (S)-2-(2-Benzoylphenylamino)-3-{4-[2-(phenylthiophen-2-ylmethylamino)-ethoxy]phenyl}propionic acid | rt: 9.11<br>MS[M+1]⁺: 577 | A |
| I_468 | II_71 | (S)-2-(2-Benzoylphenylamino)-3-{4-[3-(phenylthiophen-2-ylmethylamino)-propoxy]phenyl}propionic acid | rt: 9.251<br>MS[M+1]⁺: 591 | A |
| I_469 | IIa_396 | (S)-2-(2-Benzoylphenylamino)-3-(4-{2-[benzyl-(3-methoxypropionyl)-amino]ethoxy}phenyl)propionic acid | rt: 7.751<br>MS[M+1]⁺: 581 | A |
| I_470 | IIa_397 | (S)-2-(2-Benzoylphenylamino)-3-(4-{3-[benzyl-(3-methoxypropionyl)-amino]propoxy}phenyl)propionic acid | rt: 7.849<br>MS[M+1]⁺: 595 | A |
| I_471 | IIa_398 | (S)-2-(2-Benzoylphenylamino)-3-(4-{2-[(3-methoxypropionyl)-phenylamino]ethoxy}phenyl)propionic acid | rt: 7.665<br>MS[M+1]⁺: 567 | A |
| I_472 | IIa_399 | (S)-2-(2-Benzoylphenylamino)-3-(4-{3-[(3-methoxypropionyl)-phenylamino]propoxy}phenyl)-propionic acid | rt: 7.85<br>MS[M+1]⁺: 581 | A |
| I_473 | IIa_400 | (S)-2-(2-Benzoylphenylamino)-3-(4-{3-[(2-fluorophenyl)propionylamino]-propoxy}phenyl)propionic acid | rt: 8.169<br>MS[M+1]⁺: 569 | A |
| I_474 | IIa_401 | (S)-2-(2-Benzoylphenylamino)-3-(4-{3-[(2-fluorophenyl)pent-4-enoylamino]propoxy}phenyl)propionic acid | rt: 8.514<br>MS[M+1]⁺: 595 | A |

TABLE 6-continued

| Example Number | Starting product | Compound name | ¹H-NMR/LC-MS | HPLC Method |
|---|---|---|---|---|
| I_475 | IIa_402 | (S)-3-(4-{3-[Acryloyl-(2-fluorophenyl)-amino]propoxy}phenyl)-2-(2-benzoylphenylamino)propionic acid | rt: 8.046<br>MS[M+1]⁺: 567 | A |
| I_476 | IIa_403 | (S)-2-(2-Benzoylphenylamino)-3-(4-{3-[but-2-(E)-enoyl-(2-fluorophenyl)-amino]propoxy}phenyl)propionic acid | rt: 8.208<br>MS[M+1]⁺: 581 | A |
| I_477 | IIa_404 | (S)-2-(2-Benzoylphenylamino)-3-(4-{3-[(2-fluorophenyl)-(3-methylbutyryl)-amino]propoxy}phenyl)propionic acid | rt: 8.701<br>MS[M+1]⁺: 597 | A |
| I_478 | IIa_405 | (R)-2-(2-Benzoylphenylamino)-3-(4-{2-[phenyl(thiophene-2-carbonyl)-amino]ethoxy}phenyl)propionic acid | rt: 8.24<br>MS[M+1]⁺: 579 | A |
| I_479 | IIa_406 | (S)-2-(2-Benzoylphenylamino)-3-(4-{3-[(2-fluorophenyl)-(2-methylacryloyl)amino]propoxy}-phenyl)propionic acid | rt: 8.243<br>MS[M+1]⁺: 581 | A |
| I_480 | IIa_407 | (S)-2-(2-Benzoylphenylamino)-3-(4-{3-[(3-fluorophenyl)-(2-methylacryloyl)amino]propoxy}-phenyl)propionic acid | rt: 8.232<br>MS[M+1]⁺: 581 | A |
| I_481 | IIa_408 | (S)-2-(2-Benzoylphenylamino)-3-(4-{2-[but-2-(E)-enoyl-(2-methoxyphenyl)amino]ethoxy}phenyl)-propionic acid | rt: 8.038<br>MS[M+1]⁺: 579 | A |
| I_482 | IIa_409 | (S)-2-(2-Benzoylphenylamino)-3-(4-{2-[but-2-(E)-enoyl-(3-methoxyphenyl)amino]ethoxy}phenyl)-propionic acid | rt: 8.053<br>MS[M+1]⁺: 579 | A |
| I_483 | IIa_410 | (S)-2-(2-Benzoylphenylamino)-3-(4-{2-[(2-methoxyphenyl)-(3-methylbutyryl)amino]ethoxy}phenyl)-propionic acid | rt: 8.541<br>MS[M+1]⁺: 595 | A |
| I_484 | IIa_411 | (S)-2-(2-Benzoylphenylamino)-3-(4-{3-[(3-fluorophenyl)-(3-methylbutyryl)-amino]propoxy}phenyl)propionic acid | rt: 8.701<br>MS[M+1]⁺: 597 | A |
| I_485 | IIa_412 | (S)-2-(2-Benzoylphenylamino)-3-(4-{2-[(3-methoxyphenyl)-(3-methylbutyryl)amino]ethoxy}phenyl)-propionic acid | rt: 8.479<br>MS[M+1]⁺: 595 | A |
| I_486 | IIa_413 | (S)-2-(2-Benzoylphenylamino)-3-(4-{3-[(3-fluorophenyl)pent-4-enoylamino]propoxy}phenyl)propionic acid | rt: 8.513<br>MS[M+1]⁺: 595 | A |
| I_487 | IIa_414 | (S)-2-(2-Benzoylphenylamino)-3-(4-{3-[cyclobutanecarbonyl-(3-fluorophenyl)amino]propoxy}phenyl)-propionic acid | rt: 8.596<br>MS[M+1]⁺: 595 | A |
| I_488 | IIa_415 | (S)-2-(2-Benzoylphenylamino)-3-(4-{3-[cyclobutanecarbonyl-(4-fluorophenyl)amino]propoxy}phenyl)-propionic acid | rt: 8.583<br>MS[M+1]⁺: 595 | A |
| I_489 | IIa_416 | (R)-2-(2-Benzoylphenylamino)-3-{4-[2-(cyclobutanecarbonylphenylamino)-ethoxy]phenyl}propionic acid | rt: 8.416<br>MS[M+1]⁺: 563 | A |
| I_490 | IIa_417 | (S)-2-(2-Benzoylphenylamino)-3-(4-{2-[cyclopropanecarbonyl-(2-methoxyphenyl)amino]ethoxy}phenyl)-propionic acid | rt: 8.082<br>MS[M+1]⁺: 579 | A |
| I_491 | IIa_418 | (S)-2-(2-Benzoylphenylamino)-3-(4-{3-[cyclopropanecarbonyl-(3-fluorophenyl)amino]propoxy}phenyl)-propionic acid | rt: 8.313<br>MS[M+1]⁺: 581 | A |
| I_492 | IIa_419 | (S)-2-(2-Benzoylphenylamino)-3-(4-{3-[cyclopropanecarbonyl-(4-fluorophenyl)amino]propoxy}phenyl)-propionic acid | rt: 8.293<br>MS[M+1]⁺: 581 | A |
| I_493 | IIa_420 | (S)-2-(2-Benzoylphenylamino)-3-(4-{2-[(2-methoxyphenyl)-propionylamino]ethoxy}phenyl)-propionic acid | rt: 7.996<br>MS[M+1]⁺: 567 | A |
| I_494 | IIa_421 | (S)-2-(2-Benzoylphenylamino)-3-(4-{3-[(3-fluorophenyl)propionylamino]-propoxy}phenyl)propionic acid | rt: 8.175<br>MS[M+1]⁺: 569 | A |

TABLE 6-continued

| Example Number | Starting product | Compound name | $^1$H-NMR/LC-MS | HPLC Method |
|---|---|---|---|---|
| I_495 | IIa_422 | (S)-2-(2-Benzoylphenylamino)-3-(4-{2-[(3-methoxyphenyl)-propionylamino]ethoxy}phenyl)-propionic acid | rt: 7.947<br>MS[M+1]$^+$: 567 | A |
| I_496 | IIa_423 | (S)-2-(2-Benzoylphenylamino)-3-(4-{3-[(4-fluorophenyl)propionylamino]-propoxy}phenyl)propionic acid | rt: 8.16<br>MS[M+1]$^+$: 569 | A |
| I_497 | IIa_424 | (R)-2-(2-Benzoylphenylamino)-3-{4-[2-(phenylpropionylamino)ethoxy]-phenyl}propionic acid | rt: 7.952<br>MS[M+1]$^+$: 593 | A |
| I_498 | IIa_425 | (S)-2-(2-Benzoylphenylamino)-3-(4-{3-[(3-fluorophenyl)isobutyrylamino]-propoxy}phenyl)propionic acid | rt: 8.434<br>MS[M+1]$^+$: 583 | A |
| I_499 | IIa_426 | (S)-2-(2-Benzoylphenylamino)-3-(4-{2-[isobutyryl-(3-methoxyphenyl)-amino]ethoxy}phenyl)propionic acid | rt: 8.218<br>MS[M+1]$^+$: 581 | A |
| I_500 | IIa_427 | (S)-2-(2-Benzoylphenylamino)-3-(4-{3-[(4-fluorophenyl)isobutyrylamino]-propoxy}phenyl)propionic acid | rt: 8.424<br>MS[M+1]$^+$: 583 | A |
| I_501 | IIa_428 | (S)-2-(2-Benzoylphenylamino)-3-(4-{3-[(2-fluorophenyl)pentanoylamino]-propoxy}phenyl)propionic acid | rt: 8.73<br>MS[M+1]$^+$: 597 | A |
| I_502 | IIa_429 | (S)-2-(2-Benzoylphenylamino)-3-(4-{3-[(3-fluorophenyl)pentanoylamino]-propoxy}phenyl)propionic acid | rt: 8.726<br>MS[M+1]$^+$: 597 | A |
| I_503 | IIa_430 | (S)-2-(2-Benzoylphenylamino)-3-(4-{2-[butyryl-(2-methoxyphenyl)amino]-ethoxy}phenyl)propionic acid | rt: 8.274<br>MS[M+1]$^+$: 581 | A |
| I_504 | IIa_431 | (S)-2-(2-Benzoylphenylamino)-3-(4-{3-[butyryl-(3-fluorophenyl)amino]-propoxy}phenyl)propionic acid | rt: 8.447<br>MS[M+1]$^+$: 583 | A |
| I_505 | IIa_432 | (S)-2-(2-Benzoylphenylamino)-3-(4-{2-[butyryl-(3-methoxyphenyl)amino]-ethoxy}phenyl)propionic acid | rt: 8.222<br>MS[M+1]$^+$: 581 | A |
| I_506 | IIa_433 | (S)-2-(2-Benzoylphenylamino)-3-(4-{3-[butyryl-(4-fluorophenyl)amino]-propoxy}phenyl)propionic acid | rt: 8.436<br>MS[M+1]$^+$: 583 | A |
| I_507 | IIa_434 | (S)-2-(2-Benzoylphenylamino)-3-(4-{3-[(2,2-dimethylpropionyl)-(2-fluorophenyl)amino]propoxy}phenyl)-propionic acid | rt: 8.792<br>MS[M+1]$^+$: 597 | A |
| I_508 | IIa_435 | (S)-2-(2-Benzoylphenylamino)-3-(4-{2-[(2,2-dimethylpropionyl)-(2-methoxyphenyl)amino]ethoxy}phenyl)-propionic acid | rt: 8.656<br>MS[M+1]$^+$: 595 | A |
| I_509 | IIa_436 | (S)-2-(2-Benzoylphenylamino)-3-(4-{3-[(2,2-dimethylpropionyl)-(3-fluorophenyl)amino]propoxy}phenyl)-propionic acid | rt: 8.784<br>MS[M+1]$^+$: 597 | A |
| I_510 | IIa_437 | (S)-2-(2-Benzoylphenylamino)-3-(4-{2-[(2,2-dimethylpropionyl)-(3-methoxyphenyl)amino]ethoxy}phenyl)-propionic acid | rt: 8.61<br>MS[M+1]$^+$: 595 | A |
| I_511 | IIa_438 | (S)-2-(2-Benzoylphenylamino)-3-(4-{2-[isobutyryl-(3-methylsulfanylphenyl)amino]ethoxy}-phenyl)propionic acid | rt: 8.483<br>MS[M+1]$^+$: 597 | A |
| I_512 | IIa_439 | (S)-2-(2-Benzoylphenylamino)-3-(4-{3-[(2-methoxyphenyl)-propionylamino]propoxy}phenyl)-propionic acid | rt: 8.122<br>MS[M+1]$^+$: 581 | A |
| I_513 | IIa_440 | (S)-2-(2-Benzoylphenylamino)-3-(4-{3-[cyclopropanecarbonyl-(2-methoxyphenyl)amino]propoxy}-phenyl)propionic acid | rt: 8.213<br>MS[M+1]$^+$: 593 | A |
| I_514 | IIa_441 | (S)-2-(2-Benzoylphenylamino)-3-(4-{3-[isobutyryl-(2-methoxyphenyl)-amino]propoxy}phenyl)propionic acid | rt: 8.385<br>MS[M+1]$^+$: 595 | A |
| I_515 | IIa_442 | (S)-2-(2-Benzoylphenylamino)-3-(4-{3-[but-2-(E)-enoyl-(2-methoxyphenyl)amino]propoxy}-phenyl)propionic acid | rt: 8.159<br>MS[M+1]$^+$: 593 | A |
| I_516 | IIa_443 | (S)-2-(2-Benzoylphenylamino)-3-(4-{3-[(2-methoxyphenyl)-(2-methylacryloyl)amino]propoxy}-phenyl)propionic acid | rt: 8.163<br>MS[M+1]$^+$: 593 | A |

TABLE 6-continued

| Example Number | Starting product | Compound name | ¹H-NMR/LC-MS | HPLC Method |
|---|---|---|---|---|
| I_517 | IIa_444 | (S)-3-(4-{3-[Acryloyl-(2-methoxyphenyl)amino]propoxy}-phenyl)-2-(2-benzoylphenylamino)-propionic acid | rt: 8.015<br>MS[M+1]⁺: 579 | A |
| I_518 | IIa_445 | (S)-2-(2-Benzoylphenylamino)-3-(4-{3-[butyryl-(2-methoxyphenyl)amino]-propoxy}phenyl)propionic acid | rt: 8.395<br>MS[M+1]⁺: 595 | A |
| I_519 | IIa_446 | (S)-2-(2-Benzoylphenylamino)-3-(4-{3-[(3-methoxyphenyl)-propionylamino]propoxy}phenyl)-propionic acid | rt: 8.111<br>MS[M+1]⁺: 581 | A |
| I_520 | IIa_447 | (S)-2-(2-Benzoylphenylamino)-3-(4-{3-[cyclopropanecarbonyl-(3-methoxyphenyl)amino]propoxy}-phenyl)propionic acid | rt: 8.246<br>MS[M+1]⁺: 593 | A |
| I_521 | IIa_448 | (S)-2-(2-Benzoylphenylamino)-3-(4-{3-[isobutyryl-(3-methoxyphenyl)-amino]propoxy}phenyl)propionic acid | rt: 8.374<br>MS[M+1]⁺: 595 | A |
| I_522 | IIa_449 | (S)-2-(2-Benzoylphenylamino)-3-(4-{3-[but-2-(E)-enoyl-(3-methoxyphenyl)amino]propoxy}-phenyl)propionic acid | rt: 8.204<br>MS[M+1]⁺: 593 | A |
| I_523 | IIa_450 | (S)-2-(2-Benzoylphenylamino)-3-(4-{3-[(3-methoxyphenyl)-(2-methylacryloyl)amino]propoxy}-phenyl)propionic acid | rt: 8.134<br>MS[M+1]⁺: 593 | A |
| I_524 | IIa_451 | (S)-3-(4-{3-[Acryloyl-(3-methoxyphenyl)amino]propoxy}-phenyl)-2-(2-benzoylphenylamino)-propionic acid | rt: 8.045<br>MS[M+1]⁺: 579 | A |
| I_525 | IIa_452 | (S)-2-(2-Benzoylphenylamino)-3-(4-{3-[butyryl-(3-methoxyphenyl)amino]-propoxy}phenyl)propionic acid | rt: 8.381<br>MS[M+1]⁺: 595 | A |
| I_526 | IIa_453 | (S)-2-(2-Benzoylphenylamino)-3-(4-{2-[cyclobutanecarbonyl-(2-methoxyphenyl)amino]ethoxy}phenyl)-propionic acid | rt: 8.42<br>MS[M+1]⁺: 593 | A |
| I_527 | IIa_454 | (S)-2-(2-Benzoylphenylamino)-3-(4-{2-[isobutyryl-(2-methoxyphenyl)-amino]ethoxy}phenyl)propionic acid | rt: 8.27<br>MS[M+1]⁺: 581 | A |
| I_528 | IIa_455 | (S)-3-{4-[2-(Acryloylnaphthalen-1-ylamino)ethoxy]phenyl}-2-(2-benzoylphenylamino)propionic acid | rt: 8.35<br>MS[M+1]⁺: 585 | A |
| I_529 | IIa_456 | (S)-3-{4-[2-(Acryloylnaphthalen-2-ylamino)ethoxy]phenyl}-2-(2-benzoylphenylamino)propionic acid | rt: 8.418<br>MS[M+1]⁺: 585 | A |
| I_530 | IIa_457 | (S)-3-(4-{2-[Acryloyl-(3-methylsulfanylphenyl)amino]ethoxy}-phenyl)-2-(2-benzoylphenylamino)-propionic acidr | rt: 8.172<br>MS[M+1]⁺: 581 | A |
| I_531 | IIa_458 | (S)-3-(4-{2-[Acryloyl-(4-methylsulfanylphenyl)amino]ethoxy}-phenyl)-2-(2-benzoylphenylamino)-propionic acid | rt: 8.182<br>MS[M+1]⁺: 581 | A |
| I_532 | IIa_459 | (S)-3-(4-{3-[Acryloyl-(3-fluorophenyl)-amino]propoxy}phenyl)-2-(2-benzoylphenylamino)propionic acid | rt: 8.098<br>MS[M+1]⁺: 567 | A |
| I_533 | IIa_460 | (S)-2-(2-Benzoylphenylamino)-3-(4-{3-[but-2-(E)-enoyl-(3-fluorophenyl)-amino]propoxy}phenyl)propionic acid | rt: 8.274<br>MS[M+1]⁺: 581 | A |
| I_534 | IIa_461 | (S)-3-(4-{2-[Acryloyl-(2-methoxyphenyl)amino]ethoxy}phenyl)-2-(2-benzoylphenylamino)propionic acid | rt: 7.886<br>MS[M+1]⁺: 565 | A |
| I_535 | IIa_462 | (S)-2-(2-Benzoylphenylamino)-3-(4-{2-[(2-methoxyphenyl)-(2-methylacryloyl)amino]ethoxy}phenyl)-propionic acid | rt: 8.037<br>MS[M+1]⁺: 579 | A |
| I_536 | IIa_463 | (S)-2-(2-Benzoylphenylamino)-3-(4-{2-[cyclopropanecarbonyl-(3-methoxyphenyl)amino]ethoxy}phenyl)-poropionic acid | rt: 8.081<br>MS[M+1]⁺: 579 | A |
| I_537 | IIa_464 | (S)-2-(2-Benzoylphenylamino)-3-(4-{2-[cyclobutanecarbonyl-(3-methoxyphenyl)amino]ethoxy}phenyl)-propionic acid | rt: 8.384<br>MS[M+1]⁺: 593 | A |

TABLE 6-continued

| Example Number | Starting product | Compound name | ¹H-NMR/LC-MS | HPLC Method |
|---|---|---|---|---|
| I_538 | IIa_465 | (S)-3-(4-{2-[Acryloyl-(3-methoxyphenyl)amino]ethoxy}phenyl)-2-(2-benzoylphenylamino)propionic acid | rt: 7.884<br>MS[M+1]$^+$: 565 | A |
| I_539 | IIa_466 | (S)-2-(2-Benzoylphenylamino)-3-(4-{2-[(3-methoxyphenyl)-(2-methylacryloyl)amino]ethoxy}phenyl)-propionic acid | rt: 7.975<br>MS[M+1]$^+$: 579 | A |
| I_540 | IIa_467 | (S)-2-(2-Benzoylphenylamino)-3-(4-{2-[ethyl(naphthalene-2-carbonyl)-amino]ethoxy}phenyl)propionic acid | rt: 8.236<br>MS[M+1]$^+$: 587 | A |
| I_541 | IIa_468 | (S)-2-(2-Benzoylphenylamino)-3-(4-{2-[(naphthalene-2-carbonyl)-propylamino]ethoxy}phenyl)propionic acid | rt: 8.511<br>MS[M+1]$^+$: 601 | A |
| I_542 | IIa_469 | (S)-2-(2-Benzoylphenylamino)-3-(4-{2-[ethyl(quinoline-2-carbonyl)amino]-ethoxy}phenyl)propionic acid | rt: 7.881<br>MS[M+1]$^+$: 588 | A |
| I_543 | IIa_470 | (S)-2-(2-Benzoylphenylamino)-3-(4-{2-[propyl(quinoline-2-carbonyl)-amino]ethoxy}phenyl)propionic acid | rt: 8.2<br>MS[M+1]$^+$: 602 | A |
| I_544 | IIa_471 | (S)-2-(2-Benzoylphenylamino)-3-(4-{2-[ethyl(quinoxaline-2-carbonyl)-amino]ethoxy}phenyl)propionic acid | rt: 7.756<br>MS[M+1]$^+$: 589 | A |
| I_545 | IIa_472 | (S)-2-(2-Benzoylphenylamino)-3-(4-{2-[propyl(quinoxaline-2-carbonyl)-amino]ethoxy}phenyl)propionic acid | rt: 8.077<br>MS[M+1]$^+$: 603 | A |
| I_546 | IIa_473 | (S)-2-(2-Benzoylphenylamino)-3-(4-{2-[ethyl(thiophene-2-carbonyl)-amino]ethoxy}phenyl)propionic acid | rt: 7.732<br>MS[M+1]$^+$: 543 | A |
| I_547 | IIa_474 | (S)-2-(2-Benzoylphenylamino)-3-(4-{2-[propyl(thiophene-2-carbonyl)-amino]ethoxy}phenyl)propionic acid | rt: 8.04<br>MS[M+1]$^+$: 557 | A |
| I_548 | IIa_475 | (S)-2-(2-Benzoylphenylamino)-3-(4-{2-[ethyl(pyridine-3-carbonyl)amino]-ethoxy}phenyl)propionic acid | rt: 6.713<br>MS[M+1]$^+$: 538 | A |
| I_549 | IIa_476 | (S)-2-(2-Benzoylphenylamino)-3-(4-{2-[propyl(pyridine-3-carbonyl)amino]-ethoxy}phenyl)propionic acid | rt: 7.037<br>MS[M+1]$^+$: 552 | A |
| I_550 | IIa_477 | (S)-2-(2-Benzoylphenylamino)-3-(4-{2-[ethyl-(3-thiophen-2-ylacryloyl)-amino]ethoxy}phenyl)propionic acid | rt: 7.924<br>MS[M+1]$^+$: 569 | A |
| I_551 | IIa_478 | (S)-2-(2-Benzoylphenylamino)-3-(4-{2-[propyl-(3-thiophen-2-ylacryloyl)-amino]ethoxy}phenyl)propionic acid | rt: 8.236<br>MS[M+1]$^+$: 583 | A |
| I_552 | IIa_479 | (S)-2-(2-Benzoylphenylamino)-3-(4-{2-[(3,3-dimethylbutyryl)propylamino]-ethoxy}phenyl)propionic acid | rt: 8.572<br>MS[M+1]$^+$: 545 | A |
| I_553 | IIa_480 | (S)-2-(2-Benzoylphenylamino)-3-(4-{2-[ethyl-(3-pyridin-3-ylpropionyl)-amino]ethoxy}phenyl)propionic acid | rt: 5.866<br>MS[M+1]$^+$: 566 | A |
| I_554 | IIa_481 | (S)-2-(2-Benzoylphenylamino)-3-(4-{2-[propyl-(3-pyridin-3-ylpropionyl)-amino]ethoxy}phenyl)propionic acid | rt: 6.125<br>MS[M+1]$^+$: 580 | A |
| I_555 | IIa_482 | (S)-2-(2-Benzoylphenylamino)-3-{4-[2-(cyclobutanecarbonylpropylamino)-ethoxy]phenyl}propionic acid | rt: 8.138<br>MS[M+1]$^+$: 529 | A |
| I_556 | IIa_483 | (S)-2-(2-Benzoylphenylamino)-3-{4-[2-(isobutyrylpropylamino)ethoxy]phenyl}propionic acid | rt: 7.963<br>MS[M+1]$^+$: 517 | A |
| I_557 | IIa_484 | (S)-2-(2-Benzoylphenylamino)-3-{4-[2-butyrylpropylamino)ethoxy]phenyl}-propionic acid | rt: 7.945<br>MS[M+1]$^+$: 517 | A |
| I_558 | IIa_485 | (S)-3-{4-[2-(Benzoylethylamino)-ethoxy]phenyl}-2-(2-benzoylphenylamino)propionic acid | rt: 7.725<br>MS[M+1]$^+$: 537 | A |
| I_559 | IIa_486 | (S)-2-(2-Benzoylphenylamino)-3-{4-[2-(benzoylpropylamino)ethoxy]phenyl}-propionic acid | rt: 8.03<br>MS[M+1]$^+$: 551 | A |
| I_560 | IIa_487 | (S)-2-(2-Benzoylphenylamino)-3-(4-{2-[ethyl-(3-phenylacryloyl)amino]ethoxy}phenyl)propionic acid | rt: 8.034<br>MS[M+1]$^+$: 563 | A |
| I_561 | IIa_488 | (S)-2-(2-Benzoylphenylamino)-3-(4-{2-[(2,2-dimethylpropionyl)-ethylamino]ethoxy}phenyl)propionic acid | rt: 8.102<br>MS[M+1]$^+$: 517 | A |

| Example Number | Starting product | Compound name | ¹H-NMR/LC-MS | HPLC Method |
|---|---|---|---|---|
| I_562 | IIa_489 | (S)-2-(2-Benzoylphenylamino)-3-(4-{2-[(2,2-dimethylpropionyl)-propylamino]ethoxy}phenyl)propionic acid | rt: 8.44<br>MS[M+1]⁺: 531 | A |

The invention claimed is:

1. A compound of formula I

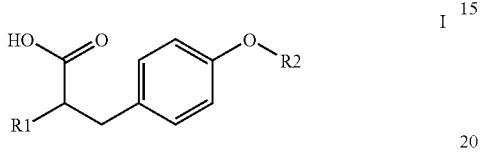

its stereoisomers and mixtures thereof, its polymorphs and mixtures thereof, and the pharmaceutically acceptable solvates and addition salts of all of them, wherein R1 represents the radical 2-benzoylphenylamino;

R2 represents —(CH$_2$)$_s$—N(COR3)-A-J-T or —(CH$_2$)$_s$—N(R4)-B-J-T;

R3 represents —(C$_1$-C$_{10}$)alkyl optionally substituted by one or more substituents selected from —F, —Cl, —Br and —O(C$_1$-C$_4$)alkyl; —(C$_2$-C$_6$)alkenyl; —(C$_2$-C$_6$)alkynyl; —(C$_1$-C$_3$)-alkylene-Y; —(C$_2$-C$_3$)alkenylene-Y; —(C$_2$-C$_3$)alkynylene-Y or —Y;

R4 represents —(C$_4$-C$_{10}$)alkyl optionally substituted by one or more substituents selected from —F, —Cl, —Br and —O(C$_1$-C$_4$)alkyl; —(C$_2$-C$_6$)alkenyl; —(C$_2$-C$_6$)alkynyl; —(C$_1$-C$_4$)-alkylene-Y; —(C$_2$-C$_4$)alkenylene-Y; —(C$_2$-C$_4$)alkynylene-Y or —Y;

s represents 2 or 3;

A represents —(C$_1$-C$_4$)alkylene-; —(C$_2$-C$_4$)alkenylene-; —(C$_2$-C$_4$)alkynylene-; —(C$_1$-C$_4$)-alkylene-Z-, wherein the alkylene part is attached to the N atom and Z is attached to J; or -Z-;

B represents —(C$_4$)alkylene-; —(C$_2$-C$_4$)alkenylene-; —(C$_2$-C$_4$)alkynylene-; —(C$_1$-C$_4$)-alkylene-Z-, wherein the alkylene part is attached to the N atom and Z is attached to J; or -Z-;

J represents a single bond or a biradical selected from the following groups:
a) —(CH$_2$)$_{1-4}$—, —O—, —S—, —SO—, —SO$_2$—, —CO—, —OCO—, —COO—, —OCONR5-, —NR5COO—, —CONR5-, —NR5CO—, —NR5-, —NR5SO$_2$—, —SO$_2$NR5-; and
b) —O—(C$_1$-C$_4$)alkyl-, —(C$_1$-C$_4$)alkyl-O—, —S—(C$_1$-C$_4$)alkyl-, —(C$_1$-C$_4$)alkyl-S—, —SO—(C$_1$-C$_4$)alkyl-, —(C$_1$-C$_4$)alkyl-SO—, —SO$_2$—(C$_1$-C$_4$)alkyl-, —(C$_1$-C$_4$)alkyl-SO$_2$—, —OCO—(C$_1$-C$_4$)alkyl-, —COO—(C$_1$-C$_4$)alkyl-, —(C$_1$-C$_4$)alkyl-OCO—, —(C$_1$-C$_4$)-alkyl-COO—, —OCONR5-(C$_1$-C$_4$)alkyl-, —NR5COO—(C$_1$-C$_4$)alkyl, —(C$_1$-C$_4$)-alkyl-OCONR5-, —(C$_1$-C$_4$)alkyl-NR5COO—, —CONR5-(C$_1$-C$_4$)alkyl-, —R5CO—(C$_1$-C$_4$)alkyl-, —(C$_1$-C$_4$)alkyl-CONR5-, —(C$_1$-C$_4$)alkyl-NR5CO—, —NR5-(C$_1$-C$_4$)alkyl-, —(C$_1$-C$_4$)alkyl-NR5-, —SO$_2$NR5-(C$_1$-C$_4$)alkyl-, —NR5SO$_2$—(C$_1$-C$_4$)-alkyl-, —(C$_1$-C$_4$)alkyl-SO$_2$NR5-, —(C$_1$-C$_4$)alkyl-NR5SO$_2$—;

T represents —H, —(C$_1$-C$_4$)alkyl, —(C$_2$-C$_4$)alkenyl, —(C$_2$-C$_4$)alkynyl or —Y;

Y represents a monoradical coming from a cycle selected from a (C$_3$-C$_6$)cycloalkane, cyclohexene, a heterocycle, benzene and a bicycle, wherein all these cycles can be optionally substituted with one or more substituents selected from the group —OH, —CHO, —SH, —NO$_2$, —CN, —F, —Cl, —Br, —CO(C$_1$-C$_4$)alkyl, —COO(C$_1$-C$_4$)alkyl, —OCO(C$_1$-C$_4$)alkyl, —S(C$_1$-C$_4$)alkyl, —SO(C$_1$-C$_4$)alkyl, —SO$_2$(C$_1$-C$_4$)alkyl, —SO$_2$—O(C$_1$-C$_4$)alkyl, —O—SO$_2$(C$_1$-C$_4$)alkyl, —NR5R6, —CONR5R6, —(C$_1$-C$_4$)alkyl optionally substituted by one or more —OH or —F and —O(C$_1$-C$_4$)alkyl optionally substituted by one or more —OH or —F, and wherein the cycles (C$_3$-C$_6$)cycloalkane, cyclohexene and bicycle can also be optionally substituted with one or more substituents oxo;

Z represents a biradical coming from a cycle selected from a (C$_3$-C$_6$)cycloalkane, cyclohexene, a heterocycle, benzene and a bicycle, wherein all these cycles can be optionally substituted with one or more substituents selected from the group —OH, —CHO, —SH, —NO$_2$, —CN, —F, —Cl, —Br, —CO(C$_1$-C$_4$)alkyl, —COO(C$_1$-C$_4$)alkyl, —OCO(C$_1$-C$_4$)alkyl, —S(C$_1$-C$_4$)alkyl, —SO(C$_1$-C$_4$)alkyl, —SO$_2$(C$_1$-C$_4$)alkyl, —SO$_2$—O(C$_1$-C$_4$)alkyl, —O—SO$_2$(C$_1$-C$_4$)alkyl, —NR5R6, —CONR5R6, —(C$_1$-C$_4$)alkyl optionally substituted by one or more —OH or —F and —O(C$_1$-C$_4$)alkyl optionally substituted by one or more —OH or —F, and wherein the cycles (C$_3$-C$_6$)cycloalkane, cyclohexene and bicycle can also be optionally substituted with one or more substituents oxo;

R5 and R6 independently represent —H or —(C$_1$-C$_4$)alkyl;

a heterocycle in the above definitions represents a five- or six-membered aromatic ring containing from one to three heteroatoms independently selected from O, S and N, wherein said ring can be attached to the rest of the molecule through a carbon or a nitrogen atom; and a bicycle in the above definitions represents a partially unsaturated, saturated or aromatic seven- to ten-membered ring optionally containing from one to three heteroatoms independently selected from O, S and N, wherein said ring or rings can be attached to the rest of the molecule through a carbon or a nitrogen atom.

2. A compound according to claim 1 wherein the configuration of the chiral carbon attached to R1 is (S), thus having the formula Ia

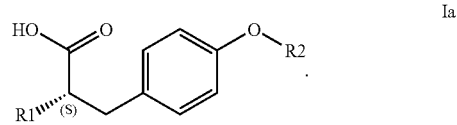

3. A compound according to claim 1, wherein R2 represents —(CH$_2$)$_s$—N(COR3)-A-J-T.

4. A compound according to claim 3, wherein R3 represents —(C$_1$-C$_{10}$)-alkyl optionally substituted by one or more substituents selected from —F, —Cl, —Br and —O($C_1$-$C_4$)-alkyl; —($C_2$-$C_6$)alkenyl; —($C_1$-$C_3$)alkylene-Y; —($C_2$-$C_3$)alkenylene-Y; —($C_2$-$C_3$)alkynylene-Y or —Y; and Y in R3 represents a monoradical coming from a cycle selected from a ($C_3$-$C_6$)cycloalkane, a heterocycle, benzene and a bicycle, wherein all these cycles can be optionally substituted as defined in claim 1.

5. A compound according to claim 3, wherein A represents —($C_1$-$C_4$)-alkylene-; —($C_1$-$C_4$)alkylene-Z- or -Z-; Z in A represents a biradical coming from a cycle selected from a ($C_3$-$C_6$)cycloalkane, a heterocycle, benzene and a bicycle, wherein all these cycles can be optionally substituted with one or more substituents selected from the group —F, —Cl, —Br, —S($C_1$-$C_4$)alkyl, —($C_1$-$C_4$)alkyl optionally substituted by one or more —OH or —F and —O($C_1$-$C_4$)alkyl optionally substituted by one or more —OH or —F; J represents a single bond; and T represents —H.

6. A compound according to claim 5 wherein Z in A represents an unsubstituted biradical coming from a cycle selected from a ($C_3$-$C_6$)cycloalkane and benzene.

7. A compound according to claim 1, wherein R2 represents —($CH_2$)$_s$—N(R4)-B-J-T.

8. A compound according to claim 7, wherein R4 represents —($C_4$-$C_{10}$)-alkyl optionally substituted by one or more substituents selected from —F, —Cl, —Br and —O($C_1$-$C_4$)-alkyl; —($C_1$-$C_4$)alkylene-Y; or —Y; and Y in R4 represents a monoradical coming from a cycle selected from a ($C_3$-$C_6$) cycloalkane, a heterocycle, benzene and a bicycle, wherein all these cycles can be optionally substituted as defined in claim 1.

9. A compound according to claim 7, wherein B represents —($C_1$-$C_4$)-alkylene-Z- or -Z-; Z in B represents a biradical coming from a cycle selected from a ($C_3$-$C_6$)cycloalkane, heterocycle, benzene and bicycle, wherein all these groups can be optionally substituted as defined in claim 1; J represents a single bond; and T represents —H.

10. A pharmaceutical composition which comprises a compound of formula I as defined in claim 1, together with appropriate amounts of pharmaceutically acceptable excipients.

* * * * *